US009049863B2

(12) United States Patent
Jakobi et al.

(10) Patent No.: US 9,049,863 B2
(45) Date of Patent: Jun. 9, 2015

(54) SUBSTITUTED (3R,4R)-4-CYAN-3,4-DIPHENYLBUTANOATES, METHOD FOR THE PRODUCTION THEREOF AND USE THEREOF AS HERBICIDES AND PLANT GROWTH REGULATORS

(75) Inventors: Harald Jakobi, Frankfurt (DE); Marc Mosrin, Frankfurt am Main (DE); Elmar Gatzweiler, Bad Nauheim (DE); Isolde Häuser-Hahn, Leverkusen (DE); Ines Heinemann, Hofheim (DE); Christopher Hugh Rosinger, Hofheim (DE); Alfred Angermann, Kriftel (DE); Michael Gerhard Hoffmann, Flörsheim (DE); Stefan Schnatterer, Hattersheim (DE); Hans-Joachim Zeiβ, Sulzbach (DE)

(73) Assignee: Bayer Intellectual Property GmbH, Monheim (DE)

( * ) Notice: Subject to any disclaimer, the term of this patent is extended or adjusted under 35 U.S.C. 154(b) by 0 days.

(21) Appl. No.: 14/005,379

(22) PCT Filed: Mar. 12, 2012

(86) PCT No.: PCT/EP2012/054292
§ 371 (c)(1),
(2), (4) Date: Oct. 16, 2013

(87) PCT Pub. No.: WO2012/126765
PCT Pub. Date: Sep. 27, 2012

(65) Prior Publication Data
US 2014/0194291 A1   Jul. 10, 2014

Related U.S. Application Data

(60) Provisional application No. 61/454,143, filed on Mar. 18, 2011.

(30) Foreign Application Priority Data

Mar. 18, 2011   (EP) ..................... 11158828

(51) Int. Cl.
*A01N 43/20*   (2006.01)
*A01N 37/34*   (2006.01)
(Continued)

(52) U.S. Cl.
CPC ............... *A01N 43/20* (2013.01); *A01N 37/34* (2013.01); *A01N 37/48* (2013.01); *A01N 41/02* (2013.01);
(Continued)

(58) Field of Classification Search
CPC ....... A01N 43/20; A01N 37/34; A01N 37/44; A01N 37/48; A01N 41/02; A01N 41/10; C07C 255/41; C07C 323/16

USPC ......... 504/100, 189, 209, 309, 310, 312, 314, 504/315, 321, 322; 514/63, 183, 506, 520, 514/521; 560/8, 239, 266; 562/400, 405
See application file for complete search history.

(56) References Cited

U.S. PATENT DOCUMENTS 4,224,052 A * 9/1980 Szucs ........................... 504/310
4,631,211 A   12/1986 Houghten
(Continued)

FOREIGN PATENT DOCUMENTS

EP   0 005 341   11/1979
EP   0005341 A2 * 11/1979 ............... A01N 9/22
(Continued)

OTHER PUBLICATIONS

International Search Report for PCT/EP2012/054292 Mailed Apr. 25, 2012.
Journal of Chemical Society (1945), London: The Society, pp. 438.
Nishimura et al., Chiral Amino Ether-Controlled Catalytic Enantioselective Arylthiol Conjugate Additions. Journal of Organic Chemistry. 2002, 67, pp. 431-434.
(Continued)

*Primary Examiner* — Jane C Oswecki
(74) *Attorney, Agent, or Firm* — Miles and Stockbridge

(57) ABSTRACT

Compounds of the formula (I) or salts thereof, in each case in the optically active (3R,4R)-threo form,

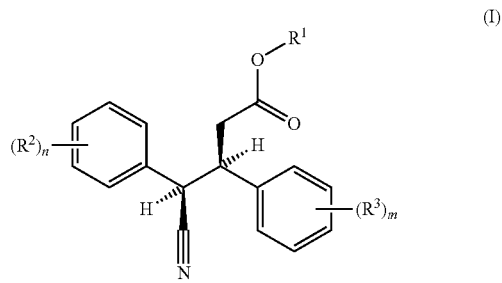

in which
R¹ is hydrogen or a hydrolysable radical, and
$(R^2)_n$, $(R^3)_m$, n and m are as defined in formula (I) according to claim 1, where the stereochemical configuration at the carbon atom in position 3 of the butanoic acid derivative has a stereochemical purity of from 60 to 100% (R), preferably 70 to 100% (R), or more preferably 80 to 100% (R), in particular 90 to 100% (R), based on a mixture of threo enantiomers present, and
the stereochemical configuration at the carbon atom in position 4 of the butanoic acid derivative has a stereochemical purity of from 60 to 100% (R), preferably 70 to 100% (R), more preferably 80 to 100% (R), in particular 90 to 100% (R), based on a mixture of threo enantiomers present, are suitable for use as herbicides and growth regulators, in particular for the selective use in plant crops, and can be prepared by the process of claim 9.

19 Claims, No Drawings

(51) Int. Cl.
| | |
|---|---|
| A01N 37/44 | (2006.01) |
| A01N 37/48 | (2006.01) |
| A01N 41/02 | (2006.01) |
| C07C 255/41 | (2006.01) |
| C07C 255/57 | (2006.01) |
| C07C 323/12 | (2006.01) |
| A01N 41/10 | (2006.01) |
| A01N 37/38 | (2006.01) |

(52) U.S. Cl.
CPC .............. *C07C 255/41* (2013.01); *C07C 255/57* (2013.01); *C07C 323/12* (2013.01); *A01N 41/10* (2013.01); *A01N 37/38* (2013.01)

(56) References Cited

U.S. PATENT DOCUMENTS

| | | | |
|---|---|---|---|
| 5,013,659 A | 5/1991 | Bedbrook et al. | |
| 2014/0087945 A1* | 3/2014 | Jakobi et al. | 504/103 |

FOREIGN PATENT DOCUMENTS

| | | | | |
|---|---|---|---|---|
| EP | 0005341 | A2 | 11/1979 | |
| EP | 0005341 | A3 | 11/1979 | |
| EP | 0086750 | A3 | 2/1983 | |
| EP | 0094349 | A2 | 5/1983 | |
| EP | 0094349 | A3 | 5/1983 | |
| EP | 0094349 | B1 | 5/1983 | |
| EP | 0086750 | B1 | 8/1983 | |
| EP | 0086750 | A2 | 11/1983 | |
| EP | 0131624 | B1 | 1/1984 | |
| EP | 0142924 | A2 | 5/1985 | |
| EP | 0142924 | A3 | 5/1985 | |
| EP | 0142924 | B1 | 5/1985 | |
| EP | 0174562 | A2 | 3/1986 | |
| EP | 0174562 | A3 | 3/1986 | |
| EP | 0174562 | B1 | 3/1986 | |
| EP | 0191736 | A2 | 8/1986 | |
| EP | 0191736 | A3 | 8/1986 | |
| EP | 0191736 | B1 | 8/1986 | |
| EP | 0193259 | A1 | 9/1986 | |
| EP | 0193259 | B1 | 9/1986 | |
| EP | 0131624 | A1 | 12/1986 | |
| EP | 0131624 | A4 | 12/1986 | |
| EP | 0221044 | A1 | 5/1987 | |
| EP | 0221044 | B1 | 5/1987 | |
| EP | 0242236 | A1 | 10/1987 | |
| EP | 0242236 | B1 | 10/1987 | |
| EP | 0242236 | B2 | 10/1987 | |
| EP | 0242246 | A1 | 10/1987 | |
| EP | 0242246 | B1 | 10/1987 | |
| EP | 0257993 | A2 | 3/1988 | |
| EP | 0257993 | A3 | 3/1988 | |
| EP | 0257993 | B1 | 3/1988 | |
| EP | 0 266 725 | | 5/1988 | |
| EP | 0266725 | A1 | 5/1988 | |
| EP | 0266725 | A1 * | 5/1988 | C07C 121/66 |
| EP | 0 270 830 | | 6/1988 | |
| EP | 0269806 | A1 | 6/1988 | |
| EP | 0269806 | B1 | 6/1988 | |
| EP | 0270830 | A1 * | 6/1988 | A01N 37/34 |
| EP | 0270830 | A1 | 6/1988 | |
| EP | 0305398 | B1 | 3/1989 | |
| EP | 0309862 | A1 | 4/1989 | |
| EP | 0309862 | B1 | 4/1989 | |
| EP | 0333131 | A1 | 9/1989 | |
| EP | 0333131 | B1 | 9/1989 | |
| EP | 0346620 | A1 | 12/1989 | |
| EP | 0365484 | A1 | 4/1990 | |
| EP | 0365484 | B1 | 4/1990 | |
| EP | 0464461 | A2 | 1/1992 | |
| EP | 0464461 | A3 | 1/1992 | |
| EP | 0464461 | B1 | 1/1992 | |
| EP | 0492366 | A2 | 7/1992 | |
| EP | 0492366 | A3 | 7/1992 | |
| EP | 0492366 | B1 | 7/1992 | |
| EP | 0582198 | A2 | 2/1994 | |
| EP | 0582198 | A3 | 2/1994 | |
| EP | 0582198 | B1 | 2/1994 | |
| JP | S060087254 | A | 5/1985 | |
| JP | 4-297454 | | 10/1992 | |
| JP | 04297455 | | 10/1992 | |
| JP | H04297454 | A | 10/1992 | |
| JP | H04297455 | A | 10/1992 | |
| JP | 5-58979 | | 3/1993 | |
| JP | H05058979 | A | 3/1993 | |
| WO | 9107874 | A1 | 6/1991 | |
| WO | 9108202 | A1 | 6/1991 | |
| WO | 9113972 | A1 | 9/1991 | |
| WO | 9119806 | A1 | 12/1991 | |
| WO | 9200377 | A1 | 1/1992 | |
| WO | 9221376 | A1 | 7/1992 | |
| WO | 9014827 | A1 | 9/1992 | |
| WO | 9507897 | A1 | 3/1995 | |
| WO | 9827049 | A1 | 6/1998 | |
| WO | 9838856 | A1 | 9/1998 | |
| WO | 9900020 | A1 | 1/1999 | |
| WO | 9916744 | A1 | 4/1999 | |
| WO | 0234048 | A1 | 5/2002 | |
| WO | 2004084631 | A1 | 10/2004 | |
| WO | 2005015994 | A1 | 2/2005 | |
| WO | 2005016001 | A1 | 2/2005 | |
| WO | 2005112630 | A1 | 12/2005 | |
| WO | 2006007981 | A1 | 1/2006 | |
| WO | 2007023719 | A1 | 3/2007 | |
| WO | 2007023764 | A1 | 3/2007 | |
| WO | 2011/003775 | | 1/2011 | |
| WO | 2011/003776 | | 1/2011 | |
| WO | 2011003775 | A2 | 1/2011 | |
| WO | 2011003776 | A2 | 1/2011 | |
| WO | 2012126765 | A1 | 9/2012 | |

OTHER PUBLICATIONS

Lebel et al., Palladium-Catalyzed Cross-Coupling Reactions in One-Pot Multicatalytic Processes. Journal of American Chemical Society. 2007, 129 (43), 13321.
Journal of Organic Chemistry. American Chemical Society 1984, 49 (22), pp. 4287-4290.
DeWitt, Sheila H., Annual Reports in Combinatorial Chemistry and Molecular Diversity: Automated Synthesis, Band 1, Verlag Escom, 1997, pp. 69-77.
Houghten et al., General Method for the rapid solid-phase synthesis of large number of peptides: Specificity of antigen-antibody interaction at the level of individual amino acids. Proc. Natl. Acad. Sci., 1985, 82, pp. 5131-5135.
Christou, Paul. Trends in Plant Science 1 (1996) pp. 423-431.
Braun et al., The general mitochondrial processing peptidase from potato is an integral part of cytochrome c reductase of the respiratory chain. The EMBO Journal. vol. 11 No. 9. (1992), 3219-3227.
Wolter et al., rbcS genes in *Solanum tuberosum*: Conservation of transit peptide and exon shuffling during evolution, Proc. Natl. Acad. Sci. USA 85 (1988), 846-850.
Sonnewald et al., Transgenic tobacco plants expressing yeast-derived invertase in either the cytosol, vacuole or apoplast. Plant Journal. vol. 1 (1991), pp. 95-106.
Browing, J.E., Agglomeration: Growing Larger in Applications, Chemical and Engineering.1967, pp. 147ff.
Snow et al., Perry's Chemical Engineer's Handbook, 5th Ed., McGraw-Hill, New York 1973, pp. 8-57.
International Search Report dated Apr. 25, 2012, issued in counterpart International Application No. PCT/EP2012/054292.
G.C. Klingmann, Weed Control as a Science, John Wiley and Sons, Inc. New York, 1961, pp. 81-96.
Freyer et al., Weed Control Handbook, 5th Ed. Blackwell Scientific Publications, Oxford, 1968, pp. 101-103.
Weed Research: Glossary of Common Names and Abbreviations of Herbicides. vol. 26 (1986) pp. 441-445.

* cited by examiner

SUBSTITUTED (3R,4R)-4-CYAN-3,4-DIPHENYLBUTANOATES, METHOD FOR THE PRODUCTION THEREOF AND USE THEREOF AS HERBICIDES AND PLANT GROWTH REGULATORS

CROSS REFERENCE TO RELATED APPLICATIONS

This application is a §371 National Stage Application of PCT/EP2012/054292, filed Mar. 12, 2012, which claims priority to European Application No. 11158828.1, filed Mar. 18, 2011, and U.S. Provisional Application No. 61/454,143, filed March 18, 2011.

BACKGROUND OF THE INVENTION

1. Field of the Invention

The invention relates to the technical field of the herbicides and plant growth regulators, for example the herbicides for controlling broad-leaved weeds and weed grasses in crops of useful plants or the plant growth regulators which can be used for influencing the growth of crop plants.

2. Description of Related Art

In their application, crop protection agents known to date for the selective control of harmful plants in crops of useful plants or active compounds for controlling unwanted vegetation sometimes have disadvantages, be it (a) that they have no or else insufficient herbicidal activity against particular harmful plants, (b) that the spectrum of harmful plants which can be controlled with an active compound is not wide enough, (c) that their selectivity in crops of useful plants is too low and/or (d) that they have a toxicologically unfavorable profile. Furthermore, some active compounds which can be used as plant growth regulators for a number of useful plants cause unwanted reduced harvest yields in other useful plants or are not compatible with the crop plant, or only within a narrow application rate range. Some of the known active compounds cannot be produced economically on an industrial scale owing to precursors and reagents which are difficult to obtain, or they have only insufficient chemical stabilities. In the case of other active compounds, the activity is too highly dependent on environmental conditions, such as weather and soil conditions.

Herbicidal cyanobutyrates are disclosed in the published patent applications EP-A-5341 (U.S. Pat. No. 4,224,052), EP-A-266725, EP-A-270830, JP-04/297454, JP-04/297455, JP-05/058979, WO 2011/003775 A2 and WO 2011/003776 A2.

The publications mentioned describe the mixtures of the diastereomeric threo and erythro forms or the erythro or threo racemates of the cyanobutyrates in more detail with respect to herbicidal properties and crop plant compatibility.

EP-A-5341 describes herbicidal esters and amides of 4-cyano-3,4-diphenylbutanoic acids which are optionally substituted at the phenyl radicals. According to EP-A-5341, the threo isomers are generally suitable for the non-selective control of harmful plants, whereas the erythro/threo isomer mixtures are suitable for the selective control of harmful plants in some crops of useful plants. Moreover, EP-A-5341 mentions that the 2 enantiomers belonging to the threo form have different activities, which was investigated in an exemplary manner of the different activities of the enantiomers of the enantiomer pair of 4-cyano-3,4-diphenylbutanoic acid unsubstituted in the phenyl radicals.

EP-A-266725 discloses some erythro/threo isomer mixtures which can be used selectively for controlling weeds in rice crops.

EP-A-270830 describes that threo isomers and erythro/threo isomer mixtures can be used as plant regulators, preventing the development of infructescence in various harmful grasses.

WO 2011/003775 discloses specific esters of 4-cyano-3,4-diphenylbutanoic acids which can be used as effective herbicides, preferably also in crops of useful plants.

WO 2011/003776 discloses 4-cyano-3,4-diphenylbutanoic acids and esters which have specific substitutions at the phenyl radicals and can be used as effective herbicides, preferably also in crops of useful plants.

With the exception of EP-A-5341, the investigations described in the literature quoted are limited to the use of racemic mixtures.

However, their herbicidal action, in particular at low application rates, and/or their compatibility with crop plants still warrant improvements.

For the reasons mentioned, there is still a need for alternative, highly active herbicides for the selective application in plant crops or use on non-crop land. It is also desirable to provide alternative chemical active compounds which may be used in an advantageous manner as herbicides or plant growth regulators.

SUMMARY

Surprisingly, it has now been found that certain enriched optically active threo compounds from the group of the cyanobutyrates mentioned have special herbicidal activities and at the same time advantageous selectivities with regard to a number of useful plants.

It is an object of the present invention to provide compounds having herbicidal activity which are highly effective against economically important harmful plants even at relatively low application rates and can be used selectively in crop plants, preferably with good activity for harmful plants.

The present invention provides compounds of the formula (I) and salts thereof, in each case in the optically active (3R, 4R)-threo form,

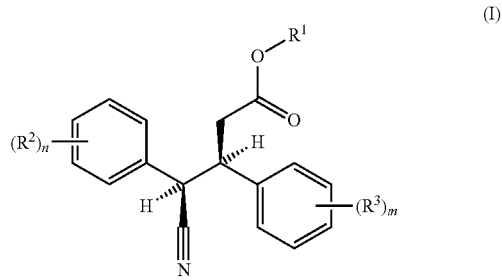

in which
R$^1$ is hydrogen or a hydrolyzable radical, preferably
   R$^1$ is hydrogen or an optionally substituted hydrocarbon radical or an optionally substituted heterocyclyl radical, where each of the two lastmentioned carbon-containing radicals including substituents has 1 to 30 carbon atoms, preferably 1 to 24 carbon atoms, in particular 1 to 20 carbon atoms,
or
   R$^1$ is a radical of the formula SiR$^a$R$^b$R$^c$, —NR$^a$R$^b$ or —N=CR$^c$R$^d$, where in the 3 lastmentioned formulae each of the radicals $R^a$, $R^b$, $R^c$ and $R^d$ independently of the others is hydrogen or an optionally substituted hydrocarbon radical, where, however, $SiH_3$ for $SiR^aR^bR^c$ is excluded, or $R^a$ and $R^b$ together with the nitrogen atom are a 3- to 9-membered heterocycle which, in addition to the nitrogen atom, may contain one or two further ring heteroatoms from the group consisting of N, O and S and which is unsubstituted or substituted, or $R^c$ and $R^d$ together with the carbon atom are a 3- to 9-membered carbocyclic radical or a heterocyclic radical which may contain 1 to 3 ring heteroatoms from the group consisting of N, O and S, where the carbocyclic or heterocyclic radical is unsubstituted or substituted, where each of the radicals $R^a$, $R^b$, $R^c$ and $R^d$ including substituents has up to 30 carbon atoms, preferably up to 24 carbon atoms, in particular up to 20 carbon atoms, or $R^1$ is a radical of the formula —C(=O)—$R^e$ or —P(=O)($R^f$)$_2$, where $R^e$ and the $R^f$ independently of one another are each hydrogen, OH, ($C_1$-$C_8$)-alkyl, ($C_1$-$C_4$)-haloalkyl, ($C_2$-$C_8$)-alkenyl, ($C_2$-$C_8$)-alkynyl, ($C_1$-$C_6$)-alkoxy, ($C_1$-$C_6$)-alkoxy-($C_1$-$C_8$)-alkyl, ($C_1$-$C_4$)-haloalkoxy, ($C_1$-$C_4$)-haloalkoxy-($C_1$-$C_8$)-alkyl, ($C_3$-$C_8$)-alkenyloxy, ($C_3$-$C_8$)-alkenyloxy-($C_1$-$C_8$)-alkyl, ($C_3$-$C_8$)-alkynyloxy, ($C_3$-$C_8$)-alkynyloxy-($C_1$-$C_8$)-alkyl, —NR*R**, where R* and R** are defined below, tri-[($C_1$-$C_4$)-alkyl]-silyl, tri-[($C_1$-$C_4$)-alkyl]-silyl-($C_1$-$C_8$)-alkyl, ($C_3$-$C_6$)-cycloalkyl, ($C_3$-$C_6$)-cycloalkyl-($C_1$-$C_8$)-alkyl, ($C_5$-$C_6$)-cycloalkenyl, ($C_5$-$C_6$)-cycloalkenyl-($C_1$-$C_8$)-alkyl, ($C_5$-$C_6$)-cycloalkynyl, ($C_5$-$C_6$)-cycloalkynyl-($C_1$-$C_8$)-alkyl, phenyl, phenyl-($C_1$-$C_8$)-alkyl, phenoxy, phenoxy-($C_1$-$C_8$)-alkyl, phenylamino, phenylamino-($C_1$-$C_8$)-alkyl, a radical $Het^1$, $Het^1$-($C_1$-$C_6$)-alkyl or $Het^1$-O—($C_1$-$C_6$)-alkyl, where the heterocyclic radical $Het^1$ is defined below, where each of the 15 lastmentioned radicals is unsubstituted in the acyclic moiety or substituted by one or more identical or different radicals $R^A$ and is unsubstituted in the cyclic moiety or substituted by one or more identical or different radicals $R^B$, ($R^2$)$_n$ is n substituents $R^2$, where $R^2$ (if n=1) or each of the substituents $R^2$ (if n is greater than 1) independently of the others is halogen, cyano, nitro, ($C_1$-$C_8$)-alkyl, ($C_1$-$C_8$)-alkoxy, ($C_1$-$C_8$)-alkylthio, ($C_1$-$C_8$)-alkylsulfinyl, ($C_1$-$C_8$)-alkylsulfonyl, ($C_1$-$C_6$)-haloalkyl, ($C_1$-$C_6$)-haloalkoxy, ($C_1$-$C_6$)-haloalkylthio, ($C_1$-$C_6$)-haloalkylsulfinyl, ($C_1$-$C_6$)-haloalkylsulfonyl, ($C_2$-$C_6$)-alkenyl, ($C_2$-$C_6$)-alkynyl, tri-[($C_1$-$C_4$)-alkyl]-silyl or tri-[($C_1$-$C_4$)-alkyl]-silyl-($C_1$-$C_4$)-alkyl or where in each case two $R^2$ located ortho at the ring together are a group of the formula —$Z^1$-A*-$Z^2$ in which A* is an alkylene group having 1 to 4 carbon atoms which is optionally substituted by one or more radicals from the group consisting of halogen, ($C_1$-$C_4$)-alkyl, ($C_1$-$C_4$)-haloalkyl, ($C_1$-$C_4$)-alkoxy and ($C_1$-$C_4$)-haloalkoxy, $Z^1$ is a direct bond, O or S and $Z^2$ is a direct bond, O or S, where the group —$Z^1$-A*-$Z^2$ together with the carbon atoms, attached to the group, of the phenyl ring form a fused-on 5- or 6-membered ring, and ($R^3$)$_m$ is m substituents $R^3$, where $R^3$ (if m=1) or each of the substituents $R^3$ (if m is greater than 1) independently of the others is halogen, cyano, nitro, ($C_1$-$C_8$)-alkyl, ($C_1$-$C_8$)-alkoxy, ($C_1$-$C_8$)-alkylthio, ($C_1$-$C_8$)-alkylsulfinyl, ($C_1$-$C_8$)-alkylsulfonyl, ($C_1$-$C_6$)-haloalkyl, ($C_1$-$C_6$)-haloalkoxy, ($C_1$-$C_6$)-haloalkylthio, ($C_1$-$C_6$)-haloalkylsulfinyl, ($C_1$-$C_6$)-haloalkylsulfonyl, ($C_2$-$C_6$)-alkenyl, ($C_2$-$C_6$)-alkynyl, NR*R**, where R* and R are defined below, tri-[($C_1$-$C_4$)-alkyl]-silyl or tri-[($C_1$-$C_4$)-alkyl]-silyl-($C_1$-$C_4$)-alkyl or where in each case two groups $R^3$ located ortho at the ring together are a group of the formula —$Z^3$-A-$Z^4$ in which A is an alkylene group having 1 to 4 carbon atoms which is optionally substituted by one or more radicals from the group consisting of halogen, ($C_1$-$C_4$)-alkyl, ($C_1$-$C_4$)-haloalkyl, ($C_1$-$C_4$)-alkoxy and ($C_1$-$C_4$)-haloalkoxy, $Z^3$ is a direct bond, O or S and $Z^4$ is a direct bond, O or S, where the group —$Z^3$-A-$Z^4$ together with the carbon atoms, attached to the group, of the phenyl ring form a fused-on 5- or 6-membered ring, where in the radicals mentioned above and in the radicals below $Het^1$ in each case independently of the others is a saturated, partially unsaturated or heteroaromatic monocyclic heterocyclyl radical having 3 to 9 ring atoms or a 9- or 10-membered bicyclic heterocycle, each containing 1, 2, 3 or 4 heteroatoms selected from the group consisting of O, N and S, R*, R** are each independently of one another (and also independently of other radicals NR*R**) H, ($C_1$-$C_8$)-alkyl, ($C_2$-$C_8$)-alkenyl, ($C_2$-$C_8$)-alkynyl, ($C_1$-$C_4$)-alkoxy-($C_1$-$C_4$)-alkyl, ($C_1$-$C_4$)-alkanoyl, [($C_1$-$C_4$)-haloalkyl]-carbonyl, [($C_1$-$C_4$)-alkoxy]-carbonyl, [($C_1$-$C_4$)-haloalkoxy]-carbonyl, ($C_3$-$C_6$)-cycloalkyl, ($C_3$-$C_6$)-cycloalkyl-($C_1$-$C_4$)-alkyl, phenyl, phenyl-($C_1$-$C_4$)-alkyl, where each of the 4 lastmentioned radicals is optionally substituted in the cycle by one or more identical or different radicals $R^{bb}$ or R* and R** together with the nitrogen atom are a 3- to 8-membered heterocycle which, in addition to the nitrogen atom, may contain one or two further ring heteroatoms from the group consisting of N, O and S and which may be unsubstituted or substituted by one or more radicals from the group consisting of ($C_1$-$C_4$)-alkyl, ($C_1$-$C_4$)-haloalkyl and oxo, $R^A$ is halogen, cyano, hydroxyl or ($C_1$-$C_6$)-alkoxy, $R^B$ is halogen, cyano, hydroxyl, oxo, nitro, ($C_1$-$C_8$)-alkyl, ($C_1$-$C_6$)-haloalkyl, cyano-($C_1$-$C_6$)-alkyl, hydroxy-($C_1$-$C_6$)-alkyl, nitro-($C_1$-$C_6$)-alkyl, ($C_2$-$C_8$)-alkenyl, ($C_2$-$C_8$)-haloalkenyl, ($C_2$-$C_8$)-alkynyl, ($C_2$-$C_8$)-haloalkynyl, ($C_1$-$C_8$)-alkoxy, ($C_2$-$C_8$)-alkenyloxy, ($C_2$-$C_8$)-alkynyloxy, ($C_1$-$C_8$)-haloalkoxy, ($C_1$-$C_6$)-alkoxy-($C_1$-$C_6$)-alkyl, ($C_1$-$C_6$)-alkoxy-($C_1$-$C_4$)-alkoxy, ($C_1$-$C_6$)-haloalkoxy-($C_1$-$C_4$)-alkyl, ($C_1$-$C_6$)-haloalkoxy-($C_1$-$C_4$)-alkoxy, ($C_1$-$C_8$)-alkylthio, ($C_2$-$C_6$)-alkenylthio, ($C_2$-$C_6$)-alkynylthio, ($C_1$-$C_8$)-alkylsulfinyl, ($C_1$-$C_6$)-haloalkylsulfinyl, ($C_1$-$C_8$)-alkylsulfonyl, ($C_1$-$C_6$)-haloalkylsulfonyl, a radical of the formula $R^{aa}$—C(=O)—, $R^{aa}$—C(=O)—($C_1$-$C_6$)-alkyl, where the $R^{aa}$ are defined below, —NR*R**, where R* and R** are defined below, tri-[($C_1$-$C_4$)-alkyl]-silyl, tri-[($C_1$-$C_4$)-alkyl]-silyl-($C_1$-$C_6$)-alkyl, ($C_3$-$C_8$)-cycloalkyl, ($C_3$-$C_8$)-cycloalkoxy, ($C_3$-$C_8$)-cycloalkyl-($C_1$-$C_8$)-alkyl, ($C_3$-$C_8$)-cycloalkyl-($C_1$-$C_8$)-alkoxy, phenyl, phenyl-($C_1$-$C_8$)-alkyl, phenoxy, phenoxy-($C_1$-$C_8$)-alkyl, phenylamino, phenylamino-($C_1$-$C_8$)-alkyl or a 5- or 6-membered monocyclic or 9- or 10-membered bicyclic heterocycle which contains 1, 2, 3 or 4 heteroatoms selected from the group consisting of O, N and S, where each of the 11 lastmentioned radicals is optionally substituted in the cyclic moiety by one or more identical or different radicals $R^{bb}$ $R^{aa}$ in each case independently of the others is hydrogen, OH, $(C_1-C_8)$-alkyl, $(C_1-C_6)$-haloalkyl, $(C_2-C_8)$-alkenyl, $(C_2-C_8)$-alkynyl, $(C_1-C_8)$-alkoxy, $(C_1-C_6)$-alkoxy-$(C_1-C_6)$-alkyl, $(C_1-C_6)$-alkoxy-$(C_1-C_6)$-alkoxy, $(C_1-C_6)$-haloalkoxy, $(C_1-C_6)$-haloalkoxy-$(C_1-C_6)$-alkyl, $(C_1-C_6)$-haloalkoxy-$(C_1-C_6)$-alkoxy, $(C_3-C_8)$-alkenyloxy, $(C_3-C_8)$-alkenyloxy-$(C_1-C_6)$-alkyl, $(C_3-C_8)$-alkenyloxy-$(C_1-C_8)$-alkoxy, $(C_3-C_8)$-alkynyloxy, $(C_3-C_8)$-alkynyloxy-$(C_1-C_6)$-alkyl, $(C_3-C_8)$-alkynyloxy-$(C_1-C_6)$-alkoxy, —NR*R*, where R* and R** are as defined above, tri-$[(C_1-C_4)$-alkyl]-silyl, tri-$[(C_1-C_4)$-alkyl]-silyl-$(C_1-C_6)$-alkyl, tri-$[(C_1-C_4)$-alkyl]-silyl-$(C_1-C_6)$-alkoxy, $(C_3-C_8)$-cycloalkyl, $(C_3-C_8)$-cycloalkoxy, $(C_3-C_8)$-cycloalkyl-$(C_1-C_8)$-alkyl, $(C_3-C_8)$-cycloalkyl-$(C_1-C_8)$-alkoxy, $(C_5-C_8)$-cycloalkenyl, $(C_5-C_8)$-cycloalkenyl-$(C_1-C_6)$-alkyl, $(C_5-C_8)$-cycloalkenyloxy, $(C_5-C_8)$-cycloalkynyl, $(C_5-C_8)$-cycloalkynyl-$(C_1-C_6)$-alkyl, $(C_5-C_8)$-cycloalkynyl-$(C_1-C_6)$-alkoxy, phenyl, phenyl-$(C_1-C_8)$-alkyl, phenyl-$(C_1-C_8)$-alkoxy, phenoxy, phenoxy-$(C_1-C_8)$-alkyl, phenoxy-$(C_1-C_8)$-alkoxy, phenylamino, phenylamino-$(C_1-C_8)$-alkyl, phenylamino-$(C_1-C_8)$-alkoxy or a 5- or 6-membered monocyclic or 9- or 10-membered bicyclic heterocycle which is optionally attached via an alkylene group or alkoxy group and contains 1, 2, 3 or 4 heteroatoms selected from the group consisting of O, N and S, where each of the 20 lastmentioned radicals is optionally substituted in the cyclic moiety by one or more identical or different radicals $R^{bb}$, and $R^{bb}$ in each case independently of the others is halogen, $(C_1-C_4)$-alkyl, $(C_1-C_4)$-haloalkyl, $(C_1-C_4)$-alkoxy or $(C_1-C_4)$-haloalkoxy or in the case of saturated or partially unsaturated cyclic base groups is also oxo and n, m are each independently of one another 0, 1, 2, 3, 4 or 5, preferably 0, 1, 2 or 3, with the proviso that the two are not simultaneously 0, where the stereochemical configuration at the carbon atom in position 3 of the butanoic acid derivative has a stereochemical purity of 60 to 100% (R), preferably 70 to 100% (R), more preferably 80 to 100% (R), in particular 90 to 100% (R), based on the mixture of threo enantiomers present, and the stereochemical configuration at the carbon atom in position 4 of the butanoic acid derivative has a stereochemical purity of 60 to 100% (R), preferably 70 to 100% (R), more preferably 80 to 100% (R), in particular 90 to 100% (R), based on the mixture of threo enantiomers present.

DETAILED DESCRIPTION OF A PREFFERED EMBODIMENT

In formula (I), the formula "$(R^2)_n$" means n radicals $R^2$ which are attached as substituents at the phenyl ring in question, where the radicals in the case of n greater than 1 may be identical or different and have the meaning mentioned in each case in more detail. In the case n=0, the phenyl ring in question is not substituted by substituents $R^2$, i.e. all ring carbon atoms of the phenyl ring in positions 2 to 6 are attached to a hydrogen atom. This applies correspondingly to the substitution of the other phenyl ring according to formula $(R^3)_m$.

In the case of $R^1$=H or in the case of suitable acidic substituents, the compounds of the formula (I) are able to form salts by reaction with bases where the acidic hydrogen is replaced by an agriculturally suitable cation.

By addition of a suitable inorganic or organic acid onto a basic group, such as, for example, amino or alkylamino, the compounds of the formula (I) are able to form salts. Suitable acidic groups present, such as, for example, carboxylic acid groups, are able to form inner salts with groups which for their part can be protonated, such as amino groups.

The compounds of the formula (I) may preferably be present in the form of agriculturally suitable salts, where the type of salt is otherwise immaterial. In general, suitable salts are the salts of those cations or the acid additions salts of those acids whose cations and anions, respectively, have no adverse effect on the herbicidal activity of the compounds (I).

Suitable cations are in particular the ions of the alkali metals, preferably lithium, sodium or potassium, of the alkaline earth metals, preferably calcium or magnesium, and of the transition metals, preferably manganese, copper, zinc or iron. The cation used may also be ammonium or substituted ammonium, where one to four hydrogen atoms may be replaced by $(C_1-C_4)$-alkyl, hydroxy-$(C_1-C_4)$-alkyl, $(C_1-C_4)$-alkoxy-$(C_1-C_4)$-alkyl, hydroxy-$(C_1-C_4)$-alkoxy-$(C_1-C_4)$-alkyl, phenyl or benzyl, preferably ammonium, dimethylammonium, diisopropylammonium, tetramethylammonium, tetrabutylammonium, 2-(2-hydroxyeth-1-oxy)eth-1-ylammonium, di(2-hydroxyeth-1-yl)ammonium, trimethylbenzylammonium. Also suitable are phosphonium ions, sulfonium ions, preferably tri$(C_1-C_4)$-alkylsulfonium, in particular trimethyl sulfonium, or sulfoxonium ions, preferably tri$(C_1-C_4)$-alkylsulfoxonium, in particular trimethyl sulfoxonium.

Anions of useful acid addition salts are primarily chloride, bromide, fluoride, hydrogensulfate, sulfate, dihydrogenphosphate, hydrogenphosphate, nitrate, bicarbonate, carbonate, hexafluorosilicate, hexafluorophosphate, benzoate and also the anions of $(C_1-C_4)$-alkanoic acids, preferably formate, acetate, propionate, butyrate or trifluoroacetate.

In formula (I) and in all subsequent formulae, chemical radicals are referred to by names which are collective terms for the individual group members or specifically refer to individual chemical radicals.

In general, terms are used which are familiar to the person skilled in the art and/or in particular have the meanings illustrated below.

A hydrolyzable radical (see definition of $R^1$) is a radical which can be hydrolyzed under application conditions, for example a radical which can be hydrolyzed even in the spray liquor or in particular under the physiological conditions in plants, where a compound of the formula (I) having the carboxylic ester group CO—$OR^1$ ($R^1$ is not hydrogen) is hydrolyzed to the compound of the formula (I) having the carboxylic acid group CO—OH (i.e. the compound (I) where $R^1$=H). Expressly, the definition of the hydrolyzable radicals also includes radicals where $R^1$=hydrocarbon radical or heterocyclyl radical, the two lastmentioned radicals being unsubstituted or substituted, even if some of them are hydrolyzable comparatively slowly.

A hydrocarbon radical is an aliphatic, cycloaliphatic or aromatic monocyclic or, in the case of an optionally substituted hydrocarbon radical, also a bicyclic or polycyclic organic radical based on the elements carbon and hydrogen, including, for example, the radicals alkyl, alkenyl, alkynyl, cycloalkyl, cycloalkenyl, aryl, phenyl, naphthyl, indanyl, indenyl, etc.; this applies correspondingly to hydrocarbon radicals in composite meanings, such as hydrocarbonoxy radicals or other hydrocarbon radicals attached via heteroatom groups.

Unless defined in more detail, the hydrocarbon radicals preferably have 1 to 20 carbon atoms, more preferably 1 to 16 carbon atoms, in particular 1 to 12 carbon atoms.

The hydrocarbon radicals, also in the special radicals alkyl, alkoxy, haloalkyl, haloalkoxy, alkylamino and alkylthio, and also the corresponding unsaturated and/or substituted radicals may in each case be straight-chain or branched in the carbon skeleton.

The expression "$(C_1-C_4)$-alkyl" is a brief notation for alkyl having from 1 to 4 carbon atoms, i.e. encompasses the methyl, ethyl, 1-propyl, 2-propyl, 1-butyl, 2-butyl, 2-methylpropyl or tert-butyl radicals. General alkyl radicals with a larger specified range of carbon atoms, e.g. "$(C_1-C_6)$-alkyl", correspondingly also encompass straight-chain or branched alkyl radicals with a greater number of carbon atoms, i.e. according to the example also the alkyl radicals having 5 and 6 carbon atoms.

Unless stated specifically, preference is given to the lower carbon skeletons, for example having from 1 to 6 carbon atoms, or having from 2 to 6 carbon atoms in the case of unsaturated groups, in the case of the hydrocarbon radicals such as alkyl, alkenyl and alkynyl radicals, including in combined radicals. Alkyl radicals, including in the combined definitions such as alkoxy, haloalkyl, etc., are, for example, methyl, ethyl, n- or i-propyl, n-, i-, t- or 2-butyl, pentyls, hexyls such as n-hexyl, i-hexyl and 1,3-dimethylbutyl, heptyls such as n-heptyl, 1-methylhexyl and 1,4-dimethylpentyl; alkenyl and alkynyl radicals are defined as the possible unsaturated radicals corresponding to the alkyl radicals; alkenyl is, for example, vinyl, allyl, 1-methyl-2-propenyl, 2-methyl-2-propenyl, 2-butenyl, pentenyl, 2-methylpentenyl or hexenyl group, preferably allyl, 1-methylprop-2-en-1-yl, 2-methylprop-2-en-1-yl, but-2-en-1-yl, but-3-en-1-yl, 1-methylbut-3-en-1-yl or 1-methylbut-2-en-1-yl.

Alkenyl also includes in particular straight-chain or branched hydrocarbon radicals having more than one double bond, such as 1,3-butadienyl and 1,4-pentadienyl, but also allenyl or cumulenyl radicals having one or more cumulated double bonds, for example allenyl (1,2-propadienyl), 1,2-butadienyl and 1,2,3-pentatrienyl.

Alkynyl is, for example, propargyl, but-2-yn-1-yl, but-3-yn-1-yl, 1-methylbut-3-yn-1-yl.

Alkynyl also includes, in particular, straight-chain or branched hydrocarbon radicals having more than one triple bond or else having one or more triple bonds and one or more double bonds, for example 1,3-butatrienyl or 3-penten-1-yn-1-yl.

A 3- to 9-membered carbocyclic ring is $(C_3-C_9)$-cycloalkyl or $(C_5-C_9)$-cycloalkenyl.

$(C_3-C_9)$-Cycloalkyl is a carbocyclic saturated ring system having preferably 3-9 carbon atoms, for example cyclopropyl, cyclobutyl, cyclopentyl, cyclohexyl, cycloheptyl, cyclooctyl or cyclononyl. In the case of substituted cycloalkyl, cyclic systems with substituents are included, where the substituents may also be bonded by a double bond on the cycloalkyl radical, for example an alkylidene group such as methylidene.

$(C_5-C_9)$-Cycloalkenyl is a carbocyclic, nonaromatic, partially unsaturated ring system having 5-9 carbon atoms, for example 1-cyclobutenyl, 2-cyclobutenyl, 1-cyclopentenyl, 2-cyclopentenyl, 3-cyclopentenyl, or 1-cyclohexenyl, 2-cyclohexenyl, 3-cyclohexenyl, 1,3-cyclohexadienyl or 1,4-cyclohexadienyl. In the case of substituted cycloalkenyl, the explanations for substituted cycloalkyl apply correspondingly.

Alkylidene, for example also in the form of $(C_1-C_{10})$-alkylidene, is the radical of a straight-chain or branched alkane which is bonded via a double bond, the position of the binding site not being fixed. In the case of a branched alkane, the only positions possible are, of course, those in which two hydrogen atoms can be replaced by the double bond; radicals are, for example, $=CH_2$, $=CH-CH_3$, $=C(CH_3)-CH_3$, $=C(CH_3)-C_2H_5$ or $=C(C_2H_5)-C_2H_5$.

Halogen is, for example, fluorine, chlorine, bromine or iodine. Haloalkyl, -alkenyl and -alkynyl are alkyl, alkenyl and alkynyl, respectively, which are partially or fully substituted by identical or different halogen atoms, preferably from the group consisting of fluorine, chlorine and bromine, in particular from the group consisting of fluorine and chlorine, for example monohaloalkyl, perhaloalkyl, $CF_3$, $CHF_2$, $CH_2F$, $CF_3CF_2$, $CH_2FCHCl$, $CCl_3$, $CHCl_2$, $CH_2CH_2Cl$; haloalkoxy is, for example, $OCF_3$, $OCHF_2$, $OCH_2F$, $CF_3CF_2O$, $OCH_2CF_3$ and $OCH_2CH_2Cl$; this applies correspondingly to haloalkenyl and other halogen-substituted radicals.

Aryl is a mono-, bi- or polycyclic aromatic system, for example phenyl, naphthyl, tetrahydronaphthyl, indenyl, indanyl, pentalenyl, fluorenyl and the like, preferably phenyl.

Optionally substituted aryl also includes polycyclic systems, such as tetrahydronaphthyl, indenyl, indanyl, fluorenyl, biphenylyl, where the point of attachment is at the aromatic system.

A heterocyclic radical (heterocyclyl) comprises at least one heterocyclic ring (=carbocyclic ring in which at least one carbon atom is replaced by a heteroatom, preferably by a heteroatom from the group consisting of N, O, S, P, B, Si, Se), which is saturated, unsaturated or heteroaromatic and may be unsubstituted or substituted, where the point of attachment is located at a ring atom.

Unless defined otherwise it preferably contains one or more, in particular 1, 2 or 3, heteroatoms in the heterocyclic ring, preferably from the group consisting of N, O, and S; it is preferably an aliphatic heterocyclyl radical having 3 to 7 ring atoms or a heteroaromatic radical having 5 or 6 ring atoms. The heterocyclic radical may, for example, be a heteroaromatic radical or ring (heteroaryl), such as, for example, a monocyclic, bicyclic or polycyclic aromatic system in which at least 1 ring contains one or more heteroatoms.

If the heterocyclyl radical or the heterocyclic ring is optionally substituted, it can be fused to other carbocyclic or heterocyclic rings. Preference is given to benzo-fused heterocyclic or heteroaromatic rings.

Optionally substituted heterocyclyl also includes polycyclic systems, such as, for example, 8-aza-bicyclo[3.2.1]octanyl or 1-aza-bicyclo[2.2.1]heptyl.

Optionally substituted heterocyclyl also includes spirocyclic systems, such as, for example, 1-oxa-5-aza-spiro[2.3]hexyl.

It is preferably a radical of a heteroaromatic ring having a heteroatom from the group consisting of N, O and S, for example the radical of a five- or six-membered ring, such as pyridyl, pyrrolyl, thienyl or furyl;
it is furthermore preferably a radical of a corresponding heteroaromatic ring having 2, 3 or 4 heteroatoms, for example pyrimidinyl, pyridazinyl, pyrazinyl, triazinyl, tetrazinyl, thiazolyl, thiadiazolyl, oxazolyl, isoxazolyl, pyrazolyl, imidazolyl or triazolyl or tetrazolyl.

Here, preference is given to a radical of a heteroaromatic five- or six-membered ring having 1 to 4 heteroatoms, such as, for example, 1,2,3-triazolyl, 1,2,4-triazolyl, tetrazolyl, isothiazolyl, 1,2,3-oxadiazolyl, 1,2,4-oxadiazolyl, 1,3,4-oxadiazolyl, 1,2,5-oxadiazolyl, 1,2,3-thiadiazolyl, 1,2,4-thiadiazolyl, 1,3,4-thiadiazolyl, 1,2,5-thiadiazolyl, tetrazolyl, 1,2,3-triazinyl, 1,2,4-triazinyl, 1,3,5-triazinyl, 1,2,3,4-tetrazinyl, 1,2,3,5-tetrazinyl, 1,2,4,5-tetrazinyl, thiazolyl, isothiazolyl, oxazolyl, isoxazolyl, pyrazolyl, imidazolyl.

More preference is given here to heteroaromatic radicals of five-membered heterocycles having 3 nitrogen atoms, such as 1,2,3-triazol-1-yl, 1,2,3-triazol-4-yl, 1,2,3-triazol-5-yl, 1,2, 5-triazol-1-yl, 1,2,5-triazol-3-yl, 1,3,4-triazol-1-yl, 1,3,4-triazol-2-yl, 1,2,4-triazol-3-yl, 1,2,4-triazol-5-yl; more preference is also given here to heteroaromatic radicals of six-membered heterocycles having 3 nitrogen atoms, such as 1,3,5-triazin-2-yl, 1,2,4-triazin-3-yl, 1,2,4-triazin-5-yl, 1,2,4-triazin-6-yl, 1,2,3-triazin-4-yl, 1,2,3-triazin-5-yl;

more preference is also given here to heteroaromatic radicals of five-membered heterocycles having two nitrogen atoms and one oxygen atom, such as 1,2,4-oxadiazol-3-yl; 1,2,4-oxadiazol-5-yl, 1,3,4-oxadiazol-2-yl, 1,2,3-oxadiazol-4-yl, 1,2,3-oxadiazol-5-yl, 1,2,5-oxadiazol-3-yl, more preference is also given here to heteroaromatic radicals of five-membered heterocycles having two nitrogen atoms and one sulfur atom, such as 1,2,4-thiadiazol-3-yl, 1,2,4-thiadiazol-5-yl, 1,3,4-thiadiazol-2-yl, 1,2,3-thiadiazol-4-yl, 1,2,3-thiadiazol-5-yl, 1,2,5-thiadiazol-3-yl;

more preference is also given here to heteroaromatic radicals of five-membered heterocycles having four nitrogen atoms, such as 1,2,3,4-tetrazol-1-yl, 1,2,3,4-tetrazol-5-yl, 1,2,3,5-tetrazol-1-yl, 1,2,3,5-tetrazol-4-yl, 2H-1,2,3,4-tetrazol-5-yl, 1H-1,2,3,4-tetrazol-5-yl, more preference is also given here to heteroaromatic radicals of six-membered heterocycles such as 1,2,4,5-tetrazin-3-yl;

more preference is also given here to heteroaromatic radicals of five-membered heterocycles having three nitrogen atoms and one oxygen or sulfur atom, such as 1,2,3,4-oxatriazol-5-yl; 1,2,3,5-oxatriazol-4-yl; 1,2,3,4-thiatriazol-5-yl; 1,2,3,5-thiatriazol-4-yl;

more preference is also given here to heteroaromatic radicals of six-membered heterocycles such as, for example, 1,2,4,6-thiatriazin-1-yl; 1,2,4,6-thiatriazin-3-yl; 1,2,4,6-thiatriazin-5-yl.

Furthermore preferably, the heterocyclic radical or ring is a partially or fully hydrogenated heterocyclic radical having one heteroatom from the group of N, O and S, for example oxiranyl, oxetanyl, oxolanyl (=tetrahydrofuryl), oxanyl, pyrrolinyl, pyrrolidyl or piperidyl.

It is also preferably a partially or fully hydrogenated heterocyclic radical having 2 heteroatoms from the group of N, O and S, for example piperazinyl, dioxolanyl, oxazolinyl, isoxazolinyl, oxazolidinyl, isoxazolidinyl and morpholinyl. Suitable substituents for a substituted heterocyclic radical are the substituents specified later on below, and additionally also oxo. The oxo group may also occur on the hetero-ring atoms which are able to exist in different oxidation states, as in the case of N and S, for example.

Preferred examples of heterocyclyl are a heterocyclic radical having from 3 to 6 ring atoms from the group of pyridyl, thienyl, furyl, pyrrolyl, oxiranyl, 2-oxetanyl, 3-oxetanyl, oxolanyl (=tetrahydrofuryl), pyrrolidyl, piperidyl, especially oxiranyl, 2oxetanyl, 3-oxetanyl or oxolanyl, or is a heterocyclic radical having two or three heteroatoms, for example pyrimidinyl, pyridazinyl, pyrazinyl, triazinyl, thiazolyl, thiadiazolyl, oxazolyl, isoxazolyl, pyrazolyl, triazolyl, piperazinyl, dioxolanyl, oxazolinyl, isoxazolinyl, oxazolidinyl, isoxazolidinyl or morpholinyl.

Preferred heterocyclic radicals are also benzo-fused heteroaromatic rings, for example benzofuryl, benzisofuryl, benzothiophenyl, benzisothiophenyl, isobenzothiophenyl, indolyl, isoindolyl, indazolyl, benzimidazolyl, benzotriazolyl, benzoxazolyl, 1,2-benzisoxazolyl, 2,1-benzisoxazolyl, benzothiazolyl, 1,2-benzisothiazolyl, 2,1-benzisothiazolyl, 1,2,3-benzoxadiazolyl, 2,1,3-benzoxadiazolyl, 1,2,3-benzothiadiazolyl, 2,1,3-benzothiadiazolyl, quinolyl (quinolinyl), isoquinolyl (isoquinolinyl), quinnolinyl, phtalazinyl, quinazolinyl, quinoxalinyl, naphthyridinyl, benzotriazinyl, purinyl, pteridinyl, indolizinyl, benzo-1,3-dioxylyl, 4H-benzo-1,3-dioxinyl and 4H-benzo-1,4-dioxinyl, and, where possible, N-oxides and salts thereof.

When a base structure is substituted "by one or more radicals" from a list of radicals (=group) or a generically defined group of radicals, this in each case includes simultaneous substitution by a plurality of identical and/or structurally different radicals.

Substituted radicals, such as a substituted alkyl, alkenyl, alkynyl, cycloalkyl, aryl, phenyl, benzyl, heterocyclyl and heteroaryl radical, are, for example, a substituted radical derived from the unsubstituted base structure, where the substituents are, for example, one or more, preferably 1, 2 or 3, radicals from the group of halogen, alkoxy, alkylthio, hydroxyl, amino, nitro, carboxyl, cyano, azido, alkoxycarbonyl, alkylcarbonyl, formyl, carbamoyl, mono- and dialkylaminocarbonyl, substituted amino such as acylamino, mono- and dialkylamino, and alkylsulfinyl, alkylsulfonyl and, in the case of cyclic radicals, also alkyl, haloalkyl, alkylthioalkyl, alkoxyalkyl, optionally substituted mono- and dialkylaminoalkyl and hydroxyalkyl; in the term "substituted radicals", such as substituted alkyl, etc., substituents include, in addition to the saturated hydrocarbon radicals mentioned, corresponding unsaturated aliphatic and aromatic radicals, such as optionally substituted alkenyl, alkynyl, alkenyloxy, alkynyloxy, phenyl and phenoxy. In the case of substituted cyclic radicals having aliphatic moieties in the ring, cyclic systems with those substituents which are bonded on the ring by a double bond are also included, for example substituted by an alkylidene group such as methylidene or ethylidene.

The term "radicals from the group consisting of (followed by the group=list of the substituents)" is, wherever used, meant to be synonymous with "radicals selected from the group consisting of ( . . . )".

The substituents given by way of example ("first substituent level") can, if they include hydrocarbon-containing fractions, be further substituted therein if desired ("second substituent level"), by for example one of the substituents as defined for the first substituent level. Corresponding further substituent levels are possible. The term "substituted radical" preferably embraces just one or two substituent levels.

"Base radical" refers to the respective base structure of a radical to which substituents of a substituent level are attached.

Preferred substituents for the substituent levels are, for example, amino, hydroxyl, halogen, nitro, cyano, mercapto, carboxyl, carbonamide, $SF_5$, aminosulfonyl, alkyl, cycloalkyl, alkenyl, cycloalkenyl, alkynyl, monoalkylamino, dialkylamino, N-alkanoylamino, alkoxy, alkenyloxy, alkynyloxy, cycloalkoxy, cycloalkenyloxy, alkoxycarbonyl, alkenyloxycarbonyl, alkynyloxycarbonyl, aryloxycarbonyl, alkanoyl, alkenylcarbonyl, alkynylcarbonyl, arylcarbonyl, alkylthio, cycloalkylthio, alkenylthio, cycloalkenylthio, alkynylthio, alkylsulfinyl, alkylsulfonyl, monoalkylaminosulfonyl, dialkylaminosulfonyl, N-alkylaminocarbonyl, N,N-dialkylaminocarbonyl, N-alkanoylaminocarbonyl, N-alkanoyl-N-alkylaminocarbonyl, aryl, aryloxy, benzyl, benzyloxy, benzylthio, arylthio, arylamino and benzylamino.

Two substituents together may also form a saturated or unsaturated hydrocarbon bridge or a corresponding bridge in which carbon atoms, CH groups or $CH_2$ groups are replaced by heteroatoms, thus forming a fused-on or fused cycle. Here, with preference benzo-fused systems based on the base structure are formed.

Optionally substituted phenyl is preferably phenyl or phenyl which is unsubstituted or substituted by one or more radicals from the group consisting of halogen, cyano, ($C_1$-

$C_4$)-alkyl, ($C_1$-$C_4$)-haloalkyl, ($C_1$-$C_4$)-alkoxy-($C_1$-$C_4$)-alkyl, ($C_1$-$C_4$)-alkoxy, ($C_1$-$C_4$)-haloalkoxy, ($C_1$-$C_4$)-alkoxy-($C_1$-$C_4$)-alkoxy, ($C_1$-$C_4$)-alkylthio and nitro, in particular phenyl which is optionally substituted by one or more radicals from the group consisting of halogen, ($C_1$-$C_4$)-alkyl, ($C_1$-$C_4$)-haloalkyl and ($C_1$-$C_4$)-alkoxy.

In the case of radicals having carbon atoms, preference is given to those having 1 to 6 carbon atoms, preferably 1 to 4 carbon atoms, in particular 1 or 2 carbon atoms. Preference is generally given to substituents from the group consisting of halogen, for example fluorine and chlorine, ($C_1$-$C_4$)-alkyl, preferably methyl or ethyl, ($C_1$-$C_4$)-haloalkyl, preferably trifluoromethyl, ($C_1$-$C_4$)-alkoxy, preferably methoxy or ethoxy, ($C_1$-$C_4$)-haloalkoxy, nitro and cyano. Particular preference is given here to the substituents methyl, methoxy, fluorine and chlorine.

Substituted amino, such as mono- or disubstituted amino, is a radical from the group of the substituted amino radicals which are N-substituted, for example, by one or two identical or different radicals from the group of alkyl, alkoxy, acyl and aryl; preferably mono- and dialkylamino, mono- and diarylamino, acylamino, Nalkyl-N-arylamino, N-alkyl-N-acylamino and N-heterocycles; preference is given to alkyl radicals having from 1 to 4 carbon atoms; aryl is preferably phenyl or substituted phenyl; acyl is as defined below, preferably ($C_1$-$C_4$)-alkanoyl. The same applies to substituted hydroxylamino or hydrazino.

Acyl is a radical of an organic acid which arises in a formal sense by removal of a hydroxyl group on the acid function, and the organic radical in the acid may also be bonded to the acid function via a heteroatom. Examples of acyl are the —CO—R radical of a carboxylic acid HO—CO—R and radicals of acids derived therefrom, such as those of thiocarboxylic acid, optionally N-substituted iminocarboxylic acids or the radical of carbonic monoesters, N-substituted carbamic acid, sulfonic acids, sulfinic acids, N-substituted sulfonamide acids, phosphonic acids or phosphinic acids.

Acyl is, for example, formyl, alkylcarbonyl such as [($C_1$-$C_4$)-alkyl]carbonyl, phenylcarbonyl, alkyloxycarbonyl, phenyloxycarbonyl, benzyloxycarbonyl, alkylsulfonyl, alkylsulfinyl, N-alkyl-1-iminoalkyl and other radicals of organic acids. The radicals may each be substituted further in the alkyl or phenyl moiety, for example in the alkyl moiety by one or more radicals from the group of halogen, alkoxy, phenyl and phenoxy; examples of substituents in the phenyl moiety are the substituents already mentioned above in general for substituted phenyl.

Acyl is preferably an acyl radical in the narrower sense, i.e. a radical of an organic acid in which the acid group is bonded directly to the carbon atom of an organic radical, for example formyl, alkylcarbonyl such as acetyl or [($C_1$-$C_4$)-alkyl]carbonyl, phenylcarbonyl, alkylsulfonyl, alkylsulfinyl and other radicals of organic acids.

More preferably, acyl is an alkanoyl radical having 1 to 6 carbon atoms, in particular 1 to 4 carbon atoms. Here, ($C_1$-$C_4$)-alkanoyl is the radical of an alkanoic acid having 1 to 4 carbon atoms formed after removal of the OH group of the acid group, i.e. formyl, acetyl, n-propionyl, isopropionyl or n-, i-, sec- or tert-butanoyl.

The "yl position" of a radical denotes the carbon atom having the free bond.

Compounds of the formula (I) according to the invention and compounds of the formula (I) used according to the invention and/or salts thereof are in short also referred to as "compounds (I)".

The invention also provides all stereoisomers which are encompassed by formula (I) and mixtures thereof. Such compounds of the formula (I) contain one or more asymmetric carbon atoms or else double bonds which are not stated specifically in the general formulae (I). The possible stereoisomers defined by their specific three-dimensional shape, such as enantiomers, diastereomers, Z- and E-isomers, are all encompassed by the formula (I) and can be obtained from mixtures of the stereoisomers by customary methods or else prepared by stereoselective reactions in combination with the use of stereochemically pure starting materials.

The invention also provides all tautomers of the compounds of the formula (I) which may result from a hydrogen atom shift (for example keto-enol tautomers). The compound of the formula (I) also includes the tautomers, even if formally the formula (I) correctly describes only one of the respective tautomers which are in equilibrium with one another or which can be converted into one another.

The compounds of the formula (I) also include all physical forms in which they may be present as a pure substance or, if appropriate, as a mixture with other compounds, in particular also polymorphic crystal forms of the compounds of the formula (I) and salts thereof and solvent adducts (for example hydrates).

Primarily for reasons of higher herbicidal activity, better selectivity and/or better producibility, compounds of the abovementioned formula (I) according to the invention or their salts or their use according to the invention are of particular interest in which individual radicals have one of the preferred meanings already specified or specified below, or in particular those in which one or more of the preferred meanings already specified or specified below occur in combination.

Irrespective of the respective other radicals from the group consisting of $R^1$, $(R^2)_n$ and $(R^3)_m$ and the subdefinitions corresponding to the general radicals, and preferably in combination with preferred definitions of one or more of these radicals, compounds according to the invention or uses according to the invention of compounds of particular interest are those with the preferred meanings listed below of the radicals in question.

Preference is given to the compounds of the formula (I) according to the invention or salts thereof in which $R^1$ is hydrogen, alkyl, alkenyl or alkynyl, where each of the 3 lastmentioned radicals is unsubstituted or substituted and, including substituents, has up to 30 carbon atoms, preferably up to 24 carbon atoms, in particular up to 20 carbon atoms, or is cycloalkyl, cycloalkenyl, cycloalkynyl or aryl, where each of the 4 lastmentioned radicals is unsubstituted or substituted and, including substituents, has up to 30 carbon atoms, preferably up to 24 carbon atoms, in particular up to 20 carbon atoms, or is a heterocyclyl radical having 3 to 9 ring atoms which contains 1 to 4 heteroatoms from the group consisting of N, O and S, which is unsubstituted or substituted and which, including substituents, has 1 to 30 carbon atoms, preferably 1 to 24 carbon atoms, in particular 1 to 20 carbon atoms.

Here, more preference is also given to compounds (I) or salts thereof in which $R^1$ is hydrogen.

Here, more preference is also given to compounds (I) or salts thereof in which $R^1$ is H, ($C_1$-$C_{18}$)-alkyl, ($C_2$-$C_{18}$)-alkenyl or ($C_2$-$C_{18}$)-alkynyl, where each of the 3 lastmentioned radicals is unsubstituted or substituted and, including substituents, has up to 30 carbon atoms, preferably up to 24 carbon atoms, in particular up to 20 carbon atoms, or ($C_3$-$C_9$)-cycloalkyl, ($C_5$-$C_9$)-cycloalkenyl, ($C_5$-$C_9$)-cycloalkynyl or phenyl, where each of the 4 lastmentioned radicals is unsubstituted or substituted and including substituents, has up to 30 carbon atoms, preferably up to 24 carbon atoms, in particular up to 20 carbon atoms.

Here, more preference is also given to compounds (I) or salts thereof in which $R^1$ is hydrogen, ($C_1$-$C_{18}$)-alkyl, ($C_2$-$C_{18}$)-alkenyl or ($C_2$-$C_{18}$)-alkynyl, where each of the 3 lastmentioned radicals is unsubstituted or substituted by one or more radicals from the group consisting of the radicals [subgroups (a)-(d)]

(a) halogen, cyano, thio, nitro, hydroxyl, carboxyl, ($C_1$-$C_8$)-alkoxy, ($C_2$-$C_8$)-alkenyloxy, ($C_2$-$C_8$)-alkynyloxy, ($C_1$-$C_8$)-haloalkoxy, ($C_1$-$C_4$)-alkoxy-($C_1$-$C_4$)-alkoxy, ($C_1$-$C_8$)-alkylthio, ($C_2$-$C_8$)-alkenylthio, ($C_2$-$C_8$)-alkynylthio, ($C_1$-$C_8$)-haloalkylthio, ($C_2$-$C_8$)-haloalkenylthio, ($C_2$-$C_8$)-haloalkynylthio, ($C_1$-$C_8$)-alkylsulfinyl, ($C_2$-$C_8$)-alkenylsulfinyl, ($C_2$-$C_8$)-alkynylsulfinyl, ($C_1$-$C_8$)-haloalkylsulfinyl, ($C_2$-$C_8$)-haloalkenylsulfinyl, ($C_2$-$C_8$)-haloalkynylsulfinyl, ($C_1$-$C_8$)-alkylsulfonyl, ($C_2$-$C_8$)-alkenylsulfonyl, ($C_2$-$C_8$)-alkynylsulfonyl, ($C_1$-$C_8$)-haloalkylsulfonyl, ($C_2$-$C_8$)-haloalkenylsulfonyl, ($C_2$-$C_8$)-haloalkynylsulfonyl, radicals of the formula —NR*R**, where R* and R** are defined below, and ($C_3$-$C_8$)-cycloalkyl, ($C_5$-$C_8$)-cycloalkenyl, ($C_5$-$C_8$)-cycloalkynyl, ($C_3$-$C_8$)-cycloalkyl-($C_1$-$C_6$)-alkoxy, ($C_3$-$C_8$)-cycloalkyl-($C_1$-$C_6$)-alkyl-S(O)$_p$—, ($C_5$-$C_8$)-cycloalkenyl-($C_1$-$C_6$)-alkoxy, ($C_5$-$C_8$)-cycloalkenyl-($C_1$-$C_6$)-alkyl-S(O)$_p$—, ($C_5$-$C_8$)-cycloalkynyl-($C_1$-$C_6$)-alkoxy, ($C_5$-$C_8$)-cycloalkynyl-($C_1$-$C_6$)-alkyl-S(O)$_p$—, ($C_3$-$C_8$)-cycloalkoxy, ($C_3$-$C_8$)-cycloalkyl-S(O)$_p$—, ($C_5$-$C_8$)-cycloalkenyloxy, ($C_5$-$C_8$)-cycloalkenyl-S(O)$_p$—, ($C_5$-$C_8$)-cycloalkynyloxy, ($C_5$-$C_8$)-cycloalkynyl-S(O)$_p$—, ($C_3$-$C_8$)-cycloalkoxy-($C_1$-$C_6$)-alkoxy, ($C_3$-$C_8$)-cycloalkoxy-($C_1$-$C_6$)-alkyl-S(O)$_p$—, phenyl, phenyl-($C_1$-$C_6$)-alkoxy, phenoxy, phenyl-S(O)$_p$—, phenyl-($C_1$-$C_6$)-alkyl-S(O)$_p$—, phenoxy-($C_1$-$C_6$)-alkoxy, phenoxy-($C_1$-$C_6$)-alkyl-S(O)$_p$—, a radical Het$^1$, Het$^1$-S(O)$_p$—, Het$^1$-($C_1$-$C_6$)-alkoxy, Het$^1$-O—, Het$^1$-O—($C_1$-$C_6$)-alkoxy, where the heterocyclic radical Het$^1$ is defined below, where each of the 29 lastmentioned radicals is unsubstituted in the acyclic moiety or substituted by one or more identical or different radicals $R^A$ and is unsubstituted in the cyclic moiety or substituted by one or more identical or different radicals $R^B$ and p is in each case independently of the others 0, 1 or 2, and preferably the radicals (a)

halogen, cyano, nitro, hydroxyl, carboxyl, ($C_1$-$C_8$)-alkoxy, ($C_1$-$C_8$)-haloalkoxy, ($C_1$-$C_4$)-alkoxy-($C_1$-$C_4$)-alkoxy, ($C_1$-$C_6$)-alkylthio, ($C_1$-$C_6$)-haloalkylthio, ($C_1$-$C_6$)-alkylsulfinyl, ($C_1$-$C_6$)-haloalkylsulfinyl, ($C_1$-$C_6$)-alkylsulfonyl, ($C_1$-$C_8$)-haloalkylsulfonyl, ($C_3$-$C_8$)-cycloalkyl, ($C_5$-$C_8$)-cycloalkenyl, ($C_5$-$C_8$)-cycloalkynyl, ($C_3$-$C_8$)-cycloalkyl-($C_1$-$C_6$)-alkoxy, ($C_5$-$C_8$)-cycloalkenyl-($C_1$-$C_6$)-alkoxy, ($C_5$-$C_8$)-cycloalkynyl-($C_1$-$C_6$)-alkoxy, ($C_3$-$C_8$)-cycloalkoxy, ($C_3$-$C_8$)-cycloalkylthio, ($C_3$-$C_8$)-cycloalkylsulfinyl, ($C_3$-$C_8$)-cycloalkylsulfonyl, ($C_3$-$C_8$)-cycloalkoxy-($C_1$-$C_6$)-alkoxy, phenyl, phenoxy, phenylthio, phenylsulfinyl, phenylsulfonyl, phenyl-($C_1$-$C_6$)-alkoxy, phenyl-($C_1$-$C_6$)-alkylthio, phenyl-($C_1$-$C_6$)-alkylsulfinyl, phenyl-($C_1$-$C_6$)-alkylsulfonyl, phenoxy-($C_1$-$C_6$)-alkoxy, phenoxy-($C_1$-$C_6$)-alkylthio, phenoxy-($C_1$-$C_6$)-alkylsulfinyl and phenoxy-($C_1$-$C_6$)-alkylsulfonyl, where each of the radicals mentioned with cyclic moieties is unsubstituted in the acyclic moiety or substituted by one or more identical or different radicals $R^A$ and is unsubstituted in the cyclic moiety or substituted by one or more identical or different radicals $R^B$, (b) radicals of the formulae —C(=O)—R$^C$, —C(=O)—O—R$^C$, —O—C(=O)—R$^C$, —O—C(=O)—O—R$^C$, C(=O)—S—R$^C$, —C(=S)—S—R$^C$, —C(=S)—S—R$^C$, —C(=O)—NR*R**, —C(=O)—O—NR*R**, —O—C(=O)—NR*R**, —N(R*)—C(=O)—R$^C$, —N(R*)—C(=O)—NR*R**, —N(R*)—C(=O)—O—R$^C$, P(=O)(R$^C$)(R$^D$), —P(=O)(OR$^C$)(R$^D$), —P(=O)(OR$^C$)(OR$^D$) or —O—P(=O)(OR$^C$)(OR$^D$), preferably a radical of the formula —C(=O)—R$^C$, —C(=O)—O—R$^C$, —O—C(=O)—R$^C$ and —O—C(=O)—O—R$^C$, in particular a radical of the formula —C(=O)—O—R$^C$, —O—C(=O)—R$^C$ and —O—C(=O)—O—R$^C$, where R*, R**, R$^C$ and R$^D$ are as defined below, preferably the radicals (b1)

[($C_1$-$C_8$)-alkoxy]-carbonyl, [($C_1$-$C_8$)-alkoxy]-thiocarbonyl, [($C_2$-$C_8$)-alkenyloxy]-carbonyl, [($C_2$-$C_8$)-alkynyloxy]-carbonyl, [($C_1$-$C_8$)-alkylthio]-carbonyl, [($C_2$-$C_8$)-alkenylthio]-carbonyl, [($C_2$-$C_8$)-alkynylthio]-carbonyl, ($C_1$-$C_8$)-alkanoyl, [($C_2$-$C_8$)-alkenyl]-carbonyl, [($C_2$-$C_8$)-alkynyl]-carbonyl, [($C_1$-$C_8$)-alkyl]-carbonylamino, [($C_2$-$C_8$)-alkenyl]-carbonylamino, [($C_2$-$C_8$)-alkynyl]-carbonylamino, [($C_1$-$C_8$)-alkoxy]-carbonylamino, [($C_2$-$C_8$)-alkenyloxy]-carbonylamino, [($C_2$-$C_8$)-alkynyloxy]-carbonylamino, [($C_1$-$C_8$)-alkylamino]-carbonylamino, [($C_1$-$C_6$)-alkyl]-carbonyloxy, [($C_2$-$C_8$)-alkenyl]-carbonyloxy, [($C_2$-$C_6$)-alkynyl]-carbonyloxy, [($C_1$-$C_8$)-alkoxy]-carbonyloxy, [($C_2$-$C_8$)-alkenyloxy]-carbonyloxy and [($C_2$-$C_8$)-alkynyloxy]-carbonyloxy, where each of the 23 lastmentioned radicals is unsubstituted or substituted by one or more radicals from the group consisting of halogen, NO$_2$, ($C_1$-$C_4$)-alkoxy and optionally halogen-, CN—, NO$_2$—, ($C_1$-$C_4$)-alkyl-, ($C_1$-$C_4$)-alkoxy- and ($C_1$-$C_4$)-alkylthio-substituted phenyl, and preferably the radicals (b2)

($C_3$-$C_8$)-cycloalkylcarbonyl, ($C_3$-$C_8$)-cycloalkyl-[($C_1$-$C_6$)-alkyl]-carbonyl, ($C_3$-$C_8$)-cycloalkyl-[($C_1$-$C_6$)-alkoxy]-carbonyl, ($C_3$-$C_8$)-cycloalkoxycarbonyl, ($C_3$-$C_8$)-cycloalkoxy-[($C_1$-$C_6$)-alkyl]-carbonyl, ($C_3$-$C_8$)-cycloalkoxy-[($C_1$-$C_6$)-alkoxy]-carbonyl, ($C_3$-$C_8$)-cycloalkylcarbonyloxy, ($C_3$-$C_8$)-cycloalkyl-[($C_1$-$C_6$)-alkyl]-carbonyloxy, ($C_5$-$C_8$)-cycloalkenyl-[($C_1$-$C_6$)-alkyl]-carbonyloxy, ($C_5$-$C_8$)-cycloalkynyl-[($C_1$-$C_6$)-alkyl]-carbonyloxy, ($C_3$-$C_8$)-cycloalkyl-[($C_1$-$C_6$)-alkoxy]-carbonyloxy, ($C_5$-$C_8$)-cycloalkenyl-[($C_1$-$C_6$)-alkoxy]-carbonyloxy, ($C_5$-$C_8$)-cycloalkynyl-[($C_1$-$C_6$)-alkoxy]-carbonyloxy, ($C_3$-$C_8$)-cycloalkoxycarbonyloxy, ($C_3$-$C_8$)-cycloalkoxy-[($C_1$-$C_6$)-alkyl]-carbonyloxy, ($C_3$-$C_8$)-cycloalkoxy-[($C_1$-$C_6$)-alkoxy]-carbonyloxy, ($C_3$-$C_8$)-cycloalkylcarbonylamino,
($C_3$-$C_8$)-cycloalkyl-[($C_1$-$C_6$)-alkyl]-carbonylamino,
($C_5$-$C_8$)-cycloalkenyl-[($C_1$-$C_6$)-alkyl]-carbonylamino,
($C_5$-$C_8$)-cycloalkynyl-[($C_1$-$C_6$)-alkyl]-carbonylamino,
($C_3$-$C_8$)-cycloalkyl-[($C_1$-$C_6$)-alkoxy]-carbonylamino,
($C_3$-$C_8$)-cycloalkoxycarbonylamino,
($C_3$-$C_8$)-cycloalkoxy-[($C_1$-$C_6$)-alkyl]-carbonylamino and
($C_3$-$C_8$)-cycloalkoxy-[($C_1$-$C_6$)-alkoxy]-carbonylamino,
phenylcarbonyl,
phenyl-[($C_1$-$C_6$)-alkyl]-carbonyl,
phenyl-[($C_1$-$C_6$)-alkoxy]-carbonyl,
phenoxycarbonyl,
phenoxy-[($C_1$-$C_6$)-alkyl]-carbonyl,
phenoxy-[($C_1$-$C_6$)-alkoxy]-carbonyl,
phenylcarbonyloxy,
phenyl-[($C_1$-$C_6$)-alkyl]-carbonyloxy,
phenyl-[($C_1$-$C_6$)-alkoxy]-carbonyloxy,
phenoxycarbonyloxy,
phenoxy-[($C_1$-$C_6$)-alkyl]-carbonyloxy,
phenoxy-[($C_1$-$C_6$)-alkoxy]-carbonyloxy,
phenylcarbonylamino,
phenyl-[($C_1$-$C_6$)-alkyl]-carbonylamino,
phenyl-[($C_1$-$C_6$)-alkoxy]-carbonylamino,
phenoxycarbonylamino,
phenoxy-[($C_1$-$C_6$)-alkyl]-carbonylamino,
phenoxy-[($C_1$-$C_6$)-alkoxy]-carbonylamino,
where each of the 42 lastmentioned radicals is optionally fused in the cyclic moiety with a carbocyclic or heterocyclic ring, preferably a carbocyclic ring having 3 to 6 carbon atoms or a heterocyclic ring having 5 or 6 ring atoms and 1 to 3 ring heteroatoms from the group consisting of N, O and S, preferably benzo-fused, and unsubstituted at the ring or at the polycyclic system or substituted by one or more radicals from the group consisting of halogen, ($C_1$-$C_4$)-alkyl, ($C_1$-$C_4$)-alkoxy, ($C_1$-$C_4$)-haloalkyl, ($C_1$-$C_4$)-haloalkoxy and nitro, and
(c) radicals of the formulae —SiR'$_3$, —O—SiR'$_3$, (R')$_3$Si—($C_1$-$C_6$)-alkoxy, —CO—O—NR'$_2$, —O—N=CR'$_2$, —N=CR'$_2$, —O—NR'$_2$, —CH(OR')$_2$ and —O—(CH$_2$)$_q$—CH(OR')$_2$,
in which each of the radicals R' independently of the others is H, ($C_1$-$C_4$)-alkyl or phenyl, which is unsubstituted or substituted by one or more radicals from the group consisting of halogen, ($C_1$-$C_4$)-alkyl, ($C_1$-$C_4$)-alkoxy, ($C_1$-$C_4$)-haloalkyl, ($C_1$-$C_4$)-haloalkoxy and nitro or at two adjacent positions by a ($C_2$-$C_6$)-alkylene bridge, and q is an integer from 0 to 6, and
(d) radicals of the formula R"O—CHR'"CH(OR")—($C_1$-$C_6$)-alkoxy,
in which each of the radicals R" independently of the others is H or ($C_1$-$C_4$)-alkyl or together the radicals are a ($C_1$-$C_6$)-alkylene group and R'" is H or ($C_1$-$C_4$)-alkyl,
or
$R^1$ is ($C_3$-$C_9$)-cycloalkyl, ($C_5$-$C_9$)-cycloalkenyl, ($C_5$-$C_9$)-cycloalkynyl or phenyl,
where each of the 4 lastmentioned radicals is unsubstituted or substituted by one or more radicals from the group consisting of the radicals [subgroups (a')-(e')]
(a') halogen, cyano, thio, nitro, hydroxyl, carboxyl, ($C_1$-$C_8$)-alkyl, ($C_1$-$C_8$)-haloalkyl, ($C_1$-$C_4$)-alkoxy-($C_1$-$C_4$)-alkyl, ($C_2$-$C_8$)-alkenyl, ($C_2$-$C_8$)-haloalkenyl, ($C_2$-$C_8$)-alkynyl, ($C_2$-$C_8$)-haloalkynyl, ($C_1$-$C_8$)-alkoxy, ($C_2$-$C_8$)-alkenyloxy, ($C_2$-$C_8$)-alkynyloxy, ($C_1$-$C_8$)-haloalkoxy, ($C_1$-$C_4$)-alkoxy-($C_1$-$C_4$)-alkoxy, ($C_1$-$C_8$)-alkylthio, ($C_2$-$C_8$)-alkenylthio, ($C_2$-$C_8$)-alkynylthio and radicals of the formula —NR*R**, where the radicals R* and R** are defined below,
(b') radicals of the formulae —C(=O)—$R^C$, —C(=O)—O—$R^C$, —O—C(=O)—$R^C$, —O—C(=O)—O—$R^C$, C(=O)—S—$R^C$, —C(=S)—S—$R^C$, —C(=S)—S—$R^C$, —C(=O)—NR*R**, —C(=O)—O—NR*R**, —O—C(=O)—NR*R**, —N(R*)—C(=O)—$R^C$, —N(R*)—C(=O)—NR*R**, —N(R*)—C(=O)—O—$R^C$, P(=O)($R^C$)($R^D$), —P(=O)(O$R^C$)($R^D$), —P(=O)(O$R^C$)(O$R^D$) or —O—P(=O)(O$R^C$)(O$R^D$),
preferably a radical of the formula —C(=O)—$R^C$, —C(=O)—O—$R^C$, —O—C(=O)—$R^C$ and —O—C(=O)—O—$R^C$, in particular a radical of the formula —C(=O)—O—$R^C$, —O—C(=O)—$R^C$ and —O—C(=O)—O—$R^C$,
where R*, R**, $R^C$ and $R^D$ are as defined below,
and preferably the radicals (b1')
[($C_1$-$C_8$)-alkoxy]-carbonyl, [($C_1$-$C_8$)-alkoxy]-thiocarbonyl, [($C_2$-$C_8$)-alkenyloxy]-carbonyl, [($C_2$-$C_8$)-alkynyloxy]-carbonyl, [($C_1$-$C_8$)-alkylthio]-carbonyl, [($C_2$-$C_8$)-alkenylthio]-carbonyl, [($C_2$-$C_8$)-alkynylthio]-carbonyl, ($C_1$-$C_8$)-alkanoyl, [($C_2$-$C_8$)-alkenyl]-carbonyl, [($C_2$-$C_8$)-alkynyl]-carbonyl, ($C_1$-$C_4$)-alkylimino, ($C_1$-$C_4$)-alkoxyimino, [($C_1$-$C_8$)-alkyl]-carbonylamino, [($C_2$-$C_8$)-alkenyl]-carbonylamino, [($C_2$-$C_8$)-alkynyl]-carbonylamino, [($C_1$-$C_8$)-alkoxy]-carbonylamino, [($C_2$-$C_8$)-alkenyloxy]-carbonylamino, [($C_2$-$C_8$)-alkynyloxy]-carbonylamino, [($C_1$-$C_8$)-alkylamino]-carbonylamino, [($C_1$-$C_6$)-alkyl]-carbonyloxy, [($C_2$-$C_6$)-alkenyl]-carbonyloxy, [($C_2$-$C_6$)-alkynyl]-carbonyloxy, [($C_1$-$C_8$)-alkoxy]-carbonyloxy, [($C_2$-$C_8$)-alkenyloxy]-carbonyloxy, [($C_2$-$C_8$)-alkynyloxy]-carbonyloxy, ($C_1$-$C_8$)-alkylsulfinyl and ($C_1$-$C_8$)-alkylsulfonyl,
where each of the 27 lastmentioned radicals is unsubstituted or substituted by one or more radicals from the group consisting of halogen, NO$_2$, ($C_1$-$C_4$)-alkoxy and optionally substituted phenyl, and preferably the radicals (b2')
($C_3$-$C_8$)-cycloalkylcarbonyl,
($C_3$-$C_8$)-cycloalkyl-[($C_1$-$C_6$)-alkyl]-carbonyl,
($C_3$-$C_8$)-cycloalkyl-[($C_1$-$C_6$)-alkoxy]-carbonyl,
($C_3$-$C_8$)-cycloalkoxycarbonyl,
($C_3$-$C_8$)-cycloalkoxy-[($C_1$-$C_6$)-alkyl]-carbonyl,
($C_3$-$C_8$)-cycloalkoxy-[($C_1$-$C_6$)-alkoxy]-carbonyl,
($C_3$-$C_8$)-cycloalkylcarbonyloxy,
($C_3$-$C_8$)-cycloalkyl-[($C_1$-$C_6$)-alkyl]-carbonyloxy,
($C_5$-$C_8$)-cycloalkenyl-[($C_1$-$C_6$)-alkyl]-carbonyloxy,
($C_5$-$C_8$)-cycloalkynyl-[($C_1$-$C_6$)-alkyl]-carbonyloxy,
($C_3$-$C_8$)-cycloalkyl-[($C_1$-$C_6$)-alkoxy]-carbonyloxy,
($C_5$-$C_8$)-cycloalkenyl-[($C_1$-$C_6$)-alkoxy]-carbonyloxy,
($C_5$-$C_8$)-cycloalkynyl-[($C_1$-$C_6$)-alkoxy]-carbonyloxy,
($C_3$-$C_8$)-cycloalkoxycarbonyloxy,
($C_3$-$C_8$)-cycloalkoxy-[($C_1$-$C_6$)-alkyl]-carbonyloxy,
($C_3$-$C_8$)-cycloalkoxy-[($C_1$-$C_6$)-alkoxy]-carbonyloxy,
($C_3$-$C_8$)-cycloalkylcarbonylamino,
($C_3$-$C_8$)-cycloalkyl-[($C_1$-$C_6$)-alkyl]-carbonylamino,
($C_5$-$C_8$)-cycloalkenyl-[($C_1$-$C_6$)-alkyl]-carbonylamino,
($C_5$-$C_8$)-cycloalkynyl-[($C_1$-$C_6$)-alkyl]-carbonylamino,
($C_3$-$C_8$)-cycloalkyl-[($C_1$-$C_6$)-alkoxy]-carbonylamino,
($C_3$-$C_8$)-cycloalkoxycarbonylamino,
($C_3$-$C_8$)-cycloalkoxy-[($C_1$-$C_6$)-alkyl]-carbonylamino and
($C_3$-$C_8$)-cycloalkoxy-[($C_1$-$C_6$)-alkoxy]-carbonylamino,
phenylcarbonyl, phenyl-[($C_1$-$C_6$)-alkyl]-carbonyl,
phenyl-[($C_1$-$C_6$)-alkoxy]-carbonyl,
phenoxycarbonyl,
phenoxy-[($C_1$-$C_6$)-alkyl]-carbonyl,
phenoxy-[($C_1$-$C_6$)-alkoxy]-carbonyl,
phenylcarbonyloxy,
phenyl-[($C_1$-$C_6$)-alkyl]-carbonyloxy,
phenyl-[($C_1$-$C_6$)-alkoxy]-carbonyloxy,
phenoxycarbonyloxy,
phenoxy-[($C_1$-$C_6$)-alkyl]-carbonyloxy,
phenoxy-[($C_1$-$C_6$)-alkoxy]-carbonyloxy,
phenylcarbonylamino,
phenyl-[($C_1$-$C_6$)-alkyl]-carbonylamino,
phenyl-[($C_1$-$C_6$)-alkoxy]-carbonylamino,
phenoxycarbonylamino,
phenoxy-[($C_1$-$C_6$)-alkyl]-carbonylamino,
phenoxy-[($C_1$-$C_6$)-alkoxy]-carbonylamino,
  where each of the 42 lastmentioned radicals is optionally fused in the cyclic moiety with a carbocyclic or heterocyclic ring, preferably a carbocyclic ring having 3 to 6 carbon atoms or a heterocyclic ring having 5 or 6 ring atoms and 1 to 3 ring heteroatoms from the group consisting of N, O and S, preferably benzo-fused, and unsubstituted at the ring or at the polycyclic system or substituted by one or more radicals from the group consisting of halogen, ($C_1$-$C_4$)-alkyl, ($C_1$-$C_4$)-alkoxy, ($C_1$-$C_4$)-haloalkyl, ($C_1$-$C_4$)-haloalkoxy and nitro, and
(c') radicals of the formulae —$SiR'_3$, —O—$SiR'_3$, ($R'$)$_3$Si—($C_1$-$C_6$)-alkoxy, —CO—O—$NR'_2$, —O—N=$CR'_2$, —N=$CR'_2$, —O—$NR'_2$, —CH($OR'$)$_2$ and —O—($CH_2$)$_q$—CH($OR'$)$_2$,
  in which each of the radicals R' independently of the others is H, ($C_1$-$C_4$)-alkyl or phenyl, which is unsubstituted or substituted by one or more radicals from the group consisting of halogen, ($C_1$-$C_4$)-alkyl, ($C_1$-$C_4$)-alkoxy, ($C_1$-$C_4$)-haloalkyl, ($C_1$-$C_4$)-haloalkoxy and nitro or at two adjacent positions by a ($C_2$-$C_6$)-alkylene bridge, and q is an integer from 0 to 6, and
(d') radicals of the formula R"O—CHR"'CH(OR")—($C_1$-$C_6$)-alkoxy,
  in which each of the radicals R" independently of the others is H or ($C_1$-$C_4$)-alkyl or together the radicals are a ($C_1$-$C_6$)-alkylene group and R"' is H or ($C_1$-$C_4$)-alkyl, and
(e') a radical of the formula $Het^1$ which is unsubstituted or substituted by one or more identical or different radicals $R^B$,
or
$R^1$ is a polycyclic radical based on ($C_3$-$C_9$)-cycloalkyl, ($C_5$-$C_9$)-cycloalkenyl, ($C_5$-$C_9$)-cycloalkynyl or phenyl, where the base ring is fused with a carbocyclic or heterocyclic ring, preferably a 5- or 6-membered ring having 0 or 1 to 3 ring heteroatoms from the group consisting of N, O and S, preferably benzo-fused, and where the base ring or the polycyclic system is unsubstituted or substituted by one or more identical or different radicals $R^B$, preferably unsubstituted or substituted by one or more radicals from the group consisting of halogen, cyano, nitro, hydroxyl, carboxyl, ($C_1$-$C_6$)-alkyl, ($C_1$-$C_6$)-haloalkyl, ($C_1$-$C_4$)-alkoxy-($C_1$-$C_4$)-alkyl, ($C_2$-$C_6$)-alkenyl, ($C_2$-$C_6$)-haloalkenyl, ($C_2$-$C_6$)-alkynyl, ($C_2$-$C_6$)-haloalkynyl, ($C_1$-$C_6$)-alkoxy, ($C_2$-$C_6$)-alkenyloxy, ($C_2$-$C_6$)-alkynyloxy, ($C_1$-$C_6$)-haloalkoxy, ($C_1$-$C_4$)-alkoxy-($C_1$-$C_4$)-alkoxy, ($C_1$-$C_6$)-alkylthio, ($C_2$-$C_6$)-alkenylthio, ($C_2$-$C_6$)-alkynylthio, ($C_3$-$C_6$)-cycloalkyl, ($C_3$-$C_6$)-cycloalkoxy, [($C_1$-$C_8$)-alkoxy]-carbonyl, [($C_1$-$C_6$)-haloalkoxy]-carbonyl and oxo,
or $R^1$ is a heterocyclic radical $Het^1$ which is unsubstituted in the ring or in the polycyclic system or substituted by one or more identical or different radicals $R^B$, preferably unsubstituted or substituted by one or more radicals from the group consisting of halogen, cyano, thio, nitro, hydroxyl, carboxyl, ($C_1$-$C_6$)-alkyl, ($C_1$-$C_6$)-haloalkyl, ($C_1$-$C_4$)-alkoxy-($C_1$-$C_4$)-alkyl, ($C_2$-$C_6$)-alkenyl, ($C_2$-$C_6$)-haloalkenyl, ($C_2$-$C_6$)-alkynyl, ($C_2$-$C_6$)-haloalkynyl, ($C_1$-$C_6$)-alkoxy, ($C_2$-$C_6$)-alkenyloxy, ($C_2$-$C_6$)-alkynyloxy, ($C_1$-$C_6$)-haloalkoxy, ($C_1$-$C_4$)-alkoxy-($C_1$-$C_4$)-alkoxy, ($C_1$-$C_6$)-alkylthio, ($C_2$-$C_6$)-alkenylthio, ($C_2$-$C_6$)-alkynylthio, ($C_3$-$C_6$)-cycloalkyl, ($C_3$-$C_6$)-cycloalkoxy, [($C_1$-$C_8$)-alkoxy]-carbonyl, [($C_1$-$C_6$)-haloalkoxy]-carbonyl and oxo,
where in the radicals mentioned above and in the radicals below
$Het^1$ in each case independently of the others is a saturated, partially unsaturated or heteroaromatic monocyclic heterocyclyl radical having 3 to 9 ring atoms, preferably having 5 or 6 ring atoms, or a 9- or 10-membered bicyclic heterocycle which contains 1, 2, 3 or 4 heteroatoms selected from the group consisting of O, N and S, preferably a 5- or 6-membered heterocycle having 1 to 3 ring heteroatoms from the group consisting of N, O and S which is optionally also fused to a carbocyclic or heterocyclic ring, preferably a carbocyclic ring having 3 to 6 carbon atoms or a heterocyclic ring having 5 or 6 ring atoms and 1 to 3 ring heteroatoms from the group consisting of N, O and S, preferably optionally benzo-fused,
R*, R** are each independently of one another (i.e. also of other groups NR*R**) H, ($C_1$-$C_8$)-alkyl, ($C_2$-$C_8$)-alkenyl, ($C_2$-$C_8$)-alkynyl, ($C_1$-$C_4$)-alkoxy-($C_1$-$C_4$)-alkyl, ($C_1$-$C_6$)-alkanoyl, [($C_1$-$C_4$)-haloalkyl]-carbonyl, [($C_1$-$C_4$)-alkoxy]-carbonyl, [($C_1$-$C_4$)-haloalkoxy]-carbonyl, ($C_3$-$C_6$)-cycloalkyl, ($C_3$-$C_6$)-cycloalkyl-($C_1$-$C_4$)-alkyl, phenyl, phenyl-($C_1$-$C_4$)-alkyl, where each of the 4 lastmentioned radicals in the cycle is optionally substituted by one or more identical or different radicals $R^{bb}$, or
R* and R** together with the nitrogen atom are a 3- to 8-membered heterocycle which, in addition to the nitrogen atom, may contain one or two further ring heteroatoms from the group consisting of N, O and S and which may be unsubstituted or substituted by one or more radicals from the group consisting of ($C_1$-$C_4$)-alkyl, ($C_1$-$C_4$)-haloalkyl and oxo,
$R^A$ is halogen, cyano, hydroxyl or ($C_1$-$C_6$)-alkoxy,
$R^B$ is halogen, cyano, hydroxyl, oxo, nitro, ($C_1$-$C_6$)-alkyl, ($C_1$-$C_4$)-haloalkyl, cyano-($C_1$-$C_4$)-alkyl, hydroxy-($C_1$-$C_4$)-alkyl, nitro-($C_1$-$C_4$)-alkyl, ($C_2$-$C_6$)-alkenyl, ($C_2$-$C_6$)-haloalkenyl, ($C_2$-$C_6$)-alkynyl, ($C_2$-$C_6$)-haloalkynyl, ($C_1$-$C_6$)-alkoxy, ($C_2$-$C_6$)-alkenyloxy, ($C_2$-$C_6$)-alkynyloxy, ($C_1$-$C_6$)-haloalkoxy, ($C_1$-$C_4$)-alkoxy-($C_1$-$C_4$)-alkyl, ($C_1$-$C_4$)-alkoxy-($C_1$-$C_4$)-alkoxy, ($C_1$-$C_4$)-haloalkoxy-($C_1$-$C_4$)-alkyl, ($C_1$-$C_4$)-haloalkoxy-($C_1$-$C_4$)-alkoxy, ($C_1$-$C_6$)-alkylthio, ($C_2$-$C_6$)-alkenylthio, ($C_2$-$C_6$)-alkynylthio, ($C_1$-$C_6$)-alkylsulfinyl, ($C_1$-$C_6$)-haloalkylsulfinyl, ($C_1$-$C_6$)-alkylsulfonyl, ($C_1$-$C_6$)-haloalkylsulfonyl, a radical of the formula $R^{aa}$—C(=O)— or $R^{aa}$—C(=O)—($C_1$-$C_6$)-alkyl, where the $R^{aa}$ are defined below, —NR*R**, where R* and R** are defined below, tri-[($C_1$-$C_4$)-alkyl]-silyl, tri-[($C_1$-$C_4$)-alkyl]-silyl-($C_1$-$C_6$)-alkyl, ($C_3$-$C_6$)-cycloalkyl, ($C_3$-$C_6$)-cycloalkoxy, ($C_3$-$C_6$)-cycloalkyl-($C_1$-$C_4$)-alkyl, ($C_3$-$C_6$)-cycloalkyl-($C_1$-$C_8$)-alkoxy, phenyl, phenyl-($C_1$-$C_6$)-alkyl, phenoxy, phenoxy-($C_1$-$C_6$)-alkyl, phenylamino, phenylamino-($C_1$-$C_6$)-alkyl or a 5- or 6-membered monocyclic or 9- or 10-membered bicyclic heterocycle which contains 1, 2, 3 or 4 heteroatoms selected from the group consisting of O, N and S, where each of the 11 lastmentioned radicals is optionally substituted in the cyclic moiety by one or more identical or different radicals $R^{bb}$ $R^C$, $R^D$ are each independently of one another (also independently of radicals $R^C$, $R^D$ in other groups)

hydrogen, $(C_1-C_8)$-alkyl, $(C_2-C_8)$-alkenyl or $(C_2-C_8)$-alkynyl, where each of the 3 lastmentioned radicals is unsubstituted or substituted by one or more radicals from the group consisting of halogen, cyano, nitro, hydroxyl, $(C_1-C_6)$-alkoxy, $(C_2-C_6)$-alkenyloxy, $(C_2-C_6)$-alkynyloxy, $(C_1-C_8)$-haloalkoxy, $(C_1-C_4)$-alkoxy-$(C_1-C_4)$-alkoxy, $(C_1-C_8)$-alkylthio, $(C_1-C_8)$-haloalkylthio, $(C_1-C_8)$-alkylsulfinyl, $(C_1-C_8)$-haloalkylsulfinyl, $(C_1-C_8)$-alkylsulfonyl, $(C_1-C_8)$-haloalkylsulfonyl and tri-[$(C_1-C_4)$-alkyl]-silyl, or $(C_3-C_8)$-cycloalkyl, $(C_5-C_8)$-cycloalkenyl, $(C_5-C_8)$-cycloalkynyl, phenyl, $(C_3-C_8)$-cycloalkyl-$(C_1-C_6)$-alkyl, $(C_5-C_8)$-cycloalkenyl-$(C_1-C_6)$-alkyl, $(C_5-C_8)$-cycloalkynyl-$(C_1-C_6)$-alkyl, phenyl-$(C_1-C_6)$-alkyl, $(C_3-C_8)$-cycloalkyloxy-$(C_1-C_6)$-alkyl, $(C_3-C_8)$-cycloalkyl-S(O)$_p$—$(C_1-C_6)$-alkyl, $(C_5-C_8)$-cycloalkenyloxy-$(C_1-C_6)$-alkyl, $(C_5-C_8)$-cycloalkynyloxy-$(C_1-C_6)$-alkyl, phenoxy-$(C_1-C_6)$-alkyl, phenyl-S(O)$_p$—$(C_1-C_6)$-alkyl, $(C_3-C_8)$-cycloalkylamino-$(C_1-C_6)$-alkyl, $(C_5-C_8)$-cycloalkenylamino-$(C_1-C_6)$-alkyl, $(C_5-C_8)$-cycloalkynylamino-$(C_1-C_6)$-alkyl, phenylamino-$(C_1-C_6)$-alkyl, Het$^1$, Het$^1$-$(C_1-C_6)$-alkyl, Het$^1$-O—$(C_1-C_6)$-alkyl or Het$^1$-S(O)$_p$—$(C_1-C_6)$-alkyl, where Het$^1$ has the meaning mentioned, where each of the 22 lastmentioned radicals is unsubstituted in the acyclic moiety or substituted by one or more identical or different radicals $R^A$ and is unsubstituted in the cyclic moiety or substituted by one or more identical or different radicals $R^B$ and p is in each case independently of the others 0, 1 or 2, $R^{aa}$ in each case independently of the others is hydrogen, OH, $(C_1-C_6)$-alkyl, $(C_1-C_4)$-haloalkyl, $(C_2-C_6)$-alkenyl, $(C_2-C_6)$-alkynyl, $(C_1-C_6)$-alkoxy, $(C_1-C_6)$-alkoxy-$(C_1-C_6)$-alkyl, $(C_1-C_6)$-alkoxy-$(C_1-C_6)$-alkyloxy, $(C_1-C_4)$-haloalkoxy, $(C_1-C_4)$-haloalkoxy-$(C_1-C_6)$-alkyl, $(C_1-C_4)$-haloalkoxy-$(C_1-C_6)$-alkoxy, $(C_3-C_6)$-alkenyloxy, $(C_3-C_6)$-alkenyloxy-$(C_1-C_6)$-alkyl, $(C_3-C_6)$-alkenyloxy-$(C_1-C_6)$-alkoxy, $(C_3-C_6)$-alkynyloxy, $(C_3-C_6)$-alkynyloxy-$(C_1-C_6)$-alkyl, $(C_3-C_6)$-alkynyloxy-$(C_1-C_6)$-alkoxy, —NR*R*, where R* and R** are as defined above, tri-[$(C_1-C_4)$-alkyl]-silyl, tri-[$(C_1-C_4)$-alkyl]-silyl-$(C_1-C_6)$-alkyl, tri-[$(C_1-C_4)$-alkyl]-silyl-$(C_1-C_6)$-alkoxy, $(C_3-C_6)$-cycloalkyl, $(C_3-C_6)$-cycloalkoxy, $(C_3-C_6)$-cycloalkyl-$(C_1-C_8)$-alkyl, $(C_3-C_6)$-cycloalkyl-$(C_1-C_8)$-alkoxy, $(C_5-C_6)$-cycloalkenyl, $(C_5-C_6)$-cycloalkenyl-$(C_1-C_6)$-alkyl, $(C_5-C_6)$-cycloalkenyloxy, $(C_5-C_6)$-cycloalkynyl, $(C_5-C_6)$-cycloalkynyl-$(C_1-C_6)$-alkyl, $(C_5-C_6)$-cycloalkynyl-$(C_1-C_6)$-alkoxy, phenyl, phenyl-$(C_1-C_6)$-alkyl, phenyl-$(C_1-C_6)$-alkoxy, phenoxy, phenoxy-$(C_1-C_6)$-alkyl, phenoxy-$(C_1-C_6)$-alkoxy, phenylthio, phenyl-S(O)$_p$—$(C_1-C_6)$-alkyl, phenyl-S(O)$_p$—$(C_1-C_6)$-alkoxy, where p in each case independently of the others is 0, 1 or 2, phenylamino, phenylamino-$(C_1-C_6)$-alkyl, phenylamino-$(C_1-C_6)$-alkoxy or a 5- or 6-membered monocyclic or 9- or 10-membered bicyclic heterocycle which is optionally attached via an alkylene group or alkoxy group and contains 1, 2, 3 or 4 heteroatoms selected from the group consisting of O, N and S, where each of the 20 lastmentioned radicals is optionally substituted in the cyclic moiety by one or more identical or different radicals $R^{bb}$, and $R^{bb}$ in each case independently of the others is halogen, $(C_1-C_4)$-alkyl, $(C_1-C_4)$-haloalkyl, $(C_1-C_4)$-alkoxy or $(C_1-C_4)$-haloalkoxy.

Here, more preference is also given to compounds (I) or salts thereof in which $R^1$ is hydrogen, $(C_1-C_{18})$-alkyl, $(C_2-C_{18})$-alkenyl or $(C_2-C_{18})$-alkynyl, preferably H, $(C_1-C_{12})$-alkyl, $(C_2-C_{12})$-alkenyl or $(C_2-C_{12})$-alkynyl, in particular H, $(C_1-C_8)$-alkyl, $(C_2-C_8)$-alkenyl or $(C_2-C_8)$-alkynyl, more preferably H or $(C_1-C_6)$-alkyl, $(C_2-C_6)$-alkenyl or $(C_2-C_6)$-alkynyl, more preferably $(C_1-C_4)$-alkyl, where each of the 13 lastmentioned radicals containing carbon atoms is unsubstituted or substituted by one or more radicals from the group consisting of the radicals [subgroups (a)-(d)]

(a) halogen, cyano, thio, nitro, hydroxyl, carboxyl, $(C_1-C_6)$-alkoxy, $(C_2-C_6)$-alkenyloxy, $(C_2-C_6)$-alkynyloxy, $(C_1-C_6)$-haloalkoxy, $(C_1-C_4)$-alkoxy-$(C_1-C_4)$-alkoxy, $(C_1-C_6)$-alkylthio, $(C_2-C_6)$-alkenylthio, $(C_2-C_6)$-alkynylthio, $(C_1-C_6)$-haloalkylthio, $(C_2-C_6)$-haloalkenylthio, $(C_2-C_6)$-haloalkynylthio, $(C_1-C_6)$-alkylsulfinyl, $(C_2-C_6)$-alkenylsulfinyl, $(C_2-C_6)$-alkynylsulfinyl, $(C_1-C_6)$-haloalkylsulfinyl, $(C_2-C_6)$-haloalkenylsulfinyl, $(C_2-C_6)$-haloalkynylsulfinyl, $(C_1-C_6)$-alkylsulfonyl, $(C_2-C_6)$-alkenylsulfonyl, $(C_2-C_6)$-alkynylsulfonyl, $(C_1-C_6)$-haloalkylsulfonyl, $(C_2-C_6)$-haloalkenylsulfonyl, $(C_2-C_6)$-haloalkynylsulfonyl, radicals of the formula —NR*R**, where R* and R** are defined below, and $(C_3-C_6)$-cycloalkyl, $(C_5-C_6)$-cycloalkenyl, $(C_5-C_6)$-cycloalkynyl, $(C_3-C_6)$-cycloalkyl-$(C_1-C_4)$-alkoxy, $(C_5-C_6)$-cycloalkenyl-$(C_1-C_4)$-alkoxy, $(C_5-C_6)$-cycloalkynyl-$(C_1-C_4)$-alkoxy, $(C_3-C_6)$-cycloalkoxy, $(C_5-C_6)$-cycloalkenyloxy, $(C_5-C_6)$-cycloalkynyloxy, $(C_3-C_6)$-cycloalkoxy-$(C_1-C_4)$-alkoxy, phenyl, phenyl-$(C_1-C_6)$-alkoxy, phenoxy, phenoxy-$(C_1-C_4)$-alkoxy, phenyl-S(O)$_p$—, phenyl-$(C_1-C_6)$-alkyl-S(O)$_p$—, phenyloxy-$(C_1-C_6)$-alkyl-S(O)$_p$—, a radical Het$^1$, Het$^1$-$(C_1-C_6)$-alkoxy, Het$^1$-O—, Het$^1$-O—$(C_1-C_4)$-alkoxy, Het$^1$-$(C_1-C_6)$-alkoxy, Het$^1$-S(O)$_p$—, Het$^1$-O—$(C_1-C_4)$-alkyl-S(O)$_p$—, where the heterocyclic radical Het$^1$ is defined below, where each of the 24 lastmentioned radicals is unsubstituted in the acyclic moiety or substituted by one or more identical or different radicals $R^A$ and is unsubstituted in the cyclic moiety or substituted by one or more identical or different radicals $R^B$ and p is in each case independently of the others 0, 1 or 2, and preferably the radicals (a1)

halogen, cyano, nitro, hydroxyl, carboxyl, $(C_1-C_6)$-alkoxy, $(C_1-C_6)$-haloalkoxy, $(C_1-C_4)$-alkoxy-$(C_1-C_4)$-alkoxy, $(C_1-C_6)$-alkylthio, $(C_1-C_6)$-haloalkylthio, $(C_1-C_6)$-alkylsulfonyl, $(C_1-C_6)$-haloalkylsulfonyl, $(C_3-C_6)$-cycloalkyl, $(C_5-C_6)$-cycloalkenyl, $(C_5-C_6)$-cycloalkynyl, $(C_3-C_6)$-cycloalkyl-$(C_1-C_4)$-alkoxy, $(C_5-C_4)$-cycloalkenyl-$(C_1-C_4)$-alkoxy, $(C_5-C_4)$-cycloalkynyl-$(C_1-C_4)$-alkoxy, $(C_3-C_4)$-cycloalkoxy, $(C_3-C_4)$-cycloalkoxy-$(C_1-C_4)$-alkoxy, phenyl, phenyl-$(C_1-C_4)$-alkoxy, phenoxy and phenoxy-$(C_1-C_4)$-alkoxy, phenylthio, phenylsulfinyl, phenylsulfonyl, where each of the radicals (a1) is unsubstituted in the acyclic moiety or substituted by one or more identical or different radicals $R^A$ and is unsubstituted in the cyclic moiety or substituted by one or more identical or different radicals $R^B$, (b) radicals of the formulae —C(=O)—$R^C$, —C(=O)—O—$R^C$, —O—C(=O)—$R^C$, —O—C(=O)—O—$R^C$, C(=O)—S—$R^C$, —C(=S)—S—$R^C$, —C(=S)—S—$R^C$, —C(=O)—NR*R**, —C(=O)—O—NR*R**, —O—C(=O)—NR*R**, —N(R*)—C(=O)—$R^C$, —N(R*)—C(=O)—NR*R**, —N(R*)—C(=O)—O—$R^C$, P(=O)($R^C$)($R^D$), —P(=O)(O$R^C$)($R^D$), —P(=O)(O$R^C$)(O$R^D$) or —O—P(=O)(O$R^C$)(O$R^D$), preferably a radical of the formula —C(=O)—$R^C$, —C(=O)—O—$R^C$, —O—C(=O)—$R^C$ and —O—C(=O)—O—$R^C$, in particular a radical of the formula —C(=O)—O—$R^C$, —O—C(=O)—$R^C$ and —O—C(=O)—O—$R^C$, where R*, R**, $R^C$ and $R^D$ are as defined below, preferably the radicals (b1)

[($C_1$-$C_6$)-alkoxy]-carbonyl, [($C_1$-$C_6$)-alkoxy]-thiocarbonyl, [($C_2$-$C_6$)-alkenyloxy]-carbonyl, [($C_2$-$C_8$)-alkynyloxy]-carbonyl, [($C_1$-$C_6$)-alkylthio]-carbonyl, [($C_2$-$C_6$)-alkenylthio]-carbonyl, [($C_2$-$C_6$)-alkynylthio]-carbonyl, ($C_1$-$C_6$)-alkanoyl, [($C_2$-$C_6$)-alkenyl]-carbonyl, [($C_2$-$C_6$)-alkynyl]-carbonyl, [($C_1$-$C_6$)-alkyl]-carbonylamino, [($C_2$-$C_6$)-alkenyl]-carbonylamino, [($C_2$-$C_6$)-alkynyl]-carbonylamino, [($C_1$-$C_6$)-alkoxy]-carbonylamino, [($C_2$-$C_6$)-alkenyloxy]-carbonylamino, [($C_2$-$C_6$)-alkynyloxy]-carbonylamino, [($C_1$-$C_6$)-alkylamino]-carbonylamino, [($C_1$-$C_6$)-alkyl]-carbonyloxy, [($C_2$-$C_6$)-alkenyl]-carbonyloxy, [($C_2$-$C_6$)-alkynyl]-carbonyloxy, [($C_1$-$C_6$)-alkoxy]-carbonyloxy, [($C_2$-$C_6$)-alkenyloxy]-carbonyloxy and [($C_2$-$C_6$)-alkynyloxy]-carbonyloxy, where each of the 23 lastmentioned radicals is unsubstituted or substituted by one or more radicals from the group consisting of halogen, $NO_2$, ($C_1$-$C_4$)-alkoxy and optionally halogen-, CN—, $NO_2$—, ($C_1$-$C_4$)-alkyl-, ($C_1$-$C_4$)-alkoxy- and ($C_1$-$C_4$)-alkylthio-substituted phenyl, and preferably the radicals (b2)
($C_3$-$C_6$)-cycloalkylcarbonyl,
($C_3$-$C_6$)-cycloalkyl-[($C_1$-$C_4$)-alkyl]-carbonyl,
($C_3$-$C_6$)-cycloalkyl-[($C_1$-$C_4$)-alkoxy]-carbonyl,
($C_3$-$C_6$)-cycloalkoxycarbonyl,
($C_3$-$C_6$)-cycloalkoxy-[($C_1$-$C_4$)-alkyl]-carbonyl,
($C_3$-$C_6$)-cycloalkoxy-[($C_1$-$C_4$)-alkoxy]-carbonyl,
($C_3$-$C_6$)-cycloalkylcarbonyloxy,
($C_3$-$C_6$)-cycloalkyl-[($C_1$-$C_4$)-alkyl]-carbonyloxy,
($C_5$-$C_6$)-cycloalkenyl-[($C_1$-$C_4$)-alkyl]-carbonyloxy,
($C_5$-$C_6$)-cycloalkynyl-[($C_1$-$C_4$)-alkyl]-carbonyloxy,
($C_3$-$C_6$)-cycloalkyl-[($C_1$-$C_4$)-alkoxy]-carbonyloxy,
($C_5$-$C_6$)-cycloalkenyl-[($C_1$-$C_4$)-alkoxy]-carbonyloxy,
($C_5$-$C_6$)-cycloalkynyl-[($C_1$-$C_4$)-alkoxy]-carbonyloxy,
($C_3$-$C_6$)-cycloalkoxycarbonyloxy,
($C_3$-$C_6$)-cycloalkoxy-[($C_1$-$C_4$)-alkyl]-carbonyloxy,
($C_3$-$C_6$)-cycloalkoxy-[($C_1$-$C_4$)-alkoxy]-carbonyloxy,
($C_3$-$C_6$)-cycloalkylcarbonylamino,
($C_3$-$C_6$)-cycloalkyl-[($C_1$-$C_4$)-alkyl]-carbonylamino,
($C_5$-$C_6$)-cycloalkenyl-[($C_1$-$C_4$)-alkyl]-carbonylamino,
($C_5$-$C_6$)-cycloalkynyl-[($C_1$-$C_4$)-alkyl]-carbonylamino,
($C_3$-$C_6$)-cycloalkyl-[($C_1$-$C_4$)-alkoxy]-carbonylamino,
($C_3$-$C_6$)-cycloalkoxycarbonylamino,
($C_3$-$C_6$)-cycloalkoxy-[($C_1$-$C_4$)-alkyl]-carbonylamino and
($C_3$-$C_6$)-cycloalkoxy-[($C_1$-$C_4$)-alkoxy]-carbonylamino,
phenylcarbonyl,
phenyl-[($C_1$-$C_4$)-alkyl]-carbonyl,
phenyl-[($C_1$-$C_4$)-alkoxy]-carbonyl,
phenoxycarbonyl,
phenoxy-[($C_1$-$C_4$)-alkyl]-carbonyl,
phenoxy-[($C_1$-$C_4$)-alkoxy]-carbonyl,
phenylcarbonyloxy,
phenyl-[($C_1$-$C_4$)-alkyl]-carbonyloxy,
phenyl-[($C_1$-$C_4$)-alkoxy]-carbonyloxy,
phenoxycarbonyloxy,
phenoxy-[($C_1$-$C_4$)-alkyl]-carbonyloxy,
phenoxy-[($C_1$-$C_4$)-alkoxy]-carbonyloxy,
phenylcarbonylamino,
phenyl-[($C_1$-$C_4$)-alkyl]-carbonylamino,
phenyl-[($C_1$-$C_4$)-alkoxy]-carbonylamino,
phenoxycarbonylamino,
phenoxy-[($C_1$-$C_4$)-alkyl]-carbonylamino,
phenoxy-[($C_1$-$C_4$)-alkoxy]-carbonylamino, where each of the 42 lastmentioned radicals is optionally fused in the cyclic moiety with a carbocyclic or heterocyclic ring, preferably a carbocyclic ring having 3 to 6 carbon atoms or a heterocyclic ring having 5 or 6 ring atoms and 1 to 3 ring heteroatoms from the group consisting of N, O and S, preferably benzo-fused, and unsubstituted at the ring or at the polycyclic system or substituted by one or more radicals from the group consisting of halogen, ($C_1$-$C_4$)-alkyl, ($C_1$-$C_4$)-alkoxy, ($C_1$-$C_4$)-haloalkyl, ($C_1$-$C_4$)-haloalkoxy and nitro, (c) radicals of the formulae —SiR'$_3$, —O—SiR'$_3$, (R')$_3$Si—($C_1$-$C_4$)-alkoxy, —CO—O—NR'$_2$, —O—N=CR'$_2$, —N=CR'$_2$, —O—NR'$_2$, —CH(OR')$_2$ and —O—($CH_2$)$_q$—CH(OR')$_2$, in which each of the radicals R' independently of the others is H, ($C_1$-$C_4$)-alkyl or phenyl, which is unsubstituted or substituted by one or more radicals from the group consisting of halogen, ($C_1$-$C_4$)-alkyl, ($C_1$-$C_4$)-alkoxy, ($C_1$-$C_4$)-haloalkyl, ($C_1$-$C_4$)-haloalkoxy and nitro or at two adjacent positions by a ($C_2$-$C_6$)-alkylene bridge, and q is an integer from 0 to 6, and (d) radicals of the formula R"O—CHR'"CH(OR")—($C_1$-$C_6$)-alkoxy, in which each of the radicals R" independently of the others is H or ($C_1$-$C_4$)-alkyl or together the radicals are a ($C_1$-$C_6$)-alkylene group and R'" is H or ($C_1$-$C_4$)-alkyl, or $R^1$ is ($C_3$-$C_6$)-cycloalkyl, ($C_5$-$C_6$)-cycloalkenyl, ($C_5$-$C_6$)-cycloalkynyl or phenyl, where each of the 4 lastmentioned radicals is unsubstituted or substituted by one or more radicals from the group consisting of the radicals [subgroups (a')-(e')]

(a') halogen, cyano, thio, nitro, hydroxyl, carboxyl, ($C_1$-$C_6$)-alkyl, ($C_1$-$C_6$)-haloalkyl, ($C_1$-$C_4$)-alkoxy-($C_1$-$C_4$)-alkyl, ($C_2$-$C_6$)-alkenyl, ($C_2$-$C_6$)-haloalkenyl, ($C_2$-$C_6$)-alkynyl, ($C_2$-$C_6$)-haloalkynyl, ($C_1$-$C_6$)-alkoxy, ($C_2$-$C_6$)-alkenyloxy, ($C_2$-$C_6$)-alkynyloxy, ($C_1$-$C_6$)-haloalkoxy, ($C_1$-$C_4$)-alkoxy-($C_1$-$C_4$)-alkoxy, ($C_1$-$C_6$)-alkylthio, ($C_2$-$C_6$)-alkenylthio, ($C_2$-$C_6$)-alkynylthio and radicals of the formula —NR*R**, where the radicals R* and R** are defined below, (b') radicals of the formulae —C(=O)—$R^C$, —C(=O)—O—$R^C$, —O—C(=O)—$R^C$, —O—C(=O)—O—$R^C$, C(=O)—S—$R^C$, —C(=S)—S—$R^C$, —C(=S)—S—$R^C$, —C(=O)—NR*R**, —C(=O)—O—NR*R**, —O—C(=O)—NR*R**, —N(R*)—C(=O)—$R^C$, —N(R*)—C(=O)—NR*R**, —N(R*)—C(=O)—O—$R^C$, P(=O)($R^C$)($R^D$), —P(=O)(O$R^C$)($R^D$), —P(=O)(O$R^C$)(O$R^D$) or —O—P(=O)(O$R^C$)(O$R^D$), preferably a radical of the formula —C(=O)—$R^C$, —C(=O)—O—$R^C$, —O—C(=O)—$R^C$ and —O—C (=O)—O—R$^C$, in particular a radical of the formula —C(=O)—O—R$^C$, —O—C(=O)—R$^C$ and —O—C(=O)—O—R$^C$, where R*, R**, R$^C$ and R$^D$ are as defined below, and preferably the radicals (b1')

[(C$_1$-C$_6$)-alkoxy]-carbonyl, [(C$_1$-C$_6$)-alkoxy]-thiocarbonyl, [(C$_2$-C$_6$)-alkenyloxy]-carbonyl, [(C$_2$-C$_6$)-alkynyloxy]-carbonyl, [(C$_1$-C$_6$)-alkylthio]-carbonyl, [(C$_2$-C$_6$)-alkenylthio]-carbonyl, [(C$_2$-C$_6$)-alkynylthio]-carbonyl, (C$_1$-C$_8$)-alkanoyl, [(C$_2$-C$_6$)-alkenyl]-carbonyl, [(C$_2$-C$_6$)-alkynyl]-carbonyl, (C$_1$-C$_4$)-alkylimino, (C$_1$-C$_4$)-alkoxyimino, [(C$_1$-C$_6$)-alkyl]-carbonylamino, [(C$_2$-C$_6$)-alkenyl]-carbonylamino, [(C$_2$-C$_6$)-alkynyl]-carbonylamino, [(C$_1$-C$_6$)-alkoxy]-carbonylamino, [(C$_2$-C$_6$)-alkenyloxy]-carbonylamino, [(C$_2$-C$_6$)-alkynyloxy]-carbonylamino, [(C$_1$-C$_6$)-alkylamino]-carbonylamino, [(C$_1$-C$_4$)-alkyl]-carbonyloxy, [(C$_2$-C$_4$)-alkenyl]-carbonyloxy, [(C$_2$-C$_4$)-alkynyl]-carbonyloxy, [(C$_1$-C$_6$)-alkoxy]-carbonyloxy, [(C$_2$-C$_6$)-alkenyloxy]-carbonyloxy, [(C$_2$-C$_6$)-alkynyloxy]-carbonyloxy, (C$_1$-C$_6$)-alkylsulfinyl and (C$_1$-C$_6$)-alkylsulfonyl, where each of the 27 lastmentioned radicals is unsubstituted or substituted by one or more radicals from the group consisting of halogen, NO$_2$, (C$_1$-C$_4$)-alkoxy and optionally substituted phenyl, and preferably the radicals (b2')

(C$_3$-C$_6$)-cycloalkylcarbonyl,
(C$_3$-C$_6$)-cycloalkyl-[(C$_1$-C$_4$)-alkyl]-carbonyl,
(C$_3$-C$_6$)-cycloalkyl-[(C$_1$-C$_4$)-alkoxy]-carbonyl,
(C$_3$-C$_6$)-cycloalkoxycarbonyl,
(C$_3$-C$_6$)-cycloalkoxy-[(C$_1$-C$_4$)-alkyl]-carbonyl,
(C$_3$-C$_6$)-cycloalkoxy-[(C$_1$-C$_4$)-alkoxy]-carbonyl,
(C$_3$-C$_6$)-cycloalkylcarbonyloxy,
(C$_3$-C$_6$)-cycloalkyl-[(C$_1$-C$_4$)-alkyl]-carbonyloxy,
(C$_5$-C$_6$)-cycloalkenyl-[(C$_1$-C$_4$)-alkyl]-carbonyloxy,
(C$_5$-C$_6$)-cycloalkynyl-[(C$_1$-C$_4$)-alkyl]-carbonyloxy,
(C$_3$-C$_6$)-cycloalkyl-[(C$_1$-C$_4$)-alkoxy]-carbonyloxy,
(C$_5$-C$_6$)-cycloalkenyl-[(C$_1$-C$_4$)-alkoxy]-carbonyloxy,
(C$_5$-C$_6$)-cycloalkynyl-[(C$_1$-C$_4$)-alkoxy]-carbonyloxy,
(C$_3$-C$_6$)-cycloalkoxycarbonyloxy,
(C$_3$-C$_6$)-cycloalkoxy-[(C$_1$-C$_4$)-alkyl]-carbonyloxy,
(C$_3$-C$_6$)-cycloalkoxy-[(C$_1$-C$_4$)-alkoxy]-carbonyloxy,
(C$_3$-C$_6$)-cycloalkylcarbonylamino,
(C$_3$-C$_6$)-cycloalkyl-[(C$_1$-C$_4$)-alkyl]-carbonylamino,
(C$_5$-C$_6$)-cycloalkenyl-[(C$_1$-C$_4$)-alkyl]-carbonylamino,
(C$_5$-C$_6$)-cycloalkynyl-[(C$_1$-C$_4$)-alkyl]-carbonylamino,
(C$_3$-C$_6$)-cycloalkyl-[(C$_1$-C$_4$)-alkoxy]-carbonylamino,
(C$_3$-C$_6$)-cycloalkoxycarbonylamino,
(C$_3$-C$_6$)-cycloalkoxy-[(C$_1$-C$_4$)-alkyl]-carbonylamino and
(C$_3$-C$_6$)-cycloalkoxy-[(C$_1$-C$_4$)-alkoxy]-carbonylamino,
phenylcarbonyl,
phenyl-[(C$_1$-C$_4$)-alkyl]-carbonyl,
phenyl-[(C$_1$-C$_4$)-alkoxy]-carbonyl,
phenoxycarbonyl,
phenoxy-[(C$_1$-C$_4$)-alkyl]-carbonyl,
phenoxy-[(C$_1$-C$_4$)-alkoxy]-carbonyl,
phenylcarbonyloxy,
phenyl-[(C$_1$-C$_4$)-alkyl]-carbonyloxy,
phenyl-[(C$_1$-C$_4$)-alkoxy]-carbonyloxy,
phenoxycarbonyloxy,
phenoxy-[(C$_1$-C$_4$)-alkyl]-carbonyloxy,
phenoxy-[(C$_1$-C$_4$)-alkoxy]-carbonyloxy,
phenylcarbonylamino,
phenyl-[(C$_1$-C$_4$)-alkyl]-carbonylamino,
phenyl-[(C$_1$-C$_4$)-alkoxy]-carbonylamino,
phenoxycarbonylamino,
phenoxy-[(C$_1$-C$_4$)-alkyl]-carbonylamino,
phenoxy-[(C$_1$-C$_4$)-alkoxy]-carbonylamino, where each of the 42 lastmentioned radicals is optionally fused in the cyclic moiety with a carbocyclic or heterocyclic ring, preferably a carbocyclic ring having 3 to 6 carbon atoms or a heterocyclic ring having 5 or 6 ring atoms and 1 to 3 ring heteroatoms from the group consisting of N, O and S, preferably benzo-fused, and unsubstituted at the ring or at the polycyclic system or substituted by one or more radicals from the group consisting of halogen, (C$_1$-C$_4$)-alkyl, (C$_1$-C$_4$)-alkoxy, (C$_1$-C$_4$)-haloalkyl, (C$_1$-C$_4$)-haloalkoxy and nitro, and (c') radicals of the formulae —SiR'$_3$, —O—SiR'$_3$, (R')$_3$Si—(C$_1$-C$_6$)-alkoxy, —CO—O—NR'$_2$, —O—N=CR'$_2$, —N=CR'$_2$, —O—NR'$_2$, —CH(OR')$_2$ and —O—(CH$_2$)$_q$—CH(OR')$_2$, in which each of the radicals R' independently of the others is H, (C$_1$-C$_4$)-alkyl or phenyl, which is unsubstituted or substituted by one or more radicals from the group consisting of halogen, (C$_1$-C$_4$)-alkyl, (C$_1$-C$_4$)-alkoxy, (C$_1$-C$_4$)-haloalkyl, (C$_1$-C$_4$)-haloalkoxy and nitro or at two adjacent positions by a (C$_2$-C$_6$)-alkylene bridge, and q is an integer from 0 to 6, and (d') radicals of the formula R"O—CHR'"CH(OR")—(C$_1$-C$_6$)-alkoxy, in which each of the radicals R" independently of the others is H or (C$_1$-C$_4$)-alkyl or together the radicals are a (C$_1$-C$_6$)-alkylene group and R'" is H or (C$_1$-C$_4$)-alkyl, and (e') a radical of the formula Het$^1$ which is unsubstituted or substituted by one or more identical or different radicals R$^B$, or R$^1$ is a polycyclic radical based on (C$_3$-C$_6$)-cycloalkyl, (C$_5$-C$_6$)-cycloalkenyl, (C$_5$-C$_6$)-cycloalkynyl or phenyl, where the base ring is fused with a carbocyclic or heterocyclic ring, preferably a 5- or 6-membered ring having 0 or 1 to 3 ring heteroatoms from the group consisting of N, O and S, preferably benzo-fused, and where the base ring or the polycyclic system is unsubstituted or substituted by one or more identical or different radicals R$^B$, preferably unsubstituted or substituted by one or more radicals from the group consisting of halogen, cyano, nitro, hydroxyl, carboxyl, (C$_1$-C$_4$)-alkyl, (C$_1$-C$_4$)-haloalkyl, (C$_1$-C$_4$)-alkoxy-(C$_1$-C$_4$)-alkyl, (C$_2$-C$_4$)-alkenyl, (C$_2$-C$_4$)-haloalkenyl, (C$_2$-C$_4$)-alkynyl, (C$_2$-C$_4$)-haloalkynyl, (C$_1$-C$_4$)-alkoxy, (C$_2$-C$_4$)-alkenyloxy, (C$_2$-C$_4$)-alkynyloxy, (C$_1$-C$_4$)-haloalkoxy, (C$_1$-C$_4$)-alkoxy-(C$_1$-C$_4$)-alkoxy, (C$_1$-C$_4$)-alkylthio, (C$_2$-C$_4$)-alkenylthio, (C$_2$-C$_4$)-alkynylthio, (C$_3$-C$_6$)-cycloalkyl, (C$_3$-C$_6$)-cycloalkoxy, [(C$_1$-C$_4$)-alkoxy]-carbonyl, [(C$_1$-C$_4$)-haloalkoxy]-carbonyl and oxo, or R$^1$ is a heterocyclic radical Het$^1$ which is unsubstituted in the ring or in the polycyclic system or substituted by one or more identical or different radicals R$^B$, preferably unsubstituted or substituted by one or more radicals from the group consisting of halogen, cyano, thio, nitro, hydroxyl, carboxyl, (C$_1$-C$_4$)-alkyl, (C$_1$-C$_4$)-haloalkyl, (C$_1$-C$_4$)-alkoxy-(C$_1$-C$_4$)-alkyl, (C$_2$-C$_4$)-alkenyl, (C$_2$-C$_4$)-haloalkenyl, (C$_2$-C$_4$)-alkynyl, (C$_2$-C$_6$)-haloalkynyl, (C$_1$-C$_4$)-alkoxy, (C$_2$-C$_4$)-alkenyloxy, (C$_2$-C$_4$)-alkynyloxy, (C$_1$-C$_4$)-haloalkoxy, (C$_1$-C$_4$)-alkoxy-(C$_1$-C$_4$)-alkoxy, (C$_1$-C$_4$)-alkylthio, (C$_2$-C$_4$)-alkenylthio, (C$_2$-C$_4$)-alkynylthio, (C$_3$-C$_6$)-cycloalkyl, (C$_3$-C$_6$)-cycloalkoxy, [(C$_1$-C$_4$)-alkoxy]-carbonyl, [(C$_1$-C$_4$)-haloalkoxy]-carbonyl and oxo, where $Het^1$, $R^*$, $R^{**}$, $R^A$, $R^B$, $R^C$, $R^D$, $R^{aa}$ and $R^{bb}$ have the meanings already mentioned above, preferably $Het^1$ in each case independently of the others is a saturated, partially unsaturated or heteroaromatic monocyclic heterocyclyl radical having 3 to 9 ring atoms, preferably having 5 or 6 ring atoms, or a 9- or 10-membered bicyclic heterocycle which contains 1, 2, 3 or 4 heteroatoms selected from the group consisting of O, N and S, preferably a 5- or 6-membered heterocycle having 1 to 3 ring heteroatoms from the group consisting of N, O and S which is optionally also fused to a carbocyclic or heterocyclic ring, preferably a carbocyclic ring having 3 to 6 carbon atoms or a heterocyclic ring having 5 or 6 ring atoms and 1 to 3 ring heteroatoms from the group consisting of N, O and S, preferably optionally benzo-fused, $R^*$, $R^{**}$ are each independently of one another (i.e. also of other groups $NR^*R^{**}$) H, $(C_1-C_6)$-alkyl, $(C_2-C_6)$-alkenyl, $(C_2-C_6)$-alkynyl, $(C_1-C_4)$-alkoxy-$(C_1-C_4)$-alkyl, $(C_1-C_6)$-alkanoyl, $[(C_1-C_4)$-haloalkyl]-carbonyl, $[(C_1-C_4)$-alkoxy]-carbonyl, $[(C_1-C_4)$-haloalkoxy]-carbonyl, $(C_3-C_6)$-cycloalkyl, $(C_3-C_6)$-cycloalkyl-$(C_1-C_4)$-alkyl, phenyl, phenyl-$(C_1-C_4)$-alkyl, where each of the 4 lastmentioned radicals in the cycle is optionally substituted by one or more identical or different radicals $R^{bb}$, or preferably H, $(C_1-C_4)$-alkyl, allyl, propargyl, $(C_1-C_4)$-alkoxy-$(C_1-C_4)$-alkyl, formyl, acetyl, n-propanoyl, i-propanoyl, trifluoroacetyl, trichloroacetyl. methoxycarbonyl, ethoxycarbonyl, n- or i-propoxycarbonyl, n-, i-, sec-, t-Butoxycarbonyl, $[(C_1-C_4)$-haloalkoxy]-carbonyl, cyclopropyl, cyclobutyl, cyclopentyl, cyclohexyl, cyclopropylmethyl, phenyl, benzyl, 1- or 2-phenylethyl, $R^*$ and $R^{**}$ together with the nitrogen atom are a preferably saturated 5- to 6-membered heterocycle which, in addition to the nitrogen atom, may contain one or two further ring heteroatoms from the group consisting of N, O and S and which may be unsubstituted or substituted by one or more radicals from the group consisting of $(C_1-C_4)$-alkyl, $(C_1-C_4)$-haloalkyl and oxo, preferably 1-piperidine, 1-piperazine, 1-pyrrolidine, 1-pyrazolidine, 1-piperazolidine or 1-morpholine radical, $R^A$ is halogen, cyano, hydroxyl or $(C_1-C_6)$-alkoxy, $R^B$ is halogen, cyano, hydroxyl, oxo, nitro, $(C_1-C_4)$-alkyl, $(C_1-C_4)$-haloalkyl, cyano-$(C_1-C_4)$-alkyl, hydroxy-$(C_1-C_4)$-alkyl, nitro-$(C_1-C_4)$-alkyl, $(C_2-C_4)$-alkenyl, $(C_2-C_4)$-alkynyl, $(C_1-C_4)$-alkoxy, $(C_2-C_4)$-alkenyloxy, $(C_2-C_4)$-alkynyloxy, $(C_1-C_4)$-haloalkoxy, $(C_1-C_4)$-alkoxy-$(C_1-C_4)$-alkyl, $(C_1-C_4)$-alkoxy-$(C_1-C_4)$-alkoxy, $(C_1-C_4)$-alkylthio, $(C_1-C_4)$-alkylsulfonyl, $(C_1-C_4)$-haloalkylsulfonyl, a radical of the formula $R^{aa}$—C(=O)— or $R^{aa}$—C(=O)—$(C_1-C_6)$-alkyl, where the $R^{aa}$ are defined below, —$NR^*R^{**}$, where $R^*$ and $R^{**}$ are defined below, cyclopropyl, cyclopropylmethyl, phenyl, benzyl, 1- or 2-phenylethyl, phenoxy, 2-phenoxy-ethyl or a 5- or 6-membered monocyclic or 9- or 10-membered bicyclic heterocycle which contains 1, 2 or 34 heteroatoms selected from the group consisting of O, N and S, where each of the 9 lastmentioned radicals is optionally substituted in the cyclic moiety by one or more identical or different radicals $R^{bb}$ $R^C$, $R^D$ are each independently of one another (also independently of radicals $R^C$, $R^D$ in other groups) hydrogen, $(C_1-C_6)$-alkyl, $(C_2-C_6)$-alkenyl or $(C_2-C_6)$-alkynyl,
where each of the 3 lastmentioned radicals is unsubstituted or substituted by one or more radicals from the group consisting of halogen, cyano, nitro, hydroxyl, $(C_1-C_4)$-alkoxy, $(C_2-C_4)$-alkenyloxy, $(C_2-C_4)$-alkynyloxy, $(C_1-C_4)$-haloalkoxy, $(C_1-C_4)$-alkoxy-$(C_1-C_4)$-alkoxy, $(C_1-C_4)$-alkylthio, $(C_1-C_6)$-alkylsulfonyl and $(C_1-C_6)$-haloalkylsulfonyl, or $(C_3-C_6)$-cycloalkyl, $(C_5-C_6)$-cycloalkenyl, $(C_5-C_6)$-cycloalkynyl, phenyl, $(C_3-C_6)$-cycloalkyl-$(C_1-C_6)$-alkyl, phenyl-$(C_1-C_4)$-alkyl, phenoxy-$(C_1-C_4)$-alkyl, or phenylamino-$(C_1-C_6)$-alkyl, radicals $Het^1$, $Het^1$-$(C_1-C_6)$-alkyl, $Het^1$-O—$(C_1-C_6)$-alkyl, where $Het^1$ has the meaning mentioned,
where each of the 12 lastmentioned radicals is unsubstituted in the acyclic moiety or substituted by one or more identical or different radicals $R^A$ and is unsubstituted in the cyclic moiety or substituted by one or more identical or different radicals $R^B$, $R^{aa}$ in each case independently of the others is hydrogen, OH, $(C_1-C_6)$-alkyl, $(C_1-C_4)$-haloalkyl, $(C_2-C_4)$-alkenyl, $(C_2-C_4)$-alkynyl, $(C_1-C_6)$-alkoxy, $(C_1-C_4)$-alkoxy-$(C_1-C_4)$-alkyl, $(C_1-C_4)$-alkoxy-$(C_1-C_4)$-alkyloxy, $(C_1-C_4)$-haloalkoxy, $(C_1-C_4)$-haloalkoxy-$(C_1-C_4)$-alkyl, $(C_1-C_4)$-haloalkoxy-$(C_1-C_4)$-alkoxy, —$NR^*R^*$, where $R^*$ and $R^{**}$ are as defined above, $(C_3-C_6)$-cycloalkyl, $(C_3-C_6)$-cycloalkoxy, $(C_3-C_6)$-cycloalkyl-$(C_1-C_6)$-alkyl, $(C_3-C_6)$-cycloalkyl-$(C_1-C_6)$-alkoxy, phenyl, phenyl-$(C_1-C_4)$-alkyl, phenyl-$(C_1-C_4)$-alkoxy, phenoxy, phenoxy-$(C_1-C_4)$-alkyl, phenoxy-$(C_1-C_4)$-alkoxy, phenylamino, phenylamino-$(C_1-C_4)$-alkyl, phenylamino-$(C_1-C_4)$-alkoxy or a 5- or 6-membered monocyclic or 9- or 10-membered bicyclic heterocycle which is optionally attached via a $(C_1-C_4)$-alkylene group or a $(C_1-C_4)$-alkoxy group and contains 1, 2, 3 or 4 heteroatoms selected from the group consisting of O, N and S, where each of the 14 lastmentioned radicals is optionally substituted in the cyclic moiety by one or more identical or different radicals $R^{bb}$ and $R^{bb}$ in each case independently of the others is halogen, $(C_1-C_4)$-alkyl, $(C_1-C_4)$-haloalkyl, $(C_1-C_4)$-alkoxy or $(C_1-C_4)$-haloalkoxy, preferably halogen, methyl, $CF_3$, $CCl_3$, methoxy, ethoxy, $OCH_2F$, $OCF_2H$ or $OCF_3$.

Here, more preference is also given to compounds (I) or salts thereof in which $R^1$ is H, $(C_1-C_6)$-alkyl, $(C_2-C_6)$-alkenyl or $(C_2-C_6)$-alkynyl,
where each of the 3 lastmentioned radicals is unsubstituted or substituted by one or more radicals from the group consisting of halogen, $(C_1-C_4)$-alkoxy, $(C_1-C_4)$-alkylthio, alkylsulfinyl, alkylsulfonyl, $(C_3-C_6)$-cycloalkyl, which is unsubstituted or substituted by one or more radicals from the group consisting of halogen and $(C_1-C_4)$-alkyl, and phenyl, phenoxy, phenylthio, phenylsulfinyl, phenylsulfonyl, where the phenyl ring in the 5 lastmentioned radicals is in each case unsubstituted or substituted by one or more radicals from the group consisting of halogen, $(C_1-C_4)$-alkyl, $(C_1-C_4)$-alkoxy and $(C_1-C_4)$-haloalkyl, or $R^1$ is $(C_3-C_6)$-cycloalkyl, unsubstituted or substituted by one or more radicals from the group consisting of $(C_1-C_4)$-alkyl, $(C_1-C_4)$-alkoxy and $(C_1-C_4)$-haloalkyl.

Here, particular preference is also given to compounds (I) or salts thereof in which $R^1$ is H, $(C_1-C_4)$-alkyl, $(C_2-C_4)$-alkenyl or $(C_2-C_4)$-alkynyl,
where each of the 3 lastmentioned radicals is unsubstituted or substituted by one or more radicals from the group consisting of halogen, $(C_1-C_4)$-alkoxy, $(C_1-C_4)$-alkylthio, cyclopropyl, cyclobutyl, where each of the two lastmentioned radicals is unsubstituted or substituted by one or more radicals from the group consisting of halogen and $(C_1-C_4)$-alkyl, and phenyl, phenylthio, phenylsulfinyl, phenylsulfonyl, where each of the 4 lastmentioned radicals is unsubstituted or substituted by one or more radicals from the group consisting of halogen, $(C_1-C_4)$-alkyl, $(C_1-C_4)$-alkoxy and $(C_1-C_4)$-haloalkyl.

More preferably $R^1$ is also a polycyclic radical based on $(C_3-C_9)$-cycloalkyl, $(C_5-C_9)$-cycloalkenyl, $(C_5-C_9)$-cycloalkynyl or phenyl, where the base ring is fused to a carbocyclic or heterocyclic ring, preferably a 5- or 6-membered ring having 0 or 1 to 3 ring heteroatoms from the group consisting of N, O and S, preferably benzo-fused, and where the base ring or the polycyclic system is unsubstituted or substituted by one or more radicals from the group consisting of halogen, cyano, nitro, $(C_1-C_6)$-alkyl, $(C_1-C_6)$-haloalkyl, $(C_1-C_4)$-alkoxy-$(C_1-C_4)$-alkyl, $(C_2-C_4)$-alkenyl, $(C_2-C_4)$-alkynyl, $(C_1-C_4)$-alkoxy, $(C_1-C_4)$-haloalkoxy, $(C_1-C_4)$-alkoxy-$(C_1-C_4)$-alkoxy, $(C_1-C_4)$-alkylthio, $(C_3-C_6)$-cycloalkyl, $(C_3-C_6)$-cycloalkoxy, $[(C_1-C_4)$-alkoxy]-carbonyl and $[(C_1-C_4)$-haloalkoxy]-carbonyl.

Preference is also given to compounds (I) or salts thereof in which $R^1$ is a saturated, partially unsaturated or heteroaromatic heterocyclyl radical having 3 to 9 ring atoms, preferably having 5 or 6 ring atoms, which contains 1 to 4 heteroatoms, preferably 1 to 3 ring heteroatoms, from the group consisting of N, O and S and which is unsubstituted or substituted by one or more radicals from the group consisting of halogen, cyano, thio, nitro, hydroxyl, $(C_1-C_6)$-alkyl, $(C_1-C_6)$-haloalkyl, $(C_1-C_4)$-alkoxy-$(C_1-C_4)$-alkyl, $(C_2-C_6)$-alkenyl, $(C_2-C_6)$-haloalkenyl, $(C_2-C_6)$-alkynyl, $(C_2-C_6)$-haloalkynyl, $(C_1-C_6)$-alkoxy, $(C_2-C_6)$-alkenyloxy, $(C_2-C_6)$-alkynyloxy, $(C_1-C_6)$-haloalkoxy, $(C_1-C_4)$-alkoxy-$(C_1-C_4)$-alkoxy, $(C_1-C_6)$-alkylthio, $(C_2-C_6)$-alkenylthio, $(C_2-C_6)$-alkynylthio, $(C_3-C_6)$-cycloalkyl, $(C_3-C_6)$-cycloalkoxy, $[(C_1-C_8)$-alkoxy]-carbonyl, $[(C_1-C_6)$-haloalkoxy]-carbonyl and oxo.

Preference is also given to compounds (I) or salts thereof in which $R^1$ is a radical of the formula $SiR^aR^bR^c$, —$NR^aR^b$ or —$N=CR^cR^d$, preferably of the formula —$NR^aR^b$ or —$N=CR^cR^d$, where in the 5 lastmentioned formulae each of the radicals $R^a$, $R^b$, $R^c$ and $R^d$ independently of the others is hydrogen, $(C_1-C_4)$-alkyl, $(C_2-C_4)$-alkenyl, $(C_2-C_4)$-alkynyl, benzyl, substituted benzyl, phenyl or substituted phenyl, but where $SiH_3$ for $SiR^aR^bR^c$ is excluded, or $R^a$ and $R^b$ together with the nitrogen atom are a 3- to 8-membered heterocycle which may, in addition to the nitrogen atom, contain one or two further ring heteroatoms from the group consisting of N, O and S and which is unsubstituted or substituted by one or more radicals from the group consisting of $(C_1-C_4)$-alkyl and $(C_1-C_4)$-haloalkyl, or $R^c$ and $R^d$ together with the carbon atom are a 3- to 8-membered carbocyclic radical or heterocyclic radical which may contain 1 to 3 ring heteroatoms from the group consisting of N, O and S, where the carbocyclic or heterocyclic radical is unsubstituted or substituted by one or more radicals from the group consisting of $(C_1-C_4)$-alkyl and $(C_1-C_4)$-haloalkyl.

Particular preference is also given to compounds (I) or salts thereof in which $R^1$ is H, methyl, ethyl, n-propyl, i-propyl, n-butyl, s-butyl, i-butyl, t-butyl, allyl, propargyl (prop-2-yn-1-yl), but-2-yn-1-yl, but-3-yn-1-yl, 2-chloroprop-2-en-1-yl, 3-phenylprop-2-yn-1-yl, 3,3-dichloroprop-2-en-1-yl, 3,3-dichloro-2-fluoroprop-2-en-1-yl, methylprop-2-yn-1-yl, 2-methylprop-2-en-1-yl, but-2-en-1-yl, but-3-en-1-yl, but-2-yn-1-yl, but-3-yn-1-yl, 4-chlorobut-2-yn-1-yl, 3-methylbut-2-en-1-yl, 3-methylbut-1-en-1-yl, 1-(2E)-1-methylbut-2-en-1-yl, (E)-pent-3-en-2-yl or (Z)-pent-3-en-2-yl, phenyl, 2-carboxyphenyl, 2-chlorophenyl, 3-chlorophenyl, 4-chlorophenyl, 2-fluorophenyl, 3-fluorophenyl, 4-fluorophenyl, 2-methoxyphenyl, 3-methoxyphenyl, 4-methoxyphenyl, 2-methoxyphenyl, 3-methoxyphenyl, 4-methoxyphenyl, benzyl, 2-fluorobenzyl, 2-fluorobenzyl, 3-fluorobenzyl, 4-fluorobenzyl, 2,3-difluorobenzyl, 2,4-difluorobenzyl, 2,5-difluorobenzyl, 2,6-difluorobenzyl, 3,4-difluorobenzyl, 3,5-difluorobenzyl, 2-phenylethyl, 1-phenylethyl, (4-chlorophenyl)-methyl [i.e. =$CH_2$(4-Cl-Ph)], (4-fluorophenyl)methyl [i.e. =$CH_2$(4-F-Ph)], (4-methoxyphenyl)methyl [i.e. =$CH_2$(4-OMe-Ph)], 2-phenoxyethyl, 2-phenylthioethyl, 2-phenylsulfinylethyl, 2-phenylsulfonylethyl, 2-methoxyethyl, 2,2,2-trifluoroethyl, 1,1,1-trifluoroprop-2-yl, 2,2-difluoroethyl, 1,3-difluoroprop-2-yl, 2,3-dimethoxypropyl, 2,3-dimethoxyprop-2-yl, 2,2-dimethoxyeth-2-yl, 2-(2,2,2-trifluoroethoxy)ethyl, 2-fluoroethyl, 2-chloroethyl, 2-bromoethyl, 2-iodoethyl, 2,2,3,3,3-pentafluoropropyl, 1-hydroxyprop-2-yl, 2-hydroxyprop-2-yl, 2-hydroxyprop-1-yl, 3-hydroxypropyl, 3-hydroxyprop-2-yl, (2-methoxyethoxy)methyl; 2-(2-methoxyethoxy)ethyl; (2-ethoxyethoxy)methyl; 2-(2-ethoxyethoxy)ethyl;

(acetoxy)methyl, (propanoyloxy)methyl, (2-methylpropanoyloxy)methyl, (2,2-dimethylpropanoyloxy)methyl, 1-(acetoxy)ethyl, 2-(acetoxy)ethyl, 2-(propanoyloxy)ethyl, 1-(propanoyloxy)ethyl, 1-(2-methylpropanoyloxy)eth-1-yl, 2-(2-methylpropanoyloxy)eth-1-yl, 2-(2,2-dimethylpropanoyloxy)ethyl [i.e. 1-(t-butylcarbonyloxy)ethyl], 2-(2,2-dimethylpropanoyloxy)ethyl;

1-(2,2-dimethylpropanoyloxy)-2-methylprop-1-yl, 1-(t-butylcarbonyloxy)-2-methylprop-1-yl, (methoxycarbonyl)methyl, (ethoxycarbonyl)methyl, (n-propoxycarbonyl)methyl, (i-propoxycarbonyl)methyl, (n-butoxycarbonyl)methyl, (s-butoxycarbonyl)methyl, (i-butoxycarbonyl)methyl, (t-butoxycarbonyl)methyl, 1-(methoxycarbonyl)ethyl, 2-(methoxycarbonyl)ethyl, 1-(ethoxycarbonyl)ethyl, 2-(ethoxycarbonyl)ethyl, 1-(n-propoxycarbonyl)ethyl, 2-(n-propoxycarbonyl)ethyl, 1-(1-propoxycarbonyl)ethyl, 2-(i-propoxycarbonyl)ethyl, 1-(n-butoxycarbonyl)ethyl, 2-(n-butoxycarbonyl)ethyl, 1-(s-butoxycarbonyl)ethyl, 2-(s-butoxycarbonyl)ethyl, 1-(1-butoxycarbonyl)ethyl, 2-(i-butoxycarbonyl)ethyl, 1-(t-butoxycarbonyl)ethyl, 2-(t-butoxycarbonyl)ethyl, (methoxycarbonyloxy)methyl, (ethoxycarbonyloxy)methyl, (n-propoxycarbonyloxy)methyl, (i-propoxycarbonyloxy)methyl, (n-butoxycarbonyloxy)methyl, (s-butoxycarbonyloxy)methyl, (i-butoxycarbonyloxy)methyl, (t-butoxycarbonyloxy)methyl, 1-(methoxycarbonyloxy)ethyl, 2-(methoxycarbonyloxy)ethyl, 1-(ethoxycarbonyloxy)ethyl, 2-(ethoxycarbonyloxy)ethyl, 1-(n-propoxycarbonyloxy)ethyl, 2-(n-propoxycarbonyloxy)ethyl, 1-(1-propoxycarbonyloxy)ethyl, 2-(1-propoxycarbonyloxy)ethyl, 1-(n-butoxycarbonyloxy)ethyl, 2-(n-butoxycarbonyloxy)ethyl, 1-(s-butoxycarbonyloxy)ethyl, 2-(s-butoxycarbonyloxy)ethyl, 1-(1-butoxycarbonyloxy)ethyl, 2-(i-butoxycarbonyloxy)ethyl, 1-(t-butoxycarbonyloxy)ethyl, 2-(t-butoxycarbonyloxy)ethyl, (cyclohexoxycarbonyloxy)methyl, 1-(cyclohexoxycarbonyloxy)eth-1-yl, 2-(cyclohexoxycarbonyloxy)eth-1-yl, (acetyl)methyl, 1-(acetyl)ethyl, 2-(acetyl)ethyl, 1-(acetyl)propyl, 2-(acetyl)propyl, 3-(acetyl)propyl, (propanoyl)methyl, 1-(propanoyl)ethyl, 2-(propanoyl)ethyl, 1-(propanoyl)propyl, 2-(propanoyl)propyl, 3-(propanoyl)propyl, 1-(propanoyl)-2-methylpropyl,
2-(ethylideneaminooxy)ethyl, 2-(prop-2-ylideneaminooxy)ethyl, 2-(but-2-ylideneaminooxy)ethyl, 2-(pent-3-ylideneaminooxy)ethyl,
(N,N-dimethylamino)methyl, 2-(N,N-dimethylamino)eth-1-yl, 1-(N,N-dimethylamino)eth-1-yl, 2-(N,N-diethylamino)eth-1-yl, 1-(N,N-diethylamino)eth-1-yl, (N,N-diethylamino)methyl,
(N,N-dimethylaminocarbonyl)methyl, 1-(N,N-dimethylaminocarbonyl)ethyl, 2-(N,N-dimethylaminocarbonyl)ethyl, (N,N-diethylaminocarbonyl)methyl, 1-(N,N-diethylaminocarbonyl)ethyl, 2-(N,N-diethylaminocarbonyl)ethyl,
1-(dimethylamino)prop-2-yl [i.e. 2-(dimethylamino)-1-methylethyl], 1-(diethylamino)prop-2-yl,
trimethylsilylmethyl, 1-(trimethylsilyl)ethyl, 2-(trimethylsilyl)ethyl, triethylsilylmethyl, 1-(triethylsilyl)ethyl, 2-(triethylsilyl)ethyl,
cyclopropyl, cyclopropylmethyl, 1-cyclopropylethyl, 2-cyclopropylethyl, (1-methylcyclopropyl)methyl, 1-(1-methylcyclopropyl)ethyl, 2-(1-methylcyclopropyl)ethyl, (2,2-dichlorcyclopropyl)methyl, 1-(2,2-dichlorcyclopropyl)ethyl, 2-(2,2-dichlorcyclopropyl)ethyl, (2,2-dimethylcyclopropyl)methyl, 1-(2,2-dimethylcyclopropyl)ethyl, 2-(2,2-dimethylcyclopropyl)ethyl, cyclobutylmethyl, cyclopentylmethyl, cyclohexylmethyl or
pyrid-2-yl, pyrid-3-yl, pyrid-4-yl, 2-chloropyrid-3-yl, 3-chloropyrid-2-yl,
thien-2-yl, thien-3-yl, 2-chlorothien-3-yl, 3-chlorothien-2-yl, 4-chlorothien-2-yl,
(1-ethyl-5-methyl-1H-pyrazol-4-yl)methyl, 1-(1-ethyl-5-methyl-1H-pyrazol-4-yl)ethyl, 2-(1-ethyl-5-methyl-1H-pyrazol-4-yl)ethyl,
(1-ethyl-3-methyl-1H-pyrazol-4-yl)methyl, 1-(1-ethyl-3-methyl-1H-pyrazol-4-yl)ethyl, 2-(1-ethyl-3-methyl-1H-pyrazol-4-yl)ethyl,
tetrahydrofuran-2-yl, tetrahydrofuran-3-yl, tetrahydrofuran-2-ylmethyl, tetrahydrofuran-3-ylmethyl, (5-methyl-2-oxo-1,3-dioxol-4-yl)methyl;
oxetan-3-yl, (oxetan-3-yl)methyl, (oxetan-2-yl)methyl, (1,3-dioxolan-2-yl)methyl, (1,3-dioxolan-4-yl)methyl, 5-methyl-2-oxo-1,3-dioxolan-4-yl)methyl, (morpholin-4-yl)methyl; 1-(morpholin-4-yl)ethyl, 2-(morpholin-4-yl)ethyl, 2,3-dihydro-1H-inden-2-yl, dihydro-1H-inden-3-yl, dihydro-1H-inden-4-yl, dihydro-1H-inden-5-yl,
1H-inden-2-yl, 1H-inden-3-yl, 1H-inden-4-yl, 1H-inden-5-yl, 1H-inden-6-yl or 1H-inden-7-yl.

Here, very particular preference is given to compounds (I) and salts thereof in which
$R^1$ is H, methyl, ethyl, n-propyl, isopropyl, n-butyl, s-butyl, isobutyl, t-butyl, phenyl, benzyl, $CH_2$(4-Cl-Ph), i.e. (4-chlorophenyl)methyl, $CH_2$(4-F-Ph), i.e. (4-fluorophenyl)methyl, $CH_2$(4-OMe-Ph), i.e. (4-methoxyphenyl)methyl, 2-fluorobenzyl, 2-fluorobenzyl, 3-fluorobenzyl, 4-fluorobenzyl, 2,3-difluorobenzyl, 2,4-difluorobenzyl, 2,5-difluorobenzyl, 2,6-difluorobenzyl, 3,4-difluorobenzyl, 3,5-difluorobenzyl, 2-phenoxyethyl, 2-phenylthioethyl, 2-phenylsulfinylethyl, 2-phenylsulfonylethyl, 2-methoxyethyl, tetrahydrofuran-2-ylmethyl, 2-(dimethylamino)ethyl, oxetan-3-yl, (3-methyloxetan-3-yl)methyl, 2,2,2-trifluoroethyl, 2,2-difluoroethyl, 2-fluoroethyl, 2,2,3,3,3-pentafluoropropyl, cyclopropylmethyl, 1-cyclopropylethyl, (1-methylcyclopropyl)methyl, (2,2-dichlorocyclopropyl)methyl, (2,2-dimethylcyclopropyl)methyl, allyl, propargyl (prop-2-yn-1-yl), 2-chloroprop-2-en-1-yl, 3-phenylprop-2-yn-1-yl, 3,3-dichloroprop-2-en-1-yl, 3,3-dichloro-2-fluoroprop-2-en-1-yl, methylprop-2-yn-1-yl, 2-methylprop-2-en-1-yl, but-2-en-1-yl, but-3-en-1-yl, but-2-yn-1-yl, but-3-yn-1-yl, 4-chlorobut-2-yn-1-yl, 3-methylbut-2-en-1-yl, 3-methylbut-1-en-1-yl, 1-(2E)-1-methylbut-2-en-1-yl, (E)-pent-3-en-2-yl or (Z)-pent-3-en-2-yl, cyclobutylmethyl, cyclopentylmethyl, cyclohexylmethyl or 1-ethyl-5-methyl-H-pyrazol-4-methyl, i.e. (1-ethyl-5-methyl-1H-pyrazol-4-yl)methyl.

Here, very particular preference is given to compounds (I) and salts thereof in which
$R^1$ is H, methyl, ethyl, n-butyl, s-butyl, isobutyl, t-butyl, allyl and propargyl, in particular methyl or ethyl.

Preference is furthermore given to compounds (I) in which
$(R^2)_n$ is n substituents $R^2$,
where $R^2$ (if n=1) or each of the substituents $R^2$ (if n is greater than 1) independently of the others is halogen, cyano, nitro, $(C_1-C_6)$-alkyl, $(C_1-C_6)$-alkoxy, $(C_1-C_6)$-alkylthio, $(C_1-C_6)$-alkylsulfinyl, $(C_1-C_6)$-alkylsulfonyl, $(C_1-C_6)$-haloalkyl, $(C_1-C_6)$-haloalkoxy, $(C_1-C_6)$-haloalkylthio, $(C_1-C_6)$-haloalkylsulfinyl, $(C_1-C_6)$-haloalkylsulfonyl, $(C_2-C_6)$-alkenyl, $(C_2-C_6)$-alkynyl, tri-[$(C_1-C_4)$-alkyl]-silyl or tri-[$(C_1-C_4)$-alkyl]-silyl-$(C_1-C_4)$-alkyl
or where in each case two $R^2$ located ortho at the ring together are a group of the formula —$Z^1$-$A^*$-$Z^2$ in which
$A^*$ is an alkylene group having 1 to 4 carbon atoms which is optionally substituted by one or more radicals from the group consisting of halogen, $(C_1-C_4)$-alkyl, $(C_1-C_4)$-haloalkyl, $(C_1-C_4)$-alkoxy and $(C_1-C_4)$-haloalkoxy,
$Z^1$ is a direct bond, O or S and
$Z^2$ is a direct bond, O or S,
where the group —$Z^1$-$A^*$-$Z^2$ together with the carbon atoms, attached to the group, of the phenyl ring form a fused-on 5- or 6-membered ring, and
$(R^3)_m$ is m substituents $R^3$,
where $R^3$ (if m=1) or each of the substituents $R^3$ (if m is greater than 1) independently of the others is halogen, cyano, nitro, $(C_1-C_6)$-alkyl, $(C_1-C_6)$-alkoxy, $(C_1-C_6)$-alkylthio, $(C_1-C_6)$-alkylsulfinyl, $(C_1-C_6)$-alkylsulfonyl, $(C_1-C_6)$-haloalkyl, $(C_1-C_6)$-haloalkoxy, $(C_1-C_6)$-haloalkylthio, $(C_1-C_6)$-haloalkylsulfinyl, $(C_1-C_6)$-haloalkylsulfonyl, $(C_2-C_6)$-alkenyl, $(C_2-C_6)$-alkynyl, $NR^*R^{**}$, tri-[$(C_1-C_4)$-alkyl]-silyl or tri-[$(C_1-C_4)$-alkyl]-silyl-$(C_1-C_4)$-alkyl
or where in each case two groups $R^3$ located ortho at the ring together are a group of the formula —$Z^3$-$A^{**}$-$Z^4$ in which
$A^{**}$ is an alkylene group having 1 to 4 carbon atoms which is optionally substituted by one or more radicals from the group consisting of halogen, $(C_1-C_4)$-alkyl, $(C_1-C_4)$-haloalkyl, $(C_1-C_4)$-alkoxy and $(C_1-C_4)$-haloalkoxy,
$Z^3$ is a direct bond, O or S and
$Z^4$ is a direct bond, O or S,
where the group —$Z^3$-$A^{**}$-$Z^4$ together with the carbon atoms, attached to the group, of the phenyl ring form a fused-on 5- or 6-membered ring,
$R^*$, $R^{**}$ each independently of one another or together with the nitrogen atom have the meaning mentioned and
n, m are each independently of one another 0, 1, 2, 3, 4 or 5, preferably 0, 1, 2 or 3, in particular 0, 1 or 2, with the proviso that the two are not simultaneously 0.

Here, preference is also given to compounds (I) and salts thereof in which $(R^2)_n$ is n substituents $R^2$,
  where, in the case that n=1, the radical $R^2$ or, in the case that n is greater than 1, each of the substituents $R^2$ independently of the others is
  halogen, cyano, nitro, $(C_1-C_4)$-alkyl, $(C_1-C_4)$-alkoxy, $(C_1-C_4)$-alkylthio, $(C_1-C_4)$-alkylsulfinyl, $(C_1-C_4)$-alkylsulfonyl, $(C_1-C_4)$-haloalkyl, $(C_1-C_4)$-haloalkoxy, $(C_1-C_4)$-haloalkylthio, $(C_1-C_4)$-haloalkylsulfinyl, $(C_1-C_4)$-haloalkylsulfonyl, $(C_2-C_4)$-alkenyl, $(C_2-C_4)$-alkynyl, tri-[$(C_1-C_4)$-alkyl]-silyl or tri-[$(C_1-C_4)$-alkyl]-silyl-$(C_1-C_4)$-alkyl,
  preferably fluorine, chlorine, bromine, iodine, cyano, nitro, methyl, ethyl, methoxy, methylthio, methylsulfinyl, methylsulfonyl, trifluoromethyl, trifluoromethoxy, trifluoroalkylthio, trifluoromethylsulfinyl or trifluoromethylsulfonyl, in particular halogen such as fluorine or chlorine, and
n is 0, 1, 2, 3, 4 or 5, preferably 0, 1, 2 or 3, in particular 0, 1 or 2, with the proviso that n and m are not both simultaneously 0.

Here, preference is also given to compounds (I) and salts thereof in which $(R^3)_m$ is m substituents $R^3$,
  where, in the case that m=1, the radical $R^3$ or, in the case that m is greater than 1, each of the substituents $R^3$ independently of the others is halogen, cyano, nitro, $(C_1-C_4)$-alkyl, $(C_1-C_4)$-alkoxy, $(C_1-C_4)$-alkylthio, $(C_1-C_4)$-alkylsulfinyl, $(C_1-C_4)$-alkylsulfonyl, $(C_1-C_4)$-haloalkyl, $(C_1-C_4)$-haloalkoxy, $(C_1-C_4)$-haloalkylthio, $(C_1-C_4)$-haloalkylsulfinyl, $(C_1-C_4)$-haloalkylsulfonyl, $(C_2-C_6)$-alkenyl, $(C_2-C_6)$-alkynyl or tri-[$(C_1-C_4)$-alkyl] silyl-$Z^b$—, where $Z^b$=a covalent bond or $(C_1-C_4)$-alkylene, or
    in each case two groups $R^3$ located ortho at the ring together are a group of the formula —$Z^3$-A**-$Z^4$, where
      A** is an alkylene group which is optionally substituted by one or more radicals from the group consisting of halogen, $(C_1-C_4)$-alkyl, $(C_1-C_4)$-haloalkyl, $(C_1-C_4)$-alkoxy and $(C_1-C_4)$-haloalkoxy,
      $Z^3$ is O or S and
$Z^4$ is O or S, where the group —$Z^3$-A**-$Z^4$ together with the carbon atoms, attached to the group, of the phenyl ring form a fused-on 5- or 6-membered ring,
  preferably each of the substituents $R^3$ independently of the others is halogen, cyano, nitro, methyl, ethyl, methoxy, ethoxy, methylthio, ethylthio, $(C_1-C_2)$-alkylsulfinyl, $(C_1-C_2)$-alkylsulfonyl, $(C_1-C_2)$-haloalkyl, $(C_1-C_2)$-haloalkoxy, $(C_1-C_2)$-haloalkylthio, $(C_1-C_2)$-haloalkylsulfinyl, $(C_1-C_2)$-haloalkylsulfonyl, $(C_2-C_4)$-alkenyl, $(C_2-C_4)$-alkynyl, tri-[$(C_1-C_2)$-alkyl]-silyl-$Z^b$, where $Z^b$=a covalent bond or $(C_1-C_2)$-alkylene,
in particular each of the substituents $R^3$ independently of the others is
  halogen, such as fluorine, chlorine, bromine, iodine, cyano, nitro, methyl, methoxy, methylthio, methylsulfinyl, methylsulfonyl, trifluoromethyl, trifluoromethoxy, trifluoroalkylthio, trifluoromethylsulfinyl or trifluoromethylsulfonyl, in particular halogen such as fluorine or chlorine, and
m is 0, 1, 2, 3, 4 or 5, preferably 0, 1, 2, 3 or 4, in particular 0, 1, 2 or 3, with the proviso that n and m in formula (I) are not both simultaneously 0.

More preference is given to compounds of the formula (I) or salts thereof in which n is 0 (=the number zero, i.e. no substituents $R^2$ are present, i.e. all free bonds at the ring are occupied by hydrogen) or preferably $(R^2)_n$ is 2-bromo, 3-bromo, 4-bromo, 2-chloro, 3-chloro, 4-chloro, 2-fluoro, 3-fluoro, 4-fluoro, 2-cyano, 3-cyano, 4-cyano, 2-methyl, 3-methyl, 4-methyl, 2-ethyl, 3-ethyl, 4-ethyl, 2-$CF_3$, 3-$CF_3$, 4-$CF_3$, 2-methoxy, 3-methoxy, 4-methoxy, 2-ethoxy, 3-ethoxy, 4-ethoxy, 2-methylthio, 3-methylthio, 4-methylthio, 2-methylsulfinyl, 3-methylsulfinyl, 4-methylsulfinyl, 2-methylsulfonyl, 3-methylsulfonyl, 4-methylsulfonyl, 2,3-dimethyl, 2,4-dimethyl, 2,5-dimethyl, 2,6-dimethyl, 3,4-dimethyl, 3,5-dimethyl, 2,3-difluoro, 2,4-difluoro, 2,5-difluoro, 2,6-difluoro, 3,4-difluoro, 3,5-difluoro, 2,3-dichloro, 2,4-dichloro, 2,5-dichloro, 2,6-dichloro, 3,4-dichloro, 3,5-dichloro, (2-Cl-3-F), (2-Cl-4-F), (2-Cl-5-F), (2-Cl-6-F), (3-Cl-2-F), (3-Cl-4-F), (3-Cl-5-F), (3-Cl-6-F), (4-Cl-2-F), (4-Cl-3-F), 2,3,4-trifluoro, 2,3,5-trifluoro, 2,3,6-trifluoro, 2,4,6-trifluoro, 3,4,5-trifluoro, 2,3,4-trichloro, 2,3,5-trichloro, 2,3,6-trichloro, 2,4,6-trichloro or 3,4,5-trichloro or else (4-Br-3-F), (3-Br-4-F), (3-Br-5-F), (4-Br-3-Cl), (3-Br-4-Cl), (4-CN-3-F), (3-CN-4-F), (3-CN-5-F), (4-CN-3-Cl) or (3-CN-4-Cl), where the numbering of the radicals refers to the position of the radical at the phenyl-1-yl radical in which the carbon atom attached to the 4-position at the butyric acid skeleton has the 1-position in the ring.

More preference is given to compounds of the formula (I) or salts thereof in which m is 0 (=the number zero, i.e. no substituents $R^3$ are present, i.e. all free bonds at the ring are occupied by hydrogen) or preferably $(R^3)_m$ is 2-bromo, 3-bromo, 4-bromo, 2-chloro, 3-chloro, 4-chloro, 2-fluoro, 3-fluoro, 4-fluoro, 2-cyano, 3-cyano, 4-cyano, 2-methyl, 3-methyl, 4-methyl, 2-ethyl, 3-ethyl, 4-ethyl, 2-$CF_3$, 3-$CF_3$, 4-$CF_3$, 2-methoxy, 3-methoxy, 4-methoxy, 2-ethoxy, 3-ethoxy, 4-ethoxy, 2-methylthio, 3-methylthio, 4-methylthio, 2-methylsulfinyl, 3-methylsulfinyl, 4-methylsulfinyl, 2-methylsulfonyl, 3-methylsulfonyl, 4-methylsulfonyl, 2,3-dimethyl, 2,4-dimethyl, 2,5-dimethyl, 2,6-dimethyl, 3,4-dimethyl, 3,5-dimethyl, 2,3-difluoro, 2,4-difluoro, 2,5-difluoro, 2,6-difluoro, 3,4-difluoro, 3,5-difluoro, 2,3-dichloro, 2,4-dichloro, 2,5-dichloro, 2,6-dichloro, 3,4-dichloro, 3,5-dichloro, (2-Cl-3-F), (2-Cl-4-F), (2-Cl-5-F), (2-Cl-6-F), (3-Cl-2-F), (3-Cl-4-F), (3-Cl-5-F), (3-Cl-6-F), (4-Cl-2-F), (4-Cl-3-F), 2,3,4-trifluoro, 2,3,5-trifluoro, 2,3,6-trifluoro, 2,4,6-trifluoro, 3,4,5-trifluoro, 2,3,4-trichloro, 2,3,5-trichloro, 2,3,6-trichloro, 2,4,6-trichloro or 3,4,5-trichloro or else 2-nitro, 3-nitro, 4-nitro, 2,5-dicyano, 2,6-dicyano, (4-Br-2-F), (4-Br-3-F), (4-CN-3-F), (4-$NO_2$-3-F), (4-OMe-3-F), (3-CN-4-F), (3-$NO_2$-4-F), (3-CN-4-Cl), (3-$NO_2$-4-Cl) or (5-CN-2-F), where the numbering of the radicals refers to the position of the radical at the phenyl-1-yl radical in which the carbon atom attached to the 3-position at the butyric acid skeleton has the 1-position in the ring.

More preference is given to compounds of the formula (I) or salts thereof in which $(R^2)_n$ is 3-bromo, 4-bromo, 3-chloro, 4-chloro, 3-fluoro, 4-fluoro, 3,4-difluoro, 3,5-difluoro, 3,4-dichloro, 3,5-dichloro, (3-Cl-4-F), (3-Cl-5-F), (4-Cl-3-F), 3,4,5-trifluoro or 3,4,5-trichloro or else 3-cyano, 4-cyano, (3-Br-4-F), (4-Br-3-F), (3-CN-4-F) or (4-CN-3-F), where the numbering of the radicals refers to the position of the radical at the phenyl-1-yl radical in which the carbon atom attached to the 4-position at the butyric acid skeleton has the 1-position in the ring.

Here, particular preference is given to:

compounds of the formula (I) or salts thereof in which $(R^2)_n$ is 3-chloro;

compounds of the formula (I) or salts thereof in which $(R^2)_n$ is 4-chloro;

compounds of the formula (I) or salts thereof in which $(R^2)_n$ is 3-fluoro;

compounds of the formula (I) or salts thereof in which $(R^2)_n$ is 4-fluoro;

compounds of the formula (I) or salts thereof in which $(R^2)_n$ is 3-cyano;

compounds of the formula (I) or salts thereof in which $(R^2)_n$ is 3,4-difluoro;

compounds of the formula (I) or salts thereof in which $(R^2)_n$ is 3,4-dichloro;

compounds of the formula (I) or salts thereof in which $(R^2)_n$ is 3,5-difluoro;

compounds of the formula (I) or salts thereof in which $(R^2)_n$ is 3,5-dichloro;

compounds of the formula (I) or salts thereof in which $(R^2)_n$ is (3-Cl-4-F);

compounds of the formula (I) or salts thereof in which $(R^2)_n$ is (3-Cl-5-F);

compounds of the formula (I) or salts thereof in which $(R^2)_n$ is (4-Cl-3-F).

More preference is given to compounds of the formula (I) or salts thereof in which $(R^3)_m$ is 2-chloro, 3-chloro, 4-chloro, 2-fluoro, 3-fluoro, 4-fluoro, 2,3-difluoro, 2,4-difluoro, 2,5-difluoro, 2,6-difluoro, 3,4-difluoro, 3,5-difluoro, 2,3-dichloro, 2,4-dichloro, 2,5-dichloro, 2,6-dichloro, 3,4-dichloro, 3,5-dichloro, (2-Cl-3-F), (2-Cl-4-F), (2-Cl-5-F), (2-Cl-6-F), (3-Cl-2-F), (3-Cl-4-F), (3-Cl-5-F), (3-Cl-6-F), (4-Cl-2-F), (4-Cl-3-F), 2,3,4-trifluoro, 2,3,5-trifluoro, 2,3,6-trifluoro, 2,4,6-trifluoro, 3,4,5-trifluoro, 2,3,4-trichloro, 2,3,5-trichloro, 2,3,6-trichloro, 2,4,6-trichloro or 3,4,5-trichloro or else 2-cyano, 3-cyano, 4-cyano, 2-nitro, 3-nitro or 4-nitro, where the numbering of the radicals refers to the position of the radical at the phenyl-1-yl radical in which the carbon atom attached to the 3-position at the butyric acid skeleton has the 1-position in the ring.

Here, particular preference is given to:

compounds of the formula (I) or salts thereof in which $(R^3)_m$ is 3-chloro;

compounds of the formula (I) or salts thereof in which $(R^3)_m$ is 4-chloro;

compounds of the formula (I) or salts thereof in which $(R^3)_m$ is 2-fluoro;

compounds of the formula (I) or salts thereof in which $(R^3)_m$ is 3-fluoro;

compounds of the formula (I) or salts thereof in which $(R^3)_m$ is 4-fluoro;

compounds of the formula (I) or salts thereof in which $(R^3)_m$ is 2,3-difluoro;

compounds of the formula (I) or salts thereof in which $(R^3)_m$ is 2,4-difluoro;

compounds of the formula (I) or salts thereof in which $(R^3)_m$ is 2,5-difluoro;

compounds of the formula (I) or salts thereof in which $(R^3)_m$ is 2,6-difluoro;

compounds of the formula (I) or salts thereof in which $(R^3)_m$ is 3,4-difluoro;

compounds of the formula (I) or salts thereof in which $(R^3)_m$ is 3,5-difluoro;

compounds of the formula (I) or salts thereof in which $(R^3)_m$ is (3-Cl-2-F);

compounds of the formula (I) or salts thereof in which $(R^3)_m$ is (3-Cl-4-F);

compounds of the formula (I) or salts thereof in which $(R^3)_m$ is (3-Cl-5-F);

compounds of the formula (I) or salts thereof in which $(R^3)_m$ is (3-Cl-6-F);

compounds of the formula (I) or salts thereof in which $(R^3)_m$ is (4-Cl-2-F);

compounds of the formula (I) or salts thereof in which $(R^3)_m$ is (4-Cl-3-F).

More preference is given to:

compounds of the formula (I) or salts thereof in which $(R^2)_n$ is 3-chloro and $(R^3)_m$ is 3-chloro, 4-chloro, 2-fluoro, 3-fluoro, 4-fluoro, 2,3-difluoro, 2,4-difluoro, 2,5-difluoro, 2,6-difluoro, 3,4-difluoro, 3,5-difluoro, (3-Cl-2-F), (3-Cl-4-F), (3-Cl-5-F), (3-Cl-6-F), (4-Cl-2-F) or (4-Cl-3-F);

compounds of the formula (I) or salts thereof in which $(R^2)_n$ is 4-chloro and $(R^3)_m$ is 3-chloro, 4-chloro, 2-fluoro, 3-fluoro, 4-fluoro, 2,3-difluoro, 2,4-difluoro, 2,5-difluoro, 2,6-difluoro, 3,4-difluoro, 3,5-difluoro, (3-Cl-2-F), (3-Cl-4-F), (3-Cl-5-F), (3-Cl-6-F), (4-Cl-2-F) or (4-Cl-3-F);

compounds of the formula (I) or salts thereof in which $(R^2)_n$ is 3-fluoro and $(R^3)_m$ is 3-chloro, 4-chloro, 2-fluoro, 3-fluoro, 4-fluoro, 2,3-difluoro, 2,4-difluoro, 2,5-difluoro, 2,6-difluoro, 3,4-difluoro, 3,5-difluoro, (3-Cl-2-F), (3-Cl-4-F), (3-Cl-5-F), (3-Cl-6-F), (4-Cl-2-F) or (4-Cl-3-F);

compounds of the formula (I) or salts thereof in which $(R^2)_n$ is 3-cyano and $(R^3)_m$ is 3-chloro, 4-chloro, 2-fluoro, 3-fluoro, 4-fluoro, 2,3-difluoro, 2,4-difluoro, 2,5-difluoro, 2,6-difluoro, 3,4-difluoro, 3,5-difluoro, (3-Cl-2-F), (3-Cl-4-F), (3-Cl-5-F), (3-Cl-6-F), (4-Cl-2-F) or (4-Cl-3-F);

compounds of the formula (I) or salts thereof in which $(R^2)_n$ is 4-fluoro and $(R^3)_m$ is 3-chloro, 4-chloro, 2-fluoro, 3-fluoro, 4-fluoro, 2,3-difluoro, 2,4-difluoro, 2,5-difluoro, 2,6-difluoro, 3,4-difluoro, 3,5-difluoro, (3-Cl-2-F), (3-Cl-4-F), (3-Cl-5-F), (3-Cl-6-F), (4-Cl-2-F) or (4-Cl-3-F);

compounds of the formula (I) or salts thereof in which $(R^2)_n$ is 3,4-difluoro and $(R^3)_m$ is 3-chloro, 4-chloro, 2-fluoro, 3-fluoro, 4-fluoro, 2,3-difluoro, 2,4-difluoro, 2,5-difluoro, 2,6-difluoro, 3,4-difluoro, 3,5-difluoro, (3-Cl-2-F), (3-Cl-4-F), (3-Cl-5-F), (3-Cl-6-F), (4-Cl-2-F) or (4-Cl-3-F);

compounds of the formula (I) or salts thereof in which $(R^2)_n$ is 3,4-dichloro and $(R^3)_m$ is 3-chloro, 4-chloro, 2-fluoro, 3-fluoro, 4-fluoro, 2,3-difluoro, 2,4-difluoro, 2,5-difluoro, 2,6-difluoro, 3,4-difluoro, 3,5-difluoro, (3-Cl-2-F), (3-Cl-4-F), (3-Cl-5-F), (3-Cl-6-F), (4-Cl-2-F) or (4-Cl-3-F);

compounds of the formula (I) or salts thereof in which $(R^2)_n$ is 3,5-difluoro and $(R^3)_m$ is 3-chloro, 4-chloro, 2-fluoro, 3-fluoro, 4-fluoro, 2,3-difluoro, 2,4-difluoro, 2,5-difluoro, 2,6-difluoro, 3,4-difluoro, 3,5-difluoro, (3-Cl-2-F), (3-Cl-4-F), (3-Cl-5-F), (3-Cl-6-F), (4-Cl-2-F) or (4-Cl-3-F);

compounds of the formula (I) or salts thereof in which $(R^2)_n$ is 3,5-dichloro and $(R^3)_m$ is 3-chloro, 4-chloro, 2-fluoro, 3-fluoro, 4-fluoro, 2,3-difluoro, 2,4-difluoro, 2,5-difluoro, 2,6-difluoro, 3,4-difluoro, 3,5-difluoro, (3-Cl-2-F), (3-Cl-4-F), (3-Cl-5-F), (3-Cl-6-F), (4-Cl-2-F) or (4-Cl-3-F);

compounds of the formula (I) or salts thereof in which $(R^2)_n$ is (3-Cl-4-F) and $(R^3)_m$ is 3-chloro, 4-chloro, 2-fluoro, 3-fluoro, 4-fluoro, 2,3-difluoro, 2,4-difluoro, 2,5-difluoro, 2,6-difluoro, 3,4-difluoro, 3,5-difluoro, (3-Cl-2-F), (3-Cl-4-F), (3-Cl-5-F), (3-Cl-6-F), (4-Cl-2-F) or (4-Cl-3-F);

compounds of the formula (I) or salts thereof in which $(R^2)_n$ is (4-Cl-3-F) and $(R^3)_m$ is 3-chloro, 4-chloro, 2-fluoro, 3-fluoro, 4-fluoro, 2,3-difluoro, 2,4-difluoro, 2,5-difluoro, 2,6-difluoro, 3,4-difluoro, 3,5-difluoro, (3-Cl-2-F), (3-Cl-4-F), (3-Cl-5-F), (3-Cl-6-F), (4-Cl-2-F) or (4-Cl-3-F).

More preference is also given to:

compounds of the formula (I) or salts thereof in which $(R^3)_m$ is 3-chloro and $(R^2)_n$ is 3-chloro, 4-chloro, 3-fluoro, 4-fluoro, 3,4-difluoro, 3,5-difluoro, 3,4-dichloro, 3,5-dichloro, (3-Cl-4-F), (3-Cl-5-F) or (4-Cl-3-F) or else 3-cyano;

compounds of the formula (I) or salts thereof in which $(R^3)_m$ is 4-chloro and $(R^2)_n$ is 3-chloro, 4-chloro, 3-fluoro, 4-fluoro, 3,4-difluoro, 3,5-difluoro, 3,4-dichloro, 3,5-dichloro, (3-Cl-4-F), (3-Cl-5-F) or (4-Cl-3-F) or else 3-cyano;

compounds of the formula (I) or salts thereof in which $(R^3)_m$ is 3-fluoro and $(R^2)_n$ is 3-chloro, 4-chloro, 3-fluoro, 4-fluoro, 3,4-difluoro, 3,5-difluoro, 3,4-dichloro, 3,5-dichloro, (3-Cl-4-F), (3-Cl-5-F) or (4-Cl-3-F) or else 3-cyano;

compounds of the formula (I) or salts thereof in which $(R^3)_m$ is 4-fluoro and $(R^2)_n$ is 3-chloro, 4-chloro, 3-fluoro, 4-fluoro, 3,4-difluoro, 3,5-difluoro, 3,4-dichloro, 3,5-dichloro, (3-Cl-4-F), (3-Cl-5-F) or (4-Cl-3-F) or else 3-cyano;

compounds of the formula (I) or salts thereof in which $(R^3)_m$ is 2,3-difluoro and $(R^2)_n$ is 3-chloro, 4-chloro, 3-fluoro, 4-fluoro, 3,4-difluoro, 3,5-difluoro, 3,4-dichloro, 3,5-dichloro, (3-Cl-4-F), (3-Cl-5-F) or (4-Cl-3-F) or else 3-cyano;

compounds of the formula (I) or salts thereof in which $(R^3)_m$ is 2,4-difluoro and $(R^2)_n$ is 3-chloro, 4-chloro, 3-fluoro, 4-fluoro, 3,4-difluoro, 3,5-difluoro, 3,4-dichloro, 3,5-dichloro, (3-Cl-4-F), (3-Cl-5-F) or (4-Cl-3-F) or else 3-cyano;

compounds of the formula (I) or salts thereof in which $(R^3)_m$ is 2,5-difluoro and $(R^2)_n$ is 3-chloro, 4-chloro, 3-fluoro, 4-fluoro, 3,4-difluoro, 3,5-difluoro, 3,4-dichloro, 3,5-dichloro, (3-Cl-4-F), (3-Cl-5-F) or (4-Cl-3-F) or else 3-cyano;

compounds of the formula (I) or salts thereof in which $(R^3)_m$ is 2,6-difluoro and $(R^2)_n$ is 3-chloro, 4-chloro, 3-fluoro, 4-fluoro, 3,4-difluoro, 3,5-difluoro, 3,4-dichloro, 3,5-dichloro, (3-Cl-4-F), (3-Cl-5-F) or (4-Cl-3-F) or else 3-cyano;

compounds of the formula (I) or salts thereof in which $(R^3)_m$ is 3,4-difluoro and $(R^2)_n$ is 3-chloro, 4-chloro, 3-fluoro, 4-fluoro, 3,4-difluoro, 3,5-difluoro, 3,4-dichloro, 3,5-dichloro, (3-Cl-4-F), (3-Cl-5-F) or (4-Cl-3-F) or else 3-cyano;

compounds of the formula (I) or salts thereof in which $(R^3)_m$ is 3,5-difluoro and $(R^2)_n$ is 3-chloro, 4-chloro, 3-fluoro, 4-fluoro, 3,4-difluoro, 3,5-difluoro, 3,4-dichloro, 3,5-dichloro, (3-Cl-4-F), (3-Cl-5-F) or (4-Cl-3-F) or else 3-cyano;

compounds of the formula (I) or salts thereof in which $(R^3)_m$ is (3-Cl-2-F) and $(R^2)_n$ is 3-chloro, 4-chloro, 3-fluoro, 4-fluoro, 3,4-difluoro, 3,5-difluoro, 3,4-dichloro, 3,5-dichloro, (3-Cl-4-F), (3-Cl-5-F) or (4-Cl-3-F) or else 3-cyano;

compounds of the formula (I) or salts thereof in which $(R^3)_m$ is (3-Cl-4-F) and $(R^2)_n$ is 3-chloro, 4-chloro, 3-fluoro, 4-fluoro, 3,4-difluoro, 3,5-difluoro, 3,4-dichloro, 3,5-dichloro, (3-Cl-4-F), (3-Cl-5-F) or (4-Cl-3-F) or else 3-cyano;

compounds of the formula (I) or salts thereof in which $(R^3)_m$ is (3-Cl-5-F) and $(R^2)_n$ is 3-chloro, 4-chloro, 3-fluoro, 4-fluoro, 3,4-difluoro, 3,5-difluoro, 3,4-dichloro, 3,5-dichloro, (3-Cl-4-F), (3-Cl-5-F) or (4-Cl-3-F) or else 3-cyano;

compounds of the formula (I) or salts thereof in which $(R^3)_m$ is (3-Cl-6-F) and $(R^2)_n$ is 3-chloro, 4-chloro, 3-fluoro, 4-fluoro, 3,4-difluoro, 3,5-difluoro, 3,4-dichloro, 3,5-dichloro, (3-Cl-4-F), (3-Cl-5-F) or (4-Cl-3-F) or else 3-cyano;

compounds of the formula (I) or salts thereof in which $(R^3)_m$ is (4-Cl-2-F) and $(R^2)_n$ is 3-chloro, 4-chloro, 3-fluoro, 4-fluoro, 3,4-difluoro, 3,5-difluoro, 3,4-dichloro, 3,5-dichloro, (3-Cl-4-F), (3-Cl-5-F) or (4-Cl-3-F) or else 3-cyano;

compounds of the formula (I) or salts thereof in which $(R^3)_m$ is (4-Cl-3-F) and $(R^2)_n$ is 3-chloro, 4-chloro, 3-fluoro, 4-fluoro, 3,4-difluoro, 3,5-difluoro, 3,4-dichloro, 3,5-dichloro, (3-Cl-4-F), (3-Cl-5-F) or (4-Cl-3-F) or else 3-cyano.

More preference is also given to compounds of the formula (I) or salts thereof in which $(R^3)_m$ is 3-chloro, 4-chloro, 2-fluoro, 3-fluoro, 4-fluoro, 2,3-difluoro, 2,4-difluoro, 2,5-difluoro, 3,4-difluoro, 3,5-difluoro, 3,4-dichloro, 3,5-dichloro, (3-Cl-2-F), (3-Cl-4-F), (3-Cl-5-F), (3-Cl-6-F), (4-Cl-2-F) or (4-Cl-3-F) or else 3-cyano, 4-cyano, 3-nitro or 4-nitro, where the numbering of the radicals refers to the position of the radical at the phenyl-1-yl radical in which the carbon atom attached to the 3-position at the butyric acid skeleton has the 1-position in the ring.

More preference is given to:

compounds of the formula (I) or salts thereof in which $(R^2)_n$ is 3-chloro and $(R^3)_m$ is 3-chloro, 4-chloro, 2-fluoro, 3-fluoro, 4-fluoro, 2,3-difluoro, 2,4-difluoro, 2,5-difluoro, 3,4-difluoro or 3,5-difluoro or else 3-cyano, 4-cyano, 3-nitro or 4-nitro;

compounds of the formula (I) or salts thereof in which $(R^2)_n$ is 4-chloro and $(R^3)_m$ is 3-chloro, 4-chloro, 2-fluoro, 3-fluoro, 4-fluoro, 2,3-difluoro, 2,4-difluoro, 2,5-difluoro, 3,4-difluoro or 3,5-difluoro or else 3-cyano, 4-cyano, 3-nitro or 4-nitro;

compounds of the formula (I) or salts thereof in which $(R^2)_n$ is 3-fluoro and $(R^3)_m$ is 3-chloro, 4-chloro, 2-fluoro, 3-fluoro, 4-fluoro, 2,3-difluoro, 2,4-difluoro, 2,5-difluoro, 3,4-difluoro or 3,5-difluoro or else 3-cyano, 4-cyano, 3-nitro or 4-nitro;

compounds of the formula (I) or salts thereof in which $(R^2)_n$ is 4-fluoro and $(R^3)_m$ is 3-chloro, 4-chloro, 2-fluoro, 3-fluoro, 4-fluoro, 2,3-difluoro, 2,4-difluoro, 2,5-difluoro, 3,4-difluoro or 3,5-difluoro or else 3-cyano, 4-cyano, 3-nitro or 4-nitro;

compounds of the formula (I) or salts thereof in which $(R^2)_n$ is 3,4-difluoro and $(R^3)_m$ is 3-chloro, 4-chloro, 2-fluoro, 3-fluoro, 4-fluoro, 2,3-difluoro, 2,4-difluoro, 2,5-difluoro, 3,4-difluoro or 3,5-difluoro or else 3-cyano, 4-cyano, 3-nitro or 4-nitro;

compounds of the formula (I) or salts thereof in which $(R^2)_n$ is 3,4-dichloro and $(R^3)_m$ is 3-chloro, 4-chloro, 2-fluoro, 3-fluoro, 4-fluoro, 2,3-difluoro, 2,4-difluoro, 2,5-difluoro, 3,4-difluoro or 3,5-difluoro or else 3-cyano, 4-cyano, 3-nitro or 4-nitro;

compounds of the formula (I) or salts thereof in which $(R^2)_n$ is 3,5-difluoro and $(R^3)_m$ is 3-chloro, 4-chloro, 2-fluoro, 3-fluoro, 4-fluoro, 2,3-difluoro, 2,4-difluoro, 2,5-difluoro, 3,4-difluoro or 3,5-difluoro or else 3-cyano, 4-cyano, 3-nitro or 4-nitro;

compounds of the formula (I) or salts thereof in which $(R^2)_n$ is 3,5-dichloro and $(R^3)_m$ is 3-chloro, 4-chloro, 2-fluoro, 3-fluoro, 4-fluoro, 2,3-difluoro, 2,4-difluoro, 2,5-difluoro, 3,4-difluoro or 3,5-difluoro or else 3-cyano, 4-cyano, 3-nitro or 4-nitro;

compounds of the formula (I) or salts thereof in which $(R^2)_n$ is (3-Cl-4-F) and $(R^3)_m$ is 3-chloro, 4-chloro, 2-fluoro, 3-fluoro, 4-fluoro, 2,3-difluoro, 2,4-difluoro, 2,5-difluoro, 3,4-difluoro or 3,5-difluoro or else 3-cyano, 4-cyano, 3-nitro or 4-nitro;

compounds of the formula (I) or salts thereof in which $(R^2)_n$ is (4-Cl-3-F) and $(R^3)_m$ is 3-chloro, 4-chloro, 2-fluoro, 3-fluoro, 4-fluoro, 2,3-difluoro, 2,4-difluoro, 2,5-difluoro, 3,4-difluoro or 3,5-difluoro or else 3-cyano, 4-cyano, 3-nitro or 4-nitro.

More preference is given to compounds of the formula (I) or salts thereof in which n=1.

More preference is given to compounds of the formula (I) or salts thereof in which n=1 and $R^2$ is halogen, such as fluorine or chlorine.

More preference is given to compounds of the formula (I) or salts thereof in which n=2 or 3, in particular 2.

More preference is given to compounds of the formula (I) or salts thereof in which n=2 and each $R^2$ is selected from the group consisting of halogen, preferably fluorine or chlorine, in particular fluorine.

In general, from among the compounds having the above-mentioned meanings for individual groups or combinations of groups $R^1$, $(R^2)_n$ and/or $(R^3)_m$, preference is given to those in which the remaining groups or combinations of groups in the compounds are defined according to the meanings mentioned as preferred.

The compounds of the formula (I) according to the invention include all stereoisomers which can occur on the basis of the centers of asymmetry or double bonds in the molecule whose configuration is not designated specifically in the formula or which are not specified explicitly, and mixtures thereof, including the racemic compounds and the mixtures enriched partly with particular stereoisomers.

The invention also includes all tautomers, such as keto and enol tautomers, and their mixtures and salts, if appropriate functional groups are present.

The compounds of the formula (I) according to the invention can be prepared by various alternative processes.

In the processes below, in some cases solvents are employed. In this context, "inert solvents" refers in each case to solvents which are inert under the particular reaction conditions, but which do not have to be inert under any reaction conditions.

In the processes below, the reactions described can alternatively also be carried out in a microwave oven.

The invention also provides processes for preparing the compounds of the general formula (I) and/or their salts. This includes processes carried out analogously to known methods.

To prepare the compounds (I) according to the invention, it is possible to use initially the corresponding diastereomer mixtures in the form of their racemic mixtures. The preparation of the diastereomer mixtures of the cyanobutyrates is known in principle; see, for example, EP-A 5341, EP-A 266725, EP-A270 830, JP 04/297454, JP 04/297455, JP 05/058979, WO 2011/003776, WO 2011/003775.

Analogously to the synthesis routes described in the publications cited, the compounds can be prepared by standard processes of organic chemistry.

Diastereomer mixtures [formula (I')] comprising the compound (I) to be prepared are obtained, for example, in that (a) compounds of the formula (II) ("cyanomethylbenzenes"/"phenylacetonitriles")

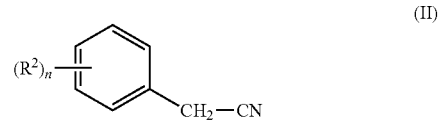

are reacted with compounds of the formula (III) (cinnamic acid derivatives) or salts thereof

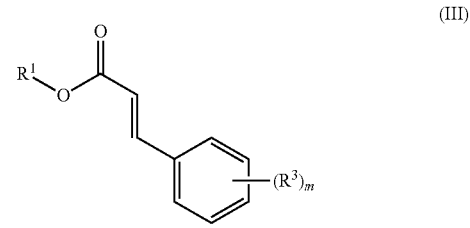

to give compounds of the formula (I') (diastereomers/racemic)

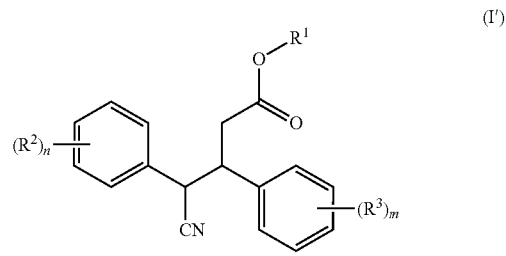

where $R^1$, $R^2$, $R^3$, m and n in the compounds (II), (III) and (I') are as defined in the respective compound of the formula (I) to be prepared.

The starting materials (II) and (III) required for preparing the compounds (I') and (I) are known from the literature cited or can be prepared analogously to the literature cited.

The reaction according to variant (a) can be carried out, for example, according to methods and under conditions like those known for Michael additions. The reaction is carried out, for example, at temperatures of from −100° C. to 150° C., preferably from −78° C. to 100° C., in an organic or inorganic solvent, generally in the presence of a base or a catalyst or both [cf. J. Chem. Soc. (1945), p. 438].

Suitable solvents are, for example, organic solvents such as:
  aliphatic hydrocarbons such as pentane, hexane, cyclohexane or petroleum ether;
  aromatic hydrocarbons such as toluene, o-, m- or p-xylene,
  halogenated hydrocarbons such as methylene chloride, chloroform or chlorobenzene,
  ethers, such as diethyl ether, diisopropyl ether, tert-butyl methyl ether, dioxane, anisole and tetrahydrofuran (THF),
  nitriles such as acetonitrile or propionitrile,
  ketones, such as acetone, methyl ethyl ketone, diethyl ketone and tert butyl methyl ketone, alcohols, such as methanol, ethanol, n-propanol, isopropanol, n butanol and tert-butanol, and also dimethyl sulfoxide, dimethylformamide, dimethylacetamide, sulfolane, mixtures of the organic solvents mentioned.

In individual cases, it is also possible to use inorganic solvents such as water or mixtures of organic solvents with water.

Preferred solvents are THF and methanol and mixtures thereof with other organic solvents.

The preparation by preparation variant (a) is preferably carried out in the presence of a base, for example from the group of the inorganic compounds such as the alkali metal and alkaline earth metal hydroxides, for example lithium hydroxide, sodium hydroxide, potassium hydroxide or calcium hydroxide, the alkali metal and alkaline earth metal oxides, for example lithium oxide, sodium oxide, calcium oxide or magnesium oxide, the alkali metal and alkaline earth metal hydrides, for example lithium hydride, sodium hydride, potassium hydride or calcium hydride, the alkali metal amides, for example lithium amide, sodium amide or potassium amide, the alkali metal and alkaline earth metal carbonates, for example lithium carbonate, potassium carbonate or calcium carbonate, the alkali metal bicarbonates, for example sodium bicarbonate, or the organometallic compounds such as, preferably, the alkali metal alkyls, for example methyllithium, butyllithium or phenyllithium, the alkylmagnesium halides, for example methylmagnesium chloride, or the alkali metal and alkaline earth metal alkoxides, for example sodium methoxide, sodium ethoxide, potassium ethoxide, potassium tert-butoxide or dimethoxymagnesium.

The bases used can also be organic bases, for example from the group of the tertiary aliphatic amines, for example trimethylamine, triethylamine, tributylamine, diisopropylethylamine or N-methylpiperidine, or the aromatic tertiary amines, for example pyridine or substituted pyridines such as collidine, lutidine or 4-dimethylaminopyridine, or the bicyclic amines such as 7-methyl-1,5,7-triazabicyclo[4.4.0]-dec-5-ene or 1,8-diazabicyclo[5.4.0]undec-7ene (DBU).

Preferred bases are, for example, potassium tert-butoxide, lithium bis(trimethylsilyl)amide or 7-methyl-1,5,7-triazabicyclo[4.4.0]-dec-5-ene.

The amount of base may generally vary within wide limits. For example, it may be expedient to employ the base in catalytic amounts, in substoichiometric amounts, in equimolar amounts or in excess. A preferably liquid organic base may optionally also be used as solvent.

Suitable catalysts for the Michael addition according to variant (a) are acidic catalysts, for example from the group of the inorganic acids, for example Broensted acids, such as hydrofluoric acid, hydrochloric acid, hydrobromic acid, sulfuric acid or perchloric acid, or Lewis acids, such as boron trifluoride, aluminum trichloride, iron(III) chloride, tin(IV) chloride, titanium(IV) chloride, scandium(III) triflate or zinc (II) chloride, and also organic acids, for example formic acid, acetic acid, propionic acid, oxalic acid, toluenesulfonic acid, benzenesulfonic acid, camphorsulfonic acid, citric acid or trifluoroacetic acid.

The amount of acidic catalyst may generally vary within wide limits. For example, it may be expedient to employ the acid in catalytic amounts, in substoichiometric amounts, in equimolar amounts or in excess. A preferably liquid acid may optionally also be used as solvent.

For example, diastereomer mixtures or racemic diastereomers [here together referred to by formula (I')] comprising the compounds (I) to be prepared may also be obtained by transesterification, in that (b) compounds of the formula (I")

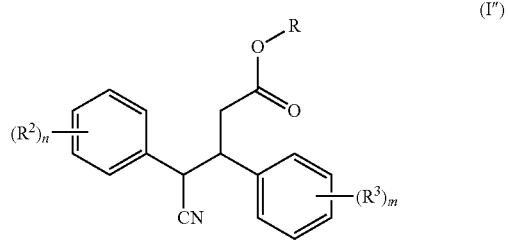

in which R is a radical from the group of the radicals possible for $R^1$, but different from the radical $R^1$ in the compound (I') to be prepared, is reacted with a compound of the formula $R^1$—OH in which $R^1$ is defined as in formula (I), to give compound (I'), where $R^2$, $R^3$, m and n in the compound (I") are as defined in the compound of the formula (I) to be prepared in each case.

By transesterification, it is also possible to obtain stereochemically enriched compounds of the formula (I) mentioned above, in that (c) stereochemically enriched compounds of the formula (I''')

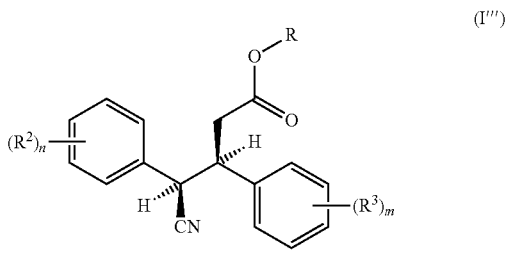

in which R is a radical from the group of the radicals possible for $R^1$, but different from the radical $R^1$ in the compound (I') to be prepared, is reacted with a compound of the formula $R^1$—OH in which $R^1$ is defined as in the compound of the formula (I) to be prepared.

The transesterifications (b) and (c) can be carried out, for example, using a suitable alcohol $R^1$—OH in the presence of a catalyst, optionally in the presence of an aprotic solvent. Furthermore, in general, those conditions are advantageous where the chemical equilibrium is shifted to the side of the desired product, for example using a large excess of the alcohol $R^1$—OH under virtually anhydrous conditions, for example in the presence of a molecular sieve.

The reactions (transesterifications) can generally be carried out at temperatures of from 0° C. to 180° C., preferably from 20° C. to 100° C., in the presence of a Lewis or Broenstedt acid or an enzyme [cf. J. Org. Chem. 2002, 67, 431].

Suitable solvents are, for example, the following organic aprotic solvents:

aliphatic hydrocarbons such as pentane, hexane, cyclohexane or petroleum ether;

aromatic hydrocarbons such as toluene, o-, m- or p-xylene, halogenated hydrocarbons such as methylene chloride (dichloromethane), chloroform or chlorobenzene, ethers, such as diethyl ether, diisopropyl ether, tert-butyl methyl ether, dioxane, anisole or tetrahydrofuran (THF), nitriles such as acetonitrile or propionitrile, ketones, such as acetone, methyl ethyl ketone, diethyl ketone and tert butyl methyl ketone, dimethyl sulfoxide, dimethylformamide, dimethylacetamide or sulfolane or mixtures of the organic solvents mentioned.

The preferred solvent is the alcohol $R^1$—OH, which is at the same time used as reaction partner for the transesterification, optionally in combination with one of the aprotic organic solvents mentioned.

Alternatively, it is also possible to obtain the desired ester from another ester in two steps by acidic or basic hydrolysis of the other esters to the free acid, i.e. to compounds (I") or (I'''), in which R is in each case H, and subsequent esterification with an alcohol $R^1$—OH.

The preparation of diastereomer mixtures or racemic diastereomers [here together referred to by formula (I')] comprising the compounds (I) to be prepared according to variant (d) or optically active compounds (I) according to variant (e) is therefore characterized in that a free acid of the abovementioned formula (I") or formula (I''') in which the radicals R are each hydrogen is esterified with an alcohol of the formula $R^1$—OH by customary methods, if appropriate combined with a previous preparation (d-1) or (e-1) of the free acid from another ester of the formula (I") or formula (I''') in which the radicals R are each not hydrogen.

The esterification from the free acid of the formula (I")/R=H or (I''')/R=H can be carried out, for example, analogously to customary methods, for example at temperatures of from 0° C. to 120° C., preferably from 20° C. to 50° C., optionally in the presence of a catalyst, in a substantially anhydrous medium or under conditions where the water including the water formed during the esterification is bound or otherwise removed. Suitable catalysts are anhydrous acids and bases, preferably organic acids or bases; see handbooks for chemical processes for esterifying carboxylic acids; see also, for example, J. Am. Chem. Soc. 2007, 129 (43), 13321; J. Org. Chem. 1984, 49 (22), 4287.

Suitable solvents for the esterification are the aprotic organic solvents mentioned above for process variants (b) and (c), including the alcohol $R^1$—OH which is at the same time used as a reaction partner for the esterification, optionally in combination with one of the aprotic organic solvents mentioned.

Suitable catalysts for the esterification are the bases or acidic or basic catalysts mentioned for process variant (a) (Michael addition), in anhydrous form or with a water content which is as low as possible. Preferred catalysts are the bases lithium hydroxide, potassium carbonate or organic amines such as pyridines, substituted pyridines and DBU.

Any hydrolysis carried out before the esterification [process variants (b-1) and (c-1)] of other esters of the formula (I") or the formula (I'''), where R is in each case not H, can be carried out analogously to customary methods, for example at temperatures of from 0° C. to 120° C., preferably from 20° C. to 50° C., if appropriate in the presence of a catalyst, in a water-containing medium/solvent; see handbooks on chemical processes for hydrolysing carboxylic esters; see also, for example, J. Am. Chem. Soc. 2007, 129 (43), 13321; J. Org. Chem. 1984, 49 (22), 4287.

A suitable solvent for the hydrolysis [process variants (b-1) and (c-1)] is water or a water-containing organic solvent, for example the organic solvent mentioned based on process variant (a) mentioned (Michael addition), preferably water or polar organic solvents containing water, such as THF.

Suitable catalysts for the hydrolysis are the acids, bases or acidic or basic catalysts mentioned for process variant (a) (Michael addition), in each case containing water. Preferred catalysts are aqueous acids and bases, in particular bases such as lithium hydroxide, sodium hydroxide, potassium carbonate, pyridines, substituted pyridines and DBU in the presence of organic solvents.

The catalysts for the esterification or the hydrolysis can generally be employed in catalytic amounts. In general, it is also possible to use relatively large amounts including equimolar amounts and a molar excess. Frequently, a use as solvent is also possible.

The reaction mixtures are worked up in a customary manner, for example by mixing with water, separating the phases and, if appropriate, chromatographic purification of the crude products. Some of the intermediates and end products are obtained in the form of colorless or slightly brownish viscous oils which are purified or freed from volatile components under reduced pressure and at moderately elevated temperature.

If the intermediates and end products are obtained as solids, the purification can also be carried out by recrystallization or digestion. If individual compounds (I') or (I) cannot be obtained by the routes described above, they can be prepared by derivatization of other compounds (I') or (I).

The compounds of the formula (I') obtained in the form of the diastereomeric mixtures contain two centers of chirality in positions 3 and 4 of the cyanobutyrate skeleton and may contain one or more further centers of chirality, depending on the substitution pattern.

Owing to the two centers of chirality in positions 3 and 4, there are 4 stereoisomers, namely two erythro enantiomers having the configurations (3S,4R) [=erythro-1] and (3R,4S) [=erythro-2], respectively, and two threo enantiomers having the configurations (3S,4S) [=threo-1] and (3R,4R) [=threo-2], respectively; see the scheme below:

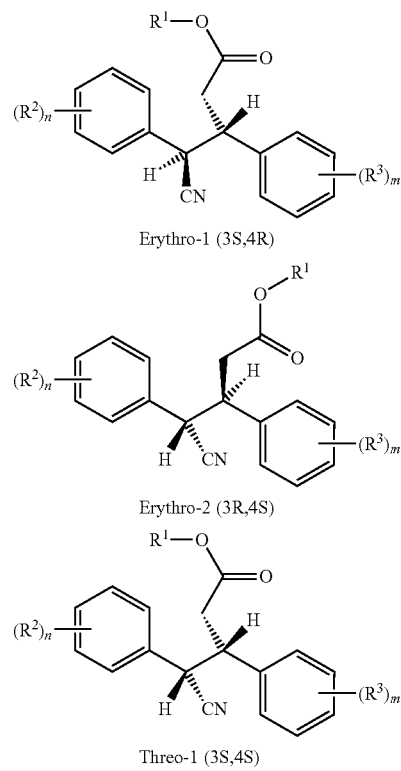

Erythro-1 (3S,4R)

Erythro-2 (3R,4S)

Threo-1 (3S,4S)

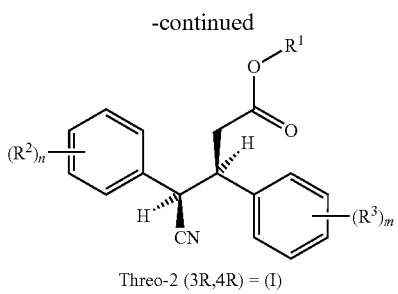

Threo-2 (3R,4R) = (I)

The compounds (I) according to the invention represent the pure enantiomers threo-2 or mixtures comprising threo-2 and threo-1 and having a stereochemical purity of from 60 to 100% threo-2, preferably from 70 to 100% threo-2, more preferably from 80 to 100% threo-2, in particular from 90 to 100% threo-2, based on the mixture of threo enantiomers present.

To prepare the compounds (I) according to the invention from the compounds (I'), it is necessary to enrich the stereoisomer (enantiomer) threo-2 from the mixture of the stereoisomers in an appropriate manner. Accordingly, an expedient process comprises the initial isolation of the threo isomers threo-1 and threo-2 from the diastereomer mixture (I') which still comprises the erythro isomers, and the subsequent optical resolution with isolation or enrichment of the enantiomer threo-2 from the mixture with the enantiomer threo-1.

The isolation of the threo isomers as a racemic mixture can be carried out analogously to the customary separation and purification processes mentioned above (diastereomer separation).

Suitable for the subsequent preparation of compounds of the formula (I) are methods for optical resolution generally known to the person skilled in the art from analogous cases (cf. handbooks of stereochemistry), for example following processes for separating mixtures into diastereomers, for example by physical processes, such as crystallization, chromatographic processes, in particular column chromatography and high-pressure liquid chromatography, distillation, if appropriate under reduced pressure, extraction and other processes, it is possible to separate remaining mixtures of enantiomers, generally by chromatographic separation on chiral solid phases. Suitable for preparative amounts or on an industrial scale are processes such as the crystallization of diastereomeric salts which can be obtained from the diastereomer mixtures using optically active acids and, if appropriate, provided that acidic groups are present, using optically active bases.

Optically active acids which are suitable for racemate separation by crystallization of diastereomeric salts are, for example, camphorsulfonic acid, camphoric acid, bromocamphorsulfonic acid, quinic acid, tartaric acid, dibenzoyltartaric acid and other analogous acids; suitable optically active bases are, for example, quinine, cinchonine, quinidine, brucine, 1-(S)- or 1-(R)-phenylethylamine and other analogous bases.

The crystallizations are then in most cases carried out in aqueous, alcoholic or aqueous-organic solvents, where the diastereomer which is less soluble precipitates first, if appropriate after seeding. One enantiomer of the compound of the formula (I) is then liberated from the precipitated salt, or the other is liberated from the crystals, by acidification or using a base.

Accordingly, the invention also provides the process for preparing the compounds (I), wherein compounds (I') are subjected to an optical resolution and the compound (I) is isolated in a stereochemical purity of from 60 to 100%, preferably from 70 to 100%, more preferably from 80 to 100%, in particular from 90 to 100%, based on the mixture of threo enantiomers present.

As an alternative to the optical resolution methods mentioned, enantioselective processes starting with stereochemically pure starting materials are in principle also possible for preparing the threo-2 enantiomers (I).

The following acids are generally suitable for preparing the acid addition salts of the compounds of the formula (I): hydrohalic acids, such as hydrochloric acid or hydrobromic acid, furthermore phosphoric acid, nitric acid, sulfuric acid, mono- or bifunctional carboxylic acids and hydroxycarboxylic acids, such as acetic acid, maleic acid, succinic acid, fumaric acid, tartaric acid, citric acid, salicylic acid, sorbic acid, or lactic acid, and also sulfonic acids, such as p-toluenesulfonic acid and 1,5-naphthalenedisulfonic acid. The acid addition compounds of the formula (I) can be obtained in a simple manner by the customary methods for forming salts, for example by dissolving a compound of the formula (I) in a suitable organic solvent, such as, for example, methanol, acetone, methylene chloride or benzene, and adding the acid at temperatures of from 0 to 100° C., and they can be isolated in a known manner, for example by filtration, and, if appropriate, purified by washing with an inert organic solvent.

The base addition salts of the compounds of the formula (I) are preferably prepared in inert polar solvents, such as, for example, water, methanol or acetone, at temperatures of from 0 to 100° C. Examples of bases which are suitable for the preparation of the salts according to the invention are alkali metal carbonates, such as potassium carbonate, alkali metal hydroxides and alkaline earth metal hydroxides, for example NaOH or KOH, alkali metal hydrides and alkaline earth metal hydrides, for example NaH, alkali metal alkoxides and alkaline earth metal alkoxides, for example sodium methoxide or potassium tert-butoxide, or ammonia, ethanolamine or quaternary ammonium hydroxide of the formula [NRR'R''R''']⁺ OH⁻.

What is meant by the "inert solvents" referred to in the above process variants are in each case solvents which are inert under the particular reaction conditions but need not be inert under all reaction conditions.

Collections of compounds of the formula (I) which can be synthesized by the aforementioned process can also be prepared in a parallel manner, it being possible for this to take place in a manual, partly automated or completely automated manner. In this connection, it is possible to automate the reaction procedure, the work-up or the purification of the products and/or intermediates. Overall, this is understood as meaning a procedure as described, for example, by S. H. DeWitt in "Annual Reports in Combinatorial Chemistry and Molecular Diversity: Automated Synthesis", Volume 1, Verlag Escom, 1997, pages 69 to 77.

For the parallelized reaction procedure and workup it is possible to use a range of commercially available instruments, of the kind offered by, for example, the companies Stem Corporation, Woodrolfe Road, Tollesbury, Essex, CM9 8SE, England, or H+P Labortechnik GmbH, Bruckmannring 28, 85764 Oberschleißheim, Germany. For the parallel purification of compounds (I) or of intermediates produced during the preparation, there are available, inter alia, chromatography apparatuses, for example from ISCO, Inc., 4700 Superior Street, Lincoln, Nebr. 68504, USA. The apparatuses listed allow a modular procedure in which the individual process steps are automated, but between the process steps manual operations have to be carried out. This can be circumvented by using partly or completely integrated automation systems in which the respective automation modules are operated, for example, by robots. Automation systems of this type can be acquired, for example, from Zymark Corporation, Zymark Center, Hopkinton, Mass. 01748, USA.

Besides the methods described here, the preparation of compounds of the formula (I) can take place completely or partially by solid-phase supported methods. For this purpose, individual intermediates or all intermediates in the synthesis or a synthesis adapted for the corresponding procedure are bonded to a synthesis resin. Solid-phase-supported synthesis methods are described extensively in the specialist literature, for example Barry A. Bunin in "The Combinatorial Index", Academic Press, 1998.

The use of solid-phase-supported synthesis methods permits a number of protocols, which are known from the literature and which for their part may be performed manually or in an automated manner, to be carried out. For example, the "teabag method" (Houghten, U.S. Pat. No. 4,631,211; Houghten et al., Proc. Natl. Acad. Sci, 1985, 82, 5131-5135) in which products from IRORI, 11149 North Torrey Pines Road, La Jolla, Calif. 92037, USA, are employed, may be semiautomated. The automation of solid-phase-supported parallel syntheses is performed successfully, for example, by apparatuses from Argonaut Technologies, Inc., 887 Industrial Road, San Carlos, Calif. 94070, USA or MultiSynTech GmbH, Wullener Feld 4, 58454 Witten, Germany.

The preparation according to the processes described herein produces compounds of the formula (I) in the form of substance collections or libraries. Accordingly, the present invention also provides libraries of compounds of the formula (I) which comprise at least two compounds of the formula (I), and precursors thereof.

The compounds of the formula (I) according to the invention (and/or their salts), above and hereinbelow also referred to together as "compounds according to the invention", "compounds (I) according to the invention" or in short as "compounds (I)", have excellent herbicidal efficacy against a broad spectrum of economically important monocotyledonous and dicotyledonous annual harmful plants. The active compounds act efficiently even on perennial harmful plants which produce shoots from rhizomes, root stocks and other perennial organs and which are difficult to control.

The present invention therefore also relates to a method for controlling unwanted plants or for regulating the growth of plants, preferably in crops of plants, where one or more compound(s) according to the invention is/are applied to the plants (for example harmful plants such as monocotyledonous or dicotyledonous weeds or undesired crop plants), to the seed (for example grains, seeds or vegetative propagules such as tubers or shoot parts with buds), to the soil in or on which the plants grow (for example the soil of cropland or non-cropland) or to the area on which the plants grow (for example the area under cultivation). In this context, the compounds according to the invention can be applied for example pre-sowing (if appropriate also by incorporation into the soil), pre-emergence or post-emergence. Specific examples may be mentioned of some representatives of the monocotyledonous and dicotyledonous weed flora which can be controlled by the compounds according to the invention, without the enumeration being restricted to certain species.

Monocotyledonous harmful plants of the genera: *Aegilops, Agropyron, Agrostis, Alopecurus, Apera, Avena, Brachiaria, Bromus, Cenchrus, Commelina, Cynodon, Cyperus, Dactyloctenium, Digitaria, Echinochloa, Eleocharis, Eleusine, Eragrostis, Eriochloa, Festuca, Fimbristylis, Heteranthera, Imperata, Ischaemum, Leptochloa, Lolium, Monochoria, Panicum, Paspalum, Phalaris, Phleum, Poa, Rottboellia, Sagittaria, Scirpus, Setaria, Sorghum.*

Dicotyledonous weeds of the genera: *Abutilon, Amaranthus, Ambrosia, Anoda, Anthemis, Aphanes, Artemisia, Atriplex, Bellis, Bidens, Capsella, Carduus, Cassia, Centaurea, Chenopodium, Cirsium, Convolvulus, Datura, Desmodium, Emex, Erysimum, Euphorbia, Galeopsis, Galinsoga, Galium, Hibiscus, Ipomoea, Kochia, Lamium, Lepidium, Lindernia, Matricaria, Mentha, Mercurialis, Mullugo, Myosotis, Papaver, Pharbitis, Plantago, Polygonum, Portulaca, Ranunculus, Raphanus, Rorippa, Rotala, Rumex, Salsola, Senecio, Sesbania, Sida, Sinapis, Solanum, Sonchus, Sphenoclea, Stellaria, Taraxacum, Thlaspi, Trifolium, Urtica, Veronica, Viola, Xanthium.*

If the compounds according to the invention are applied to the soil surface before germination, the weed seedlings are either prevented completely from emerging or else the weeds grow until they have reached the cotyledon stage, but then their growth stops, and, eventually, after three to four weeks have elapsed, they die completely.

If the active compounds are applied post-emergence to the green parts of the plants, growth stops after the treatment, and the harmful plants remain at the growth stage of the point of time of application, or they die completely after a certain time, so that in this manner competition by the weeds, which is harmful to the crop plants, is eliminated very early and in a sustained manner.

Although the compounds according to the invention display an outstanding herbicidal activity against monocotyledonous and dicotyledonous weeds, crop plants of economically important crops, for example dicotyledonous crops of the genera *Arachis, Beta, Brassica, Cucumis, Cucurbita, Helianthus, Daucus, Glycine, Gossypium, Ipomoea, Lactuca, Linum, Lycopersicon, Miscanthus, Nicotiana, Phaseolus, Pisum, Solanum, Vicia,* or monocotyledonous crops of the genera *Allium, Ananas, Asparagus, Avena, Hordeum, Oryza, Panicum, Saccharum, Secale, Sorghum, Triticale, Triticum, Zea,* in particular *Zea* and *Triticum*, are damaged only to an insignificant extent, or not at all, depending on the structure of the respective compound according to the invention and its application rate. This is why the present compounds are highly suitable for the selective control of unwanted plant growth in plant crops such as agriculturally useful plants or ornamentals.

Moreover, the compounds according to the invention (depending on their respective structure and the application rate applied) have outstanding growth-regulatory properties in crop plants. They engage in the plant's metabolism in a regulatory fashion and can therefore be employed for the influencing, in a targeted manner, of plant constituents and for facilitating harvesting, such as, for example, by triggering desiccation and stunted growth. Moreover, they are also suitable for generally controlling and inhibiting unwanted vegetative growth without destroying the plants in the process. Inhibiting the vegetative growth plays an important role in many monocotyledonous and dicotyledonous crops since for example lodging can be reduced, or prevented completely, hereby.

By virtue of their herbicidal and plant-growth-regulatory properties, the active compounds can also be employed for controlling harmful plants in crops of genetically modified plants or plants modified by conventional mutagenesis. In general, the transgenic plants are distinguished by especially advantageous properties, for example by resistances to certain pesticides, mainly certain herbicides, resistances to plant diseases or causative organisms of plant diseases, such as certain insects or microorganisms such as fungi, bacteria or viruses. Other specific characteristics relate, for example, to the harvested material with regard to quantity, quality, storability, composition and specific constituents. Thus, transgenic plants are known whose starch content is increased, or whose starch quality is altered, or those where the harvested material has a different fatty acid composition.

It is preferred with a view to trangenic crops to use the compounds according to the invention and/or their salts in economically important transgenic crops of useful plants and ornamentals, for example of cereals such as wheat, barley, rye, oats, millet, rice and corn or else crops of sugar beet, cotton, soybean, oilseed rape, potato, tomato, peas and other vegetables.

It is preferred to employ the compounds according to the invention as herbicides in crops of useful plants which are resistant, or have been made resistant by recombinant means, to the phytotoxic effects of the herbicides.

By virtue of their herbicidal and plant-growth-regulatory properties, the active compounds can also be employed for controlling harmful plants in crops of known genetically modified plants or genetically modified plants still to be developed. In general, the transgenic plants are distinguished by especially advantageous properties, for example by resistances to certain pesticides, mainly certain herbicides, resistances to plant diseases or causative organisms of plant diseases, such as certain insects or microorganisms such as fungi, bacteria or viruses. Other specific characteristics relate, for example, to the harvested material with regard to quantity, quality, storability, composition and specific constituents. Thus, transgenic plants are known whose starch content is increased, or whose starch quality is altered, or those where the harvested material has a different fatty acid composition. Other particular properties may be tolerance or resistance to abiotic stressors, for example heat, low temperatures, drought, salinity and ultraviolet radication.

It is preferred to use the compounds of the formula (I) according to the invention or salts thereof in economically important transgenic crops of useful plants and ornamental plants, for example of cereals such as wheat, barley, rye, oats, sorghum and millet, rice, cassava and corn or else crops of sugar beet, cotton, soybean, oilseed rape, potato, tomato, peas and other vegetables.

It is preferred to employ the compounds of the formula (I) according to the invention as herbicides in crops of useful plants which are resistant, or have been made resistant by recombinant means, to the phytotoxic effects of the herbicides.

Conventional methods of generating novel plants which have modified properties in comparison to plants occurring to date consist, for example, in traditional breeding methods and the generation of mutants. Alternatively, novel plants with altered properties can be generated with the aid of recombinant methods (see, for example, EP-A-0221044, EP-A-0131624). For example, the following have been described in several cases:

recombinant modifications of crop plants for the purpose of modifying the starch synthesized in the plants (e.g. WO 92/11376, WO 92/14827, WO 91/19806), transgenic crop plants which are resistant to particular herbicides of the glufosinate type (cf., for example, EP-A-0242236, EP-A-242246) or glyphosate type (WO 92/00377) or the sulfonylureas (EP-A-0257993, U.S. Pat. No. 5,013,659), transgenic crop plants, for example cotton, with the ability to produce *Bacillus thuringiensis* toxins (Bt toxins), which make the plants resistant to certain pests (EP-A-0142924, EP-A-0193259), transgenic crop plants with a modified fatty acid composition (WO 91/13972), genetically modified crop plants with novel constituents or secondary metabolites, for example novel phytoalexins, which bring about an increased disease resistance (EPA 309862, EPA0464461), genetically modified plants with reduced photorespiration which feature higher yields and higher stress tolerance (EPA 0305398), transgenic crop plants which produce pharmaceutically or diagnostically important proteins ("molecular pharming"), transgenic crop plants which are distinguished by higher yields or better quality, transgenic crop plants which are distinguished by a combination, for example of the abovementioned novel properties ("gene stacking").

A large number of molecular-biological techniques by means of which novel transgenic plants with modified properties can be generated are known in principle; see, for example, I. Potrykus and G. Spangenberg (eds.) Gene Transfer to Plants, Springer Lab Manual (1995), Springer Verlag Berlin, Heidelberg. or Christou, "Trends in Plant Science" 1 (1996) 423-431.

To carry out such recombinant manipulations, nucleic acid molecules which allow mutagenesis or a sequence change by recombination of DNA sequences can be introduced into plasmids. For example, base substitutions can be carried out, part-sequences can be removed, or natural or synthetic sequences may be added with the aid of standard methods. For the joining of the DNA fragments to one another, adaptors or linkers can be attached to the fragments; see, for example, Sambrook et al., 1989, Molecular Cloning, A Laboratory Manual, 2nd ed. Cold Spring Harbor Laboratory Press, Cold Spring Harbor, N.Y.; or Winnacker "Gene und Klone", VCH Weinheim 2nd edition 1996.

For example, the generation of plant cells with a reduced activity of a gene product can be achieved by expressing at least one corresponding antisense RNA, a sense RNA for achieving a cosuppression effect or by expressing at least one suitably constructed ribozyme which specifically cleaves transcripts of the abovementioned gene product.

To this end, it is possible to use DNA molecules which encompass the entire coding sequence of a gene product inclusive of any flanking sequences which may be present, and also DNA molecules which only encompass portions of the coding sequence, it being necessary for these portions to be long enough to have an antisense effect in the cells. The use of DNA sequences which have a high degree of homology to the coding sequences of a gene product, but are not completely identical to them, is also possible.

When expressing nucleic acid molecules in plants, the protein synthesized can be localized in any desired compartment of the plant cell. However, to achieve localization in a particular compartment, it is possible, for example, to link the coding region with DNA sequences which ensure localization in a particular compartment. Such sequences are known to those skilled in the art (see, for example, Braun et al., EMBO J. 11 (1992), 3219-3227; Wolter et al., Proc. Natl. Acad. Sci. USA 85 (1988), 846-850; Sonnewald et al., Plant J. 1 (1991), 95-106). The nucleic acid molecules can also be expressed in the organelles of the plant cells.

The transgenic plant cells can be regenerated by known techniques to give rise to entire plants. In principle, the transgenic plants can be plants of any desired plant species, i.e. not only monocotyledonous, but also dicotyledonous, plants.

Thus, transgenic plants can be obtained whose properties are altered by overexpression, suppression or inhibition of homologous (=natural) genes or gene sequences or the expression of heterologous (=foreign) genes or gene sequences.

It is preferred to employ the compounds (I) according to the invention in transgenic crops which are resistant to growth regulators such as, for example, dicamba, or against herbicides which inhibit essential plant enzymes, for example acetolactate synthases (ALS), EPSP synthases, glutamine synthases (GS) or hydroxyphenylpyruvate dioxygenases (HPPD), or against herbicides from the group of the sulfonylureas, glyphosate, glufosinate or benzoylisoxazoles and analogous active compounds.

When the active compounds according to the invention are used in transgenic crops, effects are frequently observed—in addition to the effects on harmful plants which can be observed in other crops—which are specific for the application in the transgenic crop in question, for example a modified or specifically widened spectrum of weeds which can be controlled, modified application rates which may be employed for application, preferably good combinability with the herbicides to which the transgenic crop is resistant, and an effect on growth and yield of the transgenic crop plants.

The invention therefore also relates to the use of the compounds of the formula (I) according to the invention and/or their salts as herbicides for controlling harmful plants in crops of useful plants or ornamentals, optionally in transgenic crop plants.

Preference is given to the use by the pre- or post-emergence method in cereals such as wheat, barley, rye, oats, millet and rice, in particular in wheat by the post-emergence method.

Preference is also given to the use by the pre- or post-emergence method in corn, in particular by the pre-emergence method in corn.

Preference is also given to the use by the pre- or post-emergence method in soybeans, in particular by the post-emergence method in soybeans.

The use according to the invention for the control of harmful plants or for growth regulation of plants also includes the case in which the active compound of the formula (I) or its salt is not formed from a precursor substance ("prodrug") until after application on the plant, in the plant or in the soil.

The invention also provides the method (application method) for controlling harmful plants or for regulating the growth of plants which comprises applying an effective amount of one or more compounds of the formula (I) or salts thereof onto the plants (harmful plants, if appropriate together with the useful plants), plant seeds, the soil in which or on which the plants grow or the area under cultivation.

The compounds (I) according to the invention can be used in the form of wettable powders, emulsifiable concentrates, sprayable solutions, dusting products or granules in the customary formulations. The invention therefore also provides herbicidal and plant growth-regulating compositions which comprise compounds of the formula (I) and/or salts thereof.

The compounds of the formula (I) and/or salts thereof can be formulated in various ways according to which biological and/or physicochemical parameters are required. Possible formulations include, for example: wettable powders (WP), water-soluble powders (SP), water-soluble concentrates, emulsifiable concentrates (EC), emulsions (EW) such as oil-in-water and water-in-oil emulsions, sprayable solutions, suspension concentrates (SC), oil- or water-based dispersions, oil-miscible solutions, capsule suspensions (CS), dusting products (DP), seed-dressing products, granules for scattering and soil application, granules (GR) in the form of microgranules, spray granules, coated granules and adsorption granules, water-dispersible granules (WG), water-soluble granules (SG), ULV formulations, microcapsules and waxes.

These individual types of formulation are known in principle and are described, for example, in: Winnacker-Küchler, "Chemische Technologie" [Chemical technology], volume 7, C. Hanser Verlag Munich, 4th ed. 1986; Wade van Valkenburg, "Pesticide Formulations", Marcel Dekker, N.Y., 1973; K. Martens, "Spray Drying" Handbook, 3rd ed. 1979, G. Goodwin Ltd. London.

The necessary formulation assistants, such as inert materials, surfactants, solvents and further additives, are likewise known and are described, for example, in: Watkins, "Handbook of Insecticide Dust Diluents and Carriers", 2nd Ed., Darland Books, Caldwell N. J., H. v. Olphen, "Introduction to Clay Colloid Chemistry"; 2nd Ed., J. Wiley & Sons, N.Y.; C. Marsden, "Solvents Guide"; 2nd Ed., Interscience, N.Y. 1963; McCutcheon's "Detergents and Emulsifiers Annual", MC Publ. Corp., Ridgewood N.J.; Sisley and Wood, "Encyclopedia of Surface Active Agents", Chem. Publ. Co. Inc., N.Y. 1964; Schinfeldt, "Grenzflächenaktive Äthylenoxidaddukte" [Interface-active Ethylene Oxide Adducts], Wiss. Verlagsgesell., Stuttgart 1976; Winnacker-Kiichler, "Chemische Technologie", volume 7, C. Hanser Verlag Munich, 4th ed. 1986.

Wettable powders are preparations which can be dispersed uniformly in water and, as well as the active compound, apart from a diluent or inert substance, also comprise surfactants of the ionic and/or nonionic type (wetting agents, dispersants), for example polyoxyethylated alkylphenols, polyoxyethylated fatty alcohols, polyoxyethylated fatty amines, fatty alcohol polyglycol ether sulfates, alkanesulfonates, alkylbenzenesulfonates, sodium lignosulfonate, sodium 2,2'dinaphthylmethane-6,6'-disulfonate, sodium dibutylnaphthalenesulfonate or else sodium oleoylmethyltaurinate. To prepare the wettable powders, the herbicidally active compounds are ground finely, for example in customary apparatuses such as hammer mills, blower mills and air-jet mills, and simultaneously or subsequently mixed with the formulation assistants.

Emulsifiable concentrates are prepared by dissolving the active compound in an organic solvent, for example butanol, cyclohexanone, dimethylformamide, xylene or else relatively high-boiling aromatics or hydrocarbons or mixtures of the organic solvents with addition of one or more surfactants of the ionic and/or nonionic type (emulsifiers). The emulsifiers used may, for example, be: alkylarylsulfonic calcium salts, such as calcium dodecylbenzenesulfonate, or nonionic emulsifiers such as fatty acid polyglycol esters, alkylaryl polyglycol ethers, fatty alcohol polyglycol ethers, propylene oxide-ethylene oxide condensation products, alkyl polyethers, sorbitan esters, such as, for example, sorbitan fatty acid esters, or polyoxyethylene sorbitan esters, such as, for example, polyoxyethylene sorbitan fatty acid esters.

Dusts are obtained by grinding the active compound with finely distributed solid substances, for example talc, natural clays, such as kaolin, bentonite and pyrophyllite, or diatomaceous earth.

Suspension concentrates may be water- or oil-based. They may be prepared, for example, by wet grinding by means of commercial bead mills and optional addition of surfactants as have, for example, already been listed above for the other formulation types.

Emulsions, e.g. oil-in-water emulsions (EW), can be prepared, for example, by means of stirrers, colloid mills and/or static mixers using aqueous organic solvents and if appropriate surfactants, as have for example already been listed above in connection with the other types of formulation.

Granules can be prepared either by spraying the active compound onto granulated inert material capable of adsorption or by applying active compound concentrates to the surface of carrier substances, such as sand, kaolinites or granulated inert material, by means of adhesives, for example polyvinyl alcohol, sodium polyacrylate or mineral oils. Suitable active compounds can also be granulated in the manner customary for the production of fertilizer granules—if desired as a mixture with fertilizers.

Water-dispersible granules are prepared generally by the customary processes such as spray-drying, fluidized bed granulation, pan granulation, mixing with high-speed mixers and extrusion without solid inert material.

For the production of pan granules, fluidized bed granules, extruder granules and spray granules, see, for example, processes in "Spray-Drying Handbook" 3rd ed. 1979, G. Goodwin Ltd., London; J. E. Browning, "Agglomeration", Chemical and Engineering 1967, pages 147 ff.; "Perry's Chemical Engineer's Handbook", 5th Ed., McGraw-Hill, New York 1973, pp. 8-57.

For further details regarding the formulation of crop protection agents, see, for example, G. C. Klingman, "Weed Control as a Science", John Wiley and Sons, Inc., New York, 1961, pages 81-96 and J. D. Freyer, S. A. Evans, "Weed Control Handbook", 5th ed., Blackwell Scientific Publications, Oxford, 1968, pages 101-103.

The agrochemical formulations comprise generally from 0.1 to 99% by weight, in particular from 0.1 to 95% by weight, of active compound of the formula (I) and/or salts thereof.

In wettable powders, the active compound concentration is, for example, from about 10 to 90% by weight, the remainder to 100% by weight consisting of customary formulation components. In the case of emulsifiable concentrates, the active compound concentration can be from about 1 to 90, preferably from 5 to 80, % by weight. Dust-type formulations contain from 1 to 30% by weight of active compound, preferably usually from 5 to 20% by weight of active compound; sprayable solutions contain from about 0.05 to 80% by weight, preferably from 2 to 50% by weight of active compound. In the case of water-dispersible granules, the active compound content depends partially on whether the active compound is present in liquid or solid form and on which granulation auxiliaries, fillers, etc., are used. In the water-dispersible granules, the content of active compound is, for example, between 1 and 95% by weight, preferably between 10 and 80% by weight.

In addition, the active compound formulations mentioned optionally comprise the respective customary adhesives, wetting agents, dispersants, emulsifiers, penetrants, preservatives, antifreeze agents and solvents, fillers, carriers and dyes, defoamers, evaporation inhibitors and agents which influence the pH and the viscosity. Examples of formulation auxiliaries are described, inter alia, in "Chemistry and Technology of Agrochemical Formulations", ed. D. A. Knowles, Kluwer Academic Publishers (1998).

The compounds of the formula (I) or salts thereof can be employed as such or in the form of their preparations (formulations) combined with other pesticidally active compounds, such as, for example, insecticides, acaricides, nematicides, herbicides, fungicides, safeners, fertilizers and/or growth regulators, for example as finished formulation or as tank mixes. The combination formulations can be prepared on the basis of the abovementioned formulations, while taking account of the physical properties and stabilities of the active compounds to be combined.

Active compounds which can be employed in combination with the compounds according to the invention in mixed formulations or in the tank mix are, for example, known active compounds which are based on the inhibition of, for example, acetolactate synthase, acetyl-CoA carboxylase, cellulose synthase, enolpyruvylshikimate-3-phosphate synthase, glutamine synthetase, phydroxyphenylpyruvate dioxygenase, phytoen desaturase, photosystem I, photosystem II, protoporphyrinogen oxidase, as are described in, for example, Weed Research 26 (1986) 441-445 or "The Pesticide Manual", 15th edition, The British Crop Protection Council and the Royal Soc. of Chemistry, 2006 and the literature cited therein. Known herbicides or plant growth regulators which can be combined with the compounds according to the invention are, for example, the following active compounds (the compounds are either designated by the common name according to the International Organization for Standardization (ISO) or by the chemical name, or by the code number) and always comprise all use forms such as acids, salts, esters and isomers such as stereoisomers and optical isomers. Here, by way of example, one and in some cases a plurality of use forms are mentioned:

acetochlor, acibenzolar, acibenzolar-5-methyl, acifluorfen, acifluorfen-sodium, aclonifen, alachlor, allidochlor, alloxydim, alloxydim-sodium, ametryne, amicarbazone, amidochlor, amidosulfuron, aminocyclopyrachlor, aminopyralid, amitrole, ammonium sulfamate, ancymidol, anilofos, asulam, atrazine, azafenidin, azimsulfuron, aziprotryne, beflubutamid, benazolin, benazolin-ethyl, bencarbazone, benfluralin, benfuresate, bensulide, bensulfuron, bensulfuron-methyl, bentazone, benzfendizone, benzobicyclon, benzofenap, benzofluor, benzoylprop, bicyclopyrone, bifenox, bilanafos, bilanafos-sodium, bispyribac, bispyribac-sodium, bromacil, bromobutide, bromofenoxim, bromoxynil, bromuron, buminafos, busoxinone, butachlor, butafenacil, butamifos, butenachlor, butralin, butroxydim, butylate, cafenstrole, carbetamide, carfentrazone, carfentrazone-ethyl, chlomethoxyfen, chloramben, chlorazifop, chlorazifop-butyl, chlorbromuron, chlorbufam, chlorfenac, chlorfenac-sodium, chlorfenprop, chlorflurenol, chlorflurenol-methyl, chloridazon, chlorimuron, chlorimuron-ethyl, chlormequat-chloride, chlornitrofen, chlorophthalim, chlorthal-dimethyl, chlortoluron, chlorsulfuron, cinidon, cinidon-ethyl, cinmethylin, cinosulfuron, clethodim, clodinafop, clodinafop-propargyl, clofencet, clomazone, clomeprop, cloprop, clopyralid, cloransulam, cloransulam-methyl, cumyluron, cyanamide, cyanazine, cyclanilide, cycloate, cyclosulfamuron, cycloxydim, cycluron, cyhalofop, cyhalofop-butyl, cyperquat, cyprazine, cyprazole, 2,4-D, 2,4-DB, daimuron/dymron, dalapon, daminozide, dazomet, n-decanol, desmedipham, desmetryn, detosyl-pyrazolate (DTP), diallate, dicamba, dichlobenil, dichlorprop, dichlorprop-P, diclofop, diclofop-methyl, diclofop-P-methyl, diclosulam, diethatyl, diethatyl-ethyl, difenoxuron, difenzoquat, diflufenican, diflufenzopyr, diflufenzopyr-sodium, dikegulac-sodium, dimefuron, dimepiperate, dimethachlor, dimethametryn, dimethenamid, dimethenamid-P, dimethipin, dimetrasulfuron, dinitramine, dinoseb, dinoterb, diphenamid, dipropetryn, diquat, diquat-dibromide, dithiopyr, diuron, DNOC, eglinazine-ethyl, endothal, EPTC, esprocarb, ethalfluralin, ethametsulfuron, ethametsulfuron-methyl, ethephon, ethidimuron, ethiozin, ethofumesate, ethoxyfen, ethoxyfen-ethyl, ethoxysulfuron, etobenzanid, F-5331, i.e. N-[2-chloro-4-fluoro-5-[4-(3-fluoropropyl)-4,5- dihydro-5-oxo-1H-tetrazol-1-yl]phenyl]ethanesulfonamide, F-7967, i.e. 3-[7-chloro-5-fluoro-2-(trifluoromethyl)-1H-benzimidazol-4-yl]-1-methyl-6-(trifluoromethyl)pyrimidine-2,4(1H,3H)-dione, fenoprop, fenoxaprop, fenoxaprop-P, fenoxaprop-ethyl, fenoxaprop-P-ethyl, fenoxasulfone, fentrazamide, fenuron, flamprop, flamprop-M-isopropyl, flamprop-M-methyl, flazasulfuron, florasulam, fluazifop, fluazifop-P, fluazifop-butyl, fluazifop-P-butyl, fluazolate, flucarbazone, flucarbazone-sodium, flucetosulfuron, fluchloralin, flufenacet (thiafluamide), flufenpyr, flufenpyr-ethyl, flumetralin, flumetsulam, flumiclorac, flumiclorac-pentyl, flumioxazin, flumipropyn, fluometuron, fluorodifen, fluoroglycofen, fluoroglycofen-ethyl, flupoxam, flupropacil, flupropanate, flupyrsulfuron, flupyrsulfuron-methyl-sodium, flurenol, flurenol-butyl, fluridone, fluorochloridone, fluoroxypyr, fluoroxypyr-meptyl, flurprimidol, flurtamone, fluthiacet, fluthiacet-methyl, fluthiamide, fomesafen, foramsulfuron, forchlorfenuron, fosamine, furyloxyfen, gibberellic acid, glufosinate, glufosinate-ammonium, glufosinate-P, glufosinate-P-ammonium, glufosinate-P-sodium, glyphosate, glyphosate-isopropylammonium, glyphosate-potassium, H-9201, i.e. O-(2,4-dimethyl-6-nitrophenyl) O-ethyl isopropylphosphoramidothioate, halosafen, halosulfuron, halosulfuron-methyl, haloxyfop, haloxyfop-P, haloxyfop-ethoxyethyl, haloxyfop-P-ethoxyethyl, haloxyfop-methyl, haloxyfop-P-methyl, hexazinone, HW-02, i.e. 1-(dimethoxyphosphoryl)ethyl (2,4-dichlorophenoxy)acetate, imazamethabenz, imazamethabenz-methyl, imazamox, imazamox-ammonium, imazapic, imazapyr, imazapyr-isopropylammonium, imazaquin, imazaquin-ammonium, imazethapyr, imazethapyr-ammonium, imazosulfuron, inabenfide, indanofan, indaziflam, indoleacetic acid (IAA), 4-indol-3-ylbutyric acid (IBA), iodosulfuron, iodosulfuron-methyl-sodium, ioxynil, ipfencarbazone, isocarbamid, isopropalin, isoproturon, isouron, isoxaben, isoxachlortole, isoxaflutole, isoxapyrifop, KUH-043, i.e. 3-({[5-(difluoromethyl)-1-methyl-3-(trifluoromethyl)-1H-pyrazol-4-yl]methyl}sulfonyl)-5,5-dimethyl-4,5-dihydro-1,2-oxazole, karbutilate, ketospiradox, lactofen, lenacil, linuron, maleic hydrazide, MCPA, MCPB, MCPB-methyl, -ethyl and -sodium, mecoprop, mecoprop-sodium, mecoprop-butotyl, mecoprop-P-butotyl, mecoprop-P-dimethylammonium, mecoprop-P-2-ethylhexyl, mecoprop-P-potassium, mefenacet, mefluidide, mepiquat-chloride, mesosulfuron, mesosulfuron-methyl, mesotrione, methabenzthiazuron, metam, metamifop, metamitron, metazachlor, metazasulfuron, methazole, methiopyrsulfuron, methiozolin, methoxyphenone, methyldymron, 1-methylcyclopropene, methyl isothiocyanate, metobenzuron, metobromuron, metolachlor, S-metolachlor, metosulam, metoxuron, metribuzin, metsulfuron, metsulfuron-methyl, molinate, monalide, monocarbamide, monocarbamide dihydrogensulfate, monolinuron, monosulfuron, monosulfuron ester, monuron, MT-128, i.e. 6-chloro-N-[(2E)-3-chloroprop-2-en-1-yl]-5-methyl-N-phenylpyridazine-3-amine, MT-5950, i.e. N-[3-chloro-4-(1-methylethyl)phenyl]-2-methylpentanamide, NGGC-011, naproanilide, napropamide, naptalam, NC-310, i.e. 4-(2,4-dichlorobenzoyl)-1-methyl-5-benzyloxypyrazole, neburon, nicosulfuron, nipyraclofen, nitralin, nitrofen, nitrophenolate-sodium (isomer mixture), nitrofluorfen, nonanoic acid, norflurazon, orbencarb, orthosulfamuron, oryzalin, oxadiargyl, oxadiazon, oxasulfuron, oxaziclomefone, oxyfluorfen, paclobutrazole, paraquat, paraquat dichloride, pelargonic acid (nonanoic acid), pendimethalin, pendralin, penoxsulam, pentanochlor, pentoxazone, perfluidone, pethoxamid, phenisopham, phenmedipham, phenmedipham-ethyl, picloram, picolinafen, pinoxaden, piperophos, pirifenop, pirifenop-butyl, pretilachlor, primisulfuron, primisulfuron-methyl, probenazole, profluazole, procyazine, prodiamine, prifluraline, profoxydim, prohexadione, prohexadione-calcium, prohydrojasmone, prometon, prometryn, propachlor, propanil, propaquizafop, propazine, propham, propisochlor, propoxycarbazone, propoxycarbazone-sodium, propyrisulfuron, propyzamide, prosulfalin, prosulfocarb, prosulfuron, prynachlor, pyraclonil, pyraflufen, pyraflufen-ethyl, pyrasulfotole, pyrazolynate (pyrazolate), pyrazosulfuron, pyrazosulfuron-ethyl, pyrazoxyfen, pyribambenz, pyribambenz-isopropyl, pyribambenz-propyl, pyribenzoxim, pyributicarb, pyridafol, pyridate, pyriftalid, pyriminobac, pyriminobac-methyl, pyrimisulfan, pyrithiobac, pyrithiobac-sodium, pyroxasulfone, pyroxsulam, quinclorac, quinmerac, quinoclamine, quizalofop, quizalofop-ethyl, quizalofop-P, quizalofop-P-ethyl, quizalofop-P-tefuryl, rimsulfuron, saflufenacil, secbumeton, sethoxydim, siduron, simazine, simetryn, SN-106279, i.e. methyl (2R)-2-({7-[2-chloro-4-(trifluoromethyl)phenoxy]-2-naphthyl}oxy)propanoate, sulcotrione, sulfallate (CDEC), sulfentrazone, sulfometuron, sulfometuron-methyl, sulfosate (glyphosate-trimesium), sulfosulfuron, SYN-523, SYP-249, i.e. 1-ethoxy-3-methyl-1-oxobut-3-en-2-yl 5-[2-chloro-4-(trifluoromethyl)phenoxy]-2-nitrobenzoate, SYP-300, i.e. 1-[7-fluoro-3-oxo-4-(prop-2-yn-1-yl)-3,4-dihydro-2H-1,4-benzoxazin-6-yl]-3-propyl-2-thioxoimidazolidine-4,5-dione, tebutam, tebuthiuron, tecnazene, tefuryltrione, tembotrione, tepraloxydim, terbacil, terbucarb, terbuchlor, terbumeton, terbuthylazine, terbutryne, thenylchlor, thiafluamide, thiazafluoron, thiazopyr, thidiazimin, thidiazuron, thiencarbazone, thiencarbazone-methyl, thifensulfuron, thifensulfuron-methyl, thiobencarb, tiocarbazil, topramezone, tralkoxydim, triafamone, triallate, triasulfuron, triaziflam, triazofenamide, tribenuron, tribenuron-methyl, trichloroacetic acid (TCA), triclopyr, tridiphane, trietazine, trifloxysulfuron, trifloxysulfuron-sodium, trifluralin, triflusulfuron, triflusulfuron-methyl, trimeturon, trinexapac, trinexapac-ethyl, tritosulfuron, tsitodef, uniconazole, uniconazole-P, vernolate, ZJ-0862, i.e. 3,4-dichloro-N-{2-[(4,6-dimethoxypyrimidin-2-yl)oxy]benzyl}aniline, and the following compounds:

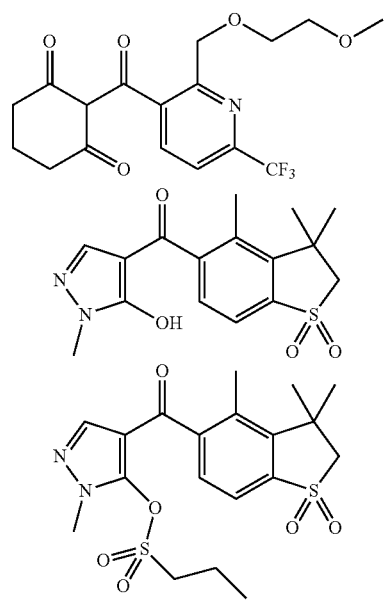

-continued

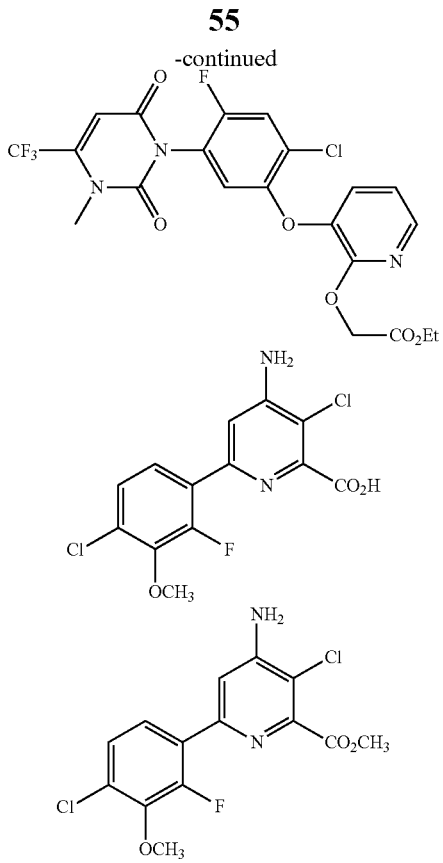

Of particular interest is the selective control of harmful plants in crops of useful plants and ornamentals. Although the compounds (I) according to the invention have already demonstrated very good to adequate selectivity in a large number of crops, in principle, in some crops and in particular also in the case of mixtures with other, less selective herbicides, phytotoxicities on the crop plants may occur. In this connection, combinations of compounds (I) according to the invention are of particular interest which comprise the compounds (I) or their combinations with other herbicides or pesticides and safeners. The safeners, which are used in an antidotically effective amount, reduce the phytotoxic side effects of the herbicides/pesticides employed, for example in economically important crops, such as cereals (wheat, barley, rye, corn, rice, millet), sugar beet, sugar cane, oilseed rape, cotton and soybeans, preferably cereals. The following groups of compounds are suitable, for example, as safeners for the compounds (I) and their combinations with further pesticides:

A) compounds of the formula (S-I)

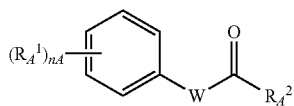 (S-I)

where the symbols and indices have the following meanings:
$n_A$ is a natural number from 0 to 5, preferably from 0 to 3;
$R_A^1$ is halogen, $(C_1-C_4)$-alkyl, $(C_1-C_4)$-alkoxy, nitro or $(C_1-C_4)$-haloalkyl;
$W_A$ is an unsubstituted or substituted divalent heterocyclic radical from the group of the partially unsaturated or aromatic five-membered heterocycles having 1 to 3 ring heteroatoms of the N or O type, where at least one nitrogen atom and at most one oxygen atom is present in the ring, preferably a radical from the group of $(W_A^1)$ to $(W_A^4)$,

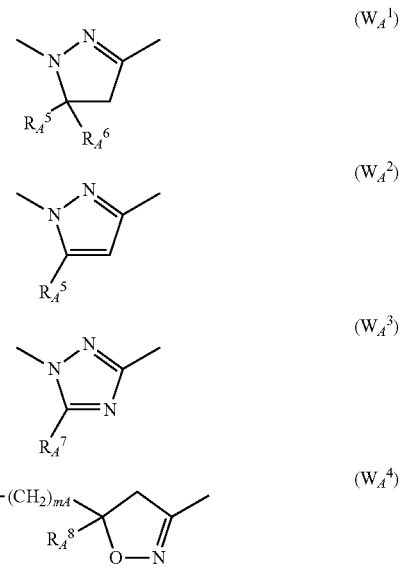

$m_A$ is 0 or 1;
$R_A^2$ is $OR_A^3$, $SR_A^3$ or $NR_A^3R_A^4$ or a saturated or unsaturated 3- to 7-membered heterocycle having at least one nitrogen atom and up to 3 heteroatoms, preferably from the group of O and S, which is joined to the carbonyl group in (S-I) via the nitrogen atom and is unsubstituted or substituted by radicals from the group of $(C_1-C_4)$-alkyl, $(C_1-C_4)$-alkoxy or optionally substituted phenyl, preferably a radical of the formula $OR_A^3$, $NHR_A^4$ or $N(CH_3)_2$, especially of the formula $OR_A^3$;
$RA^3$ is hydrogen or an unsubstituted or substituted aliphatic hydrocarbyl radical having preferably a total of 1 to 18 carbon atoms;
$R_A^4$ is hydrogen, $(C_1-C_6)$-alkyl, $(C_1-C_6)$-alkoxy or substituted or unsubstituted phenyl;
$R_A^5$ is H, $(C_1-C_8)$-alkyl, $(C_1-C_8)$-haloalkyl, $(C_1-C_4)$-alkoxy-$(C_1-C_8)$-alkyl, cyano or $COOR_A^9$, where $R_A^9$ is hydrogen, $(C_1-C_8)$-alkyl, $(C_1-C_8)$-haloalkyl, $(C_1-C_4)$-alkoxy-$(C_1-C_4)$-alkyl, $(C_1-C_6)$-hydroxyalkyl, $(C_3-C_{12})$-cycloalkyl or tri-$(C_1-C_4)$-alkyl-silyl;
$R_A^6$, $R_A^7$, $R_A^8$ are identical or different and are hydrogen, $(C_1-C_8)$-alkyl, $(C_1-C_8)$-haloalkyl, $(C_3-C_{12})$-cycloalkyl or substituted or unsubstituted phenyl;
preferably:
a) compounds of the type of the dichlorophenylpyrazoline-3-carboxylic acid, preferably compounds such as ethyl 1(2,4-dichlorophenyl)-5-(ethoxycarbonyl)-5-methyl-2-pyrazoline-3-carboxylate (S1-1) ("mefenpyr-diethyl", see Pestic. Man.), and related compounds as described in WO 91/07874;
b) derivatives of dichlorophenylpyrazolecarboxylic acid, preferably compounds such as ethyl 1-(2,4-dichlorophenyl)-5-methylpyrazole-3-carboxylate (S1-2), ethyl 1-(2,4-dichlorophenyl)-5-isopropylpyrazole-3-carboxylate (S1-3), ethyl 1-(2,4-dichlorophenyl)-5-(1,1-dimethylethyl) pyrazole-3-carboxylate (S1-4), ethyl 1-(2,4-dichlorophenyl)-5-phenylpyrazole-3-carboxylate (S1-5) and related compounds as described in EP-A-333 131 and EP-A-269 806;

c) compounds of the triazolecarboxylic acid type, preferably compounds such as fenchlorazole(-ethyl), i.e. ethyl 1-(2,4-dichlorophenyl)-5-trichloromethyl-(1H)-1,2,4-triazole-3-carboxylate (S1-6), and related compounds as described in EP-A-174 562 and EP-A-346 620;

d) compounds of the type of the 5-benzyl- or 5-phenyl-2-isoxazoline-3-carboxylic acid or the 5,5-diphenyl-2-isoxazoline-3-carboxylic acid, preferably compounds such as ethyl 5-(2,4-dichlorobenzyl)-2-isoxazoline-3-carboxylate (S1-7) or ethyl 5-phenyl-2-isoxazoline-3-carboxylate (S1-8) and related compounds, as described in WO 91/08202, or ethyl 5,5-diphenyl-2-isoxazolinecarboxylate (S1-9) ("isoxadifen-ethyl") or n-propyl 5,5-diphenyl-2-isoxazolinecarboxylate (S1-10) or ethyl 5-(4-fluorophenyl)-5-phenyl-2-isoxazoline-3-carboxylate (S1-11), as described in the patent application WO-A-95/07897.

B) Quinoline derivatives of the formula (S-II)

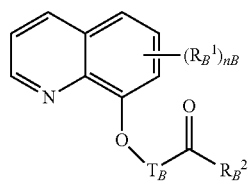

(S-II)

where the symbols and indices have the following meanings:
$R_B^1$ is halogen, $(C_1-C_4)$-alkyl, $(C_1-C_4)$-alkoxy, nitro or $(C_1-C_4)$-haloalkyl;
$n_B$ is a natural number from 0 to 5, preferably from 0 to 3;
$R_B^2$ is $OR_B^3$, $SR_B^3$ or $NR_B^3R_B^4$ or a saturated
  or unsaturated 3- to 7-membered heterocycle having at least one nitrogen atom and up to 3 heteroatoms, preferably from the group consisting of O and S, which is joined to the carbonyl group in (S-II) via the nitrogen atom and is unsubstituted or substituted by radicals from the group of $(C_1-C_4)$-alkyl, $(C_1-C_4)$-alkoxy or optionally substituted phenyl, preferably a radical of the formula $OR_B^3$, $NHR_B^4$ or $N(CH_3)_2$, especially of the formula $OR_B^3$;
$R_B^3$ is hydrogen or an unsubstituted or substituted aliphatic hydrocarbyl radical having preferably a total of 1 to 18 carbon atoms;
$R_B^4$ is hydrogen, $(C_1-C_6)$-alkyl, $(C_1-C_6)$-alkoxy or substituted or unsubstituted phenyl;
$T_B$ is a ($C_1$ or $C_2$)-alkanediyl chain which is unsubstituted or substituted by one or two $(C_1-C_4)$-alkyl radicals or by $[(C_1-C_3)$-alkoxy]-carbonyl;
preferably:
a) compounds of the type of the 8-quinolinoxyacetic acid (S2), preferably 1-methylhexyl (5-chloro-8-quinolinoxy)acetate (common name "cloquintocet-mexyl" (S2-1) (see Pestic. Man.), 1,3-dimethyl-but-1-yl (5-chloro-8-quinolinoxy)acetate (S2-2), 4-allyloxybutyl (5-chloro-8-quinolinoxy)acetate (S2-3), 1-allyloxyprop-2-yl (5-chloro-8-quinolinoxy)acetate (S2-4), ethyl (5-chloro-8-quinolinoxy)acetate (S2-5), methyl (5-chloro-8-quinolinoxy)acetate (S2-6), allyl (5-chloro-8-quinolinoxy)acetate (S2-7), 2-(2-propylideneiminoxy)-1-ethyl (5-chloro-8-quinolinoxy)acetate (S2-8), 2-oxo-prop-1-yl (5-chloro-8-quinolinoxy)acetate (S2-9) and related compounds, as described in EP-A-86 750, EP-A-94 349 and EP-A-191 736 or EP-A-0 492 366, and also their hydrates and salts, as described in WO-A-2002/034048.

b) compounds of the (5-chloro-8-quinolinoxy)malonic acid type, preferably compounds such as diethyl (5-chloro-8-quinolinoxy)malonate, diallyl (5-chloro-8-quinolinoxy)malonate, methyl ethyl (5-chloro-8-quinolinoxy)malonate and related compounds, as described in EP-A-0 582 198.

C) Compounds of the formula (S-III)

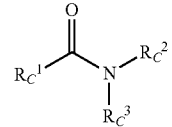

(S-III)

where the symbols and indices have the following meanings:
$R_C^1$ is $(C_1-C_4)$-alkyl, $(C_1-C_4)$-haloalkyl, $(C_2-C_4)$-alkenyl, $(C_2-C_4)$-haloalkenyl, $(C_3-C_7)$-cycloalkyl, preferably dichloromethyl;
$R_C^2$, $R_C^3$ are identical or different and are hydrogen, $(C_1-C_4)$-alkyl, $(C_2-C_4)$-alkenyl,
  $(C_2-C_4)$-alkynyl, $(C_1-C_4)$-haloalkyl, $(C_2-C_4)$-haloalkenyl, $(C_1-C_4)$-alkylcarbamoyl-$(C_1-C_4)$-alkyl, $(C_2-C_4)$-alkenylcarbamoyl-$(C_1-C_4)$-alkyl, $(C_1-C_4)$-alkoxy-$(C_1-C_4)$-alkyl, dioxolanyl-$(C_1-C_4)$-alkyl, thiazolyl, furyl, furylalkyl, thienyl, piperidyl, substituted or unsubstituted phenyl, or $R_C^2$ and $R_C^3$ together form a substituted or unsubstituted heterocyclic ring,
preferably an oxazolidine, thiazolidine, piperidine, morpholine, hexahydropyrimidine or benzoxazine ring;
preferably:
  active compounds of the type of the dichloroacetamides which are frequently used as pre-emergence safeners (soil-active safeners), such as, for example, "dichlormid" (see Pestic. Man.) (=N,N-diallyl-2,2-dichloroacetamide), "R-29148" (=3-dichloroacetyl-2,2,5-trimethyl-1,3-oxazolidine from Stauffer), "R-28725" (=3-dichloroacetyl-2,2-dimethyl-1,3-oxazolidine from Stauffer), "Benoxacor" (see Pestic. Man.) (=4-dichloroacetyl-3,4-dihydro-3-methyl-2H-1,4-benzoxazine), "PPG-1292" (=N-allyl-N-[(1,3-dioxolan-2-yl)methyl]dichloracetamide from PPG Industries), "DKA-24" (=N-allyl-N-[(allylaminocarbonyl)methyl]dichloracetamide from Sagro-Chem), "AD-67" or "MON 4660" (=3-dichloroacetyl-1-oxa-3-aza-spiro[4,5]decane from Nitrokemia or Monsanto),
  "TI-35" (=1-dichloroacetylazepane from TRI—Chemical RT) "diclonon" (dicyclonon) or "BAS145138" or "LAB145138" (=3-dichloroacetyl-2,5,5-trimethyl-1,3-diazabicyclo[4.3.0]nonane from BASF) and "Furilazol" or "MON 13900" (see Pestic. Man.) (=(RS)-3-dichloroacetyl-5-(2-furyl)-2,2-dimethyloxazolidine)

D) N-Acylsulfonamides of the formula (S-IV) and their salts

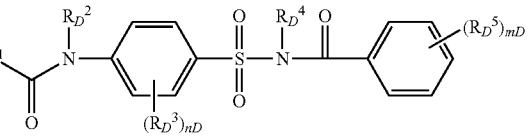

(S-IV)

in which
$R_D^1$ is hydrogen, a hydrocarbon radical, a hydrocarbonoxy radical, a hydrocarbonthio radical or a heterocyclyl radical which is preferably attached via a carbon atom, where each of the 4 lastmentioned radicals is unsubstituted or substituted by one or more identical or different radicals from the group consisting of halogen, cyano, nitro, amino, hydroxyl, carboxyl, formyl, carbonamide, sulfonamide and radicals of the formula —$Z^a$—$R^a$, where each hydrocarbon moiety has preferably 1 to 20 carbon atoms and a carbon-containing radical $R_D^1$ including substituents has preferably 1 to 30 carbon atoms;

$R_D^2$ is hydrogen or ($C_1$-$C_4$)-alkyl, preferably hydrogen, or $R_D^1$ and $R_D^2$ together with the group of the formula —CO—N— are the radical of a 3- to 8-membered saturated or unsaturated ring;

$R_D^3$ are identical of different and are halogen, cyano, nitro, amino, hydroxyl, carboxyl, formyl, $CONH_2$, $SO_2NH_2$ or a radical of the formula —$Z^b$—$R^b$;

$R_D^4$ is hydrogen or ($C_1$-$C_4$)-alkyl, preferably H;

$R_D^5$ are identical or different and are halogen, cyano, nitro, amino, hydroxyl, carboxyl, CHO, $CONH_2$, $SO_2NH_2$ or a radical of the formula —$Z^c$—$R^c$;

$R^a$ is a hydrocarbon radical or a heterocyclyl radical, where each of the two lastmentioned radicals is unsubstituted or substituted by one or more identical or different radicals from the group consisting of halogen, cyano, nitro, amino, hydroxyl, mono- and di-[($C_1$-$C_4$)-alkyl]amino, or an alkyl radical in which a plurality, preferably 2 or 3, non-adjacent $CH_2$ groups are in each case replaced by an oxygen atom;

$R^b$, $R^c$ are identical or different and are a hydrocarbon radical or a heterocyclyl radical, where each of the two lastmentioned radicals is unsubstituted or substituted by one or more identical or different radicals from the group consisting of halogen, cyano, nitro, amino, hydroxyl, phosphoryl, halo-($C_1$-$C_4$)-alkoxy, mono- and di-[($C_1$-$C_4$)-alkyl]amino, or an alkyl radical in which a plurality, preferably 2 or 3, non-adjacent $CH_2$ groups are in each case replaced by an oxygen atom;

$Z^a$ is a divalent group of the formula —O—, —S—, —CO—, —CS—, —CO—O—, —CO—S—, —O—CO—, —S—CO—, —SO—, —$SO_2$—, —NR*—, —CO—NR*—, —NR*—CO—, —$SO_2$—NR*— or —NR*—$SO_2$—, where the bond indicated on the right-hand side of the divalent group in question is the bond to the radical $R^a$ and where the R* in the 5 lastmentioned radicals independently of one another are each H, ($C_1$-$C_4$)-alkyl or halo-($C_1$-$C_4$)-alkyl;

$Z^b$, $Z^c$ are independently of one another a direct bond or a divalent group of the formula —O—, —S—, —CO—, —CS—, —CO—O—, —CO—S—, —O—CO—, —S—CO—, —SO—, —$SO_2$—, —NR*—, —$SO_2$—NR*—, —NR*—$SO_2$—, —CO—NR*— or —NR*—CO—, where the bond indicated at the right-hand side of the divalent group in question is the bond to the radical $R^b$ or $R^c$ and where the R* in the 5 lastmentioned radicals independently of one another are each H, ($C_1$-$C_4$)-alkyl or halo-($C_1$-$C_4$)-alkyl;

$n_D$ is an integer from 0 to 4, preferably 0, 1 or 2, particularly preferably 0 or 1, and $m_D$ is an integer from 0 to 5, preferably 0, 1, 2 or 3, in particular 0, 1 or 2;

E) acylsulfamoylbenzamides of the formula (S-V), if appropriate also in salt form,

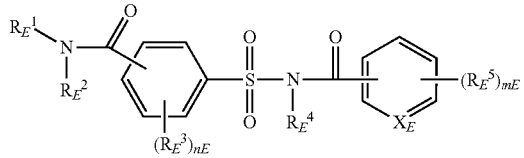

(S-V)

in which $X_E$ is CH or N;

$R_E^1$ is hydrogen, heterocyclyl or a hydrocarbon radical, where the two lastmentioned radicals are optionally substituted by one or more identical or different radicals from the group consisting of halogen, cyano, nitro, amino, hydroxyl, carboxyl, CHO, $CONH_2$, $SO_2NH_2$ and $Z^a$—$R^a$;

$R_E^2$ is hydrogen, hydroxyl, ($C_1$-$C_6$)-alkyl, ($C_2$-$C_6$)-alkenyl, ($C_2$-$C_6$)-alkynyl, ($C_1$-$C_6$)-alkoxy, ($C_2$-$C_6$)-alkenyloxy, where the five lastmentioned radicals are optionally substituted by one or more identical or different radicals from the group consisting of halogen, hydroxyl, ($C_1$-$C_4$)-alkyl, ($C_1$-$C_4$)-alkoxy and ($C_1$-$C_4$)-alkylthio, or $R_E^1$ and $R_E^2$ together with the nitrogen atom that carries them are a 3- to 8-membered saturated or unsaturated ring;

$R_E^3$ is halogen, cyano, nitro, amino, hydroxyl, carboxyl, CHO, $CONH_2$, $SO_2NH_2$ or $Z^b$—$R^b$;

$R_E^4$ is hydrogen, ($C_1$-$C_4$)-alkyl, ($C_2$-$C_4$)-alkenyl or ($C_2$-$C_4$)-alkynyl;

$R_E^5$ is halogen, cyano, nitro, amino, hydroxyl, carboxyl, phosphoryl, CHO, $CONH_2$, $SO_2NH_2$ or $Z^c$—$R^c$;

$R^a$ is a ($C_2$-$C_{20}$)-alkyl radical whose hydrocarbon chain is interrupted once or more than once by oxygen atoms, is heterocyclyl or a hydrocarbon radical, where the two lastmentioned radicals are optionally substituted by one or more identical or different radicals from the group consisting of halogen, cyano, nitro, amino, hydroxyl, mono- and di-[($C_1$-$C_4$)-alkyl]-amino;

$R^b$, $R^c$ are identical or different and are a ($C_2$-$C_{20}$)-alkyl radical whose carbon chain is interrupted once or more than once by oxygen atoms, are heterocyclyl or a hydrocarbon radical, where the two lastmentioned radicals are optionally substituted by one or more identical or different radicals from the group consisting of halogen, cyano, nitro, amino, hydroxyl, phosphoryl, ($C_1$-$C_4$)-haloalkoxy, mono- and di-[($C_1$-$C_4$)-alkyl]amino;

$Z^a$ is a divalent unit from the group consisting of O, S, CO, CS, C(O)O, C(O)S, SO, $SO_2$, $NR^d$, $C(O)NR^d$ and $SONR^d$ $Z^b$, $Z^c$ are identical or different and are a direct bond or divalent unit from the group consisting of O, S, CO, CS, C(O)O, C(O)S, SO, $SO_2$, $NR^d$, $SO_2NR^d$ and $C(O)NR^d$;

$R^d$ is hydrogen, ($C_1$-$C_4$)-alkyl or ($C_1$-$C_4$)-haloalkyl;

$n_E$ is an integer from 0 to 4, and $m_E$ if X is CH, is an integer from 0 to 5, and, if X is N, is an integer from 0 to 4 from among these, preference is given to compounds (also in the form of their salts) of the type of the acylsulfamoylbenzamides, for example of the formula (S-VI) below, which are known, for example, from WO 99/16744,

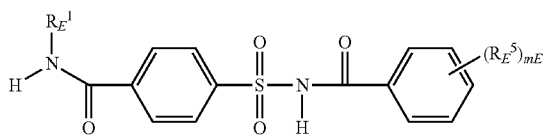

(S-VI)

for example those in which $R_E^1$=cyclopropyl and $R_E^5$=2-OMe ("cyprosulfamide", S3-1),
$R_E^1$=cyclopropyl and $R_E^5$=5-Cl-2-OMe (S3-2),
$R_E^1$=ethyl and $R_E^5$=2-OMe (S3-3),
$R_E^1$=isopropyl and $R_E^5$=5-Cl-2-OMe (S3-4) and
$R_E^1$=isopropyl and $R_E^5$=2-OMe (S3-5);

F) compounds of the type of the N-acylsulfamoylphenylureas of the formula (S-VII), which are known, for example, from EP-A-365484

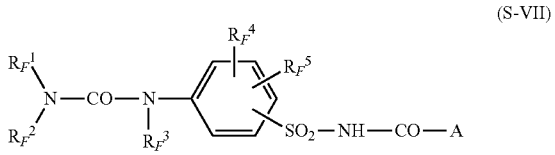

(S-VII)

in which
A is a radical from the group consisting of

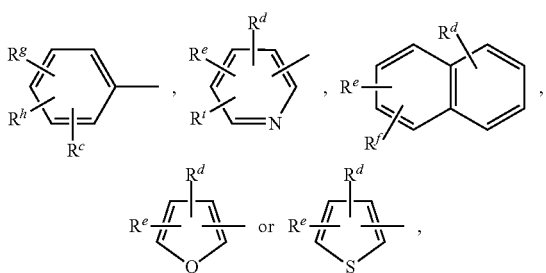

$R_F^1$ and $R_F^2$ independently of one another are hydrogen, $(C_1-C_8)$-alkyl, $(C_3-C_8)$-cycloalkyl, $(C_3-C_6)$-alkenyl, $(C_3-C_6)$-alkynyl,

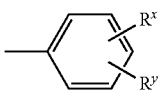

or by $(C_1-C_4)$-alkoxy or

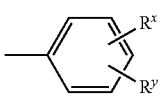

substituted $(C_1-C_4)$-alkoxy or
$R_F^1$ and $R_F^2$ together are a $(C_4-C_6)$-alkylene bridge or a $(C_4-C_6)$-alkylene bridge interrupted by oxygen, sulfur, SO, $SO_2$, NH or $-N(C_1-C_4$-alkyl)-
$R_F^3$ is hydrogen or $(C_1-C_4)$-alkyl, $R_F^4$ and $R_F^5$ independently of one another are hydrogen, halogen, cyano, nitro, trifluoromethyl, $C_1-C_4$-alkyl, $C_1-C_4$-alkoxy, $C_1-C_4$-alkylthio, $C_1-C_4$-alkylsulfinyl, $C_1-C_4$-alkylsulfonyl, $-COOR^j$, $-CONR^kR^m$, $-COR^n$, $-SO_2NR^kR^m$ or $-OSO_2-C_1-C_4$-alkyl, or $R^a$ and $R^b$ together are a $(C_3-C_4)$-alkylene bridge which may be substituted by halogen or $C_1-C_4$-alkyl, or a $(C_3-C_4)$-alkenylene bridge which may be substituted by halogen or $(C_1-C_4)$-alkyl, or a $C_4$-alkadienylene bridge which may be substituted by halogen or $(C_1-C_4)$-alkyl, and $R^g$ and $R^h$ independently of one another are hydrogen, halogen, $C_1-C_4$-alkyl, trifluoromethyl, methoxy, methylthio or $-COOR^j$, where $R^c$ is hydrogen, halogen, $(C_1-C_4)$-alkyl or methoxy,
$R^d$ is hydrogen, halogen, nitro, $(C_1-C_4)$-alkyl, $(C_1-C_4)$-alkoxy, $(C_1-C_4)$-alkylthio, $(C_1-C_4)$-alkylsulfinyl, $(C_1-C_4)$-alkylsulfonyl, $-COOR^j$ or $-CONR^kR^m$,
$R^e$ is hydrogen, halogen, $C_1-C_4$-alkyl, $-COOR^j$, trifluoromethyl or methoxy, or $R^d$ and $R^e$ together are a $(C_3-C_4)$-alkylene bridge,
$R^f$ is hydrogen, halogen or $(C_1-C_4)$-alkyl,
$R^X$ and $R^Y$ independently of one another are hydrogen, halogen, $(C_1-C_4)$-alkyl, $(C_1-C_4)$-alkoxy, $(C_1-C_4)$-alkylthio, $-COOR^4$, trifluoromethyl, nitro or cyano,
$R^j$, $R^k$ and $R^m$ independently of one another are hydrogen or $(C_1-C_4)$-alkyl,
$R^k$ and $R^m$ together are a $(C_4-C_6)$-alkylene bridge or a $C_4-C_6$-alkylene bridge interrupted by oxygen, NH or $-N(C_1-C_4$-alkyl)- and
$R^n$ is $(C_1-C_4)$-alkyl, phenyl or phenyl which is substituted by halogen, $(C_1-C_4)$-alkyl, methoxy, nitro or trifluoromethyl,
from among these, preference is given to:
1-[4-(N-2-methoxybenzoylsulfamoyl)phenyl]-3-methylurea, 1-[4-(N-2-methoxybenzoylsulfamoyl)phenyl]-3,3-dimethylurea, 1-[4-(N-4,5-dimethylbenzoylsulfamoyl)phenyl]-3-methylurea, 1-[4-(N-naphthoylsulfamoyl)phenyl]-3,3-dimethylurea,
including the stereoisomers and the salts customary in agriculture, G) active compounds from the class of the hydroxyaromatics and aromatic-aliphatic carboxylic acid derivatives, for example ethyl 3,4,5-triacetoxybenzoate, 3,5-dimethoxy-4-hydroxybenzoic acid, 3,5-dihydroxybenzoic acid, 4-hydroxysalicylic acid, 4-fluorosalicylic acid, 1,2-dihydro-2-oxo-6-trifluoromethylpyridine-3-carboxamide, 2-hydroxycinnamic acid, 2,4-dichlorocinnamic acid, as described in WO 2004084631, WO 2005015994, WO 2006007981, WO 2005016001;

H) active compounds from the class of the 1,2-dihydroquinoxalin-2-ones, for example 1-methyl-3-(2-thienyl)-1,2-dihydroquinoxalin-2-one, 1-methyl-3-(2-thienyl)-1,2-dihydroquinoxaline-2-thione, 1-(2-aminoethyl)-3-(2-thienyl)-1,2-dihydroquinoxalin-2-one hydrochloride, 1-(2-methylsulfonylaminoethyl)-3-(2-thienyl)-1,2-dihydro-quinoxalin-2-one, as described in WO 2005112630, I) active compounds which, in addition to a herbicidal action against harmful plants also have safener action on crop plants such as rice, such as, for example, "dimepiperate" or "MY-93" (see Pestic. Man.) (=S-1-methyl-1-phenylethyl piperidine-1-thiocarboxylate), which is known as safener for rice against damage caused by the herbicide molinate, "daimuron" or "SK 23" (see Pestic. Man.) (=1-(1-methyl-1-phenylethyl)-3-p-tolyl-urea), which is known as a safener for rice against damage caused by the herbicide imazosulfuron, "cumyluron"="JC-940" (=3-(2-chlorophenylmethyl)-1-(1-methyl-1-phenylethyl)urea, see JP-A-60087254), which is known as a safener for rice against damage caused by some herbicides, "methoxyphenon" or "NK 049" (=3,3'-dimethyl-4-methoxybenzophenone), which is known as a safener for rice against damage caused by some herbicides, "CSB" (=1-bromo-4-(chloromethylsulfonyl)benzene) (CAS reg. no. 54091-06-4 from Kumiai), which is known as a safener for rice against damage caused by some herbicides, K) compounds of the formula (S-IX), as described in WO-A-1998/38856,

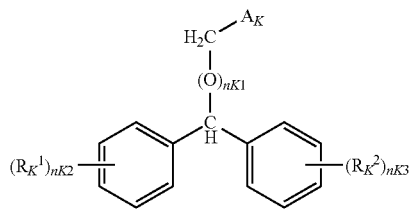

(S-IX)

where the symbols and indices have the following meanings:

$R_K^1$, $R_K^2$ independently of one another are halogen, $(C_1\text{-}C_4)$-alkyl, $(C_1\text{-}C_4)$-alkoxy, $(C_1\text{-}C_4)$-haloalkyl, $(C_1\text{-}C_4)$-alkylamino, di-$(C_1\text{-}C_4)$-alkylamino, nitro;

$A_K$ is $COOR_K^3$ or $COOR_K^4$ $R_K^3$, $R_K^4$ independently of one another are hydrogen, $(C_1\text{-}C_4)$-alkyl, $(C_2\text{-}C_6)$-alkenyl, $(C_2\text{-}C_4)$-alkynyl, cyanoalkyl, $(C_1\text{-}C_4)$-haloalkyl, phenyl, nitrophenyl, benzyl, halobenzyl, pyridinylalkyl and alkylammonium, $n_K^1$ is 0 or 1 and $n_K^2$, $n_K^3$ independently of one another are 0, 1 or 2;

preferably:

methyl (diphenylmethoxy)acetate (CAS reg no: 41858-19-9),

L) compounds of the formula (S-X)
   as described in WO A-98/27049

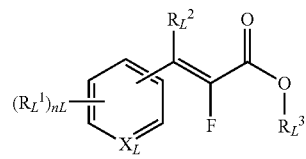

(S-X)

where the symbols and indices have the following meanings:
$X_L$ is CH or N;
$n_L$ if X=N, is an integer from 0 to 4 and
  if X=CH, is an integer from 0 to 5,
$R_L^1$ is halogen, $(C_1\text{-}C_4)$-alkyl, $(C_1\text{-}C_4)$-haloalkyl, $(C_1\text{-}C_4)$-alkoxy, $(C_1\text{-}C_4)$-haloalkoxy, nitro, $(C_1\text{-}C_4)$-alkylthio, $(C_1\text{-}C_4)$-alkylsulfonyl, $(C_1\text{-}C_4)$-alkoxycarbonyl, optionally substituted phenyl, optionally substituted phenoxy,
$R_L^2$ is hydrogen or $(C_1\text{-}C_4)$-alkyl,
$R_L^3$ is hydrogen, $(C_1\text{-}C_8)$-alkyl, $(C_2\text{-}C_4)$-alkenyl, $(C_2\text{-}C_4)$-alkynyl, or aryl, where each of the aforementioned carbon-containing radicals is unsubstituted or substituted by one or more, preferably up to three identical or different radicals from the group consisting of halogen and alkoxy; or salts thereof.

M) active compounds from the class of the 3-(5-tetrazolylcarbonyl)-2-quinolones, for example 1,2-dihydro-4-hydroxy-1-ethyl-3-(5-tetrazolylcarbonyl)-2-quinolone (CAS Reg. No.: 219479-18-2), 1,2-dihydro-4-hydroxy-1-methyl-3-(5-tetrazolylcarbonyl)-2-quinolone (CAS Reg. No.: 95855-00-8), as described in WO-A-1999000020, N) compounds of the formula (S-XI) or (S-XII)
   as described in WO-A-2007023719 and WO-A-2007023764

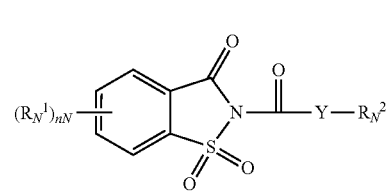

(S-XI)

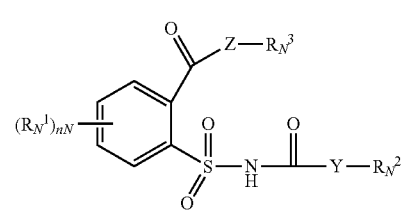

(S-XII)

in which
$R_N^1$ is halogen, $(C_1\text{-}C_4)$-alkyl, methoxy, nitro, cyano, $CF_3$, $OCF_3$
Y, Z independently of one another are O or S,
$n_N$ is an integer from 0 to 4,
$R_N^2$ is $(C_1\text{-}C_{16})$-alkyl, $(C_2\text{-}C_6)$-alkenyl, $(C_3\text{-}C_6)$-cycloalkyl, aryl; benzyl, halobenzyl,
$R_N^3$ is hydrogen or $(C_1\text{-}C_6)$-alkyl;

O) one or more compounds from the group consisting of:
1,8-naphthalic anhydride, O,O-diethyl S-2-ethylthioethyl phosphorodithioate (disulfoton), 4-chlorophenyl methylcarbamate (mephenate), O,O-diethyl O-phenyl phosphorothioate (dietholate), 4-carboxy-3,4-dihydro-2H-1-benzopyran-4-acetic acid (CL-304415, CAS Reg. No.: 31541-57-8), 2-propenyl 1-oxa-4-azaspiro[4.5]decane-4-carbodithioate (MG-838, CAS Reg. No.: 133993-74-5), methyl [(3-oxo-1H-2-benzothiopyran-4(3H)-ylidene)methoxy]acetate (from WO-A-98/13361; CAS Reg. No.: 205121-04-6), cyanomethoxyimino (phenyl)acetonitrile (cyometrinil), 1,3-dioxolan-2-ylmethoxyimino(phenyl)acetonitrile (oxabetrinil), 4'-chloro-2,2,2-trifluoroacetophenone O-1,3-dioxolan-2-ylmethyloxime (fluxofenim), 4,6-dichloro-2-phenylpyrimidine (fenclorim), benzyl 2-chloro-4-trifluoromethyl-1,3-thiazole-5-carboxylate (flurazole), 2-dichloromethyl-2-methyl-1,3-dioxolane (MG-191),
including the stereoisomers, and the salts customary in agriculture.

The weight ratios of herbicide (mixture) to safener depend generally on the herbicide application rate and the efficacy of the safener in question and may vary within wide limits, for example in the range from 200:1 to 1:200, preferably 100:1 to 1:100, especially 20:1 to 1:20. Analogously to the compounds (I) or mixtures thereof, the safener can be formulated with further herbicides/pesticides and be provided and employed as a finished formulation or tankmix with the herbicides.

For application, the herbicide or herbicide/safener formulations present in commercial form are, if appropriate, diluted in a customary manner, for example in the case of wettable powders, emulsifiable concentrates, dispersions and water-dispersible granules with water. Preparations in the form of dusts, granules for soil application or granules for broadcasting and sprayable solutions are usually not diluted further with other inert substances prior to application.

The required application rate of the compounds of the formula (I) and/or their salts varies according to the external conditions such as, inter alia, temperature, humidity and the type of herbicide used. It can vary within wide limits. For the application of herbicide for controlling harmful plants, it is, for example, in the range of from 0.001 to 10.0 kg/ha or more of active substance, preferably in the range of from 0.005 to 5 kg/ha, in particular in the range of from 0.01 to 1 kg/ha, of active substance. This applies both to the pre-emergence and the post-emergence application.

When used as plant growth regulator, for example as culm stabilizer for crop plants like those mentioned above, preferably cereal plants, such as wheat, barley, rye, triticale, millet, rice or corn, the application rate is, for example, in the range of from 0.001 to 2 kg/ha or more of active substance, preferably in the range of from 0.005 to 1 kg/ha, in particular in the range of from 10 to 500 g/ha of active substance, very particularly from 20 to 250 g/ha of active substance. This applies both to application by the pre-emergence method and the post-emergence method, the post-emergence treatment generally being preferred.

The application as culm stabilizer may take place at various stages of the growth of the plants. Preferred is, for example, the application after the tillering phase, at the beginning of the longitudinal growth.

As an alternative, application as plant growth regulator is also possible by treating the seed, which includes various techniques for dressing and coating seed. Here, the application rate depends on the particular techniques and can be determined in preliminary tests.

In an exemplary manner, some synthesis examples of compounds of the general formula (I) are described below. In the examples, the amounts (including percentages) refer to the weight, unless especially stated otherwise.

The symbols ">" and "<" mean "greater than" and "smaller than", respectively. The symbol "≥" means "greater than or equal to", the symbol "≤" means "smaller than or equal to".

If, in the context of the description and the examples, the terms "R" and "S" are given for the absolute configuration on a center of chirality of the stereoisomers of the formula (I), this RS nomenclature, follows, unless defined differently, the Cahn-Ingold-Prelog rule.

(A) SYNTHESIS EXAMPLES

Example A1 methyl (3R,4R)-3-(4-chlorophenyl)-4-cyano-4-(3-fluorophenyl)butanoate (Table 1, Example 1)

a) Preparation of the diastereomeric methyl 3-(4-chlorophenyl)-4-cyano-4-(3-fluorophenyl)butanoates:
Under protective gas (Ar), 0.824 g (6.103 mmol) of 3-(fluorophenyl)acetonitrile and 0.1 ml of sodium methoxide solution (30% in methanol) were added to 1.200 g (6.103 mmol) of methyl 3-(4-chlorophenyl)acrylate in 6.0 ml of methanol, and the mixture was stirred at 50° C. for 48 h. The solvent was removed under reduced pressure, and the residue was taken up in ethyl acetate and washed twice with in each case 25 ml of water. The combined organic phases were dried over sodium sulfate and the solvent was removed under reduced pressure. Chromatography of the residue on silica gel (ethyl acetate/heptane=15:85) gave 0.401 g (18% of theory) of the diastereomeric methyl 3-(4-chlorophenyl)-4-cyano-4-(3-fluorophenyl)butanoate (erythro:threo=60:40, comparison of the doublets in the $^1$H-NMR in CDCl$_3$ at 4.38 and 4.08 ppm).

b) Preparation of methyl (3R,4R)-3-(4-chlorophenyl)-4-cyano-4-(3-fluorophenyl)butanoate:
Preparative chromatography [(80 ml/min n-heptane/2-propanol (80:20)] of 100 mg of the diastereomer mixture obtained under a) (dissolved in 4.0 ml of methanol) on a chiral solid phase [Chiralpak IC, 20 μm, (250×50) mm column] gave 16.75 mg of the title compound which eluted as the last of the four stereoisomers (retention time=11.3 min).

The specific rotation [α] was −38°.

For $^1$H-NMR in CDCl$_3$ and retention time in analytical HPLC see Table 1.

The absolute configuration of the title compound was assigned by X-ray structural analysis.

Example A2

Methyl (3R,4R)-3-(3-chlorophenyl)-4-cyano-4-(3,4-difluorophenyl)butanoate (Table 1, Example 10)

a) Preparation of the diastereomeric methyl 3-(3-chlorophenyl)-4-cyano-4-(3,4-difluorophenyl)butanoates:
Under protective gas (Ar), 0.779 g (5.086 mmol) of (3,4-difluorophenyl)acetonitrile and 0.1 ml of sodium methoxide solution (30% in methanol) were added to 1.000 g (5.086 mmol) of methyl 3-(3-chlorophenyl)acrylate in 12.0 ml of methanol, and the mixture was stirred in a closed vessel in a microwave oven at 100° C. for 4 h. The solvent was removed under reduced pressure, the residue was taken up in dichloromethane and the mixture was washed twice with in each case 25 ml of water. The combined organic phases were dried over sodium sulfate and the solvent was removed under reduced pressure. Chromatography of the residue on silica gel (ethyl acetate/heptane=20:80) gave 0.738 g (37% of theory) of the diastereomeric methyl 3-(3-chlorophenyl)-4-cyano-4-(3,4-difluorophenyl)butanoate (erythro:threo=43:57, comparison of the doublets in the $^1$H-NMR in CDCl$_3$ at 4.40 and 4.08 ppm).

b) Preparation of methyl (3R,4R)-3-(3-chlorophenyl)-4-cyano-4-(3,4-difluorophenyl)butanoate:
Preparative chromatography [(80 ml/min n-heptane/2-propanol (90:10)] of 120 mg of the diastereomer mixture obtained under a) (dissolved in 4.0 ml of methanol) on a chiral solid phase [Chiralpak IC, 20 μm, (250×50) mm column] gave 16.40 mg of the title compound [chemical purity >95% (NMR), isomeric purity 97% (chiral HPLC)] which eluted as the last of the four stereoisomers (retention time=19.1 min). Specific rotation [α]: −43°. For $^1$H-NMR in CDCl$_3$ and retention time in analytical HPLC: see Table 1.

Example A3

(3R,4R)-3-(3-Chlorophenyl)-4-cyano-4-(3,4-difluorophenyl)butanoic acid (Table 1, Example 107)

a) Preparation of the diastereomeric 3-(3-chlorophenyl)-4-cyano-4-(3,4-difluorophenyl)butanoic acids:
Under protective gas (Ar), 0.120 g (3.000 mmol) of 2 molar aqueous sodium hydroxide solution was added to 0.525 g (1.500 mmol) of methyl (3R,4R)-3-(3-chlorophenyl)-4-cyano-4-(3,4-difluorophenyl)butanoate in 8.0 ml of methanol, and the mixture was stirred at 25° C. for 3 h.

The methanol was removed under reduced pressure. The residue was acidified with concentrated hydrochloric acid (pH=3) and extracted three times with in each case 15 ml of dichloromethane. The combined organic phases were dried over sodium sulfate and the solvent was removed under reduced pressure. This gave 0.502 g (99.7% of theory) of diastereomeric 3-(3-chlorophenyl)-4-cyano-4-(3,4-difluorophenyl)butanoic acids (erythro:threo=58:42, comparison of the doublets in the $^1$H-NMR in CDCl$_3$ at 4.35 and 4.05 ppm).

b) (3R,4R)-3-(3-Chlorophenyl)-4-cyano-4-(3,4-difluorophenyl)butanoic acid:

Preparative chromatography [(80 ml/min n-heptane/2-propanol (80:20), addition of 0.05% trifluoroacetic acid into the heptane phase] of the diastereomer mixture obtained under a) on a chiral solid phase [Chiralpak IC, 20 μm, (250×50) mm column] gave 107 mg of the title compound [chemical purity >95% (NMR), isomeric purity 96% (chiral HPLC)] which eluted as the last of the two stereoisomers formed (retention time=19.1 min). Specific rotation [α]: −40°. For $^1$H-NMR in CDCl$_3$ and retention time in analytical HPLC: see Table 1.

Example A4

Methyl (3R,4R)-3-(3-chlorophenyl)-4-cyano-4-(3,4-difluorophenyl)butanoate (Table 1, Example 109)

Under protective gas (Ar), a drop of concentrated sulfuric acid was added to 0.100 g (0.286 mmol) of methyl (3R,4R)-3-(3-chlorophenyl)-4-cyano-4-(3,4-difluorophenyl)butanoate in 3.0 ml (40.136 mmol) of n-propanol, and the mixture was stirred at 90° C. for 5 h. The solvent was removed under reduced pressure, the residue was taken up in dichloromethane and the mixture was washed twice with in each case 15 ml of saturated aqueous sodium bicarbonate solution. The combined organic phases were dried over sodium sulfate and the solvent was removed under reduced pressure. Chromatography of the residue on silica gel (gradient: start at ethyl acetate/heptane=5:95 over the course of 20 minutes increased to ethyl acetate/heptane=20:80) gave 0.082 g (76% of theory) of the title compound [chemical purity >95% (NMR), isomeric purity 96% (chiral HPLC)]. Specific rotation [α]: −38°. For $^1$H-NMR in CDCl$_3$ and retention time in analytical HPLC: see Table 1.

The compounds of the absolute configuration (3R,4R) described in Table 1 below are obtained according to or analogously to the examples described above.

In Table 1:
Ex.=example number
H=hydrogen (atom)
Me=methyl
Et=ethyl
n-Pr=n-propyl
i-Pr=isopropyl
n-Bu=n-butyl
i-Bu=isobutyl
Rt=retention time
F, Cl, Br, I=fluorine, chlorine, bromine and iodine, respectively, in accordance with the conventional chemical atom symbol
MeO or OMe=methoxy
CN=cyano
NO$_2$=nitro The position of a substituent at the phenyl ring, for example in position 2, is stated as a prefix to the symbol or the abbreviation of the radical, for example 2-Cl=2-chloro
2-Me=2-methyl Numerations of the substituent positions for di- or trisubstituted substitution patterns are analogously stated as a prefix, for example
3,5-Me$_2$=3,5-dimethyl (e.g. as substitution at the phenyl ring)
2,3-Cl$_2$=2,3-dichloro (e.g. as substitution at the phenyl ring)
3,4-F$_2$=3,4-difluoro (e.g. as substitution at the phenyl ring)

Other abbreviations are to be understood analogously to the examples stated above.
"(R$^2$)$_n$"="H"=unsubstituted cycle (n=0)
"(R$^3$)$_m$"="H"=unsubstituted cycle (m=0)

In addition, the customary chemical symbols and formulae apply, such as, for example, CH$_2$ for methylene or CF$_3$ for trifluoromethyl or OH for hydroxyl. Correspondingly, composite meanings are defined as composed of the abbreviations mentioned.

The retention times ("Rt") stated in Table 1 were obtained by analytical HPLC of the compounds (I) on a chiral solid phase under the following experimental conditions:

At a concentration of 1 mg/ml, the compounds of the formula (I) were dissolved in dichloromethane p.a. and directly subjected to HPLC.
HPLC unit: Waters AllianceHT 2795
Column: Chiralpak IC, 250×4.6 mm, 5 μm DAIC 83325
Column temperature: 25 degrees Celcius
Detector: PDA 996, measurement wavelength: 210 nm
Evaluation: Waters Empower 2 Software, SP C
Conditions (Cond.) a to d:
a: mobile phase: n-heptane/2-propanol (70/30), Chromasolv, flow rate: 1.0 ml/min
b: mobile phase: n-heptane/2-propanol (75/25), Chromasolv, flow rate: 1.0 ml/min
c: mobile phase: n-heptane/2-propanol (80/20), Chromasolv, flow rate: 1.0 ml/min
d: mobile phase: n-heptane/2-propanol (90/10), Chromasolv, flow rate: 0.6 ml/min
e: mobile phase: n-heptane/2-propanol (60/40), Chromasolv, flow rate: 1.0 ml/min The chromatographically purified compounds (I) have a stereochemical purity of more than 95%

TABLE 1

Compounds of the formula (I)

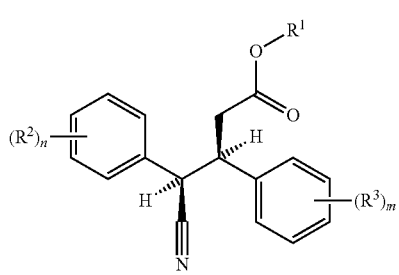

(I)

| Ex. | R$^1$ | (R$^2$)$_n$ | (R$^3$)$_m$ | Rt [min]/ Cond. |
|---|---|---|---|---|
| 1 | Me | 3-F | 4-Cl | 6.4/a |
| 2 | Me | 3-F | 3-F | 8.3/c |
| 3 | Me | 3,4-F$_2$ | 4-Cl | 8.5/c |
| 4 | Me | 3-F | 4-Br | 7.2/b |
| 5 | Me | 3-Cl | 3-F | 21.1/d |
| 6 | Me | 3,4-F$_2$ | 3-F | 24.3/d |
| 7 | Me | H | 3-F | 24.5/d |

TABLE 1-continued

Compounds of the formula (I)

| Ex. | R¹ | (R²)ₙ | (R³)ₘ | Rt [min]/Cond. |
|---|---|---|---|---|
| 8 | Me | 4-F | 3-F | 25.9/d |
| 9 | Me | 3-F | 3-Cl | 20.1/d |
| 10 | Me | 3,4-F₂ | 3-Cl | 23.1/d |
| 11 | Me | 3-Br | 3-F | 20.7/d |
| 12 | Me | 3,5-F₂ | 3-F | 16.9/d |
| 13 | Me | 3-F | 2-F | 19.2/d |
| 14 | Me | 3,4,5-F₃ | 4-Cl | 19.4/d |
| 15 | Me | 4-F | 3-Cl | 23.1/d |
| 16 | Me | 3,4-F₂ | 3-F, 4-Cl | 21.6/d |
| 17 | Me | 3,4-F₂ | 2-F | 19.9/d |
| 18 | Me | 3-F | 2,3-F₂ | 19.5/d |
| 19 | Me | 4-F | 3,5-F₂ | 20.1/d |
| 20 | Me | 3-F | 4-F | 20.6/d |
| 21 | Me | 3,4-F₂ | 3-Cl, 5-F | 20.3/d |
| 22 | Me | 3-F | 3-Cl, 5-F | 17.8/d |
| 23 | Me | 3-F | 2,5-F₂ | 18.7/d |
| 24 | Me | 3,4-F₂ | 2,3-F₂ | 21.5/d |
| 25 | Me | 3,4-F₂ | 2,5-F₂ | 20.3/d |
| 26 | Me | 3-Cl | 3-Cl, 5-F | 16.7/d |
| 27 | Me | 3-F, 4-Cl | 3-Cl | 21.2/d |
| 28 | Me | 3,4-F₂ | 3-NO₂ | 29.7/c |
| 29 | Me | 3,4-F₂ | H | 24.8/d |
| 30 | Me | 3-Cl, 4-F | 3-F | 23.4/d |
| 31 | Et | 3,4-F₂ | 4-OMe | 29.6/d |
| 32 | H | 3-F | 4-Cl | |
| 33 | Et | 3-F | 4-Cl | |
| 34 | n-Pr | 3-F | 4-Cl | |
| 35 | i-Pr | 3-F | 4-Cl | |
| 36 | n-Bu | 3-F | 4-Cl | |
| 37 | i-Bu | 3-F | 4-Cl | |
| 38 | 2,2-difluoroethyl | 3-F | 4-Cl | |
| 39 | 2,2,2-trifluoroethyl | 3-F | 4-Cl | |
| 40 | 2-fluorobenzyl | 3-F | 4-Cl | |
| 41 | 2,5-difluorobenzyl | 3-F | 4-Cl | |
| 42 | 2,5-dichlorobenzyl | 3-F | 4-Cl | |
| 43 | 3,5-dichlorobenzyl | 3-F | 4-Cl | |
| 44 | 2,4-difluorobenzyl | 3-F | 4-Cl | |
| 45 | 2,6-difluorobenzyl | 3-F | 4-Cl | |
| 46 | 2,3-difluorobenzyl | 3-F | 4-Cl | |
| 47 | Ethynyl | 3-F | 4-Cl | |
| 48 | prop-1-yn-1-yl | 3-F | 4-Cl | |
| 49 | Methoxymethyl | 3-F | 4-Cl | |
| 50 | 2-F-phenyl | 3-F | 4-Cl | |
| 51 | 3-F-phenyl | 3-F | 4-Cl | |
| 52 | 4-F-phenyl | 3-F | 4-Cl | |
| 53 | oxetan-3-yl | 3-F | 4-Cl | 18.4/d |
| 54 | 2-(phenylsulfanyl)ethyl | 3-F | 4-Cl | 23.9/d |
| 55 | 2-(phenylsulfinyl)ethyl | 3-F | 4-Cl | |
| 56 | 2-(phenylsulfonyl)ethyl | 3-F | 4-Cl | |
| 57 | H | 3-F | 3-F | |
| 58 | Et | 3-F | 3-F | |
| 59 | n-Pr | 3-F | 3-F | |
| 60 | i-Pr | 3-F | 3-F | |
| 61 | n-Bu | 3-F | 3-F | |
| 62 | i-Bu | 3-F | 3-F | |
| 63 | 2,2-difluoroethyl | 3-F | 3-F | |
| 64 | 2,2,2-trifluoroethyl | 3-F | 3-F | |
| 65 | 2-fluorobenzyl | 3-F | 3-F | |
| 66 | 2,5-difluorobenzyl | 3-F | 3-F | |
| 67 | 2,5-dichlorobenzyl | 3-F | 3-F | |
| 68 | 3,5-dichlorobenzyl | 3-F | 3-F | |
| 69 | 2,4-difluorobenzyl | 3-F | 3-F | |
| 70 | 2,6-difluorobenzyl | 3-F | 3-F | |
| 71 | 2,3-difluorobenzyl | 3-F | 3-F | |
| 72 | Ethynyl | 3-F | 3-F | |
| 73 | prop-1-yn-1-yl | 3-F | 3-F | |
| 74 | Methoxymethyl | 3-F | 3-F | |
| 75 | 2-F-phenyl | 3-F | 3-F | |
| 76 | 3-F-phenyl | 3-F | 3-F | |
| 77 | 4-F-phenyl | 3-F | 3-F | |
| 78 | oxetan-3-yl | 3-F | 3-F | |
| 79 | 2-(phenylsulfanyl)ethyl | 3-F | 3-F | |
| 80 | 2-(phenylsulfinyl)ethyl | 3-F | 3-F | |
| 81 | 2-(phenylsulfonyl)ethyl | 3-F | 3-F | |
| 82 | H | 3,4-F₂ | 3-F | |
| 83 | Et | 3,4-F₂ | 3-F | 20.7/d |
| 84 | n-Pr | 3,4-F₂ | 3-F | 18.4/d |
| 85 | i-Pr | 3,4-F₂ | 3-F | 16.9/d |
| 86 | n-Bu | 3,4-F₂ | 3-F | 18.4/d |
| 87 | i-Bu | 3,4-F₂ | 3-F | 16.2/d |
| 88 | 2,2-difluoroethyl | 3,4-F₂ | 3-F | |
| 89 | 2,2,2-trifluoroethyl | 3,4-F₂ | 3-F | |
| 90 | 2-fluorobenzyl | 3,4-F₂ | 3-F | |
| 91 | 2,5-difluorobenzyl | 3,4-F₂ | 3-F | |
| 92 | 2,5-dichlorobenzyl | 3,4-F₂ | 3-F | |
| 93 | 3,5-dichlorobenzyl | 3,4-F₂ | 3-F | |
| 94 | 2,4-difluorobenzyl | 3,4-F₂ | 3-F | |
| 95 | 2,6-difluorobenzyl | 3,4-F₂ | 3-F | |
| 96 | 2,3-difluorobenzyl | 3,4-F₂ | 3-F | |
| 97 | Ethynyl | 3,4-F₂ | 3-F | |
| 98 | prop-1-yn-1-yl | 3,4-F₂ | 3-F | |
| 99 | Methoxymethyl | 3,4-F₂ | 3-F | |
| 100 | 2-F-phenyl | 3,4-F₂ | 3-F | |
| 101 | 3-F-phenyl | 3,4-F₂ | 3-F | |
| 102 | 4-F-phenyl | 3,4-F₂ | 3-F | |
| 103 | oxetan-3-yl | 3,4-F₂ | 3-F | |
| 104 | 2-(phenylsulfanyl)ethyl | 3,4-F₂ | 3-F | |
| 105 | 2-(phenylsulfinyl)ethyl | 3,4-F₂ | 3-F | |
| 106 | 2-(phenylsulfonyl)ethyl | 3,4-F₂ | 3-F | |
| 107 | H | 3,4-F₂ | 3-Cl | 8.7/c |
| 108 | Et | 3,4-F₂ | 3-Cl | 19.7/d |
| 109 | n-Pr | 3,4-F₂ | 3-Cl | 17.6/d |
| 110 | i-Pr | 3,4-F₂ | 3-Cl | |
| 111 | n-Bu | 3,4-F₂ | 3-Cl | 17.1/d |
| 112 | i-Bu | 3,4-F₂ | 3-Cl | 15.6/d |
| 113 | 2,2-difluoroethyl | 3,4-F₂ | 3-Cl | |
| 114 | 2,2,2-trifluoroethyl | 3,4-F₂ | 3-Cl | |
| 115 | 2-fluorobenzyl | 3,4-F₂ | 3-Cl | |
| 116 | 2,5-difluorobenzyl | 3,4-F₂ | 3-Cl | |
| 117 | 2,5-dichlorobenzyl | 3,4-F₂ | 3-Cl | |
| 118 | 3,5-dichlorobenzyl | 3,4-F₂ | 3-Cl | |
| 119 | 2,4-difluorobenzyl | 3,4-F₂ | 3-Cl | |
| 120 | 2,6-difluorobenzyl | 3,4-F₂ | 3-Cl | |
| 121 | 2,3-difluorobenzyl | 3,4-F₂ | 3-Cl | |
| 122 | Ethynyl | 3,4-F₂ | 3-Cl | |
| 123 | prop-1-yn-1-yl | 3,4-F₂ | 3-Cl | |
| 124 | Methoxymethyl | 3,4-F₂ | 3-Cl | |
| 125 | 2-F-phenyl | 3,4-F₂ | 3-Cl | |

TABLE 1-continued

Compounds of the formula (I)

(I)

| Ex. | R¹ | (R²)$_n$ | (R³)$_m$ | Rt [min]/ Cond. |
|---|---|---|---|---|
| 126 | 3-F-phenyl | 3,4-F$_2$ | 3-Cl | |
| 127 | 4-F-phenyl | 3,4-F$_2$ | 3-Cl | |
| 128 | oxetan-3-yl | 3,4-F$_2$ | 3-Cl | |
| 129 | 2-(phenylsulfanyl)ethyl | 3,4-F$_2$ | 3-Cl | |
| 130 | 2-(phenylsulfinyl)ethyl | 3,4-F$_2$ | 3-Cl | |
| 131 | 2-(phenylsulfonyl)ethyl | 3,4-F$_2$ | 3-Cl | |
| 132 | H | 3-F | 3-F | |
| 133 | H | 3,4-F$_2$ | 4-Cl | |
| 134 | H | 3-F | 4-Br | |
| 135 | H | 3-Cl | 3-F | |
| 136 | H | H | 3-F | |
| 137 | H | 4-F | 3-F | |
| 138 | H | 3-F | 3-Cl | |
| 139 | H | 3-Br | 3-F | |
| 140 | H | 2,5-F$_2$ | 3-F | |
| 141 | H | 3-F | 2-F | |
| 142 | H | 3,4,5-F$_3$ | 4-Cl | |
| 143 | H | 4-F | 3-Cl | |
| 144 | H | 3,4-F$_2$ | 3-F, 4-Cl | |
| 145 | H | 3,4-F$_2$ | 2-F | |
| 146 | H | 3-F | 2,3-F$_2$ | |
| 147 | H | 4-F | 3,5-F$_2$ | |
| 148 | H | 3-F | 4-F | |
| 149 | H | 3,4-F$_2$ | 3-Cl, 5-F | |
| 150 | H | 3-F | 3-Cl, 5-F | |
| 151 | H | 3-F | 2,5-F$_2$ | |
| 152 | H | 3,4-F$_2$ | 2,3-F$_2$ | |
| 153 | H | 3,4-F$_2$ | 2,5-F$_2$ | |
| 154 | H | 3-Cl | 3-Cl, 5-F | |
| 155 | H | 3-F, 4-Cl | 3-Cl | |
| 156 | H | 3,4-F$_2$ | 3-NO$_2$ | |
| 157 | H | 3,4-F$_2$ | H | |
| 158 | H | 3-Cl, 4-F | 3-F | |
| 159 | H | 3,4-F$_2$ | 4-OMe | |
| 160 | Me | 3-F | H | |
| 161 | Me | 3-F | 2,4-F$_2$ | |
| 162 | Me | 3-F | 2,6-F$_2$ | 19.5/d |
| 163 | Me | 3-F | 3,4-F$_2$ | |
| 164 | Me | 3-F | 3,5-F$_2$ | |
| 165 | Me | 3-F | 2-Cl | |
| 166 | Me | 3-F | 2,3-Cl$_2$ | |
| 167 | Me | 3-F | 2,4-Cl$_2$ | |
| 168 | Me | 3-F | 2,5-Cl$_2$ | |
| 169 | Me | 3-F | 2,6-Cl$_2$ | |
| 170 | Me | 3-F | 3,4-Cl$_2$ | |
| 171 | Me | 3-F | 3,5-Cl$_2$ | |
| 172 | Me | 3,4-F$_2$ | 4-F | |
| 173 | Me | 3,4-F$_2$ | 2,4-F$_2$ | |
| 174 | Me | 3,4-F$_2$ | 2,6-F$_2$ | 19.3/d |
| 175 | Me | 3,4-F$_2$ | 3,4-F$_2$ | |
| 176 | Me | 3,4-F$_2$ | 3,5-F$_2$ | |
| 177 | Me | 3,4-F$_2$ | 2-Cl | |
| 178 | Me | 3,4-F$_2$ | 2,3-Cl$_2$ | |
| 179 | Me | 3,4-F$_2$ | 2,4-Cl$_2$ | |
| 180 | Me | 3,4-F$_2$ | 2,5-Cl$_2$ | |
| 181 | Me | 3,4-F$_2$ | 2,6-Cl$_2$ | |
| 182 | Me | 3,4-F$_2$ | 3,4-Cl$_2$ | |
| 183 | Me | 3,4-F$_2$ | 3,5-Cl$_2$ | |
| 184 | Me | 3-Cl | H | |
| 185 | Me | 3-Cl | 2-F | |
| 186 | Me | 3-Cl | 4-F | |
| 187 | Me | 3-Cl | 2,3-F$_2$ | |
| 188 | Me | 3-Cl | 2,4-F$_2$ | |
| 189 | Me | 3-Cl | 2,5-F$_2$ | |
| 190 | Me | 3-Cl | 2,6-F$_2$ | |
| 191 | Me | 3-Cl | 3,4-F$_2$ | |
| 192 | Me | 3-Cl | 3,5-F$_2$ | |
| 193 | Me | 3-Cl | 2-Cl | |
| 194 | Me | 3-Cl | 3-Cl | |
| 195 | Me | 3-Cl | 4-Cl | |
| 196 | Me | 3-Cl | 2,3-Cl$_2$ | |
| 197 | Me | 3-Cl | 2,4-Cl$_2$ | |
| 198 | Me | 3-Cl | 2,5-Cl$_2$ | |
| 199 | Me | 3-Cl | 2,6-Cl$_2$ | |
| 200 | Me | 3-Cl | 3,4-Cl$_2$ | |
| 201 | Me | 3-Cl | 3,5-Cl$_2$ | |
| 202 | Me | 3,4-Cl$_2$ | H | |
| 203 | Me | 3,4-Cl$_2$ | 2-F | |
| 204 | Me | 3,4-Cl$_2$ | 3-F | |
| 205 | Me | 3,4-Cl$_2$ | 4-F | |
| 206 | Me | 3,4-Cl$_2$ | 2,3-F$_2$ | |
| 207 | Me | 3,4-Cl$_2$ | 2,4-F$_2$ | |
| 208 | Me | 3,4-Cl$_2$ | 2,5-F$_2$ | 19.8/d |
| 209 | Me | 3,4-Cl$_2$ | 2,6-F$_2$ | |
| 210 | Me | 3,4-Cl$_2$ | 3,4-F$_2$ | |
| 211 | Me | 3,4-Cl$_2$ | 3,5-F$_2$ | |
| 212 | Me | 3,4-Cl$_2$ | 2-Cl | |
| 213 | Me | 3,4-Cl$_2$ | 3-Cl | |
| 214 | Me | 3,4-Cl$_2$ | 4-Cl | |
| 215 | Me | 3,4-Cl$_2$ | 2,3-Cl$_2$ | |
| 216 | Me | 3,4-Cl$_2$ | 2,4-Cl$_2$ | |
| 217 | Me | 3,4-Cl$_2$ | 2,5-Cl$_2$ | |
| 218 | Me | 3,4-Cl$_2$ | 2,6-Cl$_2$ | |
| 219 | Me | 3,4-Cl$_2$ | 3,4-Cl$_2$ | |
| 220 | Me | 3,4-Cl$_2$ | 3,5-Cl$_2$ | |
| 221 | Me | 3-Cl, 4-F | H | |
| 222 | Me | 3-Cl, 4-F | 2-F | |
| 223 | Me | 3-Cl, 4-F | 4-F | |
| 224 | Me | 3-Cl, 4-F | 2,3-F$_2$ | |
| 225 | Me | 3-Cl, 4-F | 2,4-F$_2$ | |
| 226 | Me | 3-Cl, 4-F | 2,5-F$_2$ | |
| 227 | Me | 3-Cl, 4-F | 2,6-F$_2$ | 19.2/d |
| 228 | Me | 3-Cl, 4-F | 3,4-F$_2$ | |
| 229 | Me | 3-Cl, 4-F | 3,5-F$_2$ | |
| 230 | Me | 3-Cl, 4-F | 2-Cl | |
| 231 | Me | 3-Cl, 4-F | 3-Cl | |
| 232 | Me | 3-Cl, 4-F | 4-Cl | |
| 233 | Me | 3-Cl, 4-F | 2,3-Cl$_2$ | |
| 234 | Me | 3-Cl, 4-F | 2,4-Cl$_2$ | |
| 235 | Me | 3-Cl, 4-F | 2,5-Cl$_2$ | |
| 236 | Me | 3-Cl, 4-F | 2,6-Cl$_2$ | |
| 237 | Me | 3-Cl, 4-F | 3,4-Cl$_2$ | |
| 238 | Me | 3-Cl, 4-F | 3,5-Cl$_2$ | |
| 239 | Me | 3-Cl, 4-F | H | |
| 240 | Me | 3-F, 4-Cl | 2-F | |
| 241 | Me | 3-F, 4-Cl | 3-F | |
| 242 | Me | 3-F, 4-Cl | 4-F | |
| 243 | Me | 3-F, 4-Cl | 2,3-F$_2$ | |

TABLE 1-continued

Compounds of the formula (I)

| Ex. | R¹ | (R²)ₙ | (R³)ₘ | Rt [min]/Cond. |
|---|---|---|---|---|
| 244 | Me | 3-F, 4-Cl | 2,4-F₂ | |
| 245 | Me | 3-F, 4-Cl | 2,5-F₂ | |
| 246 | Me | 3-F, 4-Cl | 2,6-F₂ | |
| 247 | Me | 3-F, 4-Cl | 3,4-F₂ | |
| 248 | Me | 3-F, 4-Cl | 3,5-F₂ | |
| 249 | Me | 3-F, 4-Cl | 2-Cl | |
| 250 | Me | 3-F, 4-Cl | 4-Cl | |
| 251 | Me | 3-F, 4-Cl | 2,3-Cl₂ | |
| 252 | Me | 3-F, 4-Cl | 2,4-Cl₂ | |
| 253 | Me | 3-F, 4-Cl | 2,5-Cl₂ | |
| 254 | Me | 3-F, 4-Cl | 2,6-Cl₂ | |
| 255 | Me | 3-F, 4-Cl | 3,4-Cl₂ | |
| 256 | Me | 3-F, 4-Cl | 3,5-Cl₂ | |
| 257 | H | 3-F | 2,6-F₂ | |
| 258 | Et | 3-F | 2,6-F₂ | |
| 259 | n-Pr | 3-F | 2,6-F₂ | |
| 260 | i-Pr | 3-F | 2,6-F₂ | |
| 261 | n-Bu | 3-F | 2,6-F₂ | |
| 262 | i-Bu | 3-F | 2,6-F₂ | |
| 263 | 2,2-difluoroethyl | 3-F | 2,6-F₂ | |
| 264 | 2,2,2-trifluoroethyl | 3-F | 2,6-F₂ | |
| 265 | 2-fluorobenzyl | 3-F | 2,6-F₂ | |
| 266 | 2,5-difluorobenzyl | 3-F | 2,6-F₂ | |
| 267 | 2,5-dichlorobenzyl | 3-F | 2,6-F₂ | |
| 268 | 3,5-dichlorobenzyl | 3-F | 2,6-F₂ | |
| 269 | 2,4-difluorobenzyl | 3-F | 2,6-F₂ | |
| 270 | 2,6-difluorobenzyl | 3-F | 2,6-F₂ | |
| 271 | 2,3-difluorobenzyl | 3-F | 2,6-F₂ | |
| 272 | Ethynyl | 3-F | 2,6-F₂ | |
| 273 | prop-1-yn-1-yl | 3-F | 2,6-F₂ | |
| 274 | Methoxymethyl | 3-F | 2,6-F₂ | |
| 275 | 2-F-phenyl | 3-F | 2,6-F₂ | |
| 276 | 3-F-phenyl | 3-F | 2,6-F₂ | |
| 277 | 4-F-phenyl | 3-F | 2,6-F₂ | |
| 278 | oxetan-3-yl | 3-F | 2,6-F₂ | |
| 279 | 2-(phenylsulfanyl)ethyl | 3-F | 2,6-F₂ | |
| 280 | 2-(phenylsulfinyl)ethyl | 3-F | 2,6-F₂ | |
| 281 | 2-(phenylsulfonyl)ethyl | 3-F | 2,6-F₂ | |
| 282 | H | 3,4-F₂ | 2,6-F₂ | |
| 283 | Et | 3,4-F₂ | 2,6-F₂ | 19.1/d |
| 284 | n-Pr | 3,4-F₂ | 2,6-F₂ | |
| 285 | i-Pr | 3,4-F₂ | 2,6-F₂ | |
| 286 | n-Bu | 3,4-F₂ | 2,6-F₂ | |
| 287 | i-Bu | 3,4-F₂ | 2,6-F₂ | |
| 288 | 2,2-difluoroethyl | 3,4-F₂ | 2,6-F₂ | |
| 289 | 2,2,2-trifluoroethyl | 3,4-F₂ | 2,6-F₂ | |
| 290 | 2-fluorobenzyl | 3,4-F₂ | 2,6-F₂ | |
| 291 | 2,5-difluorobenzyl | 3,4-F₂ | 2,6-F₂ | |
| 292 | 2,5-dichlorobenzyl | 3,4-F₂ | 2,6-F₂ | |
| 293 | 3,5-dichlorobenzyl | 3,4-F₂ | 2,6-F₂ | |
| 294 | 2,4-difluorobenzyl | 3,4-F₂ | 2,6-F₂ | |
| 295 | 2,6-difluorobenzyl | 3,4-F₂ | 2,6-F₂ | |
| 296 | 2,3-difluorobenzyl | 3,4-F₂ | 2,6-F₂ | |
| 297 | Ethynyl | 3,4-F₂ | 2,6-F₂ | |
| 298 | prop-1-yn-1-yl | 3,4-F₂ | 2,6-F₂ | |
| 299 | Methoxymethyl | 3,4-F₂ | 2,6-F₂ | |
| 300 | 2-F-phenyl | 3,4-F₂ | 2,6-F₂ | |
| 301 | 3-F-phenyl | 3,4-F₂ | 2,6-F₂ | |
| 302 | 4-F-phenyl | 3,4-F₂ | 2,6-F₂ | |
| 303 | oxetan-3-yl | 3,4-F₂ | 2,6-F₂ | |
| 304 | 2-(phenylsulfanyl)ethyl | 3,4-F₂ | 2,6-F₂ | |
| 305 | 2-(phenylsulfinyl)ethyl | 3,4-F₂ | 2,6-F₂ | |
| 306 | 2-(phenylsulfonyl)ethyl | 3,4-F₂ | 2,6-F₂ | |
| 307 | Me | H | H | |
| 308 | Me | H | 2-F | |
| 309 | Me | H | 4-F | |
| 310 | Me | H | 2,3-F₂ | |
| 311 | Me | H | 2,4-F₂ | |
| 312 | Me | H | 2,5-F₂ | |
| 313 | Me | H | 2,6-F₂ | |
| 314 | Me | H | 3,4-F₂ | |
| 315 | Me | H | 3,5-F₂ | |
| 316 | Me | H | 2-Cl | |
| 317 | Me | H | 3-Cl | |
| 318 | Me | H | 4-Cl | |
| 319 | Me | H | 2,3-Cl₂ | |
| 320 | Me | H | 2,4-Cl₂ | |
| 321 | Me | H | 2,5-Cl₂ | |
| 322 | Me | H | 2,6-Cl₂ | |
| 323 | Me | H | 3,4-Cl₂ | |
| 324 | Me | H | 3,5-Cl₂ | |
| 325 | Me | 3-CN | 3-F | |
| 326 | Me | 3-CN | 3-Cl | 33.88/a |
| 327 | Me | 3-CN | 3-CN | |
| 328 | Me | 3-CN | 4-F | |
| 329 | Me | 3-CN | 4-Cl | 32.97/a |
| 330 | Me | 3-CN | 2,5-F₂ | 18.64/e |
| 331 | Me | 3-CN | 2,6-F₂ | |
| 332 | H | 3-CN | 3-F | |
| 333 | H | 3-CN | 3-Cl | |
| 334 | H | 3-CN | 3-CN | |
| 335 | H | 3-CN | 4-F | |
| 336 | H | 3-CN | 4-Cl | |
| 337 | H | 3-CN | 2,5-F₂ | |
| 338 | H | 3-CN | 2,6-F₂ | |
| 339 | Me | 3-CN, 4-F | 3-F | 31.94/a |
| 340 | Me | 3-CN, 4-F | 3-Cl | 30.59/a |
| 341 | Me | 3-CN, 4-F | 3-CN | 37.23/a |
| 342 | Me | 3-CN, 4-F | 4-F | 12.64/e |
| 343 | Me | 3-CN, 4-F | 4-Cl | 20.15/e |
| 344 | Me | 3-CN, 4-F | 2,5-F₂ | 16.64/e |
| 345 | Me | 3-CN, 4-F | 2,6-F₂ | 17.95/a |
| 346 | H | 3-CN, 4-F | 3-F | |
| 347 | H | 3-CN, 4-F | 3-Cl | |
| 348 | H | 3-CN, 4-F | 3-CN | |
| 349 | H | 3-CN, 4-F | 4-F | |
| 350 | H | 3-CN, 4-F | 4-Cl | |
| 351 | H | 3-CN, 4-F | 2,5-F₂ | |
| 352 | H | 3-CN, 4-F | 2,6-F₂ | |
| 353 | Me | 3-Br, 4-F | 3-F | |
| 354 | Me | 3-Br, 4-F | 3-Cl | |
| 355 | Me | 3-Br, 4-F | 3-CN | |
| 356 | Me | 3-Br, 4-F | 4-F | |
| 357 | Me | 3-Br, 4-F | 4-Cl | |
| 358 | Me | 3-Br, 4-F | 2,5-F₂ | 20.01/d |
| 359 | Me | 3-Br, 4-F | 2,6-F₂ | 19.73/d |
| 360 | H | 3-Br, 4-F | 3-F | |
| 361 | H | 3-Br, 4-F | 3-Cl | |

TABLE 1-continued

Compounds of the formula (I)

(I)

| Ex. | R¹ | (R²)ₙ | (R³)ₘ | Rt [min]/ Cond. |
|---|---|---|---|---|
| 362 | H | 3-Br, 4-F | 3-CN | |
| 363 | H | 3-Br, 4-F | 4-F | |
| 364 | H | 3-Br, 4-F | 4-Cl | |
| 365 | H | 3-Br, 4-F | 2,5-F₂ | |
| 366 | H | 3-Br, 4-F | 2,6-F₂ | |
| 367 | Me | 3-F, 4-CN | 3-F | |
| 368 | Me | 3-F, 4-CN | 3-Cl | |
| 369 | Me | 3-F, 4-CN | 3-CN | |
| 370 | Me | 3-F, 4-CN | 4-F | |
| 371 | Me | 3-F, 4-CN | 4-Cl | |
| 372 | Me | 3-F, 4-CN | 2,5-F₂ | |
| 373 | Me | 3-F, 4-CN | 2,6-F₂ | |
| 374 | H | 3-F, 4-CN | 3-F | |
| 375 | H | 3-F, 4-CN | 3-Cl | |
| 376 | H | 3-F, 4-CN | 3-CN | |
| 377 | H | 3-F, 4-CN | 4-F | |
| 378 | H | 3-F, 4-CN | 4-Cl | |
| 379 | H | 3-F, 4-CN | 2,5-F₂ | |
| 380 | H | 3-F, 4-CN | 2,6-F₂ | |
| 381 | Me | 3-F | 3-CN | |
| 382 | Me | 3,4-F₂ | 3-CN | 14.71/e |
| 383 | H | 3-F | 3-CN | |
| 384 | H | 3,4-F₂ | 3-CN | |
| 385 | Me | 3-F | 4-NO₂ | |
| 386 | Me | 3,4-F₂ | 4-NO₂ | |
| 387 | H | 3-F | 4-NO₂ | |
| 388 | H | 3,4-F₂ | 4-NO₂ | |
| 389 | Me | 3-F | 3-F, 4-OMe | |
| 390 | Me | 3,4-F₂ | 3-F, 4-OMe | 43.06/a |
| 391 | H | 3-F | 3-F, 4-OMe | |
| 392 | H | 3,4-F₂ | 3-F, 4-OMe | |
| 393 | Me | 3-F | 3-NO₂ | |
| 394 | H | 3-F | 3-NO₂ | |
| 395 | Me | 3-CN, 4-F | 3,5-F₂ | 26.67/a |
| 396 | H | 3-CN, 4-F | 3,5-F₂ | |
| 397 | Me | 3,5-F₂ | 3-Cl | |
| 398 | Me | 3,5-F₂ | 3-CN | |
| 399 | Me | 3,5-F₂ | 4-F | |
| 400 | Me | 3,5-F₂ | 4-Cl | |
| 401 | Me | 3,5-F₂ | 2,5-F₂ | |
| 402 | Me | 3,5-F₂ | 2,6-F₂ | |
| 403 | H | 3,5-F₂ | 3-F | |
| 404 | H | 3,5-F₂ | 3-Cl | |
| 405 | H | 3,5-F₂ | 3-CN | |
| 406 | H | 3,5-F₂ | 4-F | |
| 407 | H | 3,5-F₂ | 4-Cl | |
| 408 | H | 3,5-F₂ | 2,5-F₂ | |
| 409 | H | 3,5-F₂ | 2,6-F₂ | |
| 410 | Me | 2,5-F₂ | 3-F | |
| 411 | Me | 2,5-F₂ | 3-Cl | |
| 412 | Me | 2,5-F₂ | 3-CN | |
| 413 | Me | 2,5-F₂ | 4-F | |
| 414 | Me | 2,5-F₂ | 4-Cl | |
| 415 | Me | 2,5-F₂ | 2,5-F₂ | |
| 416 | Me | 2,5-F₂ | 2,6-F₂ | |
| 417 | H | 2,5-F₂ | 3-Cl | |
| 418 | H | 2,5-F₂ | 3-CN | |
| 419 | H | 2,5-F₂ | 4-F | |
| 420 | H | 2,5-F₂ | 4-Cl | |
| 421 | H | 2,5-F₂ | 2,5-F₂ | |
| 422 | H | 2,5-F₂ | 2,6-F₂ | |

Further physical data for Table 1:
¹H-NMR data (CDCl₃)—chemical shift of selected characteristic signals in ppm:

Ex. 1: 2.89 (m, 2H), 3.58 (s, 3H), 3.64 (m, 1H), 4.08 (d, 1H), 7.09 (d, 2H), 7.28 (d, 2H)

Ex. 2: 2.90 (m, 2H), 3.58 (s, 3H), 3.66 (m, 1H), 4.09 (d, 1H), 6.88 (m, 1H), 6.90 (m, 1H)

Ex. 3: 2.89 (m, 2H), 3.59 (s, 3H), 3.61 (m, 1H), 4.06 (d, 1H), 7.05 (d, 2H), 7.29 (d, 2H)

Ex. 4: 2.89 (m, 2H), 3.58 (s, 3H), 3.63 (m, 1H), 4.09 (d, 1H), 7.03 (d, 2H), 7.43 (d, 2H)

Ex. 5: 2.89 (m, 2H), 3.59 (s, 3H), 3.65 (m, 1H), 4.08 (d, 1H), 7.20 (s, 1H)

Ex. 6: 2.90 (d, 2H), 3.60 (s, 3H), 3.62 (q, 1H), 4.08 (d, 1H), 7.11 (dd, 1H)

Ex. 7: 2.89 (m, 2H), 3.58 (s, 3H), 3.68 (m, 1H), 4.10 (d, 1H), 6.87 (m, 1H), 6.97 (m, 1H)

Ex. 8: 2.90 (d, 2H), 3.59 (s, 3H), 3.63 (q, 1H), 4.08 (d, 1H), 7.02 (t, 2H)

Ex. 9: 2.90 (m, 2H), 3.58 (s, 3H), 3.62 (m, 1H), 4.10 (d, 1H), 7.13 (s, 1H)

Ex. 10: 2.90 (d, 2H), 3.60 (s, 3H), 3.61 (q, 1H), 4.08 (d, 1H), 6.89 (m, 1H)

Ex. 11: 2.89 (m, 2H), 3.58 (s, 3H), 3.65 (m, 1H), 4.07 (d, 1H), 7.11 (d, 2H), 7.20 (t, 1H), 7.47 (d, 1H)

Ex. 12: 2.90 (m, 2H), 3.59 (s, 3H), 3.65 (m, 1H), 4.10 (d, 1H), 6.95 (s, 1H)

Ex. 13: 2.90 (dd, 1H), 3.03 (dd, 1H), 3.55 (s, 3H), 3.96 (m, 1H), 4.21 (d, 1H), 7.19 (t, 1H)

Ex. 14: 2.89 (d, 2H), 3.60 (s, 3H), 3.60 (q, 1H), 4.04 (d, 1H), 6.81 (t, 1H), 7.07 (d, 2H), 7.29 (d, 2H)

Ex. 15: 2.89 (d, 2H), 3.59 (s, 3H), 3.61 (q, 1H), 4.08 (d, 1H), 7.01 (m, 3H), 7.11 (m, 3H)

Ex. 16: 2.87 (d, 2H), 3.60 (s, 3H), 3.61 (q, 1H), 4.05 (d, 1H), 7.03 (m, 1H), 7.14 (dd, 1H), 7.34 (t, 1H)

Ex. 17: 2.95 (dd, 1H), 3.02 (dd, 1H), 3.57 (s, 3H), 3.91 (m, 1H), 4.17 (d, 1H), 7.08 (m, 6H)

Ex. 18: 2.90 (dd, 1H), 3.02 (dd, 1H), 3.56 (s, 3H), 3.99 (m, 1H), 4.19 (d, 1H), 7.05 (m, 6H), 7.31 (m, 1H)

Ex. 19: 2.88 (m, 2H), 3.60 (s, 3H), 3.61 (m, 1H), 4.07 (d, 1H), 7.04 (m, 2H), 7.16 (m, 2H)

Ex. 20: DMSO-d6: 2.91 (m, 2H), 3.44 (s, 3H), 3.75 (dd, 1H), 4.65 (d, 1H), 7.08 (m, 5H), 7.24 (m, 2H), 7.34 (m, 1H)

Ex. 21: 2.88 (d, 2H), 3.59 (q, 1H), 3.61 (s, 3H), 4.08 (d, 1H), 6.29 (d, 1H), 7.15 (dd, 1H)

Ex. 22: 2.88 (m, 2H), 3.59 (s, 3H), 3.62 (m, 1H), 4.08 (d, 1H), 6.78 (m, 1H), 7.34 (m, 1H)
Ex. 23: 2.90 (dd, 1H), 3.00 (dd, 1H), 3.57 (s, 3H), 3.93 (m, 1H), 4.19 (d, 1H), 7.09 (d, 1H), 7.32 (dd, 1H)
Ex. 24: 2.94 (dd, 1H), 3.01 (dd, 1H), 3.57 (s, 3H), 3.96 (m, 1H), 4.15 (d, 1H), 6.92 (t, 1H)
Ex. 25: 2.91 (dd, 1H), 2.98 (dd, 1H), 3.58 (s, 3H), 3.88 (m, 1H), 4.15 (d, 1H), 6.87 (m, 1H), 7.11 (m, 2H)
Ex. 26: 2.84 (dd, 1H), 2.89 (dd, 1H), 3.59 (s, 3H), 3.60 (m, 1H), 4.06 (d, 1H), 6.96 (s, 1H), 7.21 (s, 1H)
Ex. 27: 2.88 (m, 2H), 3.58 (s, 3H), 3.61 (dd, 1H), 4.09 (d, 1H), 6.90 (m, 1H), 7.01 (m, 2H), 7.12 (s, 1H), 7.25 (m, 2H), 7.36 (m, 1H)
Ex. 28: 2.96 (d, 2H), 3.59 (s, 3H), 3.77 (dd, 1H), 4.13 (d, 1H), 6.90 (m, 1H), 7.03 (m, 1H), 7.13 (s, 1H), 7.51 (m, 2H), 8.01 (m, 1H), 8.16 (m, 1H)
Ex. 29: 2.91 (d, 2H), 3.57 (s, 3H), 3.63 (dd, 1H), 4.07 (d, 1H), 6.87 (m, 1H), 6.96 (m, 1H), 7.15 (m, 3H), 7.28 (m, 3H)
Ex. 30: 2.89 (d, 2H), 3.58 (s, 3H), 3.62 (q, 1H), 4.06 (d, 1H), 7.09 (t, 1H)
Ex. 31: 1.13 (t, 3H), 2.85 (d, 2H), 3.57 (dd, 1H), 3.78 (s, 3H), 4.00 (q, 2H), 4.02 (d, 1H), 6.80 (d, 1H), 6.85 (m, 2H), 6.95 (m, 1H), 6.98 (d, 2H), 7.09 (m, 1H)
Ex. 53: 2.96 (m, 2H), 3.62 (q, 1H), 4.05 (d, 1H), 4.41 (m, 2H), 4.78 (q, 2H), 5.29 (quint, 1H), 7.10 (d, 2H), 7.30 (d, 2H)
Ex. 54: 2.85 (m, 2H), 2.97 (t, 2H), 3.60 (q, 1H), 4.08 (d, 1H), 4.11 (m, 2H), 7.09 (d, 2H), 7.28 (d, 2H)
Ex. 55: 2.85 (m, 2H), 2.94 (m, 2H), 3.62 (q, 1H), 4.07 (m, 1H), 4.36 (m, 2H)
Ex. 83: 1.13 (t, 3H), 2.89 (d, 2H), 3.62 (q, 1H), 4.03 (m, 3H), 6.83 (d, 1H)
Ex. 84: 0.83 (t, 3H), 1.51 (sext, 2H), 2.89 (d, 2H), 3.61 (q, 1H), 3.93 (t, 2H), 4.06 (d, 1H), 6.84 (d, 1H)
Ex. 85: 1.06 (d, 3H), 1.10 (d, 3H), 2.85 (m, 2H), 3.60 (q, 1H), 4.04 (d, 1H), 4.87 (m, 1H), 6.82 (d, 1H)
Ex. 86: 0.86 (t, 3H), 1.24 (sext, 2H), 1.47 (quint, 2H), 2.88 (d, 2H), 3.61 (q, 1H), 3.97 (t, 2H), 4.06 (d, 1H), 6.83 (d, 1H)
Ex. 87: 0.82 (d, 6H), 1.79 (sept, 1H), 2.89 (m, 2H), 3.61 (q, 1H), 3.74 (d, 2H), 4.06 (d, 1H), 6.84 (d, 1H)
Ex. 107: 2.88 (d, 2H), 3.56 (q, 1H), 4.05 (d, 1H), 6.89 (m, 1H)
Ex. 108: 1.13 (t, 3H), 2.87 (d, 2H), 3.59 (m, 1H), 4.03 (m, 3H), 6.88 (m, 1H)
Ex. 109: 0.83 (t, 3H), 1.54 (sext, 2H), 2.88 (d, 2H), 3.58 (q, 1H), 3.93 (t, 2H), 4.06 (d, 1H), 6.88 (m, 1H)
Ex. 111: 0.86 (t, 3H), 1.25 (sext, 2H), 1.45 (quint, 2H), 2.87 (d, 2H), 3.59 (q, 1H), 3.97 (t, 2H), 4.06 (d, 1H), 6.89 (m, 1H)
Ex. 112: 0.82 (d, 6H), 1.80 (sept, 1H), 2.88 (m, 2H), 3.59 (q, 1H), 3.75 (d, 2H), 4.03 (d, 1H), 6.88 (m, 1H)
Ex. 162: 3.12 (m, 1H), 3.21 (m, 1H), 3.61 (s, 3H), 4.16 (m, 2H), 6.75 (t, 2H), 6.91 (m, 2H), 6.98 (d, 1H), 7.14 (m, 1H), 7.21 (m, 1H)
Ex. 174: 3.11 (m, 1H), 3.19 (m, 1H), 3.61 (s, 3H), 4.13 (m, 2H), 6.77 (t, 2H), 6.91 (m, 1H), 7.02 (m, 2H), 7.16 (m, 1H)
Ex. 208: 2.91 (dd, 1H), 2.95 (dd, 1H), 3.58 (s, 3H), 3.89 (m, 1H), 4.15 (d, 1H), 6.88 (m, 1H), 6.96 (m, 1H), 7.02 (m, 1H), 7.11 (dd, 1H), 7.37 (d, 1H), 7.42 (d, 1H)
Ex. 227: 3.12 (m, 1H), 3.18 (m, 1H), 3.61 (s, 3H), 4.12 (m, 3H), 6.77 (t, 2H), 7.00 (t, 1H), 7.05 (m, 1H), 7.16 (m, 1H), 7.22 (m, 1H)
Ex. 283 1.13 (t, 3H), 3.09 (m, 1H), 3.20 (m, 1H), 4.08 (m, 2H), 4.13 (m, 2H), 6.77 (t, 2H), 6.91 (m, 1H), 7.02 (m, 2H), 7.16 (m, 1H)
Ex. 326: 2.90 (m, 2H), 3.59 (s, 3H), 3.64 (q, 1H), 4.14 (d, 1H), 7.00 (m, 1H), 7.06 (s, 1H), 7.25 (m, 2H), 7.44 (m, 3H), 7.63 (m, 1H)
Ex. 329: 2.89 (m, 2H), 3.58 (s, 3H), 3.64 (q, 1H), 4.13 (d, 1H), 7.03 (d, 2H), 7.26 (d, 2H), 7.37 (m, 1H), 7.45 (m, 2H), 7.63 (m, 1H)
Ex. 330: 2.98 (m, 2H), 3.58 (s, 3H), 3.92 (m, 1H), 4.21 (d, 1H), 6.83 (m, 1H), 7.00 (m, 2H), 7.51 (m, 3H), 7.62 (m, 1H)
Ex. 339: 2.92 (d, 2H), 3.61 (s, 3H), 3.62 (m, 1H), 4.13 (d, 1H), 6.79 (m, 1H), 6.87 (m, 1H), 6.99 (m, 1H), 7.19 (m, 1H), 7.28 (m, 1H), 7.37 (m, 2H)
Ex. 340: 2.90 (d, 2H), 3.61 (s, 3H), 3.61 (q, 1H), 4.14 (d, 1H), 6.97 (m, 1H), 7.06 (m, 1H), 7.23 (m, 3H), 7.48 (m, 2H)
Ex. 341: 2.92 (m, 2H), 3.58 (s, 3H), 3.89 (q, 1H), 4.17 (d, 1H), 7.21 (m, 1H), 7.48 (m, 6H)
Ex. 342: 2.89 (d, 2H), 3.60 (s, 3H), 3.63 (m, 1H), 4.12 (d, 1H), 7.02 (m, 4H), 7.19 (m, 1H), 7.32 (m, 2H)
Ex. 343: 2.89 (d, 2H), 3.61 (s, 3H), 3.61 (m, 1H), 4.13 (d, 1H), 7.01 (m, 2H), 7.18 (m, 1H), 7.38 (m, 4H)
Ex. 344: 2.97 (m, 2H), 3.60 (s, 3H), 3.88 (m, 1H), 4.21 (d, 1H), 6.83 (m, 1H), 7.01 (m, 2H), 7.21 (m, 1H), 7.49 (m, 2H)
Ex. 345: 3.17 (m, 2H), 3.62 (s, 3H), 4.14 (m, 1H0, 4.19 (d, 1H), 6.79 (m, 2H), 7.17 (m, 2H), 7.33 (m, 1H), 7.49 (m, 1H)
Ex. 358: 2.94 (d, 2H), 3.61 (s, 3H), 3.62 (m, 1H), 4.15 (d, 1H), 6.87 (m, 1H), 6.98 (m, 2H), 7.08 (m, 1H), 7.19 (m, 1H), 7.47 (m, 1H)
Ex. 359: 3.17 (m, 2H), 3.61 (s, 3H), 4.13 (m, 2H), 6.78 (t, 2H), 6.99 (6, 1H), 7.16 (m, 2H), 7.46 (m, 1H)
Ex. 382: 2.92 (d, 2H), 3.59 (s, 3H), 3.68 (q, 1H), 4.09 (d, 1H), 6.89 (m, 1H), 7.01 (m, 1H), 7.13 (m, 1H), 7.42 (m, 3H), 7.59 (m, 1H)
Ex. 390: 2.85 (m, 2H), 3.53 (q, 1H), 3.59 (s, 3H), 3.86 (s, 3H), 4.03 (d, 1H), 6.83 (m, 4H), 6.99 (m, 1H), 7.11 (m, 1H)
Ex. 395: 2.89 (d, 2H), 3.60 (q, 1H), 3.62 (s, 3H), 4.14 (d, 1H), 6.65 (m, 2H), 6.75 (m, 1H), 7.21 (m, 1H), 7.42 (m, 2H)

B) FORMULATION EXAMPLES a) A dust is obtained by mixing 10 parts by weight of a compound of the formula (I) and 90 parts by weight of talc as inert substance and comminuting the mixture in a hammer mill.
b) A wettable powder which is readily dispersible in water is obtained by mixing 25 parts by weight of a compound of the formula (I), 64 parts by weight of kaolin-containing quartz as inert substance, 10 parts by weight of potassium lignosulfonate and 1 part by weight of sodium oleoylmethyltaurate as wetting agent and dispersant, and grinding the mixture in a pinned-disk mill.
c) A readily water-dispersible dispersion concentrate is obtained by mixing 20 parts by weight of a compound of the formula (I) with 6 parts by weight of alkylphenol polyglycol ether (®Triton X 207), 3 parts by weight of isotridecanol polyglycol ether (8 EO) and 71 parts by weight of paraffinic mineral oil (boiling range for example about 255 to above 277° C.) and grinding the mixture in a ball mill to a fineness of below 5 microns.
d) An emulsifiable concentrate is obtained from 15 parts by weight of a compound of the formula (I), 75 parts by weight of cyclohexanone as solvent and 10 parts by weight of oxethylated nonylphenol as emulsifier.
e) Water-dispersible granules are obtained by mixing
   75 parts by weight of a compound of the formula (I),
   10 parts by weight of calcium lignosulfonate,
   5 parts by weight of sodium laurylsulfate,
   3 parts by weight of polyvinyl alcohol and
   7 parts by weight of kaolin, grinding the mixture in a pinned-disk mill, and granulating the powder in a fluidized bed by spraying on water as granulating liquid.

f) Water-dispersible granules are also obtained by homogenizing and precomminuting 25 parts by weight of a compound of the formula (I),
5 parts by weight of sodium 2,2'-dinaphthylmethane-6,6'-disulfonate,
2 parts by weight of sodium oleoylmethyltaurinate,
1 part by weight of polyvinyl alcohol,
17 parts by weight of calcium carbonate and
50 parts by weight of water
on a colloid mill, subsequently grinding the mixture in a bead mill and atomizing and drying the resulting suspension in a spray tower by means of a single-substance nozzle.

(C) BIOLOGICAL EXAMPLES

1. Herbicidal Pre-emergence Action

Seeds of monocotyledonous and dicotyledonous weed plants and crop plants are placed in wood-fiber pots in sandy loam and covered with soil. The compounds (I) according to the invention, formulated in the form of wettable powders (WP), are then applied as aqueous suspension or emulsion at a water application rate of 600 l/ha (converted) with the addition of 0.2% of wetting agent to the surface of the covering soil.

After the treatment, the pots are placed in a greenhouse and kept under good growth conditions for the test plants. After about 3 weeks, the effect of the preparations is scored visually in comparison with untreated controls as percentages. For example, 100% activity=the plants have died, 50% herbicidal activity or damage=the plants have been reduced by 50% or the plant mass has been reduced by 50%, 0% activity=like control plants.

Compounds (I) according to the invention, such as, for example, the compounds Nos. 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 53, 54, 55, 83, 84, 85, 86, 87, 107, 108, 109, 111, 112, 162, 174, 208, 227, 283, 326, 329, 330, 339, 340, 343, 344, 358, 359 and 390 from Table 1, have good herbicidal activity against a plurality of harmful plants at an application rate of 320 g or less of active substance per hectare when applied by the pre-emergence method. For example, these compounds have very good activity (90-100%) against harmful plants such as *Alopecurus myosuroides*, *Echinochloa crus galli* and *Setaria viridis* when applied by the pre-emergence method at an application rate of 0.32 kg of active substance per hectare.

Moreover, the compounds Nos. 1, 2, 3, 4, 5, 6, 8, 10, 12, 13, 16, 17, 18, 20, 21, 22, 23, 24, 25, 26, 27, 28, 29, 31, 53, 54, 83, 84, 85, 86, 87, 108, 109, 162, 174, 283, 326, 329, 330, 339, 340, 343, 344, 345, 358 and 359 have very good herbicidal activity (90-100%) against harmful plants such as *Lolium multiflorum* and *Veronica persica* when applied by the pre-emergence method at an application rate of 0.32 kg of active substance per hectare.

Moreover, the compounds Nos. 2, 3, 4, 5, 6, 8, 9, 10, 11, 12, 13, 15, 17, 18, 20, 21, 22, 23, 24, 25, 26, 29, 31, 53, 54, 83, 84, 85, 86, 87, 108, 109, 111, 162, 174, 208, 227, 283, 326, 329, 330, 339, 340, 343, 344, 345, 358, 359 and 390 have very good herbicidal activity (90-100%) against harmful plants such as *Amaranthus retroflexus* when applied by the pre-emergence method at an application rate of 0.32 kg of active substance per hectare.

Moreover, the compounds Nos. 2, 3, 5, 6, 8, 13, 17, 18, 20, 21, 22, 23, 24, 25, 28, 83, 84, 85, 87, 108, 162, 174, 227, 283, 326, 329, 330, 340, 343, 344, 345, 358 and 359 have very good herbicidal activity (90 to 100%) against harmful plants such as *Avena fatua* when applied by the pre-emergence method at an application rate of 0.32 kg of active substance per hectare.

Moreover, the compounds Nos. 1, 2, 3, 5, 6, 8, 10, 13, 16, 17, 19, 20, 21, 22, 23, 24, 25, 26, 29, 30, 31, 54, 83, 84, 85, 87, 109, 111, 162, 174, 208, 227, 283, 330, 340, 343, 344, 345, 358, 359 and 390 have very good herbicidal activity (90 to 100%) against harmful plants such as *Polygonum convolvulus* when applied by the pre-emergence method at an application rate of 0.32 kg of active substance per hectare.

Moreover, the compounds Nos. 1, 2, 3, 5, 8, 10, 13, 17, 19, 20, 21, 22, 24, 25, 26, 27, 29, 31, 53, 54, 83, 84, 85, 87, 108, 109, 111, 162, 174, 283, 330, 340, 343, 344, 345, 358 and 359 have very good herbicidal activity (90 to 100%) against harmful plants such as *Stellaria media* when applied by the pre-emergence method at an application rate of 0.32 kg of active substance per hectare.

In general, the active compounds mentioned and other active compounds of Table 1 even have a substantially broader activity spectrum 2. Herbicidal Post-emergence Action Seeds of monocotyledonous and dicotyledonous weed and crop plants are placed in sandy loam in wood-fiber pots, covered with soil and cultivated in a greenhouse under good growth conditions. 2 to 3 weeks after sowing, the test plants are treated at the one-leaf stage, where the compounds (I) according to the invention, formulated in the form of wettable powders (WP), are applied by spraying as aqueous suspension or emulsion at a water application rate of 600 l/ha (converted) with the addition of 0.2% of wetting agent to the green parts of the plants. After the test plants have been kept in the greenhouse under optimum growth conditions for about 3 weeks, the activity of the preparations is rated visually in comparison to untreated controls in percent (%): For example, 100% activity=the plants have died, 50% herbicidal activity or damage=the plants have been reduced by 50% or the plant mass has been reduced by 50%, 0% activity=like control plants.

As shown by the results, the compounds (I) according to the invention, such as, for example, the compounds Nos. 1, 2, 3, 5, 6, 7, 8, 9, 10, 13, 15, 16, 17, 18, 19, 20, 21, 22, 23, 24, 25, 26, 29, 30, 83, 84, 87, 108, 109, 111, 112, 162, 174, 208, 283, 326, 329, 358, 359, 330, 339, 340, 343, 344, 345, 359 and 390 from Table 1, have very good herbicidal activity (90-100%) against harmful plants such as *Echinochloa crus galli* when applied by the post-emergence method at an application rate of 0.32 kg of active substance per hectare.

Moreover, the compounds Nos. 1, 2, 5, 6, 7, 10, 13, 16 18, 23, 24, 25, 26, 29, 30, 53, 54, 174, 283, 329, 339, 340 and 345 from Table 1, for example, have very good herbicidal activity (90 to 100%) against harmful plants such as *Lolium multiflorum* when applied by the post-emergence method at an application rate of 0.32 kg of active substance per hectare.

Moreover, the compounds Nos. 5, 6, 7, 8, 9, 10, 18, 19, 20, 21, 22, 25, 29, 53, 54, 55, 108, 109, 111, 208, 329, 339, 340, 343, 344, 345 and 359 from Table 1, for example, have very good herbicidal activity (90 to 100%) against harmful plants such as *Setaria viridis* when applied by the post-emergence method at an application rate of 0.32 kg of active substance per hectare.

Moreover, the compounds Nos. 1, 3, 6, 8, 9, 10, 15, 18, 23, 24, 25, 26, 27, 28, 29, 30, 162, 174, 339, 340, 341, 344, 345 and 359 from Table 1, for example, have very good herbicidal activity (90 to 100%) against harmful plants such as *Alopecurus myosuroides* when applied by the post-emergence method at an application rate of 0.32 kg of active substance per hectare.

Moreover, the compounds Nos. 1, 5, 6, 7, 8, 10, 15, 18, 21, 23 25, 26, 27, 29, 339, 340, 344, 345 and 358 from Table 1, for example, have very good herbicidal activity (90 to 100%) against harmful plants such as *Veronica persica* when applied by the post-emergence method at an application rate of 0.32 kg of active substance per hectare.

In general, the active compounds mentioned and other active compounds of Table 1 even have a substantially broader activity spectrum.

3. Herbicidal Action and Crop Plant Compatibility 3.1 In further trails in the greenhouse, seeds of crop plants are placed in pots in sandy loam soil, covered with soil and cultivated under good growth conditions and treated by the pre-emergence method and scored analogously to the harmful plants in section 1. The results show that the compounds according to the invention do not cause any damage to dicotyledonous crops such as soybeans, cotton, oilseed rape, sugar beet and potatoes when applied by the pre-emergence method, even at high dosages of active compound. In addition, some substances spare graminaceous crops such as barley, wheat, rye, sorghum millets, corn or rice.

For example, the compounds Nos. 1, 2, 3, 4, 7, 9, 11, 13, 19, 20 and 23 of Table 1 show selectivity in corn (no damage or less than 30% damage) when applied by the pre-emergence method at 320 g/ha. With respect to the herbicidal action at 320 g/ha mentioned in section 1, the compounds are suitable for controlling unwanted vegetation in corn crops when applied by the pre-emergence method.

For example, the compounds Nos. 1, 15 and 27 of Table 1 show selectivity in wheat (no damage or less than 30% damage) when applied by the pre-emergence method at 320 g/ha. With respect to the herbicidal action at 320 g/ha mentioned in section 1, the compounds are suitable for controlling unwanted vegetation in cereal crops when applied by the pre-emergence method.

For example, the compounds Nos. 19, 29, 30 and 55 of Table 1 show selectivity in oilseed rape (no damage or less than 30% damage) when applied by the pre-emergence method at 320 g/ha. With respect to the herbicidal action at 320 g/ha mentioned in section 1, the compounds are suitable for controlling unwanted vegetation in oilseed rape crops when applied by the pre-emergence method.

3.2 In further trials in the greenhouse, seeds of crop plants and seeds of harmful plants are placed in pots in sandy loam soil, covered with earth and cultivated under good growth conditions. The compounds (I) according to the invention, formulated in the form of wettable powders (WP), are then applied as aqueous suspension or emulsion at a water application rate of 300 l/ha (converted) with the addition of 0.2% of wetting agent to the surface of the covering soil. After the test plants have been kept in the greenhouse under optimum growth conditions for about 4 weeks, the activity of the preparations is rated visually in comparison to untreated controls in percent (%): For example, 100% activity=the plants have died, 50% herbicidal activity or damage=the plants have been reduced by 50% or the plant mass has been reduced by 50%, 0% activity=like control plants.

The results show that the compounds (I) can be used effectively for controlling harmful plants in dicotyledonous crops such as soybeans, cotton, oilseed rape, sugar beet and potatoes and also graminaceous crops such as barley, wheat, rye, sorghum millets, corn or rice when applied by the pre-emergence method.

For example, the compounds Nos. 1, 4, 6, 8 and 10 of Table 1 show selectivity in wheat (no damage or less than 10% damage) when applied by the pre-emergence method at 80 g/ha, and at the same time have good to very good herbicidal activity (75 to 100%) against harmful plants such as *Alopecurus myosuroides, Lolium multiflorum* and *Amaranthus retroflexus*.

For example, the compounds Nos. 1, 6, 7, 8, 10, 11 and 111 of Table 1 show selectivity in wheat (no damage or less than 10% damage) when applied by the pre-emergence method at 80 g/ha, and at the same time have good to very good herbicidal activity (75 to 100%) against harmful plants such as *Echinochloa crus-galli, Setaria viridis* and *Veronica persica*.

In addition, the compounds Nos. 1, 4, 6, 14, 15 and 111 from Table 1 show selectivity in wheat (no damage or less than 10% damage) when applied by the pre-emergence method at 80 g/ha, and at the same time have good to very good herbicidal activity (75 to 100%) against harmful plants such as *Echinochloa crus-galli, Setaria viridis* and *Viola tricolor*.

For example, the compounds Nos. 1, 7, 11, 13, 19, 29, 30, 55, 85 and 87 of Table 1 show selectivity in oilseed rape (no damage or less than 10% damage) when applied by the pre-emergence method at 80 g/ha, and at the same time have good to very good herbicidal activity (75 to 100%) against harmful plants such as *Echinochloa crus-galli, Setaria viridis* and *Veronica persica*.

For example, the compounds Nos. 1, 7, 11, 13, 85 and 87 of Table 1 show selectivity in oilseed rape (no damage or less than 10% damage) when applied by the pre-emergence method at 80 g/ha, and at the same time have good to very good herbicidal activity (75 to 100%) against harmful plants such as *Alopecurus myosuroides*.

For example, the compounds Nos. 1, 2, 3, 4, 5, 9, 11, 13, 14, 23, 27, 29 and 162 of Table 1 show selectivity in corn (no damage or less than 10% damage) when applied by the pre-emergence method at 80 g/ha, and at the same time have good to very good herbicidal activity (75 to 100%) against harmful plants such as *Alopecurus myosuroides*.

For example, the compounds Nos. 1, 2, 3, 4, 5, 9, 11, 13, 14, 19, 23, 27, 29, 30, 31, 111, 162, 227 and 339 of Table 1 show selectivity in corn (no damage or less than 10% damage) when applied by the pre-emergence method at 80 g/ha, and at the same time have good to very good herbicidal activity (75 to 100%) against harmful plants such as *Echinochloa crus-galli* and *Setaria viridis*.

Furthermore, the compounds Nos. 1, 2, 23 and 29 of Table 1 show selectivity in corn (no damage or less than 10% damage) when applied by the pre-emergence method at 80 g/ha, and at the same time have good to very good herbicidal activity (75 to 100%) against harmful plants such as *Lolium multiflorum, Amaranthus retroflexus* and *Veronica persica*.

For example, the compounds Nos. 1, 2, 3, 5, 7, 9, 11, 12, 13, 18, 19, 20, 22, 23 and 174 of Table 1 show selectivity in corn (0-20% damage) when applied by the pre-emergence method at 50-62 g/ha. At these application rates, the compounds have good to very good herbicidal activity (75 to 100%) against harmful plants such as *Brachiaria platyphylla, Echinochloa crus-galli, Eleusine indica, Setaria faberi, Setaria viridis* and *Sorghum halepense* when applied by the pre-emergence method. Accordingly, the compounds are suitable for controlling unwanted vegetation in corn crops when applied by the pre-emergence method.

For example, the compounds Nos. 1, 2, 3, 5, 7, 11, 12, 13 and 20 of Table 1 also show selectivity in soybeans (0-20% damage) when applied by the pre-emergence method at 50-62 g/ha. At these application rates, the compounds have good to very good herbicidal activity (75 to 100%) against harmful plants such as *Brachiaria platyphylla, Echinochloa crus-galli, Eleusine indica, Setaria faberi, Setearia viridis* and *Sorghum halepense* when applied by the pre-emergence method. Accordingly, the compounds are suitable for controlling unwanted vegetation in soybeans when applied by the pre-emergence method.

Comparative Test (Pre-emergence Method):

When applied by the pre-emergence method according to the first paragraph of section 3.2 at an application rate of 80 g/ha, the compound of example No. 1 of Table 1 (a threo-2 enantiomer) has an activity of 80 to 100% against harmful plants such as *Alopecurus myosuroides, Avena fatua, Echinochloa crus-galli, Lolium multiflorum, Setaria virides, Amaranthus retroflexus, Polygonum convolvulus, Veronica persica* and *Viola tricolor*, and at the same time very good selectivity in wheat (0% damage). In contrast, the corresponding erythro/threo mixture (erythro:threo in a weight ratio of 64:36) of the compound No. 1 shows, at the same application rate of 80 g/ha, hardly any herbicidal activity against the harmful plants mentioned, i.e. 30 to 50% activity against harmful plants such as *Echinochloa crus-galli, Setaria virides* and *Viola tricolor* and 0% activity against the other harmful plants mentioned.

The test example shows that the threo-2 isomer according to the invention is not only more active than the corresponding diastereomer mixture but, in contrast to indications from EP-0005341, may, surprisingly, also be used for the selective control of weeds.

3.3 In further trials in the greenhouse, seeds of crop plants and seeds of harmful plants are placed in pots in sandy loam soil, covered with earth and cultivated under good growth conditions. The test plants are treated at the 2-3-leaf stage, where the compounds (I) according to the invention, formulated in the form of wettable powders (WP), are applied by spraying as aqueous suspension or emulsion at a water application rate of 300 l/ha (converted) with the addition of 0.2% of wetting agent to the green parts of the plants. 4 weeks after the treatment and after the test plants have been kept in the greenhouse under optimum growth conditions, the activity of the preparations is rated visually in comparison to untreated controls in percent (%): For example, 100% activity=the plants have died, 50% herbicidal activity or damage=the plants have been reduced by 50% or the plant mass has been reduced by 50%, 0% activity=like control plants.

The results show that the compounds (I) can be used effectively for controlling harmful plants in dicotyledonous crops such as soybeans, cotton, oilseed rape, sugar beet and potatoes and also graminaceous crops such as barley, wheat, rye, sorghum millets, corn or rice when applied by the post-emergence method.

For example, the compounds Nos. 1, 13 and 20 of Table 1 show selectivity in corn (0-30% damage) when applied by the post-emergence method at 100 g/ha. At these application rates, the compounds have good to very good herbicidal activity (70 to 95%) against harmful plants such as *Echinochloa crus-galli, Setaria faberi, Setaria viridis, Sorghum halepense, Euphorbia heterophylla, Solanum nigrum* and *Polygonum convolvulus* when applied by the post-emergence method. Accordingly, the compounds are suitable for controlling unwanted vegetation in corn crops when applied by the post-emergence method.

Furthermore, the compounds Nos. 1, 2, 3, 5, 6, 8, 11, 12, 13, 18, 19, 20 and 23 of Table 1 show selectivity in soybeans (0-30% damage) when applied by the pre-emergence method at 100 g/ha. At these application rates, the compounds have good to very good herbicidal activity (70 to 99%) against harmful plants such as *Echinochloa crus-galli, Setaria* spp., *Sorghum halepense, Solanum nigrum* and *Polygonum convolvulus* when applied by the post-emergence method. Accordingly, the compounds are suitable for controlling unwanted vegetation in soybean crops when applied by the post-emergence method.

In addition, the compounds Nos. 1 and 20 of Table 1 show selectivity in corn (no damage or less than 10% damage) when applied by the post-emergence method at 80 g/ha, and at the same time have good to very good herbicidal activity (75 to 100%) against harmful plants such as *Avena fatua, Echinochloa crus-galli* and *Veronica persica*.

The compounds Nos. 1, 4, 19, 21, 26, 27, 55, 85, 86, 87, 111, 112 and 208 of Table 1 also show selectivity in rice (no damage or less than 20% damage) when applied by the post-emergence method at 80 g/ha, and at the same time have good to very good herbicidal activity (75 to 100%) against harmful plants such as *Echinochloa crus-galli*.

Comparative Test (Post-Emergence Method):

When applied by the post-emergence method according to the first paragraph of section 3.3 at an application rate of 80 g/ha, the compound of example No. 86 of Table 1 (a threo-2 enantiomer) shows good herbicidal activity of 70 to 90% against harmful plants such as *Avena fatua* (90%), *Echinochloa crus-galli* (80%), *Setaria virides* (80%), *Polygonum convolvulus* (80%), *Veronica persica* (70%) and *Viola tricolor* (80%), and at the same time good selectivity in wheat (up to 10% damage), rice (up to 10% damage) and oilseed rape (0% damage).

In contrast, the erythro/threo mixture (erythro:threo in a weight ratio of 58:42) corresponding to the compound No. 86 shows, at the same application rate of 80 g/ha, an overall weaker herbicidal activity against the harmful plants mentioned, i.e. *Avena fatua* (40%), *Echinochloa crus-galli* (80%), *Setaria virides* (80%), *Polygonum convolvulus* (60%), *Veronica persica* (0%) and *Viola tricolor* (10%), and at the same time surprisingly poorer selectivity in wheat (80% damage) and oilseed rape (20% damage).

The test example shows that the threo-2 isomer according to the invention is not only more active than the corresponding diastereomer mixture but, in contrast to indications from EP-0005341, may, surprisingly, also be employed with better results for the selective control of weeds.

The invention claimed is:

1. A 4-cyano-3,4-diphenylbutanoate compound of formula (I) and/or a salt thereof, in each case in the optically active (3R,4R)-threo form,

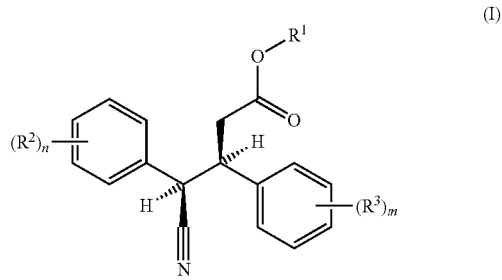

in which
R$^1$ is hydrogen or a hydrolyzable radical,
(R$^2$)$_n$ is n substituents R$^2$, where each of the substituents R$^2$ independently is halogen, cyano, nitro, (C$_1$-C$_8$)-alkyl, (C$_1$-C$_8$)-alkoxy, (C$_1$-C$_8$)-alkylthio, (C$_1$-C$_8$)-alkylsulfinyl, (C$_1$-C$_8$)-alkylsulfonyl, (C$_1$-C$_6$)-haloalkyl, (C$_1$-C$_6$)- haloalkoxy, $(C_1-C_6)$-haloalkylthio, $(C_1-C_6)$-haloalkylsulfinyl, $(C_1-C_6)$-haloalkylsulfonyl, $(C_2-C_6)$-alkenyl, $(C_2-C_6)$-alkynyl, tri-$[(C_1-C_4)$-alkyl]-silyl or tri-$[(C_1-C_4)$-alkyl]-silyl-$(C_1-C_4)$-alkyl or if n is greater than 1,where two groups $R^2$ located ortho at the ring together are optionally a group of the formula —$Z^1$-$A^*$-$Z^2$ in which $A^*$ is an alkylene group having from 1 to 4 carbon atoms which is optionally substituted by at least one radical selected from the group consisting of halogen, $(C_1-C_4)$-alkyl, $(C_1-C_4)$-haloalkyl, $(C_1-C_4)$-alkoxy and $(C_1-C_4)$-haloalkoxy, $Z^1$ is a direct bond, O or S and $Z^2$ is a direct bond, O or S, where the group —$Z^1$-$A^*$-$Z^2$ together with the carbon atoms of the phenyl ring to which they are attached form a fused-on 5- or 6-membered ring, and $(R^3)_m$ is m substituents $R^3$, where each of the substituents $R^3$ independently is halogen, cyano, nitro, $(C_1-C_8)$-alkyl, $(C_1-C_8)$-alkoxy, $(C_1-C_8)$-alkylthio, $(C_1-C_8)$-alkylsulfinyl, $(C_1-C_8)$-alkylsulfonyl, $(C_1-C_6)$-haloalkyl, $(C_1-C_6)$-haloalkoxy, $(C_1-C_6)$-haloalkylthio, $(C_1-C_6)$-haloalkylsulfinyl, $(C_1-C_6)$-haloalkylsulfonyl, $(C_2-C_6)$-alkenyl, $(C_2-C_6)$-alkynyl, NR*R, tri-$[(C_1-C_4)$-alkyl]-silyl or tri-$[(C_1-C_4)$-alkyl]-silyl-$(C_1-C_4)$-alkyl or if m is greater than 1, where two groups $R^3$ located ortho at the ring together are optionally a group of the formula —$Z^3$-$A^{}$-$Z^4$ in which $A^{}$ is an alkylene group having from 1 to 4 carbon atoms which is optionally substituted by at least one radical selected from the group consisting of halogen, $(C_1-C_4)$-alkyl, $(C_1-C_4)$-haloalkyl, $(C_1-C_4)$-alkoxy and $(C_1-C_4)$-haloalkoxy, $Z^3$ is a direct bond, O or S and $Z^4$ is a direct bond, O or S, where the group —$Z^3$-$A^{}$-$Z^4$ together with the carbon atoms of the phenyl ring to which they are attached form a fused-on 5- or 6-membered ring, R* and R** each independently are H, $(C_1-C_8)$-alkyl, $(C_2-C_8)$-alkenyl, $(C_2-C_8)$-alkynyl, $(C_1-C_4)$-alkoxy-$(C_1-C_4)$-alkyl, $(C_1-C_6)$-alkanoyl, $[(C_1-C_4)$-haloalkyl]-carbonyl, $[(C_1-C_4)$-alkoxy]-carbonyl, or $[(C_1-C_4)$-haloalkoxy]-carbonyl, or are optionally substituted $(C_3-C_6)$-cycloalkyl, $(C_3-C_6)$-cycloalkyl-$(C_1-C_4)$-alkyl, phenyl, phenyl-$(C_1-C_4)$-alkyl that is optionally substituted in the cycle by at least one identical or different radical $R^{bb}$ or R* and R** together with the nitrogen atom to which they are attached are a 3-to 8-membered heterocycle which, in addition to the nitrogen atom, optionally contain one or two further ring heteroatoms selected from the group consisting of N, O and S and which are unsubstituted or substituted by at least one radical from the group consisting of $(C_1-C_4)$-alkyl, $(C_1-C_4)$-haloalkyl and oxo, $R^{bb}$ in each case independently is halogen, $(C_1-C_4)$-alkyl, $(C_1-C_4)$-haloalkyl, $(C_1-C_4)$-alkoxy or $(C_1-C_4)$-haloalkoxy or in the case of saturated or partially unsaturated cyclic base groups is optionally oxo, and n and m are each independently of one another 0, 1, 2, 3, 4 or 5, optionally 0, 1, 2 or 3, with the proviso that n and m are not simultaneously 0, where the stereochemical configuration at the carbon atom in position 3 of the 4-cayano-3,4-diphenylbutanoate compound has a stereochemical purity of from 60 to 100% (R), optionally from 70 to 100% (R), or optionally from 80 to 100% (R), or even optionally from 90 to 100% (R), based on a mixture of threo enantiomers present, and the stereochemical configuration at the carbon atom in position 4 of the 4-clano-3,4-diphenylbutanoate compound has a stereochemical purity of from 60 to 100% (R), optionally from 70 to 100% (R), or optionally from 80 to 100% (R), or even optionally from 90 to 100% (R), based on a mixture of threo enantiomers present.

2. The compound and/or a salt thereof as claimed in claim 1, wherein $R^1$ is hydrogen, or $R^1$ is a hydrolyzable optionally substituted hydrocarbon radical or optionally substituted heterocyclyl radical, where each of the carbon-containing radicals, including any substituent attached thereto, has from 1 to 30 carbon atoms, optionally from 1 to 24 carbon atoms, or optionally 1 to 20 carbon atoms, or $R^1$ is a hydrolysable radical of the formula Si$R2^aR^bR^c$, —NR$^a$R$^b$ or —N=CR$^c$R$^d$, where each of the radicals $R^a$, $R^b$, $R^c$ and $R^d$ independently of the others is hydrogen or an optionally substituted hydrocarbon radical, where, however, SiR$^a$R$^b$R$^c$ is not SiH$_3$, or $R^a$ and $R^b$ together with the nitrogen atom to which they are attached are a 3- to 9-membered heterocycle which, in addition to the nitrogen atom, optionally contains one or two further ring heteroatoms selected from the group consisting of N, O and S and which is unsubstituted or substituted, or $R^c$ and $R^d$ together with the carbon atom to which they are attached are a 3- to 9-membered carbocyclic radical or a heterocyclic radical which optionally contains from 1 to 3 ring heteroatoms selected from the group consisting of N, O and S, where the carbocyclic or heterocyclic radical is unsubstituted or substituted, where each of the radicals $R^a$, $R^b$, $R^c$ and $R^d$, including any substituents attached thereto, has not more than 30 carbon atoms, to optionally not more then 24 carbon atoms, or optionally not more than 20 carbon atoms, or $R^1$ is a hydroyxable radical of the formula —C(=O)—$R^e$ or —P(=O)(R$^f$)$_2$, where R$^e$ and the R$^f$ independently of one another are each hydrogen, OH, $(C_1-C_8)$-alkyl, $(C_1-C_4)$-haloalkyl, $(C_2-C_8)$-alkenyl, $(C_2-C_8)$-alkynyl, $(C_1-C_6)$-alkoxy, $(C_1-C_6)$-alkoxy-$(C_1-C_8)$-alkyl, $(C_1-C_4)$-haloalkoxy, $(C_1-C_4)$-haloalkoxy-$(C_1-C_8)$-alkyl, $(C_3-C_8)$-alkenyloxy, $(C_3-C_8)$-alkenyloxy-$(C_1-C_8)$-alkyl, $(C_3-C_8)$-alkynyloxy, $(C_3-C_8)$-alkynyloxy-$(C_1-C_8)$-alkyl, —NR*R**, tri-$[(C_1-C_4)$-alkyl]-silyl, or tri-$[(C_1-C_4)$-alkyl]-silyl-$(C_1-C_8)$-alkyl, or independently of one another are each potionally substituted $(C_3-C_6)$-cycloalkyl, $(C_3-C_6)$-cycloalkyl-$(C_1-C_8)$-alkyl, $(C_5-C_6)$-cycloalkenyl, $(C_5-C_6)$-cycloalkenyl-$(C_1-C_8)$-alkyl, $(C_5-C_6)$-cycloalkynyl, $(C_5-C_6)$-cycloalkynyl-$(C_1-C_8)$-alkyl, phenyl, phenyl-$(C_1-C_8)$-alkyl, phenoxy, phenoxy-$(C_1-C_8)$-alkyl, phenylamino, phenylamino-$(C_1-C_8)$-alkyl, a radical Het$^1$, Het$^1$-$(C_1-C_6)$-alkyl or Het$^1$—O—$(C_1-C_6)$-alkyl that is unsubstituted in the acyclic moiety or substituted by at least one identical or different radical $R^A$ and is unsubstituted in the cyclic moiety or substituted by at least one identical or different radical $R^B$, Het$^1$ in each case independently is a saturated, partially unsaturated or heteroaromatic monocyclic heterocyclyl radical having from 3 to 9 ring atoms or a 9-or 10-membered bicyclic heterocycle, each containing 1, 2, 3 or 4 heteroatoms selected from the group consisting of O, N and S, R* and R** each independently are H, $(C_1-C_8)$-alkyl, $(C_2-C_8)$-alkenyl, $(C_2-C_8)$-alkynyl, $(C_1-C_4)$-alkoxy-$(C_1-C_4)$-alkyl, $(C_1-C_6)$-alkanoyl, $[(C_1-C_4)$-haloalkyl]-carbonyl,

[($C_1$-$C_4$)-alkoxy]-carbonyl, or [($C_1$-$C_4$)-haloalkoxy]-carbonyl, or are optionally substited ($C_3$-$C_6$)-cycloalkyl, ($C_3$-$C_6$-cycloalkyl-($C_1$-$C_4$)-alkyl, phenyl, or phenyl-($C_1$-$C_4$)-alkyl that is optionally substituted in the cycle by at least one identical or different radical $R^{bb}$ or R* and R** together with the nitrogen atom to which they are attached are a 3- to 8-membered heterocycle which, in addition to the nitrogen atom, optionally contains one or two further ring heteroatoms selected from the group consisting of N, O and S and which are unsubstituted or substituted by at least one radical selected from the group consisting of ($C_1$-$C_4$)-alkyl, ($C_1$-$C_4$)-haloalkyl and oxo, $R^A$ is halogen, cyano, hydroxyl or ($C_1$-$C_6$)-alkoxy, $R^B$ is halogen, cyano, hydroxyl, oxo, nitro, ($C_1$-$C_8$)-alkyl, ($C_1$-$C_6$)-haloalkyl, cyano-($C_1$-$C_6$)-alkyl, hydroxy-($C_1$-$C_6$)-alkyl, nitro-($C_1$-$C_6$)-alkyl, ($C_2$-$C_8$)-alkenyl, ($C_2$-$C_8$)-haloalkenyl, ($C_2$-$C_8$)-alkynyl, ($C_2$-$C_8$)-haloalkynyl, ($C_1$-$C_8$)-alkoxy, ($C_2$-$C_8$)-alkenyloxy, ($C_2$-$C_8$)-alkynyloxy, ($C_1$-$C_8$)-haloalkoxy, ($C_1$-$C_6$)-alkoxy-($C_1$-$C_6$)-alkyl, ($C_1$-$C_6$)-alkoxy-($C_1$-$C_4$)-alkoxy, ($C_1$-$C_6$)-haloalkoxy-($C_1$-$C_4$)-alkyl, ($C_1$-$C_6$)-haloalkoxy-($C_1$-$C_4$)-alkoxy, ($C_1$-$C_8$)-alkylthio, ($C_2$-$C_6$)-alkenylthio, ($C_2$-$C_6$)-alkynylthio, ($C_1$-$C_8$)-alkylsulfinyl, ($C_1$-$C_6$)-haloalkylsulfinyl, ($C_1$-$C_8$)-alkylsulfonyl, ($C_1$-$C_6$)-haloalkylsulfonyl, a radical of the formula $R^{aa}$—C(=O)—, $R^{aa}$—C(=O)—($C_1$-$C_6$)-alkyl, —NR*R**, tri-[($C_1$-$C_4$)-alkyl]-silyl, or tri-[($C_1$-$C_4$)-alkyl]-silyl-($C_1$-$C_6$)-alkyl, or is optionally substituted ($C_3$-$C_8$)-cycloalkyl, ($C_3$-$C_8$)-cycloalkoxy, ($C_3$-$C_8$)-cycloalkyl-($C_1$-$C_8$)-alkyl, ($C_3$-$C_8$)-cycloalkyl-($C_1$-$C_8$)-alkoxy, phenyl, phenyl-($C_1$-$C_8$)-alkyl, phenoxy, phenoxy-($C_1$-$C_8$)-alkyl, phenylamino, phenylamino-($C_1$-$C_8$)-alkyl or a 5- or 6-membered monocyclic or 9- or 10-membered bicyclic heterocycle which contains 1, 2, 3 or 4 heteroatoms selected from the group consisting of O, N and S, that is optionally substituted in the cyclic moiety by at least one identical or different radical $R^{bb}$, $R^{aa}$ in each case independently of the others is hydrogen, OH, ($C_1$-$C_8$)-alkyl, ($C_1$-$C_6$)-haloalkyl, ($C_2$-$C_8$)-alkenyl, ($C_2$-$C_8$)-alkynyl, ($C_1$-$C_8$)-alkoxy, ($C_1$-$C_6$)-alkoxy-($C_1$-$C_6$)-alkyl, ($C_1$-$C_6$)-alkoxy-($C_1$-$C_6$)-alkyloxy, ($C_1$-$C_6$)-haloalkoxy, ($C_1$-$C_6$)-haloalkoxy-($C_1$-$C_6$)-alkyl, ($C_1$-$C_6$)-haloalkoxy-($C_1$-$C_6$)-alkoxy, ($C_3$-$C_8$)-alkenyloxy, ($C_3$-$C_8$)-alkenyloxy-($C_1$-$C_6$)-alkyl, ($C_3$-$C_8$)-alkenyloxy-($C_1$-$C_6$)-alkoxy, ($C_3$-$C_8$)-alkynyloxy, ($C_3$-$C_8$)-alkynyloxy-($C_1$-$C_6$)-alkyl, ($C_3$-$C_8$)-alkynyloxy-($C_1$-$C_6$)-alkoxy, —NR*R*, tri-[($C_1$-$C_4$)-alkyl]-silyl, tri-[($C_1$-$C_4$)-alkyl]-silyl-($C_1$-$C_6$)-alkyl, or tri-[($C_1$-$C_4$)-alkyl]-silyl-($C_1$-$C_6$)-alkoxy, or is optionally substituted ($C_3$-$C_8$)-cycloalkyl, ($C_3$-$C_8$)-cycloalkoxy, ($C_3$-$C_8$)-cycloalkyl-($C_1$-$C_8$)-alkyl, ($C_3$-$C_8$)-cycloalkyl-($C_1$-$C_8$)-alkoxy, $C_5$-$C_8$)-cycloalkenyl, ($C_5$-$C_8$)-cycloalkenyl-($C_1$-$C_6$)-alkyl, ($C_5$-$C_8$)-cyclo-alkenyloxy, ($C_5$-$C_8$)-cycloalkynyl, ($C_5$-$C_8$)-cycloalkynyl-($C_1$-$C_6$)-alkyl, ($C_5$-$C_8$)-cycloalkynyl-($C_1$-$C_6$)-alkoxy, phenyl, phenyl-($C_1$-$C_8$)-alkyl, phenyl-($C_1$-$C_8$)-alkoxy, phenoxy, phenoxy-($C_1$-$C_8$)-alkyl, phenoxy-($C_1$-$C_8$)-alkoxy, phenylamino, phenylamino-($C_1$-$C_8$)-alkyl, phenylamino-($C_1$-$C_8$)-alkoxy, phenylamino, phenylamino ($C_1$-$C_8$)-alkyl, phenylamino-($C_1$-$C_8$)-alkoxy or a 5- or a 5- or 6-membered monocyclic or 9-or 10-membered bicyclic heterocycle which is optionally attached via an alkylene group or alkoxy group and contains 1, 2, 3 or 4 heteroatoms selected from the group consisting of O, N and S, that is optionally substituted in the cyclic moiety by at least one identical or different radical $R^{bb}$, and $R^{bb}$ in each case independently of the others is halogen, ($C_1$-$C_4$)-alkyl, ($C_1$-$C_4$)-haloalkyl, ($C_1$-$C_4$)-alkoxy or ($C_1$-$C_4$)-haloalkoxy or in the case of saturated or partially unsaturated cyclic base groups is optionally oxo.

3. The compound and/or a salt thereof as claimed in claim 1, wherein $R^1$ is hydrogen, or $R^1$ is ($C_1$-$C_{18}$)-alkyl, ($C_2$-$C_{18}$)-alkenyl or ($C_2$-$C_{18}$)-alkynyl, where each of the radicals is unsubstituted or substituted by at least one radical selected from the group consisting of the radicals [subgroups (a)-(d)]

(a) halogen, cyano, thio, nitro, hydroxyl, carboxyl, ($C_1$-$C_8$)-alkoxy, ($C_2$-$C_8$)-alkenyloxy, ($C_2$-$C_8$)-alkynyloxy, ($C_1$-$C_8$)-haloalkoxy, ($C_1$-$C_4$)-alkoxy-($C_1$-$C_4$)-alkoxy, ($C_1$-$C_8$)-alkylthio, ($C_2$-$C_8$)-alkenylthio, ($C_2$-$C_8$) alkynylthio, ($C_1$-$C_8$)-haloalkylthio, ($C_2$-$C_8$)-haloalkenylthio, ($C_2$-$C_8$)-haloalkynylthio, ($C_1$-$C_8$)-alkylsulfinyl, ($C_2$-$C_8$)-alkenylsulfinyl, ($C_2$-$C_8$)-alkynylsulfinyl, ($C_1$-$C_8$)-haloalkylsulfinyl, ($C_2$-$C_8$)-haloalkenylsulfinyl, ($C_2$-$C_8$)-haloalkynylsulfinyl, ($C_1$-$C_8$)-alkylsulfonyl, ($C_2$-$C_8$)-alkenylsulfonyl, ($C_2$-$C_8$)-alkynylsulfonyl, ($C_1$-$C_8$)-haloalkylsulfonyl, ($C_2$-$C_8$)-haloalkenylsulfonyl, ($C_2$-$C_8$)-haloalkynylsulfonyl, radicals of the formula —NR*R**, and a cyclic moiety selected from the group consisting of optionally substituted ($C_3$-$C_8$)-cyclo-alkyl, ($C_5$-$C_8$)-cycloalkenyl, ($C_5$-$C_8$)-cycloalkynyl, ($C_3$-$C_8$)-cycloalkyl-($C_1$-$C_6$)-alkoxy, ($C_3$-$C_8$)-cycloalkyl-($C_1$-$C_6$)-alkyl-S(O)$_p$—, ($C_5$-$C_8$)-cycloalkenyl-($C_1$-$C_6$)-alkoxy, ($C_5$-$C_8$)-cycloalkenyl-($C_1$-$C_6$)-alkyl-S(O)$_p$—, ($C_5$-$C_8$)-cycloalkynyl-($C_1$-$C_6$)-alkoxy, ($C_5$-$C_8$)-cycloalkynyl-($C_1$-$C_6$)-alkyl-S(O)$_p$—, ($C_3$-$C_8$)-cycloalkoxy, ($C_3$-$C_8$)-cycloalkyl-S(O)$_p$—, ($C_5$-$C_8$)-cycloalkenyloxy, ($C_5$-$C_8$)-cycloalkenyl-S(O)$_p$-,($C_5$-$C_8$)-cycloalkynyloxy, ($C_5$-$C_8$)-cycloalkynyl-S(O)$_p$—, ($C_3$-$C_8$)-cycloalkoxy-($C_1$-$C_6$)-alkoxy, ($C_3$-$C_8$)-cycloalkoxy-($C_1$-$C_6$)-alkyl S(O)$_p$—, phenyl, phenyl-($C_1$-$C_6$)-alkoxy, phenoxy, phenyl-S(O)$_p$—, phenyl-($C_1$-$C_6$)-alkyl-S(O)$_p$—, phenoxy-($C_1$-$C_6$)-alkoxy, phenoxy-($C_1$-$C_6$)-alkyl-S(O)$_p$—, a radical Het$^1$, Het$^1$-S(O)$_p$—, Het$^1$-($C_1$-$C_6$)-alkoxy, Het$^1$—O—, Het$^1$—O—($C_1$-$C_6$)-alkoxy that is unsubstituted in the acyclic moiety or substituted by at least one identical or different radical $R^A$ and is unsubstituted in the cyclic moiety or substituted by at least one identical or different radical $R^B$ and p is in each case independently of the others 0, 1 or 2, (b) a radical of the formulae —C(=O)—R$^C$, —C(=O)—O—R$^C$, —O—C(=O)—R$^C$, —O—C(=O)—O—R$^C$, —C(=O)—S—R$^C$, —C(=S)—S—R$^C$, —C(=S)—S—R$^C$, —C(=O)—NR*R**, —C(=O)—O—NR*R**, —O—C(=O)—NR*R**, —N(R*)—C(=O)—R$^C$, —N(R*)—C(=O)—NR*R**, —N(R*)—C(=O)—O—R$^C$, —P(=O)(R$^C$)(R$^D$), —P(=O)(OR$^C$)(R$^D$), —P(=O)(OR$^C$)(OR$^D$) or —O—P(=O)(OR$^C$)(OR$^D$), (c) a radical of the formulae —SiR'$_3$, —O—SiR'$_3$, (R')$_3$Si—($C_1$-$C_6$)-alkoxy, —CO—O—NR'$_2$, —O—N=CR'$_2$, —N=CR'$_2$, —O—NR'$_2$, —CH(OR')$_2$ and —O—(CH$_2$)$_q$—CH(OR')$_2$, in which each of the radicals R' independently of the others is H, ($C_1$-$C_4$)-alkyl or phenyl, which is unsubstituted or substituted by at least one radical selected from the group consisting of halogen, ($C_1$-$C_4$)-alkyl, ($C_1$-$C_4$)-alkoxy, ($C_1$-$C_4$)-haloalkyl, ($C_1$-$C_4$)-haloalkoxy and nitro or at two adjacent positions by a $(C_2-C_6)$-alkylene bridge, and q is an integer from 0 to 6, and
  (d) radical of the formula R"O—CHR'"CH(OR")—$(C_1$-$C_6)$-alkoxy, in which each of the radicals R" independently of the others is H or $(C_1-C_4)$-alkyl or together the radicals are a $(C_1-C_6)$-alkylene group and R'" is H or $(C_1-C_4)$-alkyl,
  or
$R^1$ is $(C_3-C_9)$-cycloalkyl, $(C_5-C_9)$-cycloalkenyl, $(C_5-C_9)$-cycloalkynyl or phenyl, where each of the radicals is unsubstituted or substituted by at least one radical selected from the group consisting of radicals [subgroups (a')-(e')]
  (a') halogen, cyano, thio, nitro, hydroxyl, carboxyl, $(C_1-C_8)$-alkyl, $(C_1-C_8)$-haloalkyl, $(C_1-C_4)$-alkoxy-$(C_1-C_4)$-alkyl, $(C_2-C_8)$-alkenyl, $(C_2-C_8)$-haloalkenyl, $(C_2-C_8)$-alkynyl, $C_2-C_8)$-haloalkynyl, $(C_1-C_8)$-alkoxy, $(C_2-C_8)$-alkenyloxy, $(C_2-C_8)$-alkynyloxy, $(C_1-C_8)$-haloalkoxy, $(C_1-C_4)$-alkoxy-$(C_1-C_4)$-alkoxy, $(C_1-C_8)$-alkylthio, $(C_2-C_8)$-alkenylthio, $(C_2-C_8)$-alkynylthio and radicals of the formula —NR*R**,
  (b') a radical of the formulae —C(=O)—$R^C$, —C(=O)—O—$R^C$, —O—C(=O)—$R^C$, —O—C(=O)—O—$R^C$, —C(=O)—S—$R^C$, —C(=S)—S—$R^C$, —C(=S)—S—$R^C$, —C(=O)—NR*R**, —C(=O)—O—NR*R**, —O—C(=O)—NR*R**, —N(R*)—C(=O)—$R^C$, —N(R*)—C(=O)—NR*R**, —N(R*)—C(=O)—O—$R^C$, —P(=O)($R^C$)($R^D$), —P(=O)(O$R^C$)($R^D$), P(=O)(O$R^C$)(O$R^D$) or —O—P(=O)(O$R^C$)(O$R^D$),
  (c') a radical of the formulae —SiR'$_3$, —O—SiR'$_3$, (R')$_3$Si—$(C_1-C_6)$-alkoxy, —CO—O—NR'$_2$, —O—N=CR'$_2$, —N=CR'$_2$, —O—NR'$_2$, —CH(OR')$_2$ and —O—(CH$_2$)$_q$—CH(OR')$_2$, in which each of the radicals R' independently of the others is H, $(C_1-C_4)$-alkyl or phenyl, which is unsubstituted or substituted by at least one radical selected from the group consisting of halogen, $(C_1-C_4)$-alkyl, $(C_1-C_4)$-alkoxy, $(C_1-C_4)$-haloalkyl, $(C_1-C_4)$-haloalkoxy and nitro or at two adjacent positions by a $(C_2-C_6)$-alkylene bridge, and q is an integer from 0 to 6, and
  (d') a radical of the formula R"O—CHR'"CH(OR")—$(C_1-C_6)$-alkoxy, in which each of the radicals R" independently of the others is H or $(C_1-C_4)$-alkyl or together the radicals are a $(C_1-C_6)$-alkylene group and R'" is H or $(C_1-C_4)$-alkyl, and
  (e') a radical of the formula Het$^1$ which is unsubstituted or substituted by at least one identical or different radical $R^B$,
  or
$R^1$ is a polycyclic radical based on $(C_3-C_9)$-cycloalkyl, $(C_5-C_9)$-cycloalkenyl, $(C_5-C_9)$-cycloalkynyl or phenyl, where the base ring is fused with a carbocyclic or heterocyclic ring, optionally a 5- or 6-membered ring having 0 or from 1 to 3 ring heteroatoms selected from the group consisting of N, O and S, optionally benzo-fused, and where the base ring or the polycyclic system is unsubstituted or substituted by at least one identical or different radical $R^B$, optionally unsubstituted or substituted by at least one radical selected from the group consisting of halogen, cyano, nitro, hydroxyl, carboxyl, $(C_1-C_6)$-alkyl, $(C_1-C_6)$-haloalkyl, $(C_1-C_4)$-alkoxy-$(C_1-C_4)$-alkyl, $(C_2-C_6)$-alkenyl, $(C_2-C_6)$-haloalkenyl, $(C_2-C_6)$-alkynyl, $(C_2-C_6)$-haloalkynyl, $(C_1-C_6)$-alkoxy, $(C_2-C_6)$-alkenyloxy, $(C_2-C_6)$-alkynyloxy, $(C_1-C_6)$-haloalkoxy, $(C_1-C_4)$-alkoxy-$(C_1-C_4)$-alkoxy, $(C_1-C_6)$-alkylthio, $(C_2-C_6)$-alkenylthio, $(C_2-C_6)$-alkynylthio, $(C_3-C_6)$-cycloalkyl, $(C_3-C_6)$-cycloalkoxy, [$(C_1-C_8)$-alkoxy]-carbonyl, [$(C_1-C_6)$-haloalkoxy]-carbonyl and oxo,
  or
$R^1$ is a heterocyclic radical Het$^1$ which is unsubstituted in the ring or in the polycyclic system or is substituted by at least one identical or different radical $R^B$, optionally unsubstituted or substituted by at least one radical selected from the group consisting of halogen, cyano, thio, nitro, hydroxyl, carboxyl, $(C_1-C_6)$-alkyl, $(C_1-C_6)$-haloalkyl, $(C_1-C_4)$-alkoxy-$(C_1-C_4)$-alkyl, $(C_2-C_6)$-alkenyl, $(C_2-C_6)$-haloalkenyl, $(C_2-C_6)$-alkynyl, $(C_2-C_6)$-haloalkynyl, $(C_1-C_6)$-alkoxy, $(C_2-C_6)$-alkenyloxy, $(C_2-C_6)$-alkynyloxy, $(C_1-C_6)$-haloalkoxy, $(C_1-C_4)$-alkoxy-$(C_1-C_4)$-alkoxy, $(C_1-C_6)$-alkylthio, $(C_2-C_6)$-alkenylthio, $(C_2-C_6)$-alkynylthio, $(C_3-C_6)$-cycloalkyl, $(C_3-C_6)$-cycloalkoxy, [$(C_1-C_8)$-alkoxy]-carbonyl, [$(C_1-C_6)$-haloalkoxy]-carbonyl and oxo,
Het$^1$ in each case independently of the others is a saturated, partially unsaturated or heteroaromatic monocyclic heterocyclyl radical having from 3 to 9 ring atoms, optionally having 5 or 6 ring atoms, or a 9- or 10-membered bicyclic heterocycle which contains 1, 2, 3 or 4 heteroatoms selected from the group consisting of O, N and S, optionally a 5- or 6-membered heterocycle having from 1 to 3 ring heteroatoms selected from the group consisting of N, O and S which is optionally also fused to a carbocyclic or heterocyclic ring, optionally a carbocyclic ring having from 3 to 6 carbon atoms or a heterocyclic ring having 5 or 6 ring atoms and 1 to 3 ring heteroatoms selected from the group consisting of N, O and S, optionally benzo-fused,
R* and R** are each independently H, $(C_1-C_8)$-alkyl, $(C_2-C_8)$-alkenyl, $(C_2-C_8)$-alkynyl, $(C_1-C_4)$-alkoxy-$(C_1-C_4)$-alkyl, $(C_1-C_6)$-alkanoyl, [$(C_1-C_4)$-haloalkyl]-carbonyl, [$(C_1-C_4)$-alkoxy]-carbonyl, [$(C_1-C_4)$-haloalkoxy]-carbonyl, or are optionally substituted $(C_3-C_6)$-cycloalkyl, $(C_3-C_6)$-cycloalkyl-$(C_1-C_4)$-alkyl, phenyl, phenyl-$(C_1-C_4)$-alkyl, where each of the radicals in the cycle is optionally substituted by at least one identical or different radicals $R^{bb}$, or
R* and R** together with the nitrogen atom to which they are attached are a 3- to 8-membered heterocycle which, in addition to the nitrogen atom, optionally contains one or two further ring heteroatoms selected from the group consisting of N, O and S and which may be unsubstituted or substituted by at least one radical selected from the group consisting of $(C_1-C_4)$-alkyl, $(C_1-C_4)$-haloalkyl and oxo,
$R^A$ is halogen, cyano, hydroxyl or $(C_1-C_6)$-alkoxy,
$R^B$ is halogen, cyano, hydroxyl, oxo, nitro, $(C_1-C_6)$-alkyl, $(C_1-C_4)$-haloalkyl, cyano-$(C_1-C_4)$-alkyl, hydroxy-$(C_1-C_4)$-alkyl, nitro-$(C_1-C_4)$-alkyl, $(C_2-C_6)$-alkenyl, $(C_2-C_6)$-haloalkenyl, $(C_2-C_6)$-alkynyl, $(C_2-C_6)$-haloalkynyl, $(C_1-C_6)$-alkoxy, $(C_2-C_6)$-alkenyloxy, $(C_2-C_6)$-alkynyloxy, $(C_1-C_6)$-haloalkoxy, $(C_1-C_4)$-alkoxy-$(C_1-C_4)$-alkyl, $(C_1-C_4)$-alkoxy-$(C_1-C_4)$-alkoxy, $(C_1-C_4)$-haloalkoxy-$(C_1-C_4)$-alkyl, $(C_1-C_4)$-haloalkoxy-$(C_1-C_4)$-alkoxy, $(C_1-C_6)$-alkylthio, $(C_2-C_6)$-alkenylthio, $(C_2-C_6)$-alkynylthio, $(C_1-C_6)$-alkylsulfinyl, $(C_1-C_6)$-haloalkylsulfinyl, $(C_1-C_6)$-alkylsulfonyl, $(C_1-C_6)$-haloalkylsulfonyl, a radical of the formula $R^{aa}$—C(=O)— or $R^{aa}$—C(=O)—$(C_1-C_4)$-alkyl, —NR*R**, tri-[$(C_1-C_4)$-alkyl]-silyl, or tri-[$(C_1-C_4)$-alkyl]-silyl-$(C_1-C_6)$-alkyl, or is optionally substuted $(C_3-C_6)$-cycloalkyl, $(C_3-C_6)$-cycloalkoxy, $(C_3-C_6)$-cycloalkyl-$(C_1$-

$C_4$)-alkyl, ($C_3$-$C_6$)-cycloalkyl-($C_1$-$C_8$)-alkoxy, phenyl, phenyl-($C_1$-$C_6$)-alkyl, phenoxy, phenoxy-($C_1$-$C_6$)-alkyl, phenylamino, phenylamino-($C_1$-$C_6$)-alkyl or a 5- or 6-membered monocyclic or 9- or 10-membered bicyclic heterocycle which contains 1, 2, 3 or 4 heteroatoms selected from the group consisting of O, N and S, where each of the radicals is optionally substituted in the cyclic moiety by at least one identical or different radical $R^{bb}$, $R^C$ and $R^D$ each independently are hydrogen, or are optionally substituted ($C_1$-$C_8$)-alkyl, ($C_2$-$C_8$)-alkenyl or ($C_2$-$C_8$)-alkynyl, that is unsubstituted or substituted by at least one radical selected from the group consisting of halogen, cyano, nitro, hydroxyl, ($C_1$-$C_6$)-alkoxy, ($C_2$-$C_6$)-alkenyloxy, ($C_2$-$C_6$)-alkynyloxy, ($C_1$-$C_8$)-haloalkoxy, ($C_1$-$C_4$)-alkoxy-($C_1$-$C_4$)-alkoxy, ($C_1$-$C_8$)-alkylthio, ($C_1$-$C_8$)-haloalkylthio, ($C_1$-$C_8$)-alkylsulfinyl, ($C_1$-$C_8$)-haloalkylsulfinyl, ($C_1$-$C_8$)-alkylsulfonyl, ($C_1$-$C_8$)-haloalkylsulfonyl and tri-[($C_1$-$C_4$)-alkyl]-silyl, or are optionally substuted ($C_3$-$C_8$)-cycloalkyl, ($C_5$-$C_8$)-cycloalkenyl, ($C_5$-$C_8$)-cyclo-alkynyl, phenyl, ($C_3$-$C_8$)-cycloalkyl-($C_1$-$C_6$)-alkyl, ($C_5$-$C_8$)-cycloalkenyl-($C_1$-$C_6$)-alkyl, ($C_5$-$C_8$)-cycloalkynyl-($C_1$-$C_6$)-alkyl, phenyl-($C_1$-$C_6$)-alkyl, ($C_3$-$C_8$)-cycloalkyloxy-($C_1$-$C_6$)-alkyl, ($C_3$-$C_8$)-cycloalkyl-S(O)$_p$—($C_1$-$C_6$)-alkyl, ($C_5$-$C_8$)-cycloalkenyloxy-($C_1$-$C_6$)-alkyl, ($C_5$-$C_8$)-cycloalkynyloxy-($C_1$-$C_6$)-alkyl, phenoxy-($C_1$-$C_6$)-alkyl, phenyl-S(O)$_p$—($C_1$-$C_6$)-alkyl, ($C_3$-$C_8$)-cycloalkylamino-($C_1$-$C_6$)-alkyl, ($C_5$-$C_8$)-cycloalkenylamino-($C_1$-$C_6$)-alkyl, ($C_5$-$C_8$)-cycloalkynylamino-($C_1$-$C_6$)-alkyl, phenylamino-($C_1$-$C_6$)-alkyl, Het$^1$, Het$^1$-($C_1$-$C_6$)-alkyl, Het$^1$—O—($C_1$-$C_6$)-alkyl or Het$^1$—S(O)$_p$—($C_1$-$C_6$)-alkyl, where each of the radicals is unsubstituted in the acyclic moiety or substituted by at least one identical or different radicals $R^A$ and is unsubstituted in the cyclic moiety or substituted by at least one identical or different radicals $R^B$ and p is in each case independently of the others 0, 1 or 2, $R^{aa}$ in each case independently of the others is hydrogen, OH, ($C_1$-$C_6$)-alkyl, ($C_1$-$C_4$)-haloalkyl, ($C_2$-$C_6$)-alkenyl, ($C_2$-$C_6$)-alkynyl, ($C_1$-$C_6$)-alkoxy, ($C_1$-$C_6$)-alkoxy-($C_1$-$C_6$)-alkyl, ($C_1$-$C_6$)-alkoxy-($C_1$-$C_6$)-alkyloxy, ($C_1$-$C_4$)-haloalkoxy, ($C_1$-$C_4$)-haloalkoxy-($C_1$-$C_6$)-alkyl, ($C_1$-$C_4$)-haloalkoxy-($C_1$-$C_6$)-alkoxy, ($C_3$-$C_6$)-alkenyloxy, ($C_3$-$C_6$)-alkenyloxy-($C_3$-$C_6$)-alkyl, ($C_3$-$C_6$)-alkenyloxy-($C_1$-$C_6$)-alkoxy, ($C_3$-$C_6$)-alkynyloxy, ($C_3$-$C_6$)-alkynyloxy-($C_1$-$C_6$)-alkyl, ($C_3$-$C_6$)-alkynyloxy-($C_1$-$C_6$)-alkoxy, —NR*R*, where R* and R** are as defined above, tri-[($C_1$-$C_4$)-alkyl]-silyl, tri-[($C_1$-$C_4$)-alkyl]-silyl-($C_1$-$C_6$)-alkyl, or tri-[($C_1$-$C_4$)-alkyl]-silyl-($C_1$-$C_6$)-alkoxy, or is optionally substituted ($C_3$-$C_6$)-cycloalkyl, ($C_3$-$C_6$)-cycloalkoxy, ($C_3$-$C_6$)-cycloalkyl-($C_1$-$C_8$)-alkyl, ($C_3$-$C_6$)-cycloalkyl-($C_1$-$C_8$)-alkoxy, ($C_5$-$C_6$)-cycloalkenyl, ($C_5$-$C_6$)-cycloalkenyl-($C_1$-$C_6$)-alkyl, ($C_5$-$C_6$)-cycloalkenyloxy, ($C_5$-$C_6$)-cycloalkynyl, ($C_5$-$C_6$)-cycloalkynyl-($C_1$-$C_6$)-alkyl, ($C_5$-$C_6$)-cycloalkynyl-($C_1$-$C_6$)-alkoxy, phenyl, phenyl-($C_1$-$C_6$)-alkyl, phenyl-($C_1$-$C_6$)-alkoxy, phenoxy, phenoxy-($C_1$-$C_6$)-alkyl, phenoxy-($C_1$-$C_6$)-alkoxy, phenylthio, phenyl-S(O)$_p$—($C_1$-$C_6$)-alkyl, phenyl-S(O)$_p$—($C_1$-$C_6$)-alkoxy, where p in each case independently of the others is 0, 1 or 2, phenylamino, phenylamino-($C_1$-$C_6$)-alkyl, phenylamino-($C_1$-$C_6$)-alkoxy or a 5- or 6-membered monocyclic or 9- or 10-membered bicyclic heterocycle which is optionally attached via an alkylene group or alkoxy group and contains 1, 2, 3 or 4 heteroatoms selected from the group consisting of O, N and S, where each of the radicals is optionally substituted in the cyclic moiety by at least one identical or different radicals $R^{bb}$, and $R^{bb}$ in each case independently of the others is halogen, ($C_1$-$C_4$)-alkyl, ($C_1$-$C_4$)-haloalkyl, ($C_1$-$C_4$)-alkoxy or ($C_1$-$C_4$)-haloalkoxy.

4. The compound and/or a salt thereof as claimed in claim 1, wherein ($R^2$)$_n$ is n substituents $R^2$, where each of the substituents $R^2$ independently is halogen, cyano, nitro, ($C_1$-$C_6$)-alkyl, ($C_1$-$C_6$)-alkoxy, ($C_1$-$C_6$)-alkylthio, ($C_1$-$C_6$)-alkylsulfinyl, ($C_1$-$C_6$)-alkylsulfonyl, ($C_1$-$C_6$)-haloalkyl, ($C_1$-$C_6$)-haloalkoxy, ($C_1$-$C_6$)-haloalkylthio, ($C_1$-$C_6$)-haloalkylsulfinyl, ($C_1$-$C_6$)-haloalkylsulfonyl, ($C_2$-$C_6$)-alkenyl, ($C_2$-$C_6$)-alkynyl, tri-[($C_1$-$C_4$)-alkyl]-silyl or tri-[($C_1$-$C_4$)-alkyl]-silyl-($C_1$-$C_4$)-alkyl or if n is greater than 1, where two groups $R^2$ located ortho at the ring together are optionally a group of the formula —$Z^1$-$A^*$-$Z^2$ in which $A^*$ is an alkylene group having from 1 to 4 carbon atoms which is optionally substituted by at least one radical selected from the group consisting of halogen, ($C_1$-$C_4$)-alkyl, ($C_1$-$C_4$)-haloalkyl, ($C_1$-$C_4$)-alkoxy and ($C_1$-$C_4$)-haloalkoxy, $Z^1$ is a direct bond, O or S and $Z^2$ is a direct bond, O or S, where the group —$Z^1$-$A^*$-$Z^2$ together with the carbon atoms of the phenyl ring to which they are attached form a fused-on 5- or 6-membered ring, and ($R^3$)$_m$ is m substituents $R^3$, where each of the substituents $R^3$ independently is halogen, cyano, nitro, ($C_1$-$C_6$)-alkyl, ($C_1$-$C_6$)-alkoxy, ($C_1$-$C_6$)-alkylthio, ($C_1$-$C_6$)-alkylsulfinyl, ($C_1$-$C_6$)-alkylsulfonyl, ($C_1$-$C_6$)-haloalkyl, ($C_1$-$C_6$)-haloalkoxy, ($C_1$-$C_6$)-haloalkylthio, ($C_1$-$C_6$)-haloalkylsulfinyl, ($C_1$-$C_6$)-haloalkylsulfonyl, ($C_2$-$C_6$)-alkenyl, ($C_2$-$C_6$)-alkynyl, tri-[($C_1$-$C_4$)-alkyl]-silyl or tri-[($C_1$-$C_4$)-alkyl]-silyl-($C_1$-$C_4$)-alkyl or if m is greater than 1, where two groups $R^3$ located ortho at the ring together are optionally a group of the formula —$Z^3$-$A^{}$-$Z^4$ in which $A^{}$ is an alkylene group having from 1 to 4 carbon atoms which is optionally substituted by at least one radical selected from the group consisting of halogen, ($C_1$-$C_4$)-alkyl, ($C_1$-$C_4$)-haloalkyl, ($C_1$-$C_4$)-alkoxy and ($C_1$-$C_4$)-haloalkoxy, $Z^3$ is a direct bond, O or S and $Z^4$ is a direct bond, O or S, where the group —$Z^3$-$A^{**}$-$Z^4$ together with the carbon atoms of the phenyl ring to which they are attached form a fused-on 5- or 6-membered ring, and n and m are each independently of one another 0, 1, 2, 3, 4 or 5, optionally 0, 1, 2 or 3, with the proviso that n and m are not simultaneously 0.

5. The compound and/or a salt thereof as claimed in claim 1, wherein ($R^2$)$_n$ is n substituents $R^2$, where each of the substituents $R^2$ independently is halogen, cyano, nitro, ($C_1$-$C_4$)-alkyl, ($C_1$-$C_4$)-alkoxy, ($C_1$-$C_4$)-alkylthio, ($C_1$-$C_4$)-alkylsulfinyl, ($C_1$-$C_4$)-alkylsulfonyl, ($C_1$-$C_4$)-haloalkyl, ($C_1$-$C_4$)-haloalkoxy, ($C_1$-$C_4$)-haloalkylthio, ($C_1$-$C_4$)-haloalkylsulfinyl, ($C_1$-$C_4$)-haloalkylsulfonyl, ($C_2$-$C_4$)-alkenyl, ($C_2$-$C_4$)-alkynyl, tri-[($C_1$-$C_4$)-alkyl]-silyl or tri-[($C_1$-$C_4$)-alkyl]-silyl-($C_1$-$C_4$)-alkyl and n is 0, 1, 2, 3, 4 or 5, optionally 0, 1, 2 or 3, optionally 0, 1 or 2, with the proviso that n and m are not both simultaneously 0.

6. The compound and/or a salt thereof as claimed in claim 1, wherein $(R^3)_m$ is m substituents $R^3$, where each of the substituents $R^3$ independently is halogen, cyano, nitro, $(C_1-C_4)$-alkyl, $(C_1-C_4)$-alkoxy, $(C_1-C_4)$-alkylthio, $(C_1-C_4)$-alkylsulfinyl, $(C_1-C_4)$-alkylsulfonyl, $(C_1-C_4)$-haloalkyl, $(C_1-C_4)$-haloalkoxy, $(C_1-C_4)$-haloalkylthio, $(C_1-C_4)$-haloalkylsulfinyl, $(C_1-C_4)$-haloalkylsulfonyl, $(C_2-C_6)$-alkenyl, $(C_2-C_6)$-alkynyl or tri-$[(C_1-C_4)$-alkyl]silyl-$Z^b$—, where $Z^b$ is a covalent bond or $(C_1-C_4)$-alkylene, or if n is greater than 1, where two groups $R^3$ located ortho at the ring together are optionally a group of the formula —$Z^3$-A-$Z^4$, where A is an alkylene group which is optionally substituted by at least one radical selected from the group consisting of halogen, $(C_1-C_4)$-alkyl, $(C_1-C_4)$-haloalkyl, $(C_1-C_4)$-alkoxy and $(C_1-C_4)$-haloalkoxy, $Z^3$ is O or S and $Z^4$ is O or S, where the group —$Z^3$-A**-$Z^4$ together with the carbon atoms, attached to the group, of the phenyl ring form a fused-on 5- or 6-membered ring, m is 0, 1, 2, 3, 4 or 5, optionally 0, 1, 2, 3 or 4, or optionally 0, 1, 2 or 3, with the proviso that n and m in formula (I) are not both simultaneously 0.

7. The compound and/or a salt thereof as claimed in claim 1, wherein $(R^2)_n$ is n substituents $R^2$, where each of the substituents $R^2$ independently is fluorine, chlorine, bromine, iodine, cyano, nitro, methyl, ethyl, methoxy, methylthio, methylsulfinyl, methylsulfonyl, trifluoromethyl, trifluoromethoxy, trifluoroalkylthio, trifluoromethylsulfinyl or trifluoromethylsulfonyl, and $(R^3)_m$ is m substituents $R^3$, where each of the substituents $R^3$ independently is halogen, cyano, nitro, methyl, methoxy, methylthio, methylsulfinyl, methylsulfonyl, trifluoromethyl, trifluoromethoxy, trifluoroalkylthio, trifluoromethylsulfinyl or trifluoromethylsulfonyl, and m is 0, 1, 2, 3, 4 or 5, optionally 0, 1, 2, 3 or 4, or optionally 0, 1, 2 or 3 and n is 0, 1, 2, 3, 4 or 5, optionally 0, 1, 2 or 3, or optionally 0, 1 or 2, with the proviso, that n and m are not simultaneously 0.

8. The compound and/or a salt thereof as claimed in claim 1, wherein $(R^2)_n$ is 2-bromo, 3-bromo, 4-bromo, 2-chloro, 3-chloro, 4-chloro, 2-fluoro, 3-fluoro, 4-fluoro, 2-cyano, 3-cyano, 4-cyano, 2-methyl, 3-methyl, 4-methyl, 2-ethyl, 3-ethyl, 4-ethyl, 2-$CF_3$, 3-$CF_3$, 4-$CF_3$, 2-methoxy, 3-methoxy, 4-methoxy, 2-ethoxy, 3-ethoxy, 4-ethoxy, 2-methylthio, 3-methylthio, 4-methylthio, 2-methylsulfinyl, 3-methylsulfinyl, 4-methylsulfonyl, 2-methylsulfonyl, 3-methylsulfonyl, 4-methylsulfonyl, 2,3-dimethyl, 2,4-dimethyl, 2,5-dimethyl, 2,6-dimethyl, 3,4-dimethyl, 3,5-dimethyl, 2,3-difluoro, 2,4-difluoro, 2,5-difluoro, 2,6-difluoro, 3,4-difluoro, 3,5-difluoro, 2,3-dichloro, 2,4-dichloro, 2,5-dichloro, 2,6-dichloro, 3,4-dichloro, 3,5-dichloro, (2-Cl-3-F), (2-Cl-4-F), (2-Cl-5-F), (2-Cl-6-F), (3-Cl-2-F), (3-Cl-4-F), (3-Cl-5-F), (3-Cl-6-F), (4-Cl-2-F), (4-Cl-3-F), (4-Br-3-F), (3-Br-4-F), (3-Br-5-F), (4-Br-3-Cl), (3-Br-4-Cl), (4-CN-3-F), (3-CN-4-F), (3-CN-5-F), (3-CN-3-Cl), (3-CN-4-Cl), 2,3,4-trifluoro, 2,3,5-trifluoro, 2,3,6-trifluoro, 2,4,6-trifluoro, 3,4,5-trifluoro, 2,3,4-trichloro, 2,3,5-trichloro, 2,3,6-trichloro, 2,4,6-trichloro or 3,4,5-trichloro and $(R^3)_m$ is 2-bromo, 3-bromo, 4-bromo, 2-chloro, 3-chloro, 4-chloro, 2-fluoro, 3-fluoro, 4-fluoro, 2-cyano, 3-cyano, 4-cyano, 2-methyl, 3-methyl, 4-methyl, 2-ethyl, 3-ethyl, 4-ethyl, 2-$CF_3$, 3-$CF_3$, 4-$CF_3$, 2-methoxy, 3-methoxy, 4-methoxy, 2-ethoxy, 3-ethoxy, 4-ethoxy, 2-methylthio, 3-methylthio, 4-methylthio, 2-methylsulfinyl, 3-methylsulfinyl, 4-methylsulfonyl, 2-methylsulfonyl, 3-methylsulfonyl, 4-methylsulfonyl, 2-nitro, 3-nitro, 4-nitro, 2,3-dimethyl, 2,4-dimethyl, 2,5-dimethyl, 2,6-dimethyl, 3,4-dimethyl, 3,5-dimethyl, 2,3-difluoro, 2,4-difluoro, 2,5-difluoro, 2,6-difluoro, 3,4-difluoro, 3,5-difluoro, 2,3-dichloro, 2,4-dichloro, 2,5-dichloro, 2,6-dichloro, 3,4-dichloro, 3,5-dichloro, 2,5-dicyano, 2,6-dicyano, (2-Cl-3-F), (2-Cl-4-F), (2-Cl-5-F), (2-Cl-6-F), (3-Cl-2-F), (3-Cl-4-F), (3-Cl-5-F), (3-Cl-6-F), (4-Cl-2-F), (4-Cl-3-F), (4-Br-2-F), (4-Br-3-F), (4-CN-3-F), (4-$NO_2$-3-F), (4-OMe-3-F), (3-CN-4-F), (3-$NO_2$-4-F), (3-CN-4-Cl), (3-$NO_2$-4-Cl), (5-CN-2-F), 2,3,4-trifluoro, 2,3,5-trifluoro, 2,3,6-trifluoro, 2,4,6-trifluoro, 3,4,5-trifluoro, 2,3,4-trichloro, 2,3,5-trichloro, 2,3,6-trichloro, 2,4,6-trichloro or 3,4,5-trichloro.

9. A process for preparing a compound of formula (I) as defined in claim 1, and/or a salt thereof comprising (a) reacting a compound of formula (II)

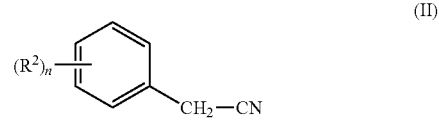

with a compound of formula (III) and/or a salt thereof

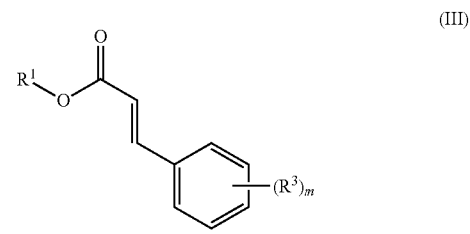

to give a compound of formula (I')

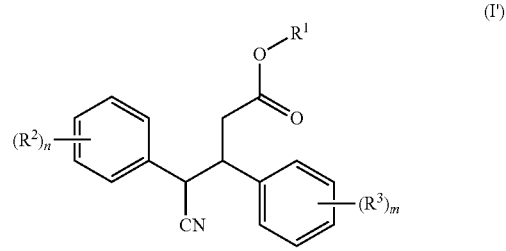

where $R^1$, $R^2$, $R^3$, m and n in the compounds (II), (III) and (I') are as defined in the respective compound of formula (I) to be prepared, and sepqrqting and isolating the (3R,4R)-threo isomer from an isomer mixture (I')

or (b) reacting a compound of formula (I")

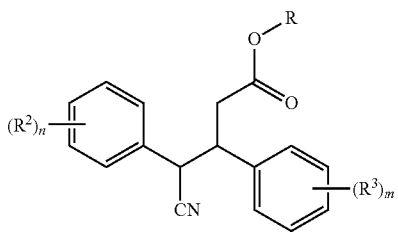

(I")

in which R is a radical selected from the group of radicals possible for $R^1$, but different from the radical $R^1$ in the compound (I') to be prepared,
with a compound of formula $R^1$—OH in which $R^1$ is defined as in the compound of formula (I) to be prepared, to give compound (I'), where $R^2$, $R^3$, m and n in the compound (I") are as defined in the compound of formula (I) to be prepared in each case, and separating and isolating the (3R,4R)-threo isomer is from the isomer mixture (I')

or (c) reacting a stereochemically enriched compound of the (3R,4R)-threo isomers of formula (I"')

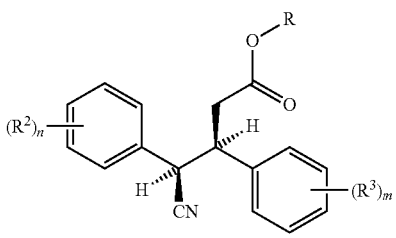

(I"')

in which R is a radical selected from the group of the radicals possible for $R^1$, but different from the radical $R^1$ in the compound (I) to be prepared, with a compound of formula $R^1$—OH in which $R^1$ is defined as in the compound of formula (I) to be prepared, to give compound (I), where $R^2$, $R^3$, m and n in the compound (I"') are as defined in the compound of formula (I) to be prepared.

10. A herbicidal and/or a plant growth-regulating composition which comprises at least one compound of formula (I) and/or a salt thereof as defined in claim 1, and at least one formulation auxiliary said auxiliary being customary in crop protection.

11. A method for controlling a harmful plant and/or for regulating the growth of a plant which comprises applying an effective amount of at least one compound of formula (I) and/or a salt thereof as defined in claim 1, onto a plant, a plant seed, soil in which and/or on which a plant grows and/or an area under cultivation.

12. The method as claimed in claim 11, wherein a compound of formula (I) and/or a salt thereof is employed for controlling a harmful plant and/or for regulating growth in a crop of a useful plant and/or an ornamental plant.

13. The method as claimed in claim 12, wherein the crop plant is a transgenic crop plant.

14. A compound of formula (I) and/or a salt thereof as claimed in claim 1, capable of being used as a herbicide and/or a plant growth regulator.

15. A compound of the formula (I) and/or a salt thereof capable of being used as claimed in claim 14, wherein the compound and/or salt is capable of being applied to a crop of a useful and/or an ornamental plant.

16. A method for regulating the growth of a plant which comprises applying an effective amount of at least one compound of formula (I) and/or a salt thereof as defined in claim 1, onto a plant, a plant seed, or soil in which and/or on which a plant grows and/or an area under cultivation.

17. The method as claimed in claim 16, wherein the compound of formula (I) and/or a salt thereof is employed for regulating growth in a crop of a useful plant and/or an ornamental plant.

18. A method for controlling a harmful plant which comprises applying an effective amount of at least one compound of formula (I) and/or a salt thereof as defined in claim 1, onto a plant, a plant seed, or soil in which and/or on which a plant grows and/or an area under cultivation.

19. The method as claimed in claim 18, wherein the compound of formula (I) and/or a salt thereof is employed for controlling a harmful plant in a crop of a useful plant and/or an ornamental plant.

* * * * *